US009301974B2

(12) United States Patent  
Cope et al.

(10) Patent No.: US 9,301,974 B2
(45) Date of Patent: *Apr. 5, 2016

(54) METHODS AND COMPOSITIONS FOR SELECTIVELY REMOVING POTASSIUM ION FROM THE GASTROINTESTINAL TRACT OF A MAMMAL

(71) Applicant: Relypsa, Inc., Redwood City, CA (US)

(72) Inventors: Michael J. Cope, Berkeley, CA (US); Paul Mansky, San Francisco, CA (US); Futian Liu, Sunnyvale, CA (US); Han-Ting Chang, Livermore, CA (US); Dominique Charmot, Campbell, CA (US); Eric Connor, Los Gatos, CA (US); Kalpesh Biyani, Fremont, CA (US); Mingjun Liu, Campbell, CA (US); Tony Kwok-Kong Mong, Hsinchu (TW); Yan Chen, Cupertino, CA (US)

(73) Assignee: Relypsa, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/053,725

(22) Filed: Oct. 15, 2013

(65) Prior Publication Data

US 2014/0044804 A1  Feb. 13, 2014

Related U.S. Application Data

(63) Continuation of application No. 13/901,918, filed on May 24, 2013, now abandoned, which is a continuation of application No. 12/088,625, filed as application No. PCT/US2006/038602 on Oct. 2, 2006, now Pat. No. 8,617,609.

(60) Provisional application No. 60/723,073, filed on Sep. 30, 2005.

(51) Int. Cl.

| | |
|---|---|
| *A61K 9/14* | (2006.01) |
| *A61K 33/06* | (2006.01) |
| *A61K 9/50* | (2006.01) |
| *A61K 31/75* | (2006.01) |
| *A61K 31/785* | (2006.01) |
| *A61K 31/74* | (2006.01) |
| *A61K 9/16* | (2006.01) |

(52) U.S. Cl.

CPC ............... *A61K 33/06* (2013.01); *A61K 9/5026* (2013.01); *A61K 31/74* (2013.01); *A61K 31/75* (2013.01); *A61K 31/785* (2013.01); *A61K 9/1694* (2013.01)

(58) Field of Classification Search

None  
See application file for complete search history.

(56) References Cited

U.S. PATENT DOCUMENTS

| | | | |
|---|---|---|---|
| 2,611,730 A | 9/1952 | Heming | |
| 2,909,462 A | 10/1959 | Warfield et al. | |
| 3,416,884 A * | 12/1968 | Stynes et al. | 423/181 |
| 3,499,960 A | 3/1970 | Macek et al. | |
| 3,874,907 A | 4/1975 | Gardon et al. | |
| 3,974,272 A | 8/1976 | Polli et al. | |
| 4,143,130 A | 3/1979 | Imondi et al. | |
| 4,380,590 A | 4/1983 | Chong | |
| 4,470,975 A | 9/1984 | Berger et al. | |
| 4,492,205 A | 1/1985 | Jundt et al. | |
| 4,605,701 A | 8/1986 | Harada et al. | |
| 4,747,881 A | 5/1988 | Shaw et al. | |
| 4,837,015 A | 6/1989 | Olsen | |
| 4,902,501 A | 2/1990 | Bandi et al. | |
| 4,942,205 A | 7/1990 | Ohmori et al. | |
| 5,051,253 A | 9/1991 | Lloyd-Jones et al. | |
| 5,091,175 A | 2/1992 | Imondi et al. | |
| 5,141,927 A | 8/1992 | Krotkiewski | |
| 5,186,937 A | 2/1993 | Sparks et al. | |
| 5,281,631 A | 1/1994 | Horwitz et al. | |
| 5,374,422 A | 12/1994 | St. Pierre et al. | |
| 5,413,782 A | 5/1995 | Warchol et al. | |
| 5,487,888 A | 1/1996 | Mandeville, III et al. | |
| 5,502,232 A | 3/1996 | Buysch et al. | |
| 5,607,669 A | 3/1997 | Mandeville, III et al. | |
| 5,618,530 A | 4/1997 | Mandeville, III et al. | |

(Continued)

FOREIGN PATENT DOCUMENTS

| | | |
|---|---|---|
| EP | 0 349 453 A1 | 1/1990 |
| EP | 0730494 A1 | 9/1996 |
| JP | 1998-059851 A | 3/1998 |
| JP | 1998-130154 A | 5/1998 |
| JP | 2004-149525 A | 5/2004 |

(Continued)

OTHER PUBLICATIONS

Wrong, O., et al., "The Electrolyte Content Faeces", Proc. R. Soc. Med., 1965, pp. 1007-1009, vol. 58, No. 12.

(Continued)

*Primary Examiner* — Susan Tran  
(74) *Attorney, Agent, or Firm* — Senniger Powers LLP

(57) ABSTRACT

The present invention provides methods and compositions for the treatment of ion imbalances using core-shell composites and compositions comprising such core-shell composites. In particular, the invention provides core-shell particles and compositions comprising potassium binding polymers, and core-shell particles and compositions comprising sodium binding polymers, and in each case, pharmaceutical compositions thereof. Methods of use of the polymeric and pharmaceutical compositions for therapeutic and/or prophylactic benefits are also disclosed. The compositions and methods of the invention offer improved approaches for treatment of hyperkalemia and other indications related to potassium ion homeostasis, and for treatment of hypertension and other indicates related to sodium ion homeostasis.

26 Claims, 25 Drawing Sheets

(56) References Cited

U.S. PATENT DOCUMENTS

| | | | |
|---|---|---|---|
| 5,633,344 A | 5/1997 | Figuly | |
| 5,667,775 A | 9/1997 | Holmes-Farley et al. | |
| 5,679,717 A | 10/1997 | Mandeville, III et al. | |
| 5,693,675 A | 12/1997 | Mandeville, III et al. | |
| 5,702,696 A | 12/1997 | Mandeville, III et al. | |
| 5,718,920 A | 2/1998 | Notenbomer | |
| 5,824,339 A | 10/1998 | Shimizu et al. | |
| 5,846,990 A | 12/1998 | Murugesan et al. | |
| 5,888,472 A | 3/1999 | Bem et al. | |
| 5,891,417 A | 4/1999 | Bem et al. | |
| 5,935,599 A | 8/1999 | Dadey | |
| 6,099,737 A | 8/2000 | Sherman et al. | |
| 6,280,717 B1 | 8/2001 | Kamakura et al. | |
| 6,294,163 B1 | 9/2001 | Dhal et al. | |
| 6,332,985 B1 | 12/2001 | Sherman et al. | |
| 6,558,665 B1 | 5/2003 | Cohen et al. | |
| 6,579,460 B1 | 6/2003 | Willis et al. | |
| 6,814,871 B1 | 11/2004 | Bem et al. | |
| 6,881,484 B2 | 4/2005 | Kataoka et al. | |
| 7,488,495 B2 | 2/2009 | Charmot et al. | |
| 7,566,432 B2 * | 7/2009 | Wong | 423/305 |
| 2002/0054903 A1 | 5/2002 | Tyler et al. | |
| 2002/0054913 A1 | 5/2002 | Heese et al. | |
| 2002/0146386 A1 | 10/2002 | Simon et al. | |
| 2003/0027789 A1 | 2/2003 | Yamaoka et al. | |
| 2003/0065090 A1 | 4/2003 | Kelly et al. | |
| 2004/0105895 A1 * | 6/2004 | Ash | 424/617 |
| 2004/0166156 A1 | 8/2004 | Tyler et al. | |
| 2004/0251204 A1 | 12/2004 | Paananen et al. | |
| 2005/0036983 A1 | 2/2005 | Simon et al. | |
| 2005/0106267 A1 * | 5/2005 | Frykman et al. | 424/684 |
| 2005/0220751 A1 * | 10/2005 | Charmot et al. | 424/78.1 |
| 2005/0220752 A1 | 10/2005 | Charmot et al. | |
| 2005/0220889 A1 | 10/2005 | Charmot et al. | |
| 2005/0220890 A1 | 10/2005 | Charmot et al. | |
| 2006/0024336 A1 | 2/2006 | Charmot et al. | |

FOREIGN PATENT DOCUMENTS

| | | |
|---|---|---|
| WO | 82/00257 A1 | 2/1982 |
| WO | 92/10522 A1 | 6/1992 |
| WO | 94/27619 A1 | 12/1994 |
| WO | 95/05184 A2 | 2/1995 |
| WO | 95/14531 A1 | 6/1995 |
| WO | 97/49387 A1 | 12/1997 |
| WO | 97/49736 A2 | 12/1997 |
| WO | 00/40224 A1 | 7/2000 |
| WO | 01/51063 A1 | 7/2001 |
| WO | 02/12160 A1 | 2/2002 |
| WO | 02/40039 A2 | 5/2002 |
| WO | 02/062356 A2 | 8/2002 |
| WO | 2005/065291 A2 | 7/2005 |

OTHER PUBLICATIONS

Wrong, O. M., "Role of the Human Colon in Homeostasis," Scientific Basis of Medicine Annual Reviews, 1971, pp. 192-215.
Wrong, et al., "In Vivo Dialysis of Feces as a Method of Stool Analysis", Clinical Science, 1965, pp. 357-375, vol. 28.
Agarwal, et al., "Pathophysiology of Potassium Absorption and Secretion by the Human Intestine", Gastroenterology, 1994, pp. 548-571, vol. 107, American Gastroenterological Association.
Arshady, R., "Biodegradable Microcapsular Drug Delivery Systems: Manufacturing Methodology, Release Control and Targeting Prospects," Journal of Bioactive and Compatible Polymers, Jul. 1990, pp. 315-342, vol. 5.
Berlyne, G. M., et al., "Cation Exchange Resins in Hyperkalaemic Renal Failure", Israel J. Med Sci., 1967, pp. 45-52, vol. 3, No. 1.
Blake, J., M.D., et al., "Differential Effects of Direct Antagonism of All Compared to ACE Inhibitors on Serum Potassium Levels and Azotemia in Patients with Severe Congestive Heart Failure," Congestive Heart Failure, Jul./Aug. 2000, pp. 193-196, vol. 6, No. 4, CHF, Inc., Darien, Connecticut.
Chourasia, M. K., et al., "Pharmaceutical Approaches to Colon Targeted Drug Delivery Systems", J. Pharm Pharm Sci., 2003, pp. 33-66, vol. 6, No. 1.
Coli, L., et al., "Phosphate Removal by Resin Hemoperfusion Efficacy and Biocompatibility of a New Exchange Resin", Biomaterials, Artificial Cells, and Immobilization Biotechnology, 1992, pp. 1153-1163, vol. 20, No. 5.
Corcoran, A. C., et al., "Controlled Observations on the Effect of Low Sodium Dietotherapy in Essential Hypertension", Circulation, 1951, pp. 1-16, vol. 3, No. 1.
Cuna, M. et al., "Controlled-Release Liquid Suspensions Based on Ion-Exchange Particles Entrapped Within Acrylic Microcapusles", International Journal of Pharmaceutics, 2000, pp. 151-158, vol. 199, Elsevier Science.
Dai, et al., "Controlling Ion Transport through Mulitlayer Polyelectrolyte Membranes by Derivatization with Photolabile Functional Groups", Macromolecules, 2002, pp. 3164-3170, vol. 35, American Chemical Society.
Danowski, T. S., et al., "Changes in Fecal and Serum Constituents During Ingestion of Cation and Anion Exchangers", Ann N Y Acad. Sci., 1953, pp. 273-279, vol. 57, No. 3.
Emerson Jr., K., et al., "The Role of the Gastro-Intestinal Tract in the Adaptation of the Body to the Prevention of Sodium Depletion by Cation Exchange Resins", Ann N Y Acad Sci., 1953, pp. 280-290, vol. 57, No. 3.
Emmett, M., et al., "Effect of Three Laxatives and a Cation Exchange Resin on Fecal Sodium and Potassium Excretion", Gastroenterology, 1995, pp. 752-760, vol. 108, No. 3.
EP Search Report for counterpart foreign Application No. 05731099 dated May 8, 2007, 3 pages.
EP Search Report for counterpart foreign Application No. 05732849 dated May 8, 2007.
Estrela-Lopis, et al., "SANS Studies of Polyelectrolyte Multilayers on Colloidal Templates", Langmuir, 2002, pp. 7861-7866, vol. 18, American Chemical Society.
Evans, B. M., et al., "Ion-Exchange Resins in the Treatment of Anuria", Lancet, 1953, pp. 791-795, vol. 265, No. 6790.
Field, Jr., H., et al., "Electrolyte Changes in Ileal Contents and in Feces During Restriction of Dietary Sodium With and Without the Administration of Cation-Exchange Resin", Circulation, 1955, pp. 625-629, vol. 12, No. 4.
Field, Jr., H., et al., "Mechanisms Regulating the Retention of Sodium in the Feces by Cation-Exchange Resin: Release of Base from the Resin by Bacterial Fermentation in the Terminal Ileum", J. Lab Clin Med., 1958, pp. 178-184, vol. 51, No. 2.
Forrest, M. L., et al., "A Degradable Polyethylenimine Derivative with Low Toxicity for Highly Efficient Gene Delivery", Bioconjugate Chem., 2003, pp. 934-940, vol. 14, No. 5.
Fourman, P., "Capacity of a Cationic Exchange Resin (zeo-karb 225) In Vivo" British Medical Journal, 1953, pp. 544-546, vol. 1, No. 4809.
Friedman, E. A., "Clinical Aspects of Uremia and Dialysis/Sorbent Therapy in Uremia", 1976, pp. 671-687.
Friedman, E. A., et al., "Combined Oxystarch-Charcoal Trial in Uremia: Sorbent-induced Reduction in Serum Cholesterol", Kidney International, 1976, pp. S273-S276, vol. 10.
Gerstman, et al., "Use of Sodium Polystyrene Sulfonate in Sorbitol in the United States", American Journal of Kidney Diseases, Nov. 1991, pp. 619-621, vol. XVIII, No. 5.
Greenman, L., et al., "Biochemical Changes Accompanying the Ingestion of a Carboxylic Cation Exchanger in the Hydrogen, Ammonium, Sodium, Potassium, or Calcium Form", J. Clin Invest., 1951, pp. 995-1008, vol. 30, No. 9.
Gruy-Kapral, C., et al., "Effect of Single Dose Resin-Cathartic Therapy on Serum Potassium Concentration in Patients With End-Stage Renal Disease", J. Am. Soc. Nephrol, 1998, pp. 1924-1930, vol. 9, No. 10.
Harthon, J. G. L., et al., "A Case of Uremia and Hyperpotassemia Treated With Sulphonic Cation-Exchange Resin", Acta Med. Scan, 1952, pp. 230-236, vol. 144, No. 3.
Heming, A. E., et al., "Considerations in the Selection of Cation Exchange Resins for Therapeutic Use", Ann N Y Acad Sci., 1953, pp. 239-251, vol. 57, No. 3.

(56) References Cited

OTHER PUBLICATIONS

Ichikawa, H. et al., "Use of Ion-Exchange Resins to Prepare 100 μm-sized Microcapsules with Prolonged Drug-Release by the Wurster Process", International Journal of Pharmaceutics, 2001, pp. 67-76, vol. 216, Elsevier Science.
Imondi, A. R., et al., "Gastrointestinal Sorbents for the Treatment of Uremia I. Lightly Cross-Linked Carboxyvinyl Polymers", Ann Nutr Metabol., 1981, pp. 311-319, vol. 25, No. 5.
Irwin, L., et al., "The Effect of a Cation Exchange Resin on Electrolyte Balance and Its Use in Edematous States", J. Clin Invest., 1949, pp. 1403-1411, vol. 28, No. 6, Part 2.
Ishibashi, M., et al., "Application of Synthetic Hydrated Aluminum Silicates as Orally Administered Absorbents of Ammonium Ion," Chemical & Pharmaceutical Bulletin, 1986, pp. 806-812, vol. 34, No. 2.
Ishibashi, M., et al., "Synthetic Hydrated Aluminum Silicates as Oral Absorbents of Potassium Ion," Chemical & Pharmaceutical Bulletin, 1986, pp. 2973-2978, vol. 34, No. 7.
Johnson, K., et al., "Sodium Polystyrene Sulfonate Resin Candy for Control of Potassium in Chronic Dialysis Patients," Clinical Nephrology, 1976, pp. 266-268, vol. 5, No. 6.
Kim, et al., "Therapeutic Approach to Hyperkalemia", Nephron, 2002, pp. 33-40, vol. 92, Supplement 1, Division of Nephrology, Department of Internal Medicine, Hanyang University Kuri Hospital, Kuri, Korea.
Kohlstaedt, K. G., et al., "Clinical Experience With Mixtures of Anion and Cation Exchange Resins", Ann N Y Acad Sci., 1953, pp. 260-272, vol. 57, No. 3.
Koping-Hoggard, M., et al., "Chitosan as a Nonviral Gene Delivery System. Structure-Property Relationships and Characteristics Compared with Polyethylenimine In Vitro and After Lung Administration In Vivo", Gene Therapy, 2001, pp. 1108-1121, vol. 8.
Mason, N. S., et al., "A New Ion Exchanger With High In Vivo Sodium Capacity" Kidney Int. Suppl., 1985, pp. S178-S182, vol. 28, No. 17.
Mateer, F. M., et al., "Sodium Restriction and Cation Exchange Resin Therapy in Nephrotic Children", J Clin Invest, 1951, pp. 1018-1026, vol. 30, No. 9.
McChesney, E.W., "Effects of Long-Term Feeding of Sulfonic Ion Exchange Resin on the Growth and Mineral Metabolism of Rats", Am. J. Physiol., 1954, pp. 395-400, vol. 177, No. 3.
McChesney, E. W., et al., "Some Aspects of Cation Exchange Resins as Therapeutic Agents for Sodium Removal", Ann N Y Aced Sci., 1953, pp. 252-259, vol. 57, No. 3.
Meszaros, et al., "Adsorption of Poly(ethyleneimine) on Silica Surfaces: Effect of pH on the Reversibility of Adsorption", Langmuir, 2004, pp. 5026-5029, vol. 20, American Chemical Society.
Moustafine, R. I., et al., "Characteristics of Interpolyelectrolyte Complexes of Eudragit E 100 With Sodium Alginate", Int. J. Pharm., 2005, pp. 113-120, vol. 294, Nos. 1-2.
Picart, et al., "Microinterferometric Study of the Structure, Interfacial Potential, and Viscoelastic Properties of Polyelectrolyte Multilayer Films on a Planar Substrate", J. Phys. Chem. B, 2004, pp. 7196-7205, vol. 108, American Chemical Society.
Root, M. A., "Comparison of the In Vivo Sodium-Removing Activity of Various Types of Ion Exchange Resins in Rats", J. Lab. Clin. Med., 1953, pp. 430-437, vol. 42, No. 3.
Ross, E. J., et al., "Observations on Cation Exchange Resins in the Small and Large Intestines", 1954, pp. 555-566, Medical Unit, University College Hospital Medical School, London, W.C.1.
Salas-Coll, et al., "Potassium Transport Across the Distal Colon in Man", Clinical Science and Molecular Medicine, 1976, pp. 287-296, vol. 51.
Spencer, et al., "Cation Exchange in the Gastrointestinal Tract", 1954, pp. 603-606, Medical Unit, University College Hospital Medical School, London, W.C.1.
Thies, C., "Microcapsules as Drug Delivery Devices," Crit Rev Biomed Eng., 1982, pp. 335-383, vol. 8, No. 4.
Thomas, M., et al., "Cross-Linked Small Polyethylenimines: While Still Nontoxic, Deliver DNA Efficiently to Mammalian Cells In Vitro and In Vivo", Pharmaceutical Research, 2005, pp. 373-380, vol. 22, No. 3.
Tust, R. H., et al., "The Effects of Malethamer on the Excretion and Plasma Levels of Sodium, Potassium, and Chloride (34990)", Proc. Soc. Exp. Biol. Med., 1970, pp. 72-76, vol. 135, No. 1.
Ash, Stephen R., "Cation Exchangers as Oral Sorbents for Ammonium and Potassium: PSS, ZP and ZS (Zirconium Silicate)," Clarian Arnett Health, Wellbound and HemoCleanse, Inc., Lafayette, Indiana, Presented at the ASAIO Innovation Conference, Chicago, Illinois, 2007, 25 pages.
Brown, T. L., et al., Chemistry, The Central Science, Fifth Edition, 1991, p. 256.
Cattaneo, M. V., et al., "The Potential of a Microencapsulated Urease-Zeolite Oral Sorbent for the Removal of Urea in Uremia," ASAIO Transactions, Apr.-Jun. 1991, pp. 80-87, vol. 37, No. 2.
Gardner, D. L., et al., "An Orally Administered Microcapsule System for Treating Chronic Renal Failure Patients," Applied Biochemistry and Biotechnology, 1984, pp. 27-40, vol. 10.
Kjellstrand, C., et al., "On the Clinical Use of Microencapsulated Zirconium Phosphate-Urease for the Treatment of Chronic Uremia," Transactions—American Society for Artificial Internal Organs, 1981, pp. 24-29, vol. 27.
Wolfe, E. A., et al., "Orally Ingested Microencapsulated Urease and an Adsorbent, Zirconium Phosphate, to Remove Urea in Kidney Failure," The International Journal of Artificial Organs, 1987, pp. 269-274, vol. 10, No. 4.
Baerlocher, C., et al., Atlas of Zeolite Framework Types, Fifth Revised Edition, 2001, Elsevier.
McCUSKER, L. B., et al., "Nomenclature of Structural and Compositional Characteristics of Ordered Microporous and Mesoporous Materials With Inorganic Hosts (IUPAC Recommendations 2001)," Pure and Applied Chemistry, 2001, pp. 381-394, vol. 73, No. 2.
Clearfield et al., "Journal of Molecular Structure," 1998, vol. 470:207-213.

* cited by examiner

BINDING DATA FOR DOWEX(Na) AT 37 C IN NI CONDITION
([Mg2+], 50 mM;[K+], 50 mM)

BINDING DATA FOR DOWEX(Na) WITH A CROSSLINKED PVAm SHELL
(2gm COATING BATCH) AT 37 C IN NI CONDITION
[Mg2+], 50 mM;[K+], 50 mM)

BINDING DATA FOR DOWEX(Na) WITH A CROSSLINKED PVAm SHELL
(100gm COATING BATCH) AT 37 C IN NI CONDITION
[Mg2+], 50 mM;[K+], 50 mM)

BINDING DATA FOR DOWEX(Na) WITH A PVAm SHELL CROSSLINKED BY N,DGA
(4.0gm COATING BATCH) AT 37 C IN NI CONDITION
[Mg2+], 50 mM;[K+], 50 mM)

FIG. 5
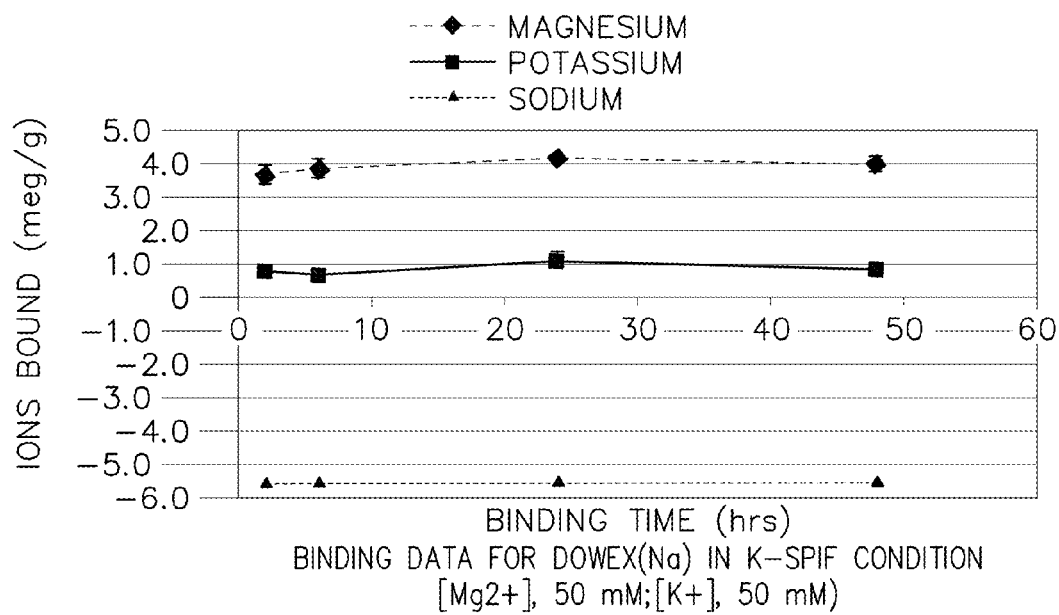
BINDING DATA FOR DOWEX(Na) IN K-SPIF CONDITION
[Mg2+], 50 mM;[K+], 50 mM)
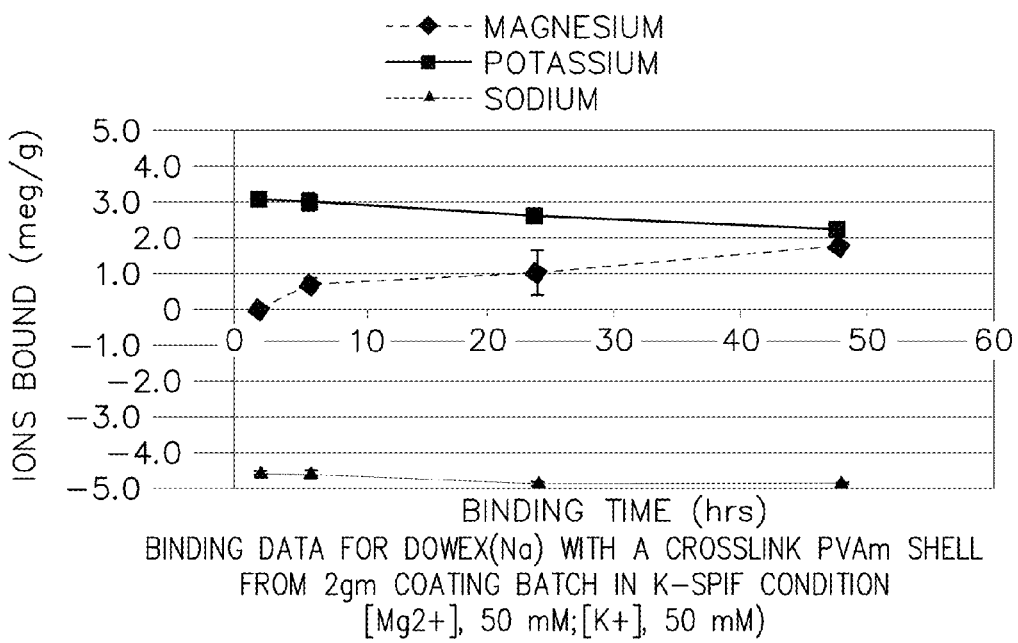
BINDING DATA FOR DOWEX(Na) WITH A CROSSLINK PVAm SHELL
FROM 2gm COATING BATCH IN K-SPIF CONDITION
[Mg2+], 50 mM;[K+], 50 mM)
FIG. 6

BINDING DATA FOR DOWEX(Na) WITH A CROSSLINK PVAm SHELL
FROM 100gm COATING BATCH AT 37 C IN K-SPIF CONDITION
[Mg2+], 50 mM;[K+], 50 mM)

BINDING DATA FOR DOWEX(Na) WITH A PVAm SHELL CROSSLINKED BY N, N-DGA
(4.0gm COATING BATCH) AT 37 C IN K-SPIF CONDITION
[Mg2+], 50 mM;[K+], 50 mM)

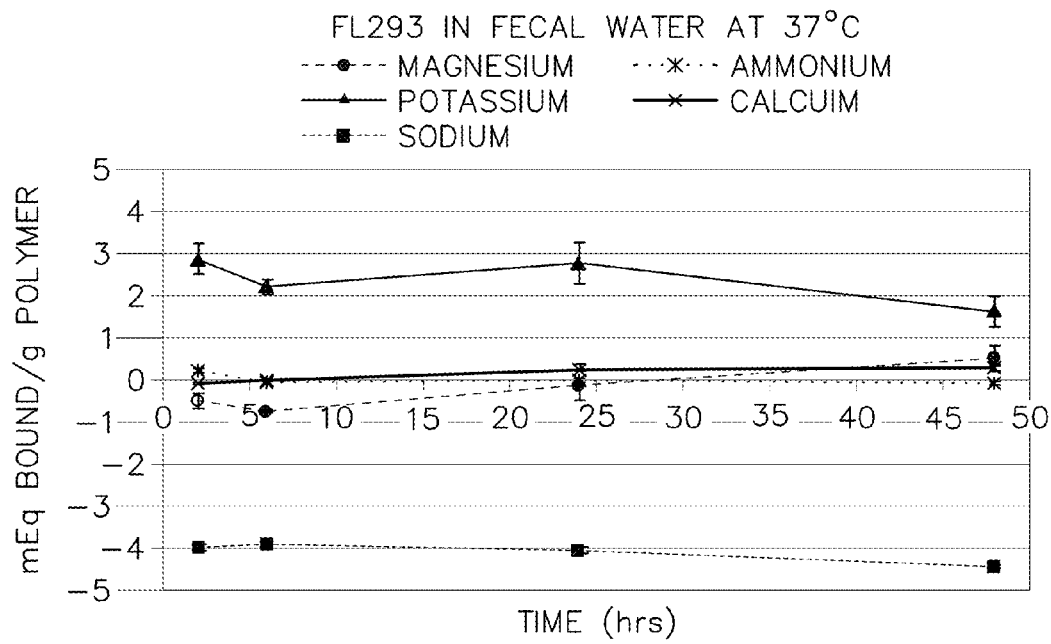
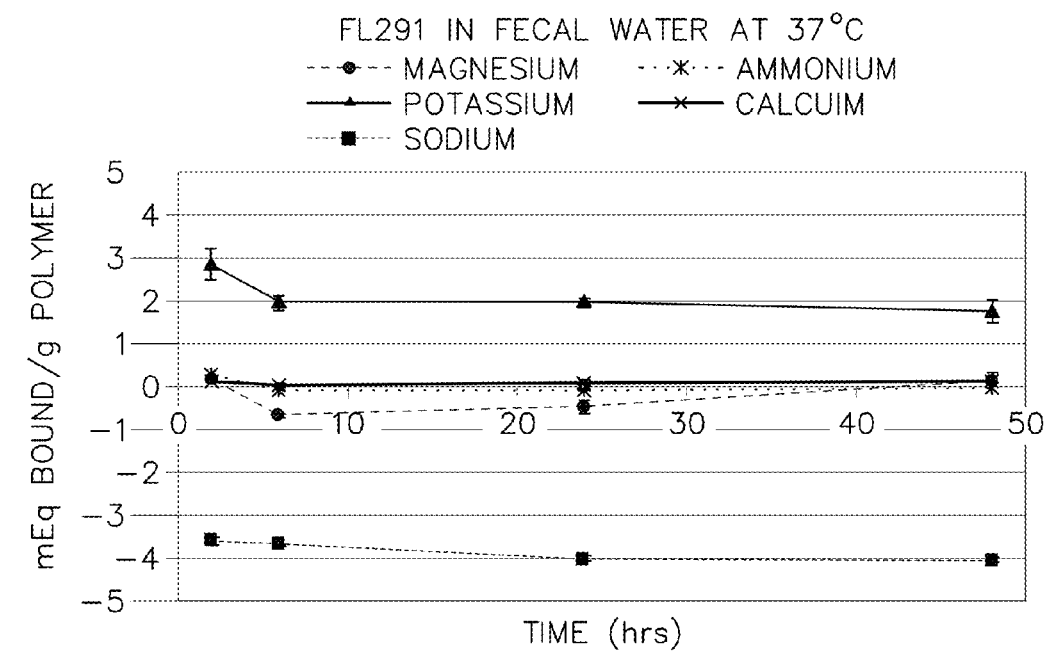

FIG. 13A
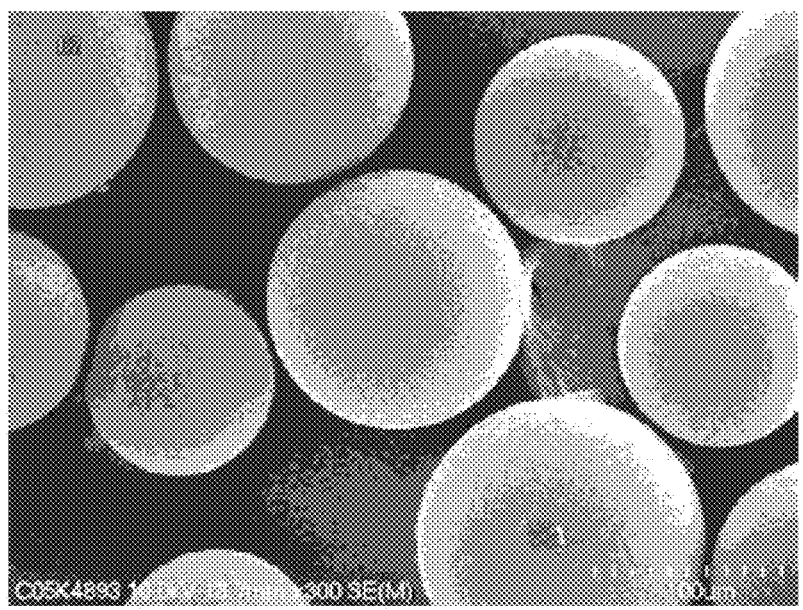
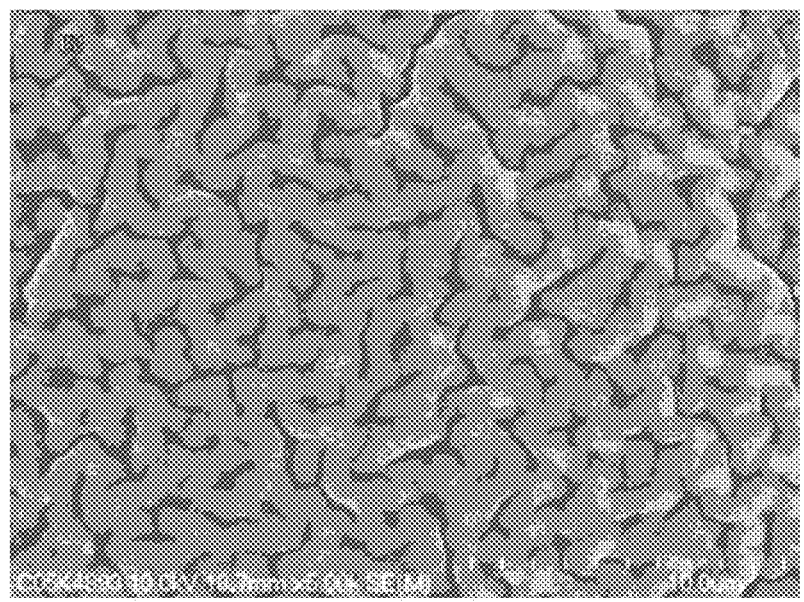
FIG. 13B

FIG. 14A
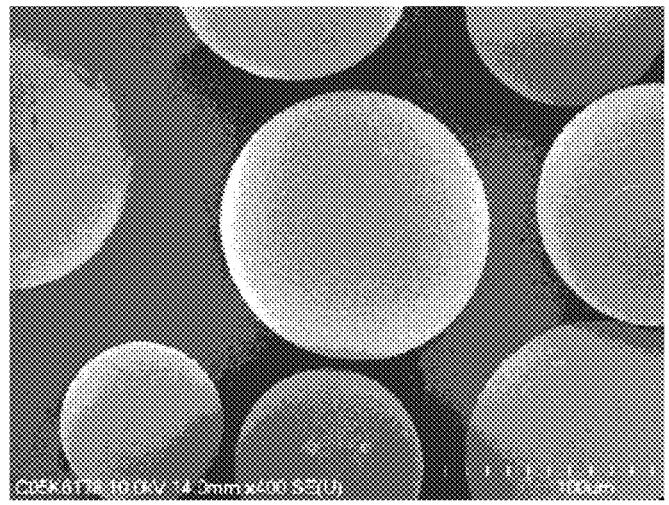
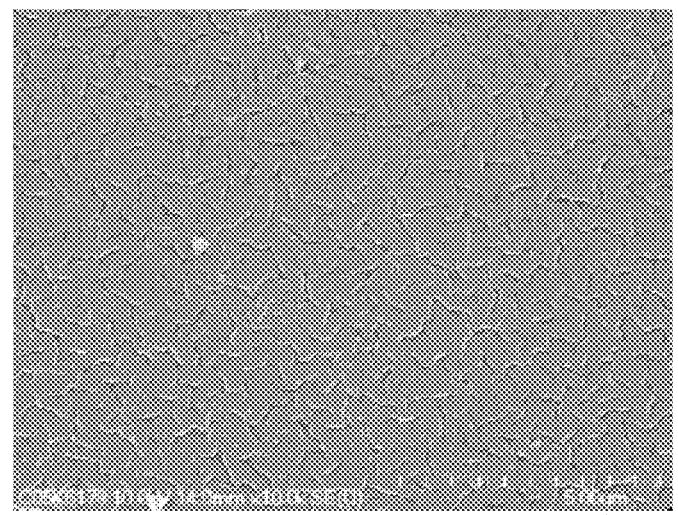
FIG. 14B

FIG. 15A
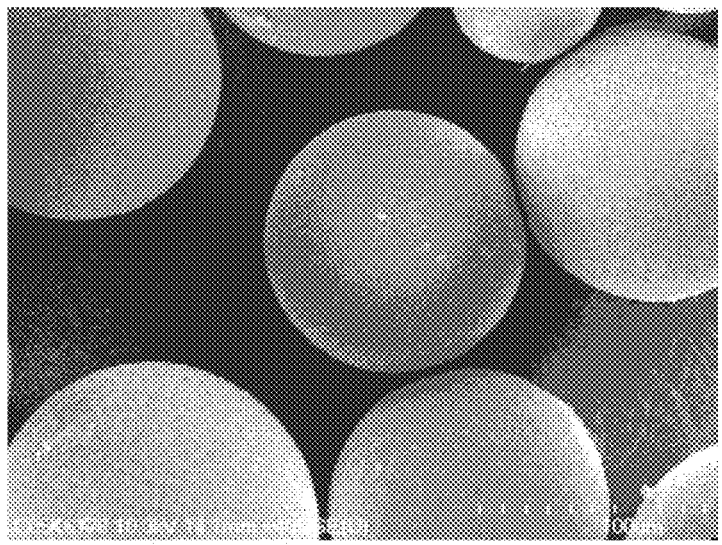
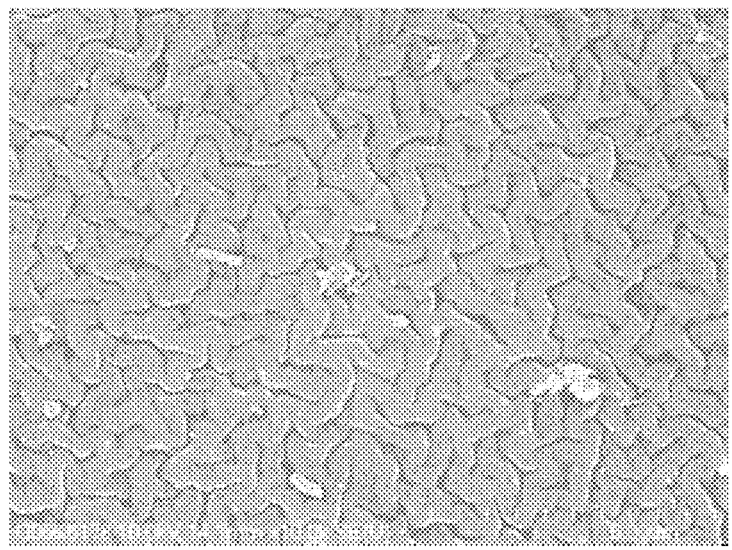
FIG. 15B

FIG. 16A
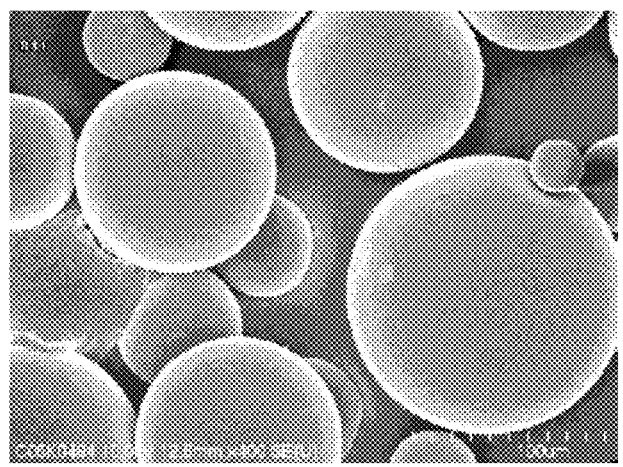
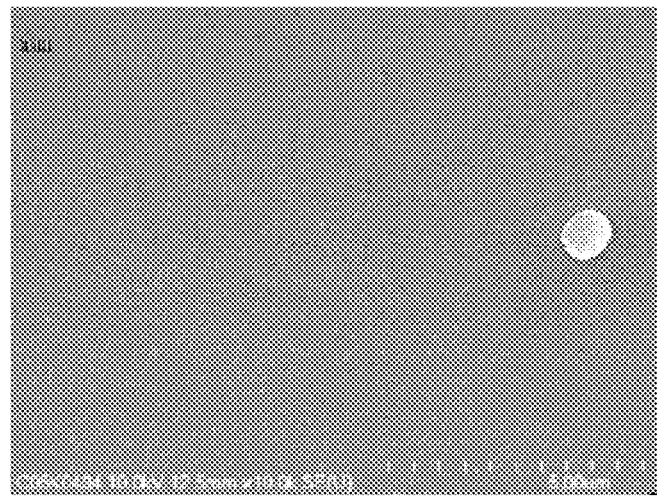
FIG. 16B

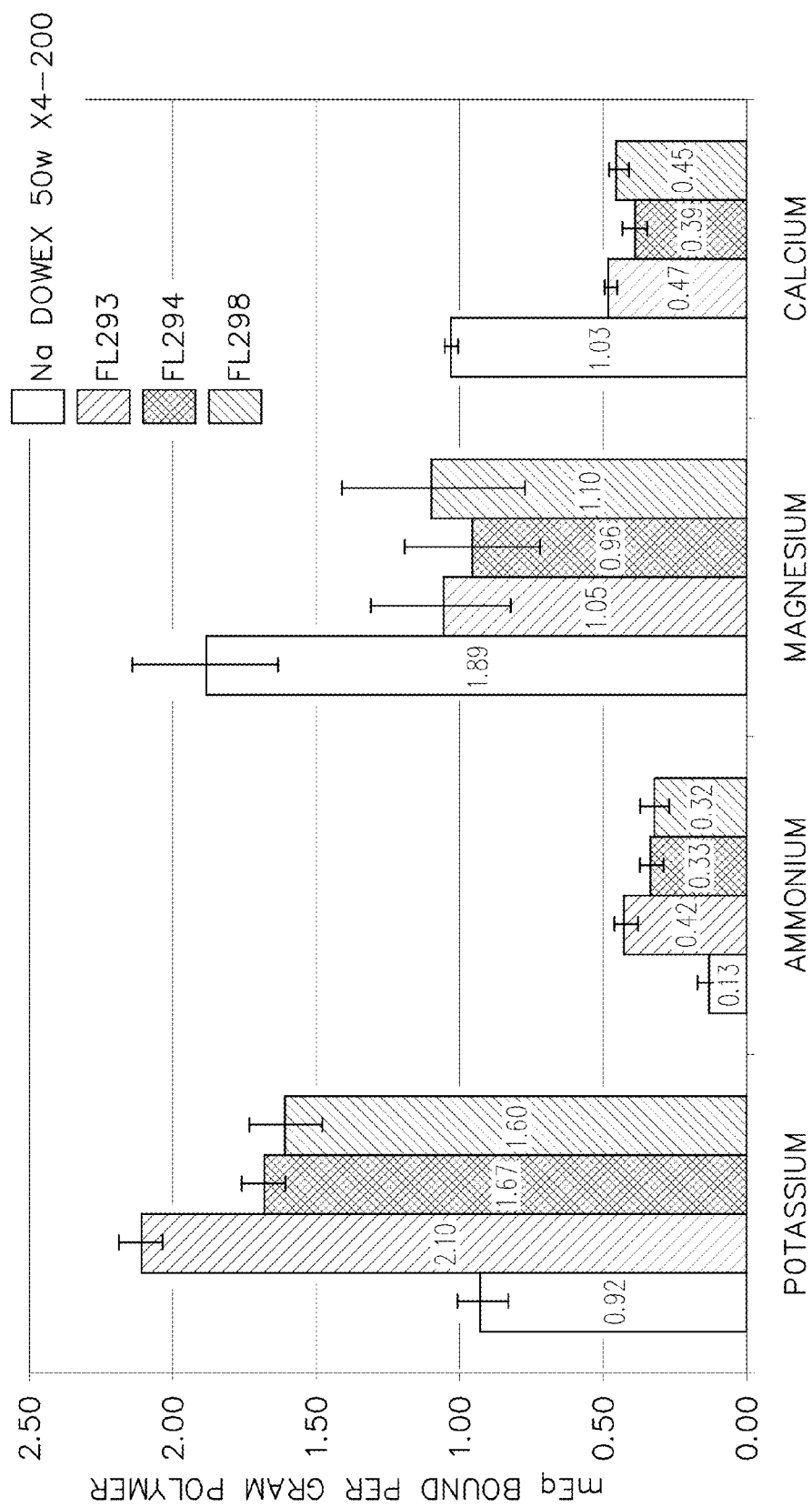

METHODS AND COMPOSITIONS FOR SELECTIVELY REMOVING POTASSIUM ION FROM THE GASTROINTESTINAL TRACT OF A MAMMAL

CROSS-REFERENCE TO RELATED APPLICATIONS

This application is a continuation of U.S. patent application Ser. No. 13/901,918, filed May 24, 2013, which is a continuation of U.S. patent application Ser. No. 12/088,625, filed Sep. 30, 2008, which is a U.S. PCT National of PCT/US2006/038602, filed Mar. 30, 2005, which claims the benefit of U.S. Provisional Application Ser. No. 60/723,073 which was filed Sep. 30, 2005. The entire content of these applications is incorporated herein by reference.

BACKGROUND OF THE INVENTION

Potassium ($K^+$) is the most abundant intracellular cation, comprising ~35-40 mEq/kg in humans. See Agarwal, R, et al. (1994) Gastroenterology 107: 548-571; Mandal, A K (1997) Med Clin North Am 81: 611-639. Only 1.5-2.5% of this is extracellular. Potassium is obtained through the diet, mainly through vegetables, fruits, meats and dairy products, with certain food such as potatoes, beans, bananas, beef and turkey being especially rich in this element. See Hunt, C D and Meacham, S L (2001) J Am Diet Assoc 101: 1058-1060; Hazell, T (1985) World Rev Nutr Diet 46: 1-123. In the US, intake is ~80 mEq/day. About 80% of this intake is absorbed from the gastrointestinal tract and excreted in the urine, with the balance excreted in sweat and feces. Thus, potassium homeostasis is maintained predominantly through the regulation of renal excretion. Where renal excretion of $K^+$ is impaired, elevated serum $K^+$ levels will occur. Hyperkalemia is a condition wherein serum potassium is greater than about 5.0 mEq/L.

While mild hyperkalemia, defined as serum potassium of about 5.0-6 mEq/L, is not normally life threatening, moderate to severe hyperkalemia (with serum potassium greater than (about) 6.1 mEq/L) can have grave consequences. Cardiac arrythmias and altered ECG waveforms are diagnostic of hyperkalemia. See Schwartz, M W (1987) Am J Nurs 87: 1292-1299. When serum potassium levels increases above about 9 mEq/L, atrioventricular dissociation, ventricular tachycardia, or ventricular fibrillation can occur.

Hyperkalemia is rare in the general population of healthy individuals. However, certain groups definitely exhibit a higher incidence of hyperkalemia. In patients who are hospitalized, the incidence of hyperkalemia ranges from about 1-10%, depending on the definition of hyperkalemia. Patients at the extremes of life, either premature or elderly, are at high risk. The presence of decreased renal function, genitourinary disease, cancer, severe diabetes, and polypharmacy can also predispose patients to hyperkalemia.

Most of the current treatment options for hyperkalemia are limited to use in hospitals. For example, exchange resins, such as Kayexalate, are not suitable for outpatient or chronic treatment, due to the large doses necessary that leads to very low patient compliance, severe GI side effects and significant introduction of sodium (potentially causing hypernatremia and related fluid retention and hypertension). Diuretics that can remove sodium and potassium from patients via the kidneys are often limited in their efficacy due to underlying kidney disease and frequently related diuretic resistance. Diuretics are also contraindicated in patients where a drop in blood pressure and volume depletion are undesired (e.g. CHF patients that in addition to suffering from low blood pressure are often on a combination of drugs such as ACE inhibitors and potassium sparing diuretics such as spironolactone that can induce hyperkalemia).

The use of cation-binding resins for binding inorganic monovalent cations such as potassium ion and sodium ion has been reported. For example, U.S. Pat. No. 5,718,920 to Notenbomer discloses polymeric core-shell particles said to be effective for binding cations such as sodium ion and potassium ion.

WO 05/097081 and WO 05/020752 describe core-shell particles for binding target solutes. WO 05/020752 describes core-shell particles having shell components comprising polymers, including in one embodiment polymers produced by free radical polymerization of ethylenic monomers. In another embodiment, commercially available polymers, such as Eudragit polymers, are described. Although WO 05/020752 describes core-shell particles that represent an advance in core-shell technology and the use thereof, further improvement with respect to the selective binding and retention of monovalent cations over divalent cations remains desirable, especially as applied to core-shell particles advantaged for use in treating hyperkalemia. Similarly, WO 05/097081 describes potassium binding core-shell particles wherein the shell component comprises polymers, including for example commercially available Eudragit polymer, or (in an alternative embodiment), benzylated polyethyleneimine polymers. Although WO 05/020752 likewise represents an advance in core-shell technology and the use thereof, further opportunity exists for improvement with respect to permselectivity, especially as applied to core-shell particles advantaged for use in treating hyperkalemia.

Notwithstanding the progress made in the art, there remains a need for improved compositions for binding inorganic monovalent cations such as potassium ion and sodium ion, and especially, for binding such monovalent cations selectively over divalent cations such as magnesium ion and calcium ion. In particular, there remains a need for improved core-shell particles having a therapeutically effective binding capacity in the physiologically relevant pH range for potassium ion or sodium ion, where such core-shell particles are substantially non-degradable, substantially non-absorbable and are suitable with respect to lack of toxicity. Likewise, there remains a need in the art for improved methods applying such improved compositions, for example in pharmaceutical and other applications involving the removal of monovalent cations from an environment. In particular, there remains a significant need for improved treatment of hyperkalemia, and related indications using such improved compositions.

SUMMARY OF THE INVENTION

Methods.

The present invention is directed, in a first general aspect, to methods for removal of monovalent cations, preferably inorganic monovalent cations such as potassium ions and sodium ions, from an environment comprising such cations, such as the gastrointestinal tract of a mammal. Preferably, the environment comprises one or more competing solutes, in particular one or more competing divalent cations, preferably inorganic divalent cations such as magnesium ion or calcium ion. The methods are preferably applied for removing potassium ion from a gastrointestinal tract of a mammal.

In one first embodiment within this first aspect of the invention, the method comprises administering a pharmaceutical composition (such as a core-shell particle) to the mammal, where the pharmaceutical composition comprises a permselective polymer for binding potassium ion over magnesium ion (and preferably for binding both sodium ion and potassium ion over both magnesium ion and calcium ion). The permselectivity of the pharmaceutical composition persists during transit of the core-shell particle through the small intestine and the colon. The pharmaceutical composition preferentially exchanges and retains potassium ion over sodium ion in a lower colon of the gastrointestinal tract. A therapeutically effective amount of potassium ion is from the gastrointestinal tract of the mammal Preferably in this embodiment, the core-shell particle can transit through the gastrointestinal tract of the mammal over a period of at least (about) 30 hours, or in some cases, over a longer period of at least (about) 36 hours, or 42 hours or 48 hours.

In another second embodiment within this aspect of the invention, a core-shell particle is administered to mammal, preferably to a human. The core-shell particle comprises a core component and a shell component, the core component being a polymer having a capacity for binding potassium ion, and the shell component being a permselective polymer for binding potassium ion over magnesium ion (and preferably for binding both sodium ion and potassium ion over both magnesium ion and calcium ion). The permselectivity of the core-shell particle for potassium ion over magnesium ion persists during transit of the core-shell particle through the small intestine and the colon. The core-shell particle preferentially binds (e.g. exchanges) and retains potassium ion over sodium ion in a lower colon of the gastrointestinal tract. A therapeutically effective amount of potassium ion is removed from the gastrointestinal tract of the mammal. Preferably in this embodiment, the core-shell particle can transit through the gastrointestinal tract of the mammal over a period of at least (about) 30 hours, or in some cases, over a longer period of at least (about) 36 hours, or 42 hours or 48 hours.

In a further third embodiment of the first aspect of the invention, the invention is directed to methods for treating a pharmaceutical indication based on or derived directly or indirectly from abnormally elevated monovalent cation, such as abnormally elevated serum potassium ion or abnormally elevated serum sodium ion. The method comprises removing potassium ion from a gastrointestinal tract of a mammal according to the first or second embodiments of this invention, as set forth above and as more specifically described hereinafter. The methods and compositions of the invention are suitable for therapeutic and/or prophylactic use in such treatments. For example, the pharmaceutical compositions of the invention can be used to treat hyperkalemia using potassium-binding core-shell particles. In one embodiment, the core-shell particles comprising potassium binding compositions are used in combination with drugs that cause potassium retention, such as potassium-sparing diuretics, angiotensin-converting enzyme inhibitors (ACEIs), Angiotensin receptor blockers (ARBs), non-steroidal anti-inflammatory drugs, heparin, or trimethoprim.

In a further fourth embodiment of this first general (methods) aspect of the invention, the invention is directed to the use of a composition comprising a core-shell particle for manufacture of a medicament. The medicament is preferably for use for prophylactic or therapeutic treatment of various indications, as described herein. The composition can comprise core-shell particles, optionally in combination with one or more pharmaceutically acceptable excipients. The medicament can be used to remove potassium ion from a gastrointestinal tract of a mammal according to the first or second embodiments of this invention, as set forth above and as more specifically described hereinafter.

Compositions of Matter.

In another, second general aspect, the present invention provides compositions of matter, such as pharmaceutical compositions, for removing potassium ion from a gastrointestinal tract of a mammal.

In a first embodiment within the second aspect of the invention, the pharmaceutical composition the pharmaceutical composition can comprise a polymer having a capacity for binding potassium ion, and the pharmaceutical composition can have a persistent selectivity for potassium ion over magnesium ion. The pharmaceutical composition is further characterized by one or more of (a) the pharmaceutical composition having a specific binding for potassium ion of at least (about) 1.0 mmol/gm, preferably at least (about) 1.5 mmol/gm, preferably at least (about) 2.0 mmol/gm achieved within a potassium-binding period of less than (about) 24 hours, preferably less than (about) 18 hours, preferably less than (about) 12 hours, preferably less than (about) six hours, and the pharmaceutical composition having a specific binding for magnesium ion of not more than (about) 3.0, preferably not more than (about) 2.0, preferably not more than (about) 1.0 mmol/gm maintained over a magnesium-binding period of more than (about) eighteen hours, preferably more than (about) 24 hours, (b) the pharmaceutical composition having a relative binding for potassium ion of at least (about) 20%, preferably at least (about) 30%, more preferably at least (about) 40%, in each case by mole of the total bound cation, achieved within a potassium-binding period of less than (about) 24 hours, preferably less than (about) 18 hours, preferably less than (about) 12 hours, preferably less than (about) six hours, and the pharmaceutical composition having a relative binding for magnesium ion of not more than (about) 70%, preferably not more than (about) 60%, preferably not more than (about) 50%, preferably not more than (about) 40%, in each case by mole of the total bound cation, maintained over a magnesium-binding period of more than (about) eighteen hours, preferably more than (about) 24 hours, or (c) the pharmaceutical composition having a time persistence for potassium ion defined as the time needed to reach (about) 80% of the equilibrium binding, $t_{80}$, of not more than (about) 24 hours, preferably not more than (about) 18 hours, preferably not more than (about) 12 hours, preferably not more than (about) 6 hours, and the pharmaceutical composition having a time persistence for magnesium ion defined as the time needed to reach (about) 80% of the equilibrium binding, $t_{80}$, of more than (about) 18 hours, preferably more than (about) 24 hours.

In each case (a), (b) or (c), values are determined in vitro in an assay selected from the group consisting of (i) a first assay consisting essentially of incubating the pharmaceutical composition at a concentration of 4 mg/ml in a solution consisting essentially of 55 mM KCl, 55 mM $MgCl_2$ and 50 mM 2-morpholinoethanesulfonic acid, monohydrate, at a pH of 6.5 and a temperature of 37° C. for 48 hrs with agitation, and directly or indirectly measuring cations bound to the pharmaceutical composition over time, (ii) a second assay consisting essentially of incubating the pharmaceutical composition at a concentration of 4 mg/ml in a solution consisting essentially of 50 mM KCl, 50 mM $MgCl_2$, 50 mM 2-morpholinoethanesulfonic acid, monohydrate, 5 mM sodium taurocholate, 30 mM oleate and 1.5 mM citrate, at a pH of 6.5 and a temperature of 37° C. for 48 hrs with agitation, and directly or indirectly measuring cations bound to the pharmaceutical composition over time, and (iii) a third assay consisting essentially of incubating the pharmaceutical composition at a concentration of 4 mg/ml in fecal water solution, the fecal water solution being a filtered centrifugal supernatant derived by centrifuging human feces for 16 hours at 50,000 g at 4° C. and then filtering the supernatant through a 0.2 um filter, the pharmaceutical composition being incubated in the fecal water solution at a temperature of 37° C. for 48 hrs with agitation, and directly or indirectly measuring cations bound to the pharmaceutical composition over time, and combinations of one or more of the first assay, the second assay and the third assay. In one approach within this first embodiment of the second aspect of the invention, for each case (a) and (b), the potassium-binding period is preferably less than (about) 24 hours and the magnesium-binding period is preferably more than (about) 24 hours. In another approach within such embodiment, for each case (a) and (b), the potassium-binding period is preferably less than (about) 18 hours and the magnesium-binding period is preferably more than (about) 18 hours. In a further approach within such embodiment, for each case (a) and (b), the potassium-binding period is preferably less than (about) 12 hours and the magnesium-binding period is preferably more than (about) 18 hours.

In an additional approach within such embodiment, for each case (a) and (b), the potassium-binding period is preferably less than (about) 6 hours and the magnesium-binding period is preferably more than (about) 18 hours. Similarly, in one approach within this first embodiment of the second aspect of the invention, for case (c), the potassium-binding period is preferably not more than (about) 24 hours and the magnesium-binding period is preferably more than (about) 24 hours. In another approach within such embodiment, for case (c), the potassium-binding period is preferably not more than (about) 18 hours and the magnesium-binding period is preferably more than (about) 18 hours. In a further approach within such embodiment, for case (c), the potassium-binding period is preferably not than (about) 12 hours and the magnesium-binding period is preferably more than (about) 18 hours. In an additional approach within such embodiment, for case (c), the potassium-binding period is preferably not more than (about) 6 hours and the magnesium-binding period is preferably more than (about) 18 hours.

A further third embodiment of the second general aspect of the present invention is directed to a core-shell particle comprising an inner core component and a shell component. The inner core component comprises a cation exchange polymer. The shell component encapsulates the core component and comprises a net positively charged crosslinked amine polymer containing amine moieties, at least 1% and preferably at least 2% of the amine moieties being quaternary ammonium. Preferably in such embodiment, the core-shell particle has a size of (about) 1 μm to (about) 500 μm and a binding capacity for potassium of at least (about) 1.5 mmol/g at a pH greater than 5.5. Such core-shell particles are, in preferred use aspects, administered to a mammal for passage through the gastrointestinal tract of the mammal.

A further fourth embodiment of the second general aspect of the present invention is directed to a core-shell particle comprising and inner core component and a shell component. The inner core component comprises a cation exchange polymer. The shell component encapsulates the core component and comprises a net positively charged crosslinked amine polymer, the polymer comprising amine moieties substituted by an (alk)heterocyclic moiety having the formula —$(CH_2)_m$-HET-$(R_x)_t$ or an (alk)aryl moiety having the formula —$(CH_2)_m$—Ar—$(R_x)_t$, wherein m is 0-10, t is 0-5, HET is a heterocyclic moiety, Ar is an aryl moiety, and $R_x$ is hydrocarbyl or substituted hydrocarbyl, and —$(CH_2)_m$—Ar—$(R_x)_t$ is other than benzyl. Such core-shell particles are, in preferred use aspects, administered to a mammal for passage through the gastrointestinal tract of the mammal.

In a further fifth embodiment of the second general aspect of the invention, the invention is directed to a composition for use as a pharmaceutical. Preferably, the invention is directed to a composition for use in therapy (including for use in prophylactic or therapeutic therapy) for treatment of various indications, as described above below with respect to the first aspect (methods) of the invention. The composition can comprise a pharmaceutical composition such as a core-shell particles, for example as described above in connection with the first, second, third and fourth embodiments of this aspect of the invention. The composition can optionally comprise one or more pharmaceutically acceptable excipients and additionally or alternatively, optionally can be applied in combination with a liquid media for suspending or dispersing the composition (e.g., core-shell particles). The composition can be formulated into any suitable form (e.g., tablets, etc., as more fully described below). The core-shell particle can be used as described above with respect to the one first embodiment of the first aspect of the invention.

In the various embodiments of the first and second aspects of the invention, the selectivity (e.g., permselectivity) of the pharmaceutical composition (such as core-shell particles) of the invention is sufficiently persistent to have a beneficial effect, such as a beneficial prophylactic or a beneficial therapeutic effect. In particular, in applications involving the gastrointestinal environment, the compositions (and core-shell particles) of the invention can remove a greater amount of potassium ion than sodium ion from the gastrointestinal tract (within a potassium-binding period representative of the transit time for the lower colon), and can have a persistent selectivity for potassium ion over one or more divalent ions, e.g., magnesium ion, calcium ion (over a divalent ion-binding period representative of the transit time through the gastrointestinal tract or a relevant portion there of (e.g., through the small intestine and the colon)).

In any embodiment of the first general aspect or of the second general aspect of the present invention, the core shell particle can be further characterized as being or as having one or more additional features, described as follows in the paragraphs included hereinafter within the Summary of the Invention and as detailed in the Detailed Description of the Invention. Such additional features are considered to be part of the invention in any and all possible combinations with each other and with one or more embodiments of the invention as mentioned in connection with the first or second aspect thereof.

Shell Component.

In particularly preferred embodiments, the shell component comprises a crosslinked polyvinylic (e.g., polyvinylamine) polymer having one or more further features or characteristics (alone or in various combinations), as described herein. In some embodiments, the polyvinylic polymer can be a densely crosslinked polyvinylic polymer. In some embodiments, for example, the polyvinylic polymer can be a product of a crosslinking reaction comprising crosslinking agent and polyvinylic polymer (e.g., of repeat units of the polymer or of crosslinkable functional groups of the polymer) in a ratio of not less than (about) 2:1, and preferably in a ratio ranging from (about) 2:1 to (about) 10:1, ranging from (about) 2.5:1 to (about) 6:1, or ranging from (about) 3:1 to (about) 5:1 and in some embodiments in a ratio of (about) 4:1, in each case on a molar basis. In some embodiments, the crosslinked shell polymer can be a crosslinked polyvinylamine polymer comprising a crosslinking moieties and amine moieties in a ratio of not less than (about) 0.05:1, preferably not less than (about)

0.1:1, and preferably in a ratio ranging from (about) 0.1:1 to (about) 1.5:1, more preferably ranging from (about) 0.5:1 to (about) 1.25:1, or from (about) 0.75:1 to (about) 1:1, in each case based on mole equivalent of crosslinking moiety to amine moiety in the crosslinked polyvinylamine polymer.

Shell Crosslinking Agents.

The shell can be crosslinked with a crosslinking agent. Generally, the crosslinking agent comprises a compound having at least two amine reactive moieties. In some embodiments, the crosslinking agent for the shell component can be a hydrophobic crosslinking agent.

Robustness.

The core-shell particle of any aspect or embodiment of the invention is preferably sufficiently robust to survive in the environment of use—for example, to pass through the gastrointestinal system (or an in-vitro assay representative thereof) for pharmaceutical applications—without substantially disintegrating such core shell particle, and/or preferably without substantially degrading physical characteristics and/or performance characteristics of the core-shell particle. In preferred embodiments, the shell component of the core-shell composition is essentially not disintegrated and/or has physical characteristics and/or performance characteristics that are essentially not degraded under physiological conditions of the gastrointestinal tract (or in vitro representations or mimics thereof) during a period of time for residence in and passage through the environment of interest, such as the gastrointestinal tract.

Deformable Polymer.

In some embodiments, the shell component is preferably a deformable polymer, and more preferably deformable crosslinked polymer that can accommodate changes in the core component dimensions (e.g., due to swelling—such as from hydration in an aqueous environment; or e.g., do to manufacturing protocols—such as drying; or e.g., due to storage—such as in a humid environment).

Non-Absorbed.

Preferably core-shell particles and the compositions comprising such core-shell particles are not absorbed from the gastro-intestinal tract. Preferably, (about) 90% or more of the polymer is not absorbed, more preferably (about) 95% or more is not absorbed, even more preferably (about) 97% or more is not absorbed, and most preferably (about) 98% or more of the polymer is not absorbed.

Potassium Binding Capacity.

The core-shell particle of any aspect or embodiment of the invention can have an effective amount of a potassium binding core, such as a potassium binding polymer (e.g., a polymer having a capacity for binding potassium). In some embodiments, the core-shell particle can have a therapeutically effective amount of a potassium binding core, such that upon being administered to a mammal subject, such as a human, the core-shell particle effectively binds and removes an average of at least (about) 1.5 mmol (or 1.5 mEq) or higher of potassium per gm of core-shell particle. The core-shell particle can also be characterized by its binding capacity based on in vitro binding capacity for potassium, as described hereinafter in the Detailed Description of the Invention.

Selectivity.

Advantageously, core-shell particles of the invention are selective to monovalent cations over divalent cations. The crosslinked shell polymer can be a permselective polymer, having a permselectivity for inorganic monovalent cations over inorganic divalent cations. In preferred embodiments, the relative permeability of the shell polymer for monovalent ion versus divalent ion can be characterized by a permeability ratio of permeability for monovalent ions (e.g., potassium ions) to permeability for divalent cations (e.g., $Mg^{++}$ and $Ca^{++}$), as measure in suitable environment-representative in vitro assays. For example, as measured in gastrointestinal representative assays, the permeability ratio can be at least (about) at least (about) 2:1, and preferably at least (about) 5:1, or at least (about) 10:1 or at least (about) 100:1, or at least (about) 1,000:1 or at least (about) 10,000:1. As measured in gastrointestinal representative assays, the permeability ratio can range, for example, from (about) 1:0.5 to (about) 1:0.0001 (i.e., from (about) 2:1 to (about) 10,000:1), and can preferably range from (about) 1:0.2 and (about) 1:0.01 (i.e., from (about) 5:1 to (about) 100:1).

Shell Amount/Thickness/Particle Size.

The core-shell particle can preferably comprise a shell component and a core component in a relative amount generally ranging from (about) 1:1000 to (about) 1:2 by weight. In preferred embodiments, the relative amount of shell component to core component can range from (about) 1:500 to (about) 1:4 by weight, or ranging from (about) 1:100 to (about) 1:5 by weight, or ranging from (about) 1:50 to (about) 1:10 by weight. In some embodiments, shell component can have a thickness ranging from (about) 0.002 micron to (about) 50 micron, preferably (about) 0.005 micron to (about) 20 microns, or from (about) 0.01 microns to (about) 10 microns.

Product-by-Process.

The core-shell particles and compositions of the invention can be a product resulting from a process comprising steps for preparing a core-shell composite (such as a core-shell particle) comprising a core component and a crosslinked shell polymer formed over a surface of the core component. In particular, the core-shell particles and compositions of the invention can be a product resulting from a certain multiphase process with in situ crosslinking. A preferred process can comprise, in one general embodiment, forming a core-shell intermediate comprising a core component, and a shell polymer associated with a surface of the core component. The core-shell intermediate is formed for example in a first liquid phase. The core-shell intermediate is phase-isolated from a bulk portion of the first liquid phase. Preferably, the core-shell intermediate is phase-isolated using a second liquid phase, the second liquid phase being substantially immiscible with the first liquid phase. The phase-isolated core-shell intermediate is contacted with a crosslinking agent under crosslinking conditions (to crosslink the shell polymer associated with the surface of the core component). The resulting product is the core-shell composite comprising a cross-linked shell polymer over a surface of a core component. Additional embodiments of such process are described in further detail below, and products resulting from such embodiments are likewise within the invention.

Polymeric Components.

In embodiments where the core component comprises a polymer, the polymer can be a homopolymer or a copolymer (e.g., binary, tertiary or higher-order polymer), and can optionally be crosslinked. Copolymers of the core component can be random copolymers, block copolymers, or copolymers having a controlled architecture prepared by living free radical polymerization. The crosslinked polyvinylic polymer of the shell component can likewise be a homopolymer or a copolymer (e.g., binary, tertiary or higher-order polymer). Copolymers of the shell component can be random copolymers, block copolymers, or copolymers having a controlled architecture prepared by living free radical polymerization.

Core Component.

In some embodiments, the core can be a commercially available cation exchange resin, such as polystyrenesulfonate (e.g., available commercially as a Dowex resin (Aldrich)), or such as polyacrylic acid (e.g., available commercially as Amberlite (Rohm and Haas)). In some embodiments, the core component can comprise a polymer selected from a polyfluoroacrylic acid polymer, a poly-difluoromaleic acid polymer, polysulfonic acid, and combinations thereof, in each case optionally (and generally preferably) crosslinked. In some preferred embodiments the core-component polymer comprises 2-fluoroacrylic acid crosslinked with a crosslinking agent. The crosslinking agent for a polymeric core component can be selected from the group consisting of divinylbenzene, 1,7-octadiene, 1,6-heptadiene, 1,8-nonadiene, 1,9-decadiene, 1,4-divinyloxybutane, 1,6-hexamethylenebisacrylamide, ethylene bisacrylamide, N,N'-bis(vinylsulfonylacetyl)ethylene diamine, 1,3-bis(vinylsulfonyl) 2-propanol, vinylsulfone, N,N'-methylenebisacrylamide polyvinyl ether, polyallylether, and combinations thereof. In some preferred embodiments the crosslinking agent are selected from divinylbenzene, 1,7-octadiene, 1,4-divinyloxybutane, and combinations thereof. In some embodiments, the core can be in its proton form, sodium form, potassium form, calcium form, ammonium form, or combinations thereof.

Advantageously, the compositions and methods of the invention provide substantial advantages for removing monovalent ions from an environment, such as from a gastrointestinal tract of a mammal. In particular, the compositions and methods of the invention provide improved selectivity for binding monovalent ions preferentially over competing solutes, particularly over divalent cations such as magnesium ion and/or calcium ion present in the environment. The compositions and methods of the invention also provide improved retention of monovalent ions, even in the presence of substantial concentrations of competing solutes such as divalent cations, and even over long periods of time. The improvements in performance characteristics realized by the compositions and methods of the invention translate to substantial benefits for treatment of ion balance disorders in humans and other mammals. In particular, for example, the compositions and methods of the invention offer improved approaches (compositions and methods) for (prophylactic or therapeutic) treatment of hyperkalemia and other indications related to potassium ion homeostasis, and for treatment of hypertension and other indicates related to sodium ion homeostasis. Notably, such prophylactic and/or therapeutic benefits can be realized using the compositions and methods of the invention, while also reducing the risk of potential off-target effects (e.g., the risk of hypocalcemia and hypomagnesemia).

BRIEF DESCRIPTION OF THE DRAWINGS

FIG. 1 through FIG. 12 are each graphs showing the binding profiles of core-shell particles of the invention for certain cations—shown as the amount of cation bound per unit weight of core-shell particle (meq/gm) over time. Data is shown for three core-shell particles comprising a crosslinked polyvinylamine shell over a polystyrenesulfonate core [xPVAm/Dowex(Na)] (prepared as in Examples 1 through 3) and for a control particle comprising polystyrene sulfonate—without a shell [Dowex(Na)], in each case as determined by three different in vitro assays representative of the gastrointestinal tract—as detailed in Example 4A (FIGS. 1 through 4), Example 4B (FIGS. 5 through 8), and Example 4C (FIGS. 9 through 12).

FIGS. 13A and 13B show SEM images of the core-shell particle [xPVAm/Dowex (Na)] prepared in Example 1 (Ref #253) at relatively low magnification (FIG. 13A) and at relatively high magnification (FIG. 13B).

FIGS. 14A and 14B show SEM images of the core-shell particle [xPVAm/Dowex (Na)] prepared in Example 2 (Ref #293) at relatively low magnification (FIG. 14A) and at relatively high magnification (FIG. 14B).

FIGS. 15A and 15B show SEM images of the core-shell particle [xPVAm/Dowex (Na)] prepared in Example 3 (Ref #291) at relatively low magnification (FIG. 15A) and at relatively high magnification (FIG. 15B).

FIGS. 16A and 16B show SEM images of the a [Dowex (Na)] particle—without a shell component (used as a control in the experiment of Example 4) at relatively low magnification (FIG. 16A) and at relatively high magnification (FIG. 16B).

FIG. 19 is a graph showing the binding profile in fecal extract of A Dowex 50W X4-200 core without a shell and various test material containing the same core, but with various crosslinked polyvinylamine shells.

FIG. 25(b) further shows the stability of a Ben(84)-PEI shell on a Dowex(K) core after contact with an acidic aqueous solution.

DETAILED DESCRIPTION OF THE INVENTION

Figure 1:
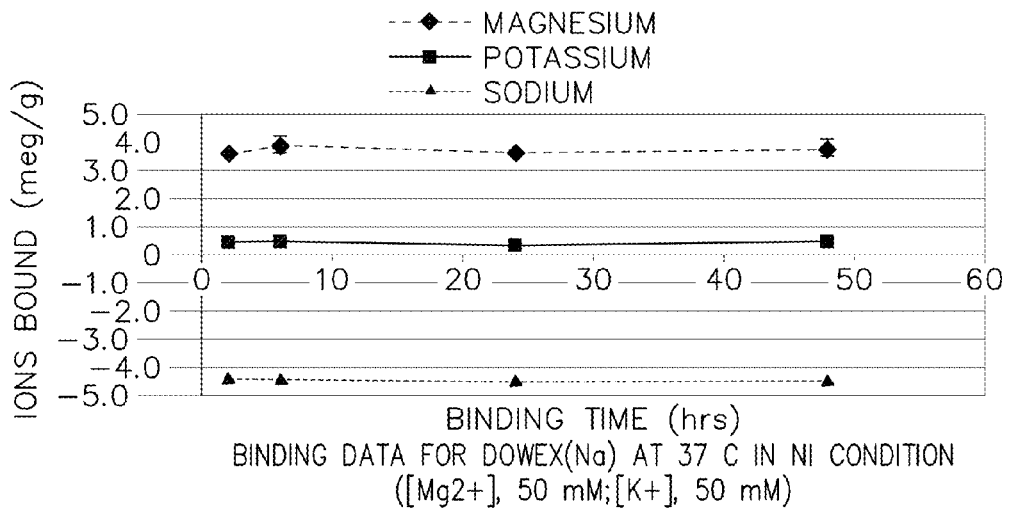

The present invention provides compositions of matter, including pharmaceutical compositions and compositions for use as a pharmaceutical or for use in therapy, in each case, said composition comprising a core-shell particle. The present invention also provides methods, including methods for removing monovalent cation, such as inorganic monovalent cation, from an environment comprising such cation, and in some embodiments, removing such cation from a gastrointestinal tract of a mammal. The invention also provides methods for treating a pharmaceutical indication based on or derived directly or indirectly from abnormally elevated monovalent cation, such as abnormally elevated serum potassium ion (e.g., hyperkalemia) or abnormally elevated serum sodium ion (e.g., hypertension). The invention also provides for the use of a composition comprising a core-shell particle for manufacture of a medicament. The medicament is preferably for use for prophylactic or therapeutic treatment of various indications, as described herein (in this paragraph, in earlier paragraphs above, and in later paragraphs following). The invention also provides kits for the treatment of animal subjects, and preferably mammals.

The compositions and methods of the invention offer improvements over prior art approaches, in particular with respect to binding capacity for, selectivity for and retention of monovalent ions. The compositions and methods of the invention also provide substantial benefits for treatment of ion balance disorders in humans and other mammals.

Core-Shell Particle

In general, the various aspects of the invention comprise a core-shell particle. The core-shell particle comprises a core component and shell component.

Because the core component has a net negative charge under physiological conditions (to provide the capacity for binding monovalent cation) and the shell polymer has a net positive charge under physiological conditions, the core and shell components are significantly attracted to each other and, as a result, there is a potential for the shell polymer and core component to form an interpenetrating polymer network. Interpenetration of the two components, however, will tend to reduce the capacity of the core component for potassium. Interpenetration of the two components may also reduce the integrity of the shell layer and thereby reduce the permselectivity of the core-shell particles for monovalent cations over divalent cations. Thus, it is generally preferred that the interpenetration of the material used for the shell and core components be minimized.

One factor affecting whether the core and shell components, especially polyelectrolyte polymers interpenetrate is the size of the shell polyelectrolyte relative to the pore size of the core. In general, the potential for interpenetration increases as the molecular weight of the shell polymer decreases or the pore size of the core increases. In some embodiments, therefore, the shell polymer molecular weight is greater than (about) 1500 daltons, preferably, greater than (about) 5000 daltons, and still more preferably, greater than (about) 10,000 daltons. Similarly, in some embodiments, the average pore size of the cation exchange polymer core is less than (about) 1 µm; preferably, less than (about) 500 nm, still more preferably, less than (about) 250 nm; and even more preferably, less than (about) 50 nm. In some embodiments, the core-shell particle comprises a shell component comprising or consisting essentially of a shell polymer having a molecular weight greater than (about) 1500 daltons, preferably, greater than (about) 5000 daltons, and still more preferably, greater than (about) 10,000 daltons, in each case crosslinked with a suitable crosslinker, and a core component comprising or consisting essentially of a cation exchange resin which is a crosslinked polymer having an average pore size of less than (about) 1 µm; preferably, less than (about) 500 nm, still more preferably, less than (about) 250 nm; and even more preferably, less than (about) 50 nm, including each permutation of combinations of the foregoing molecular weights and average pore sizes. The embodiments described in this paragraph are general features of the invention, and can be used in combination with each other feature of the invention, as described herein.

The core component can generally comprise an organic material (e.g., an organic polymer) or an inorganic material. Preferably, the core component can comprise a capacity (e.g., the core component can comprise a polymer having a capacity) for binding monovalent cation (e.g., an inorganic monovalent cation such a potassium ion or sodium ion). In preferred embodiments, the core component will be a cation exchange resin (sometimes referred to as a cation exchange polymer), preferably comprising a crosslinked polymer. Suitable organic and inorganic core materials are described below.

In general, the shell component comprises a crosslinked polymer, such as a crosslinked hydrophilic polymer. Preferably, the shell component comprises a crosslinked polymer having a vinylic repeat unit, such as a vinylamine repeat unit or other amine-containing monomer derived repeat unit. The shell polymer can also comprise hydrophobic moieties, such as a copolymer (e.g., a random copolymer or block copolymer) having both hydrophilic and hydrophobic repeat units. The shell component can comprise a cationic polyelectrolyte, the polyelectrolyte comprising a polymer having a vinylamine repeat unit. In particularly preferred embodiments of the various aspects of the invention, the shell component comprises crosslinked polyvinylamine.

Shell Component

The shell component comprises a crosslinked shell polymer. Generally, the sequence of polymerization of a shell polymer, crosslinking of a shell polymer and/or coating of a shell polymer onto a core component is not narrowly critical. In one embodiment, the shell polymer is crosslinked during the polymerization reaction to form the crosslinked polymer; in an alternative embodiment, the monomer(s) is(are) polymerized and the resulting (uncrosslinked) polymer is subsequently treated with a crosslinking agent to form the crosslinked polymer. In connection with the former of the immediately-aforementioned embodiments of this paragraph, the crosslinked polymer can be prepared before the shell polymer is coated onto the core; or alternatively, the crosslinked polymer can be coated onto the core, in situ, during the polymerization reaction. In connection with the latter of the aforementioned embodiments of this paragraph, the shell polymer can be treated with crosslinking agent to form a crosslinked polymer before the shell polymer is coated onto the core, or alternatively, the (uncrosslinked) shell polymer can be coated onto the core before the shell polymer is treated with the crosslinking agent to form the crosslinked polymer). The following description applies with respect to each possible sequence of polymerization, crosslinking and/or coating as described in this paragraph, and explained in further detail below. The shell polymer can comprise a hydrophilic polymer. The shell polymer can have an amine functional group. The shell polymer can comprise a polyvinylic polymer. The shell polymer can comprise a polyvinylamine polymer. Alternatively, the shell polymer may comprise a polyalkyleneimine polymer (e.g., polyethyleneimine) polymer. Although polyvinylic polymers such as polyvinylamine polymers and polyalkyleneimine polymers are preferred shell polymers, other shell polymers can be used in some embodiments of the invention. Some other shell polymers are described below, without being limiting to the invention.

The polymer (e.g., hydrophilic polymer or polyvinylic polymer, such as polyvinylamine polymer or polyalkyleneimine polymer such as polyethyleneimine) of the shell component can generally be a homopolymer or a copolymer (e.g., binary, tertiary or higher-order polymer). Copolymers of the shell component can be random copolymers, block copolymers, or controlled-architecture copolymers (e.g., copolymers having a controlled architecture prepared by living free radical polymerization).

In one embodiment, the shell is a polymer containing repeat units derived from a vinyl monomer, and preferably from a monomer containing a vinylamine group. In another embodiment, the shell is a polymer containing repeat units derived from an alkyleneimine monomer. In general, permselectivity of the core-shell particle for monovalent cation over divalent cation can be influenced, at least in part, by the electronic character of the shell component which, in turn, can be influenced by the relative number of repeat units in the shell component derived from vinylamine, alkyleneimine or other amine-containing monomers. Under physiological conditions, the amine moieties of such repeat units can be protonated, providing a source of a net positive charge; by increasing the number density of amine derived repeat units relative to other monomer derived repeat units, therefore, the cationic charge density of the shell polymer can be increased under physiological conditions. Thus, in one embodiment it is preferred that the shell component comprise a polymer having at least 10% of the repeat units of the polymer derived from amine containing monomers. In this embodiment, it is even more preferred that the shell component comprise a polymer having at least 20% of the repeat units of the polymer derived from amine containing monomers. In this embodiment, it is even more preferred that the shell component comprise a polymer and that at least 30% of the repeat units of the polymer be derived from amine containing monomers. Still more preferably in this embodiment, at least 50% of the repeat units of the polymer be derived from amine containing monomers. Still more preferably in this embodiment, at least 75% of the repeat units of the polymer be derived from amine containing monomers. In some approaches in this embodiment, it is preferable that least 100% of the repeat units of the polymer are derived from amine containing monomers. In each of the aforementioned, preferred amine-containing monomers are vinylamine monomer and/or alyleneimine monomers. In copolymer systems, vinylamine monomer derived repeat units, alkyleneimine monomer derived repeat units, or other amine-containing monomer derived repeat units can, each independently or in various combination, be included within a copolymer comprising other non-amine-containing monomer derived repeat units, such as other non-amine-containing viniylic monomer derived repeat units. Such non-amine-containing vinylic monomer from which such a copolymer can be derived include, for example, vinylamide monomers. Hence, in one embodiment of the invention, the shell polymer can comprise a copolymer comprising a repeat unit derived from an amine-containing monomer and a repeat unit derived from an amide-containing monomer; particularly for example, a copolymer comprising repeat units derived from vinylamine and vinylamide monomers Still more preferably in this embodiment, the polymer is a homopolymer derived from a vinylamine containing monomer, a homopolymer derived from an alkyleneimine (e.g., ethyleneimine) monomer, or a copolymer derived from a vinylamine containing monomer and an alkyleneimine (e.g., ethyleneimine) monomer. In each embodiment described in this paragraph, it is preferred that the polymer be crosslinked.

The amine moiety of vinyl amine monomer derived units of a polymer contained by the shell component may be in the form of a primary, secondary, tertiary, or quaternary amine. Similarly, the amine moiety of alkyleneimine monomer derived units of a polymer contained by the shell component may be in the form of a secondary or tertiary amine, or quaternary ammonium. In some embodiments, at least a portion of the amine moieties are quaternary ammonium moieties, as described hereinafter. The extent of substitution of the amine moiety, as well as the hydrophilic/hydrophobic character of any such substituents can also influence the permselectivity of the shell component under physiological conditions. For example, in one embodiment, it is preferred that the shell component contain a polymer having vinylamine monomer derived repeat units, alkyleneimine monomer derived repeat units, or other amine-containing monomer derived repeat units and that more than 10% of the amine moieties of such repeat units contain a hydrocarbyl, substituted hydrocarbyl, or heterocyclic substituent, preferably in each case, such substituent being a hydrophobic moiety. In some of these embodiments, vinylamine monomer derived repeat units, alkyleneimine monomer derived repeat units, or other amine-containing monomer derived repeat units can, each independently or in various combination, be included within a copolymer comprising other non-amine-containing monomer derived repeat units, such as other non-amine-containing viniylic monomer derived repeat units. Such non-amine-containing viniylic monomer from which such a copolymer can be derived includes, for example, vinylamide monomers. Hence, in one embodiment of the invention, the shell polymer can comprise a copolymer comprising a repeat unit derived from an amine-containing monomer and a repeat unit derived from an amide-containing monomer; particularly for example, a copolymer comprising repeat units derived from vinylamine and vinylamide monomers. In general, the relative percentage of amine moieties containing a hydrocarbyl, substituted hydrocarbyl, or heterocyclic substituent (e.g., in each case, as a hydrophobic moiety) can be inversely related to the amount of amine-containing repeat units in the shell component; thus, for example, when the percentage of repeat units derived from amine-containing monomer is relatively low, the percentage of amine-containing monomer derived units containing hydrocarbyl, substituted hydrocarbyl or heterocyclic substitutents (as compared to the total number of amine-containing monomer derived repeat units) tends to be greater. Thus, for example, in certain embodiments, it is preferred that more than 25% of the amine-containing monomer derived repeat units contain a hydrocarbyl, substituted hydrocarbyl, or heterocyclic substituent. In certain embodiments, it is preferred that more than 50% of the amine-containing monomer derived repeat units contain a hydrocarbyl, substituted hydrocarbyl, or heterocyclic substituent. In certain embodiments, it is preferred that more than 98% or more than 99% or (about) 100% of the amine-containing monomer derived repeat units contain a hydrocarbyl, substituted hydrocarbyl, or heterocyclic substituent. The percentage of amine-containing monomer derived repeat units containing hydrocarbyl, substituted hydrocarbyl or heterocyclic substitutents, therefore, will typically be between 10 and (about) 100%, alternatively ranging from 25-75%, and for some approaches ranging from 30-60% of the amine-containing monomer derived repeat units in the shell component. In each such embodiment described in this paragraph, it is preferred that the polymer be crosslinked.

Preferably, the shell polymer can be a polyvinylamine polymer modified or derivitized to comprise one more alkyl moieties and/or one more N-alkyl-aryl moieties.

A polyvinylamine shell polymer can, in one embodiment, be characterized as a polymer or preferably a crosslinked polymer, in each case where the polymer is represented by Formula I:

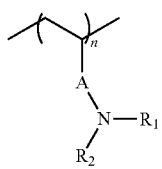

Formula I or a copolymer thereof, wherein n is at least 4, $R_1$ and $R_2$ are independently selected from hydrogen, alkyl, phenyl, aryl, or heterocyclic, and A is a linker wherein A is nothing (i.e., represents a covalent bond between the N atom and the C atom of the polymer backbone) or is selected from alkyl, aryl, heterocyclic, carboxyalkyl (—$CO_2$-alkyl), carboxamidoalkyl (—CON-alkyl), or aminoalkyl. In one embodiment, $R_1$ and $R_2$ are independently selected from hydrogen, hydrocarbyl, substituted hydrocarbyl, heterocyclic moieties, and the residue of crosslinking agents (described elsewhere herein to crosslink the polymer) or together, in combination with the nitrogen atom to which they are bonded, form a heterocylic (i.e., a vinylheterocyclic). For example, in this embodiment $R_1$ and $R_2$ may be independently selected from hydrogen, optionally substituted alkyl, alkenyl, alkynyl, (alk)heterocyclic or (alk)aryl wherein (alk)heterocyclic has the formula —$(CH_2)_m$-HET-$(R_x)_t$, (alk)aryl has the formula —$(CH_2)_m$—Ar—$(R_x)_t$, m is 0-10, t is 0-5, HET is a heterocyclic moiety, Ar is an aryl moiety, and $R_x$ is hydrocarbyl or substituted hydrocarbyl. When $R_1$ or $R_2$ is —$(CH_2)_m$-HET-$(R_x)_t$ and the heterocyclic moiety, HET, is heteroaromatic or, when $R_1$ or $R_2$ is —$(CH_2)_m$—Ar—$(R_x)_t$, it is sometimes preferred that m be at least 1. In addition, when $R_1$ or $R_2$ is —$(CH_2)_m$—Ar—$(R_x)_t$ and m is 1, it is sometimes preferred that t be at least 1. Further, when one of $R_1$ and $R_2$ is —$(CH_2)_m$—Ar—$(R_x)_t$ or —$(CH_2)_m$-HET-$(R_x)_t$, it is sometimes preferred that the other be hydrogen, lower alkyl (e.g., methyl, ethyl or propyl) or the residue of a crosslinking agent. In one embodiment, $R_1$ is optionally substituted alkyl and $R_2$ is —$(CH_2)_m$-HET-$(R_x)_t$ or —$(CH_2)_m$—Ar—$(R_x)_t$, wherein m is 0-10, t is 0-5, HET is a heterocyclic moiety, Ar is an aryl moiety, and $R_x$ is hydrocarbyl or substituted hydrocarbyl. In another embodiment, $R_1$ and $R_2$ may be hydrogen, optionally substituted alkyl, —$(CH_2)_m$-HET-$(R_x)_t$ or —$(CH_2)_m$—Ar—$(R_x)_t$, and A is hydrocarbylene (e.g., methylene or ethylene), substituted hydrocarbylene (e.g., substituted methylene or substituted ethylene), heterocyclic, carboxyalkyl (—$CO_2$-alkyl), carboxamidoalkyl (—CON-alkyl), or aminoalkyl. In each of these embodiments in which a hydrocarbyl(ene) or heterocyclic moiety is substituted, a carbon atom is substituted with a hetero atom such as nitrogen, oxygen, silicon, phosphorous, boron, sulfur, or a halogen atom; thus, for example, the hydrocarbyl(ene) or heterocyclic moiety may be substituted with halogen, heterocyclo, alkoxy, alkenoxy, alkynoxy, or aryloxy. In each of these embodiments of the polymer of Formula I, n is preferably at least 10, or at least 20, or at least 40, or at least 100, or at least 400, or at least 1000, or at least 4000, or at least 10,000. In the polymer of Formula I, n can preferably range from 4 to 100,000, and preferably from 10 to 10,000.

In various embodiments, $R_1$ or $R_2$ have the formula —$(CH_2)_m$-HET-$(R_x)_t$ or the formula —$(CH_2)_m$—Ar—$(R_x)_t$ and t is 1-5; additionally, $R_x$ may be $C_1$-$C_{18}$ alkyl. Further, $R_1$ or $R_2$ may correspond to Formula VI

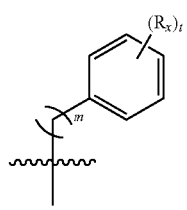

Formula VI wherein m is 0 to 10; $R_x$ is linear or branched $C_1$-$C_{18}$ alkyl, $C_1$-$C_{18}$ alkenyl, $C_1$-$C_{18}$ alkynyl, or $C_1$-$C_{20}$ aryl; and t is 0 to 5. In some embodiments, the (alk)aryl group corresponding to Formula VI is other than benzyl. Preferably, when $R_1$ or $R_2$ corresponds to Formula VI, $R_x$ is linear or branched $C_1$-$C_{18}$ alkyl or $C_1$-$C_{18}$ alkenyl; more preferably $C_1$-$C_3$ alkyl or $C_1$-$C_3$ alkenyl. In various preferred embodiments, when $R_1$ or $R_2$ corresponds to Formula VI, m is 1 to 3 and when m is 1 to 3, t is 1.

Preferred polymers of Formula I include:

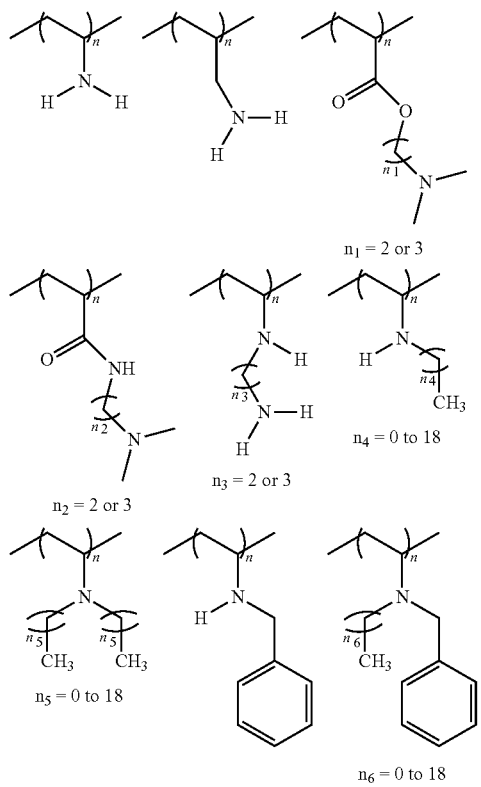

Other examples of preferred polymers of Formula I include each of the structures shown in the previous paragraph with alternative alkyl group (e.g., ethyl, propyl, butyl, pentyl, hexyl, etc.) substituted for methyl. Other preferred polymers of Formula I include:

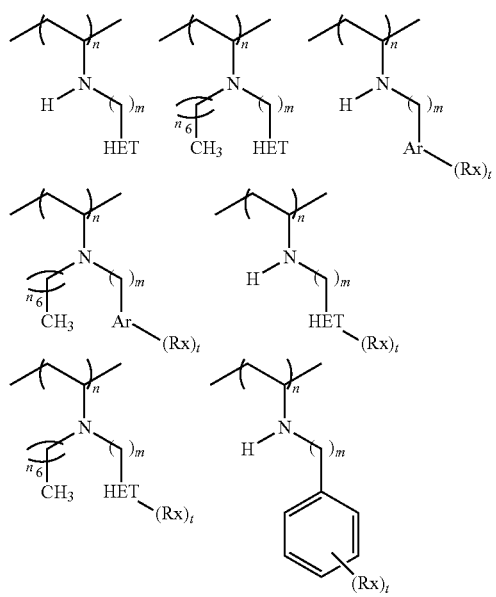

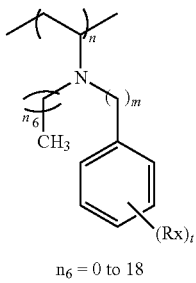

wherein HET is heterocyclic, Ar is aryl, $R_x$ is optionally substituted alkyl, alkenyl, alkynyl or aryl, m is 0 to 10; and t is 1 to 5. In some embodiments, m is 1 to 10.

Even more preferred polymers of Formula I include:

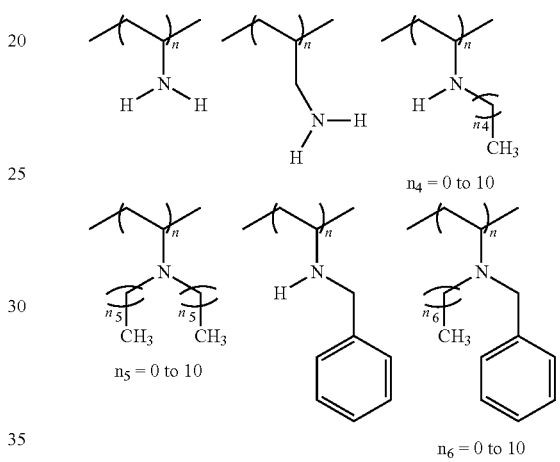

In a second embodiment, the polymer can be characterized as a polymer or preferably a crosslinked polymer, in each case where the polymer is represented by Formula II:

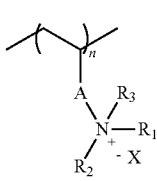

Formula II or a copolymer thereof, wherein n is at least 4; $R_1$, $R_2$, and $R_3$ are independently selected from hydrogen, alkyl, phenyl, aryl, or heterocyclic or a moiety —C(=NH)—NH2; X are independently selected from hydroxide, halid, sulfonate, sulfate, carboxlate, and phosphate; A is a linker wherein A is nothing or is selected from alkyl, aryl, heterocyclic, carboxyalkyl (—CO$_2$-alkyl), carboxamidoalkyl (—CON-alkyl), or aminoalkyl. In one embodiment, $R_1$, $R_2$ and $R_3$ are independently selected from hydrogen, hydrocarbyl, substituted hydrocarbyl, heterocyclic and the residue of a crosslinking agent or, $R_1$ and $R_2$ together, in combination with the nitrogen atom to which they are bonded, form a heterocylic (i.e., a vinylheterocyclic). For example, in this embodiment $R_1$, $R_2$ and $R_3$ may be independently selected from hydrogen, optionally substituted alkyl, alkenyl, alkynyl, (alk)heterocyclic or (alk)aryl wherein (alk)heterocyclic has the formula —(CH$_2$)$_m$-HET-(R$_x$)$_t$, (alk)aryl has the formula —(CH$_2$)$_m$—Ar—(R$_x$)$_t$, m is 0-10, t is 0-5, HET is a heterocyclic moiety, Ar is an aryl moiety, and $R_x$ is hydrocarbyl or substituted hydrocarbyl. When $R_1$, $R_2$, or $R_3$ is —$(CH_2)_m$—HET-$(R_x)_t$ and the heterocyclic moiety, HET, is heteroaromatic or, when $R_1$, $R_2$ or $R_3$ is —$(CH_2)_m$—Ar—$(R_x)_t$, it is sometimes preferred that m be at least 1. In addition, when $R_1$, $R_2$ or $R_3$ is —$(CH_2)_m$—Ar—$(R_x)_t$ and m is 1, it is sometimes preferred that t be at least 1. Further, when one of $R_1$, $R_2$ and $R_3$ is —$(CH_2)_m$—Ar—$(R_x)_t$ or —$(CH_2)_m$-HET-$(R_x)_t$, it is sometimes preferred that the others be hydrogen, lower alkyl (e.g., methyl, ethyl or propyl) or the residue of a crosslinking agent. In one embodiment, $R_1$ and $R_3$ are optionally substituted alkyl and $R_2$ is —$(CH_2)_m$-HET-$(R_x)_t$ or —$(CH_2)_m$—Ar—$(R_x)_t$, wherein m is 0-10, t is 0-5, HET is a heterocyclic moiety, Ar is an aryl moiety, and $R_x$ is hydrocarbyl or substituted hydrocarbyl. In another embodiment, $R_1$, $R_2$ and $R_3$ may be hydrogen, optionally substituted alkyl, —$(CH_2)_m$-HET-$(R_x)_t$ or —$(CH_2)_m$—Ar—$(R_x)_t$, and A is hydrocarbylene (e.g., methylene or ethylene), substituted hydrocarbylene (e.g., substituted methylene or substituted ethylene), heterocyclic, carboxyalkyl (—$CO_2$-alkyl), carboxamidoalkyl (—CON-alkyl), or aminoalkyl. In each of these embodiments in which a hydrocarbyl(ene) or heterocyclic moiety is substituted, a carbon atom is substituted with a hetero atom such as nitrogen, oxygen, silicon, phosphorous, boron, sulfur, or a halogen atom; thus, for example, the hydrocarbyl(ene) or heterocyclic moiety may be substituted with halogen, heterocyclo, alkoxy, alkenoxy, alkynoxy, or aryloxy. In each of these embodiments of Formula II, n is preferably at least 10, or at least 20, or at least 40, or at least 100, or at least 400, or at least 1000, or at least 4000, or at least 10,000. In the polymer of Formula II, n can preferably range from 4 to 100,000, and preferably from 10 to 10,000.

Preferred polymers of Formula II include:

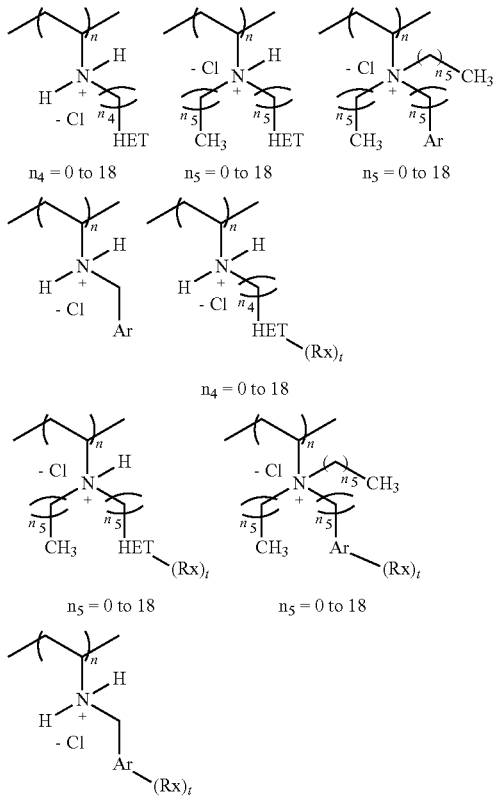

Even more preferred polymers of Formula II include:

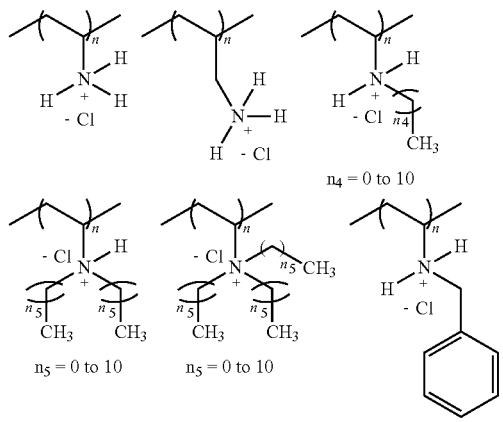

The aforementioned polyvinylamine polymers are exemplary, and not limiting. Other preferred polyvinylamine polymers will be apparent to a person of skill in the art.

In one embodiment, the shell is a polymer containing repeat units derived from an alkyleneimine monomer, such as ethyleneimine or propyleneimine monomers.

A polyalkyleneimineamine shell polymer can, in one embodiment, be characterized as a polymer or preferably a crosslinked polymer, in each case where the polymer is represented by Formula IV:

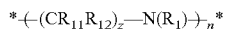    Formula IV or a copolymer thereof, wherein n is at least 2, $R_1$ is selected from hydrogen, hydrocarbyl, substituted hydrocarbyl, heterocyclic and the residue of crosslinking agents, and $R_{11}$ and $R_{12}$ are independently hydrogen, alkyl or aryl. In one embodiment, z is 2 to 10; for example, when z is 2, the repeat unit is an ethyleneimine repeat unit and when z is 3, the repeat unit is a propyleneimine repeat unit. In a preferred embodiment, $R_{11}$ and $R_{12}$ are hydrogen or alkyl (e.g., C1-C3 alkyl); in one particular preferred embodiment, $R_{11}$ and $R_{12}$ are hydrogen or methyl and z is 2 or 3. In each of these embodiments, $R_1$ may be, for example, selected from hydrogen, optionally substituted alkyl, alkenyl, alkynyl, (alk)heterocyclic or (alk)aryl wherein (alk)heterocylic has the formula —$(CH_2)_m$-HET-$(R_x)_t$, (alk)aryl has the formula —$(CH_2)_m$—Ar—$(R_x)_t$, m is 0-10, t is 0-5, HET is a heterocyclic moiety, Ar is an aryl moiety, and $R_x$ is hydrocarbyl or substituted hydrocarbyl. When $R_1$—$(CH_2)_m$-HET-$(R_x)_t$ and the heterocyclic moiety, HET, is heteroaromatic or, when $R_1$ is —$(CH_2)_m$—Ar—$(R_x)_t$, it is sometimes preferred that m be at least 1. In addition, when $R_1$ is —$(CH_2)_m$—Ar—$(R_x)_t$ and m is 1, it is sometimes preferred that t be at least 1. In one embodiment, $R_1$ is —$(CH_2)_m$-HET-$(R_x)_t$ or —$(CH_2)_m$—Ar—$(R_x)_t$, wherein m is 0-10, t is 0-5, HET is a heterocyclic moiety, Ar is an aryl moiety, and $R_x$ is hydrocarbyl or substituted hydrocarbyl. In each of these embodiments in which a hydrocarbyl(ene) or heterocyclic moiety is substituted, a carbon atom is substituted with a hetero atom such as nitrogen, oxygen, silicon, phosphorous, boron, sulfur, or a halogen atom; thus, for example, the hydrocarbyl(ene) or heterocyclic moiety may be substituted with halogen, heterocyclo, alkoxy, alkenoxy, alkynoxy, or aryloxy. In each of these embodiments of the polymer of Formula IV, n is preferably at least 10, or at least 20, or at least 40, or at least 100, or at least 400, or at least 1000, or at least 4000, or at least 10,000. In the polymer of Formula IV, n can preferably range from 4 to 100,000, and preferably from 10 to 10,000.

A polyalkyleneimineamine shell polymer can also, in one embodiment, be characterized as a polymer or preferably a crosslinked polymer containing quaternary ammonium repeat units, in each case where the polymer is represented by Formula V:

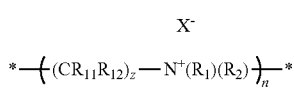

Formula V or a copolymer thereof, wherein n is at least 2, $R_1$ and $R_2$ are independently selected from hydrocarbyl, substituted hydrocarbyl, heterocyclic and the residue of crosslinking agents, $R_{11}$ and $R_{12}$ are independently hydrogen, alkyl or aryl, and $X^-$ is anion (preferably independently selected from hydroxide, halid, sulfonate, sulfate, carboxlate, and phosphate). In one embodiment, z is 2 to 10; for example, when z is 2, the repeat unit is an ethyleneimine repeat unit and when z is 3, the repeat unit is a propyleneimine repeat unit. In a preferred embodiment, $R_{11}$ and $R_{12}$ are hydrogen or alkyl (e.g., C1-C3 alkyl); in one particular preferred embodiment, $R_{11}$ and $R_{12}$ are hydrogen or methyl and z is 2 or 3. In each of these embodiments, $R_1$ and $R_2$ may be independently selected from optionally substituted alkyl, alkenyl, alkynyl, (alk)heterocyclic or (alk)aryl wherein (alk)heterocylic has the formula —$(CH_2)_m$-HET-$(R_x)_t$, (alk)aryl has the formula —$(CH_2)_m$—Ar—$(R_x)_t$, m is 0-10, t is 0-5, HET is a heterocyclic moiety, Ar is an aryl moiety, and $R_x$ is hydrocarbyl or substituted hydrocarbyl. When $R_1$ or $R_2$ is —$(CH_2)_m$-HET-$(R_x)_t$ and the heterocyclic moiety, HET, is heteroaromatic or, when $R_1$ or $R_2$ is —$(CH_2)_m$—Ar—$(R_x)_t$, it is sometimes preferred that m be at least 1. In addition, when $R_1$ or $R_2$ is —$(CH_2)_m$—Ar—$(R_x)_t$ and m is 1, it is sometimes preferred that t be at least 1 (e.g., that the (alk)aryl moiety be other than benzyl). Further, when one of $R_1$ and $R_2$ is —$(CH_2)_m$—Ar—$(R_x)_t$ or —$(CH_2)_m$-HET-$(R_x)_t$, it is sometimes preferred that the other be hydrogen, lower alkyl (e.g., methyl, ethyl or propyl) or the residue of a crosslinking agent. In one embodiment, $R_1$ is hydrocarbyl or substituted hydrocarbyl, and $R_2$ is —$(CH_2)_m$-HET-$(R_x)_t$ or —$(CH_2)_m$—Ar—$(R_x)_t$, wherein m is 0-10, t is 0-5, HET is a heterocyclic moiety, Ar is an aryl moiety, and $R_x$ is hydrocarbyl or substituted hydrocarbyl. In each of these embodiments in which a hydrocarbyl(ene) or heterocyclic moiety is substituted, a carbon atom is substituted with a hetero atom such as nitrogen, oxygen, silicon, phosphorous, boron, sulfur, or a halogen atom; thus, for example, the hydrocarbyl(ene) or heterocyclic moiety may be substituted with halogen, heterocyclo, alkoxy, alkenoxy, alkynoxy, or aryloxy. In each of these embodiments of the polymer of Formula V, n is preferably at least 10, or at least 20, or at least 40, or at least 100, or at least 400, or at least 1000, or at least 4000, or at least 10,000. In the polymer of Formula V, n can preferably range from 4 to 100,000, and preferably from 10 to 10,000.

The shell polymer can, in some preferred embodiments, comprise a copolymer comprising two or more polymers having different monomer repeat units, where (i) at least one of the polymers is a crosslinked or non-crosslinked polymer represented by Formula I, or (ii) at least one of the polymers is a crosslinked or non-crosslinked polymer represented by Formula II, or (iii) at least one of the polymers is a crosslinked or non-crosslinked polymer represented by Formula I and at least one of the polymers is a crosslinked or non-crosslinked polymer represented by Formula II.

In some embodiments, the polyvinylamine polymer can be a vinylheterocyclic amine polymer, such as polymers having repeat units selected from a group consisting of vinylpyridines, vinylimidazoles, vinyl pyrrazoles, vinylindoles, vinyltriazoles, vinyltetrazoles, as well as alkyl derivatives thereof, and combinations thereof. For example, polyvinylamine shell polymer can be a polymer having repeat units selected from vinylpyridines, vinylimidazole, vinylindoles, including for example polymers represented by one or more of Formula IIIA through IIIE:

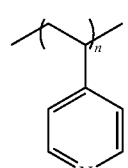

Formula IIIA

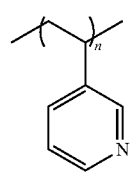

Formula IIIB

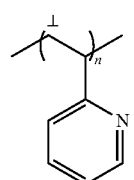

Formula IIIC

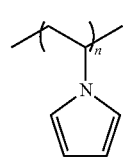

Formula IIID

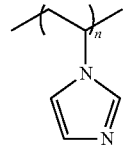

Formula IIIE wherein in each case n is at least 4. The compounds of Formulas IIIA through IIIE can optionally be substituted or derivatized to include one or more additional moieties (not shown in the formulas), for example with an R-group on the heterocycle, where such moieties are independently selected from hydrogen, alkyl, phenyl, aryl, or heterocyclic, hydroxide, halide, sulfonate, sulfate, carboxlate, and phosphate. In the polymer of Formulas IIIA through IIIE, n is preferably at least 10, or at least 20, or at least 40, or at least 100, or at least 400, or at least 1000, or at least 4000, or at least 10,000. In the polymer of Formula I, n can preferably range from 4 to 100,000, and preferably from 10 to 10,000.

In some embodiments, the polyamine polymer can comprise a polybenzylamine polymer.

In some embodiments, the polyamine polymer can comprise cyclopolymers, for example as formed from diallyl amine monomers. Preferred polymers include

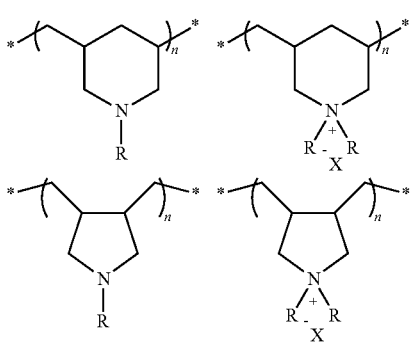

wherein n is at least 4; R are independently selected from hydrogen, alkyl, phenyl, aryl, or heterocyclic; X are independently selected from hydroxide, halide, sulfonate, sulfate, carboxlate, and phosphate. n is preferably at least 10, or at least 20, or at least 40, or at least 100, or at least 400, or at least 1000, or at least 4000, or at least 10,000.

In some embodiments, the amine polymers can comprise a guanilylated compound. In some embodiments, for example, polyvinylamine moieties (e.g., as disclosed herein) can have a guanylated counterpart produced by treatment of the precursor amine moiety with, for example, pyrazole guanidine. For example, such treatment could proceed by a mechanism represented schematically as follows:

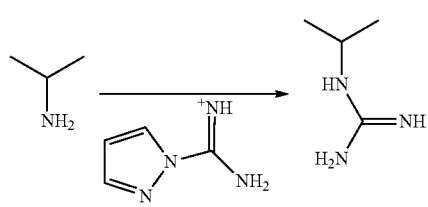

The polyvinylic (e.g., polyvinylamine) polymer can have a weight average molecular weight or a number average molecular weight of at least (about) 1000, preferably at least (about) 10,000. In any such embodiment, the polyvinylic polymer can have a weight average molecular weight or a number average molecular weight ranging from (about) 1,000 to (about) 2,000,000, preferably from (about) 1,000 to (about) 1,000,000, or from (about) 10,000 to (about) 1,000,000, and preferably from (about) 10,000 to (about) 500,000. Preferably, the polyvinylic (e.g., polyvinylamine) polymer can have a polydispersity index (PDI) ranging from (around) 1 to 10, and preferably ranging from 1 to 5, or from 1 to 2.

The shell component can comprise, in some embodiments, the polyvinylic polymer (e.g., such as polyvinylamine polymer) as a densely crosslinked polyvinylic polymer. In some embodiments, for example, the polyvinylic (e.g., polyvinylamine) polymer can be a product of a crosslinking reaction comprising crosslinking agent and polyvinylic polymer in a ratio of crosslinking agent to crosslinkable functional groups of the polymer not less than (about) 2:1, and preferably in a ratio ranging from (about) 2:1 to (about) 10:1, ranging from (about) 2.5:1 to (about) 6:1, or ranging from (about) 3:1 to (about) 5:1 and in some embodiments in a ratio of (about) 4:1, by mole. In some embodiments, the crosslinked shell polymer can be a crosslinked polyvinylamine polymer comprising a crosslinking moieties and amine moieties in a ratio of not less than (about) 0.05:1, preferably not less than (about) 0.1:1, and preferably in a ratio ranging from (about) 0.1:1 to (about) 1.5:1, more preferably ranging from (about) 0.5:1 to (about) 1.25:1, or from (about) 0.75:1 to (about) 1:1, in each case based on mole equivalent of crosslinking moiety to amine moiety in the crosslinked polyvinylamine polymer.

The shell polymer can be crosslinked with a crosslinking agent. Generally, the crosslinking agent can be a compound having two or more moieties reactive with a functional group of the shell polymer.

For shell polymers comprising repeat units having amine functional groups, the crosslinking agent can generally be a compound having two or more amine reactive moieties. Suitable compound having an amine reactive moiety can include, for example and without limitation, compounds or moieties selected from epoxides, alkyl halide, benzyl halide, acylhalide, activated olefin, isocyanate, isothiocyanate, activated ester, acid anhydrides, and lactone, etc.

In some embodiments, the shell polymer (e.g., polyvinylic polymer such as a polyvinylamine polymer) can be crosslinked with a small molecule crosslinking agent having a molecular weight of not more than (about) 500, preferably not more than (about) 300, or not more than (about) 200, or not more than (about) 100. In some embodiments, the shell polymer (e.g., polyvinylic polymer such as a polyvinylamine polymer) can be crosslinked with oligomer or polymer bearing amine reactive moieties.

In preferred embodiments, the crosslinking agent can be selected from the group consisting of epoxides, halides, activated esters, isocyanate, anhydrides, and combinations thereof. Suitable crosslinking agents include epichlorohydrine, alkyl diisocyanates, alkyl dihalides, or diesters. Preferably, the crosslinking agent can be a di-functional or multi-functional-epoxide, -halide, -isocyanate, -anhydride, -ester and combinations thereof.

In some embodiments, the crosslinking agent for the shell component can be a hydrophobic crosslinking agent. For example, the crosslinking agent can be N,N diglycidylaniline (N,N-DGA), or 2,2'-[(1-methylethylidene)bis(4,1-phenyleneoxymethylene)]bis-oxirane, or 2,4 diisocyanate (TID), among others.

In some embodiments, the crosslinking agent for the shell component can be selected from the group consisting of epichlorohydrine (ECH), 1,2-bis-(2-iodoethoxy)ethane (BIEE) and N,N diglycidylaniline (N,N-DGA) and combinations thereof.

In some embodiments, the crosslinking agent can be selected from one or more of the following crosslinking agents (alone or in various permutations and combinations):

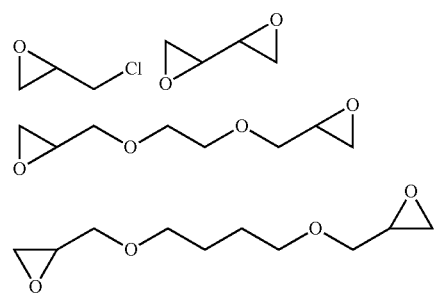

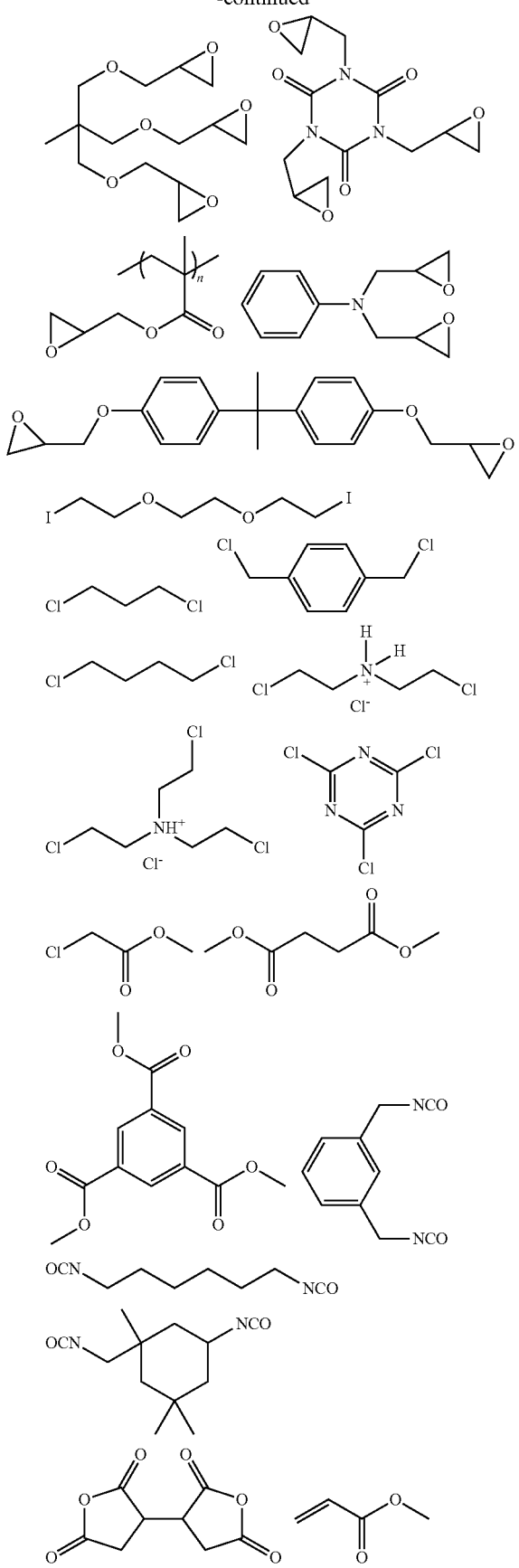
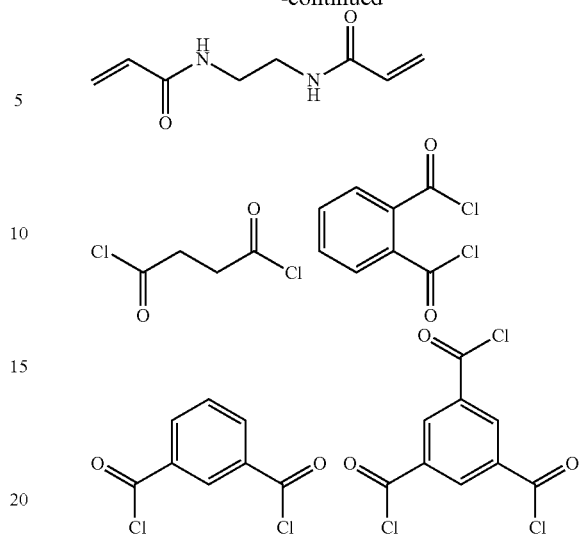

Crosslinking agents are commercially available, for example, from commercial sources, such as Aldrich, Acros, TCI, or Lancaster.

The shell component can be (e.g. situated or formed) over a surface of the core component. The shell component can be physically or chemically attached (e.g., physically or chemically adhered or bonded) to the core component. In some embodiments for example, the shell component can be adhered to the core component by ionic bonding. In other embodiments for example, the shell component can be covalently bonded to the core component. As a nonlimiting example, the shell component can be covalently bonded to the core component through ester, amide, or urethane linkages. In some cases, the shell polymer is attached to the core through physical bonds, chemical bonds, or a combination of both. In the former case, the electrostatic interaction between negatively charged core and positively charged shell can maintain the core-shell composition during use (e.g., during transit in the gastrointestinal tract). In the latter case a chemical reaction can be carried out at the core-shell interface to form covalent bonds between the crosslinked shell polymer and the core component.

Shell polymers (generally), such as hydrophilic polymers, polyvinylic polymers (e.g., polyvinylamine) and other polymers described herein are generally commercially available. For example, polyvinylamine polymers are commercially available from BASF (e.g., under the trade name Lupramin). Preferred polyvinylic polymers are described above.

One method for determining the percentage of nitrogen atoms in the solid polymer that are quaternary ammonium nitrogens is to analyze a sample using X-ray photoelectron spectroscopy (XPS). The XPS data generally indicates the composition of the core-shell particles tested and differentiates the primary, secondary, tertiary, and quaternary nitrogen atoms in the amine functional polymer shell. The XPS can generally further distinguish between nitrogen atoms bonded to three organic groups and protonated from nitrogen atoms bonded to four organic groups. Various polymeric systems containing quaternary ammonium ions have demonstrated the use of XPS to determine the extent of those nitrogens that are bonded to four organic groups. (*Adv. Polymer Sci.* 1993, 106, 136-190; *Adv. Mater.* 2000, 12(20), 1536-1539; *Langmuir* 2000, 16(26), 10540-10546; *Chem. Mater.* 2000, 12, 1800-1806).

Core Component

The core component generally comprises an organic material (e.g., an organic polymer) or an inorganic material. Preferably, the core component can comprise a capacity for binding monovalent cation (e.g., an inorganic monovalent cation such a potassium ion or sodium ion).

Organic core materials preferably include organic polymers, and especially a polymer having a capacity for binding monovalent cation (e.g., an inorganic monovalent cation), such a potassium ion or sodium ion. Polyacrylic acid polymers, polyhaloacrylic acid polymers, polystyrenic polymers, polysulfonic polymers and polystyrenesulfonate polymers are preferred core polymers.

Inorganic core materials can include ceramics, microporous and mesoporous materials (e.g. zeolites).

In particularly preferred embodiments, the core component can comprise a polymer selected from a poly-fluoroacrylic acid polymer, a poly-difluoromaleic acid polymer, polysulfonic acid, and combinations thereof, in each case optionally (and generally preferably) crosslinked. In some preferred embodiments the core-component polymer comprises 2-fluoroacrylic acid crosslinked with a crosslinking agent. The crosslinking agent for a polymeric core component can be selected from the group consisting of divinylbenzene, 1,7-octadiene, 1,6-heptadiene, 1,8-nonadiene, 1,9-decadiene, 1,4-divinyloxybutane, 1,6-hexamethylenebisacrylamide, ethylene bisacrylamide, N,N'-bis(vinylsulfonylacetyl)ethylene diamine, 1,3-bis(vinylsulfonyl) 2-propanol, vinylsulfone, N,N'-methylenebisacrylamide polyvinyl ether, polyallylether, and combinations thereof. In some preferred embodiments, the crosslinking agents are selected from divinylbenzene, 1,7-octadiene, 1,4-divinyloxybutane, and combinations thereof. In some embodiments, the core can be in its proton form, sodium form, potassium form, calcium form, ammonium form, or combinations thereof.

Preferred monomer repeat units of the core polymers, such as α-fluoroacrylate and difluoromaleic acid can be prepared from a variety of routes. See for example, Gassen et al, J. Fluorine Chemistry, 55, (1991) 149-162, K F Pittman, C. U., M. Ueda, et al. (1980). *Macromolecules* 13(5): 1031-1036. Difluoromaleic acid is preferred by oxidation of fluoroaromatic compounds (Bogachev et al, Zhurnal Organisheskoi Khimii, 1986, 22(12), 2578-83), or fluorinated furans derivatives (See U.S. Pat. No. 5,112,993). A preferred mode of synthesis of α-fluoroacrylate is given in EP 415214. Other methods comprise the step-growth polymerization from phosphonate, carboxylic, phosphate, sulfinate, sulfate and sulfonate functionals compounds. High density polyphosphonates such as Briquest, marketed by Rhodia, are particularly useful.

Another process to produce alpha-fluoroacrylate beads is direct suspension polymerization. Typically, suspension stabilizers, such as polyvinyl alcohol or polyacrylic acid, are used to prevent coalescence of particles during the process. It has been observed that the addition of NaCl and/or aqueous phase polymerization inhibitor such as sodium nitrite (NaNO$_2$) in the aqueous phase decreased coalescence and particle aggregation. Other suitable salts for this purpose include salts that solubilize in the aqueous phase. Other suitable inhibitors for the purpose include inhibitors that are soluble in the aqueous phase or are surface active. In this embodiment, water soluble salts are added at a weight % comprised between (about) 0.1 to (about) 10, preferably comprised between (about) 1 to (about) 7.5 and even more preferably between (about) 2.5 to (about) 5. In this embodiment, polymerization inhibitors are added at a weight ppm comprised between (about) 0 ppm to (about) 500 ppm, preferably comprised between (about) 10 ppm to (about) 200 ppm and even more preferably between (about) 50 to (about) 200 ppm. In this embodiment, buffer reagent such as phosphate buffer can also be used to maintain reaction pH. The buffer reagents are added at a weight % comprised between 0 to 2%. It has been observed that in the case of alpha-fluoroacrylate esters (e.g. MeFA) suspension polymerization, the nature of the free radical initiator plays a role in the quality of the suspension in terms of particle stability, yield of beads, and the conservation of a spherical shape. Use of water-insoluble free radical initiators, such as lauryl peroxide, led to the quasi absence of gel and produced beads in a high yield. It was found that free radical initiators with water solubility lower than 0.1 g/L preferably lower than 0.01 g/L led to optimal results. In preferred embodiments, polyMeFA beads are produced with a combination of a low water solubility free radical initiator, the presence of salt in the aqueous phase, such as NaCl, and/or the presence of aqueous polymerization inhibitor such as sodium nitrite and a buffer solution.

Generally, the core component can comprise a crosslinked core polymer. The core polymers can be crosslinked using a multifunctional crosslinking agent. As non-limiting examples, the crosslinking agent for a polymeric core component can be selected from the group consisting of divinylbenzene, 1,7-octadiene, 1,6-heptadiene, 1,8-nonadiene, 1,9-decadiene, 1,4-divinyloxybutane, 1,6-hexamethylenebisacrylamide, ethylene bisacrylamide, N,N'-bis(vinylsulfonylacetyl)ethylene diamine, 1,3-bis(vinylsulfonyl) 2-propanol, vinylsulfone, N,N'-methylenebisacrylamide polyvinyl ether, polyallylether, and combinations thereof. In some preferred embodiments the crosslinking agent are selected from divinylbenzene, 1,7-octadiene, 1,4-divinyloxybutane, and combinations thereof. In some embodiments, the core can be in its proton form, sodium form, potassium form, calcium form, ammonium form, or combinations thereof.

Other preferred core polymers are disclosed below.

Binding Capacity

The core-shell particles of the invention have a high binding capacity (and as described below, preferably also a high (and persistent) selectivity and a high retention) for monovalent cation such as potassium ion and sodium ion.

The core-shell particle of the invention can have an effective amount of a potassium binding core, such as a potassium binding polymer (e.g., a polymer having a capacity for binding potassium), such that upon being administered to a mammal subject, such as a human, the core-shell particle effectively binds and removes an average of at least (about) 1.5 mmol (or 1.5 mEq) or higher of potassium per gm of core-shell particle. Preferably the binding capacity or amount of potassium bound in vivo in a human (in other mammal of interest) and removed from the human (or other mammal) is (about) 2 mmol or more per gm, more preferred is (about) 3 mmol or more per gm, even more preferred is (about) 4 mmol or more per gm, or (about) 5 mmol per gm, or (about) 6 mmol or more per gm, in each case per gm of core-shell particle. In a preferred embodiment, the average binding capacity or average amount of potassium bound in vivo in a human (in other mammal of interest) can range from (about) 1.5 mmol per gm to (about) 8 mmol per gm, preferably from (about) 2 mmol per gm to (about) 6 mmol per gm, in each case per gm of core-shell particle.

In some embodiments, the core-shell particle has an average in vitro binding capacity for potassium or an average amount of potassium bound of greater than (about) 1.5 mmol/gm of core-shell composite (e.g., core-shell particle) at a pH of greater than (about) 5.5. In other preferred embodiments, the core-shell particle can have an average in vitro binding capacity or amount of potassium bound of at least (about) 2.0 mmol/gm, preferably greater than (about) 2.0 mmol/gm, such as preferably at least (about) 2.5 mmol/gm, or at least (about) 3.0 mmol/gm, or at least (about) 3.5 mmol/gm or at least (about) 4.0 mmol/gm or at least (about) 4.5 mmol/gm or at least (about) 5.0 mmol/gm, in each case where mmol/gm refers to per gram of core-shell composite (e.g., core-shell particle), and in each case as determined an in vitro assay mimicking physiological conditions of the gastrointestinal tract. Preferably, the in vitro binding capacity/amount of potassium bound can be determined from an assay selected from GI Assay No. I, GI Assay No. II, GI Assay No. III, and combinations thereof, in each case as defined and described in detail below.

The core-shell particle of the invention can additionally or alternatively have an effective amount of a sodium binding core, such as a sodium binding polymer (e.g., a polymer having a capacity for binding sodium), such that upon being administered to a mammal subject, such as a human, the core-shell particle effectively binds and removes an average of at least (about) 1.5 mmol (or 1.5 mEq) or higher of sodium per gm of core-shell particle. Preferably the in vivo sodium binding capacity or amount of sodium bound in a human (or other mammal of interest) is (about) 2 mmol or more per gm, more preferred is (about) 3 mmol or more per gm, even more preferred is (about) 4 mmol or more per gm, or (about) 5 mmol per gm, or (about) 6 mmol or more per gm, in each case per gram of core-shell particle. In a preferred embodiment, the average in vivo sodium binding capacity or amount of sodium bound in a human (or other mammal of interest) ranges (about) 2 mmol to (about) 6 mmol per gm, preferably from (about) 3 mmol to (about) 6 mmol per gram, in each case per gram of core-shell particle.

In some embodiments, the core-shell particle has an average in vitro binding capacity for sodium or amount of sodium bound of greater than (about) 1.0 mmol/gm, or preferably greater than (about) 1.5 mmol/gm of core-shell particle at a pH of greater than (about) 2 or in some embodiments at a pH of greater than (about) 5.5. In other preferred embodiments, the core-shell particle can have an average in vitro binding capacity or amount of sodium bound of at least (about) 2.0 mmol/gm, preferably greater than (about) 2.0 mmol/gm, such as preferably at least (about) 2.5 mmol/gm, or at least (about) 3.0 mmol/gm, or at least (about) 3.5 mmol/gm or at least (about) 4.0 mmol/gm or at least (about) 4.5 mmol/gm or at least (about) 5.0 mmol/gm, in each case where mmol/gm refers to per gram of core-shell composite (e.g., core-shell particle), and in each case as determined an in vitro assay mimicking physiological conditions of the gastrointestinal tract. Preferably, the in vitro binding capacity or amount of sodium bound can be determined from an assay selected from GI Assay No. I, GI Assay No. II, GI Assay No. III, and combinations thereof, in each case as defined and described in detail below.

Typically, in vivo binding capacity or amount of ion bound (e.g., a specific binding for a particular ion) is determined in a mammal such as a human. Techniques for determining in vivo potassium or sodium binding capacity in a human are well known in the art. For example, following administration of a potassium-binding or sodium-binding polymer to a patient, the amount of potassium or sodium in the feces can be compared to the amount of the ion found in the feces of subjects who to whom the polymer has not been administered. The increase in the ion excreted in the presence of the polymer versus in its absence can be used to calculate the in vivo potassium or sodium binding per gram of core-shell particle. The average in vivo binding is preferably calculated in a set of normal human subjects, this set being (about) 5 or more human subjects, preferably (about) 10 or more human subjects, even more preferably (about) 25 or more human subjects, and most preferably (about) 50 or more human subjects, and in some instances even 100 or more human subjects.

The binding of potassium or sodium to the core shell particles, in the presence of interfering divalent ions and other species, can also be determined in vitro. It is preferred that the in vitro potassium or sodium binding is determined in conditions that mimic the physiological conditions of the gastrointestinal tract, in particular the colon. Generally, the in vitro binding capacity/specific binding for a particular monovalent ion of interest can be determined from an assay selected from GI Assay No. I, GI Assay No. II, GI Assay No. III, and combinations thereof, in each case as defined and described in detail below.

The higher monovalent ion binding of the polymeric core-shell particles or composition enables the administration of a lower dose of the composition, to remove a therapeutically beneficial amount of sodium or potassium, as described below.

Selectivity/Permselectivity

Advantageously, core-shell particles of the invention are selective to monovalent cations over divalent cations. Such selectivity is preferably persistent over a meaningful period, including over a period allowing for effective application of the compositions and methods of the invention for treatment of various conditions and/or disorders as described below.

Without being bound by theory not specifically recited in the claims, the crosslinked polyvinylic (e.g., polyvinylamine) shell polymer modulates entry of competing solutes such as magnesium and/or such as calcium across the shell to the core component. The crosslinked shell polymer is permselective for inorganic monovalent cations over inorganic divalent cations. Competing cations have a lower permeability from the external environment across the shell compared to that of monovalent ions such as potassium ion or sodium ion. Examples of such competing cations include, but are not limited to, $Mg^{++}$, $Ca^{++}$, and protonated amines. In some embodiments, the shell is permeable to both mono- and divalent cations; however, the core-shell particle remains selective for binding of monovalent cations due to difference in permeation rates—i.e., due to kinetics affecting the rate of permeation—rather than as a result of an equilibrium preference for binding of the monovalent cation.

The relative permeability of the shell polymer for monvalent ion versus divalent ion can be characterized by a permeability ratio of permeability for monovalent ions (e.g., potassium ions) to permeability for divalent cations (e.g., $Mg^{++}$ and $Ca^{++}$), as measure in suitable environment-representative in vitro assays. For example, as measured in gastrointestinal representative assays, the permeability ratio can range from (about) 1:0.5 to (about) 1:0.0001 (i.e., from (about) 2:1 to (about) 10,000:1), and can preferably range from (about) 1:0.2 and (about) 1:0.01 (i.e., from (about) 5:1 to (about) 100:1). Further details on methods for determining permeability are disclosed below.

Permselectivity of the crosslinked polyvinylic polymers, such as crosslinked polyvinylamine, for inorganic monovalent ion over inorganic divalent ion can, generally be engineered and optimized (i.e., tuned) for an environment of interest. In particular, the shell component can be adapted to have a reduced permeability for higher valency cations (divalent cations such as magnesium ion and calcium ion) compared to permeability for monovalent cations, for an environment in which the core-shell particles will be applied. Generally, the permeability of the shell polymer to alkaline-earth cations can be altered by changing the average pore size, charge density and hydrophobicity of the membrane. Further details regarding approaches for tuning permselectivity (as well as persistence, discussed hereinafter, are set forth below.

Retention/Persistence

Preferably, the core-shell particles and compositions comprising such core-shell particles (e.g., such as potassium binding polymeric compositions and sodium-binding polymeric compositions described herein) bind the target inorganic monovalent ion and retain the target ion for a meaningful period within the environment of interest. For example, in applications involving binding of potassium ion or sodium ion in the gastrointestinal tract, the core-shell particle can bind potassium ion or sodium ion in the regions of the gastrointestinal tract having a relatively high concentration of potassium ion or sodium ion, respectively. Such bound potassium ion or sodium ion preferably remains bound to the core-shell particles and is excreted out of the body, in sufficient quantity to have a therapeutic benefit. From an alternative perspective, the core-shell particles do not significantly release the bound monovalent cation in the environment of interest such as in the gastrointestinal tract, prior to obtaining a desired beneficial effect. The core-shell particles and compositions described herein can retain a significant amount of the bound monovalent ion such as potassium ion or sodium ion. The term "significant amount" as used herein is not intended to mean that the entire amount of the bound potassium is retained. It is preferred that at least some of the bound monovalent ion is retained, such that a therapeutic and/or prophylactic benefit is obtained. Preferred amounts of bound monovalent ion that can be retained range from (about) 5% to (about) 100%, relative to amount initially bound. It is preferred that the polymeric compositions retain (about) 25% of the bound monovalent ion, more preferred is (about) 50%, even more preferred is (about) 75% and most preferred is retention of (about) 100% of the bound monovalent ion.

The period of retention is generally preferred to be during the time that the core-shell particle or composition is being used, in the environment of interest. For example, for applications involving ion binding in the gastrointestinal tract the time is a period sufficient for a therapeutically and/or prophylactically beneficial effect. In the embodiment in which the composition is used to bind and remove monovalent ion from the gastrointestinal tract, the retention period can be generally the time of residence of the composition in the gastrointestinal tract and more particularly the average residence time in the colon.

Advantageously, the selectivity (e.g., permselectivity) of the core-shell particles of the invention is sufficiently persistent to have a beneficial effect, such as a beneficial prophylactic or a beneficial therapeutic effect. The persistent selectivity (e.g. persistent permselectivity) of the core-shell particles is particularly advantageous for binding monovalent ions, and especially for binding potassium ion, in the gastrointestinal tract. The persistent selectivity (e.g. persistent permselectivity) of the core-shell particles is also advantageous for binding sodium ion in the gastrointestinal tract.

Notably, the gastrointestinal tract comprises a substantially diverse set of environments—particularly with respect to cation concentration. The concentration of cations varies substantially in the stomach and in the small intestine according to diet. However, estimates can be drawn based on average diets. See, for example, Hunt, C. D. et al., "Aluminum, boron, calcium, copper, iron, magnesium, manganese, molybdenum, phosphorus, potassium, sodium, and zinc: concentrations in common western foods and estimated daily intakes by infants; toddlers; and male and female adolescents, adults, and seniors in the United States." *J Am Diet Assoc* 101(9): 1058-60 (2001). See also USDA National Nutrient Database for Standard References, Release 16-1. Generally, in the small intestine (e.g., as measured at the end of the ileum), sodium ion and potassium ion concentration approximate the concentration of these ions in serum (as physiologically regulated), whereas calcium ion and magnesium ion depend on diet and secretion, and therefore vary over a wider range. Ion concentrations in the lower colon (e.g., sigmoid colon) are generally known. See, for example, Wrong, O., A. Metcalfe-Gibson, et al. (1965). "In Vivo Dialysis of Faeces as a Method of Stool Analysis. I. Technique and Results in Normal Subjects." Clin Sci 28: 357-75. See also, Wrong, O. M. (1971). "Role of the human colon in Homeostasis." Scientific Basis of Medicine: 192-215. See also, Salas-Coll, C. A., J. C. Kermode, et al. (1976). "Potassium transport across the distal colon in man." Clin Sci Mol Med 51(3): 287-96. See also Agarwal, R., R. Afzalpurkar, et al. (1994). "Pathophysiology of potassium absorption and secretion by the human intestine." Gastroenterology 107(2): 548-71.

Table 1 shows typical concentrations of various inorganic monovalent and divalent cations at various regions of the gastrointestinal tract, as reported in literature.

TABLE 1

|  | [Na+] | [K+] | [Mg++] | [Ca++] | pH |
|---|---|---|---|---|---|
| Stomach* | ~30 mM | ~15 mM | ~5 mM | ~10 mM | 2-6 |
| Ileum | ~120 mM | ~5 mM | ~10-50 mM | ~10-50 mM | 7-7.5 |
| Sigmoid Colon | ~30 mM | ~75 mM | ~20-40 mM | ~10-40 mM | 6-7.5 |

*values are diet dependent; reported ranges based on US average diet.

With respect to monovalent cation binding, for example: hydrogen ion is especially prevalent in the stomach (e.g. gastric acids); sodium ion is particularly prevalent in the ileum and earlier regions of the colon (e.g., ascending colon), but is less prevalent in the latter regions of the colon (e.g., descending colon and Sigmoid colon) (See, e.g., Ross, E. J. et al. "Observations on cation exchange resins in the small and large intestines." *Clin Sci (Lond)* 13(4): 555-66 (1954); see also Spencer, A. G. et al., "Cation exchange in the gastrointestinal tract." *Br Med J* 4862: 603-6 (1954)); and potassium ion is particularly prevalent in latter regions of the colon (e.g. descending colon and Sigmoid colon) (See, e.g., Wrong, O., A. et al., "In Vivo Dialysis of Faeces as a Method of Stool Analysis. I. Technique and Results in Normal Subjects." Clin Sci 28: 357-75 (1965); see also Wrong, O. M., "Role of the human colon in Homeostasis." Scientific Basis of Medicine: 192-215 (1971); see also Salas-Coll, C. A. et al., "Potassium transport across the distal colon in man." Clin Sci Mol Med 51(3): 287-96 (1976); see also Agarwal, R., R. et al., "Pathophysiology of potassium absorption and secretion by the human intestine." Gastroenterology 107(2): 548-71 (1994).

Divalent cations, such as Mg++ and Ca++ are generally prevalent throughout the small intestine and the colon (See Shiga, A., T. et al., "Correlations among pH and Mg, Ca, P, Na, K, Cl— and HCO3- contents of digesta in the gastrointestinal tract of rats." Nippon Juigaku Zasshi 49(6): 973-9 (1987); see also McCarthy, J. et al., "Divalent Cation Metabolism: Calcium", in Atlas of Diseases of the Kidney. Vol. 1. R. W. Schrier, editor. Blackwell Sciences, Philadelphia (1999); see also McCarthy, J. et al., "Divalent Cation Metabolism: Magnesium" in Atlas of Diseases of the Kidney. Vol. 1. R. W. Schrier, editor. Blackwell Sciences, Philadelphia (1999)).

Persistent Selectivity—Potassium

Significantly, the compositions (e.g., pharmaceutical compositions) and the core-shell particles of the present invention selectively bind potassium ion over competing inorganic divalent ions such as magnesium and/or calcium, and the selectivity is persistent. The persistent selectivity of the compositions (and the core-shell particles) of the invention for potassium ion over one or more divalent ions (e.g., magnesium ion, calcium ion) is realized by effectively reducing (e.g., substantially minimizing, retarding or precluding) the extent of binding of inorganic divalent ions (especially magnesium ion and/or calcium ion), and maintaining such reduced extent of binding over a period of time meaningful for the application of interest. For example, in applications involving potassium-ion binding in the gastrointestinal tract, the portion of the binding capacity (e.g., on a cation exchange resin) occupied by such divalent ions is preferably minimized (or precluded) over a period of time required for the composition to transit the small intestine and the colon, where divalent ions such as magnesium ion and calcium ion are prevalent. Notably, divalent cations are preferentially bound by cation exchange resins (e.g., by a core component comprising a cation exchange resin as a core polymer) in comparison to monovalent cations; as such, the significance of divalent ions as interferents for monovalent ion binding is substantial, and is not directly correlated to relative concentration of divalent ion versus monovalent ion. In preferred embodiments, such persistent selectivity over divalent ions is realized, for example, using a permselective shell over a potassium-binding core, where the shell has a persistent permselectivity for potassium over inorganic divalent ion, including magnesium ion and/or calcium ion.

Also significantly, in applications for core-shell particles and compositions in the gastrointestinal tract, the core-shell particles and compositions of the invention can be effective for removing potassium preferentially (even over potentially-competing sodium ion) from the gastrointestinal tract, based on a capability to exchange monovalent ions relatively quickly from the core-shell particle. Specifically, the core-shell particles and compositions can be effective for binding potassium ion, based on the relative concentrations of potassium and sodium in various regions of the gastrointestinal environment coupled with a capability to bind potassium ion at a rate that allows a cation exchange resin to become preferentially loaded with potassium ion over sodium ion in regions of the gastrointestinal environment where potassium ion concentration exceeds sodium ion concentration. In particular, the core-shell particles and compositions of the invention can be effective for binding potassium ion preferentially over competing sodium ion in the lower colon (e.g., distal colon), preferably within the period of time the composition resides in the lower colon. In the gastrointestinal tract, sodium ion is present in relatively high concentrations compared to potassium ion in the small intestine (e.g., ileum); however, the relationship inverts as the composition transits further down the gastrointestinal tract—with potassium ion present in relatively high concentrations compared to sodium ion in the lower colon (e.g., distal colon). Hence, a monovalent cation exchange resin can preferentially bind potassium over sodium in the gastrointestinal tract if the exchange kinetics for potassium are sufficiently fast to allow for meaningful potassium binding within the period of passage through the lower colon (e.g., the distal colon).

Accordingly, the compositions (and core-shell particles) of the present invention are preferably applied as potassium binders, and especially in the gastrointestinal tract of a mammal.

In a preferred embodiment, the compositions (and core-shell particles) of the invention bind a greater amount of potassium ion than sodium ion (within a potassium-binding period representative of the transit time for the lower colon), and also have a persistent selectivity for potassium ion over one or more divalent ions, e.g., magnesium ion, calcium ion (over a divalent ion-binding period representative of the transit time through the gastrointestinal tract or a relevant portion there of (e.g., through the small intestine and the colon)). For example, in one embodiment, the composition can comprise a core-shell particle comprising a core component and a shell component. The core component can be a polymer having a capacity for binding potassium ion. The shell component can be a persistent permselective polymer for potassium ion over magnesium ion and/or calcium ion. The composition (and core-shell particle) can be further characterized by (i) binding an effective amount of potassium ion within a relatively short potassium-binding period (e.g., generally less than (about) ten hours), in combination with (ii) retarding binding of divalent cation (e.g., magnesium ion and/or calcium ion) with such retarded binding maintained over a relatively long magnesium-binding period and/or calcium-binding period (e.g., generally more than (about) twelve hours).

Generally, for embodiments of the invention in which the core component comprises a core polymer which is a cation exchange resin, the ion-binding period for a particular ion of interest (e.g., a potassium-binding period for potassium ion) can be understood by a person of ordinary skill in the art as reflecting a time scale for cation exchange (e.g., a cation-exchange period)—specifically for example, a time scale for monovalent cation exchange (with respect to monovalent ion-binding periods), or for example, a time scale for divalent cation exchange (with respect to divalent ion-binding periods). Also, the reference to "binding" of monovalent or divalent ions in the context of such embodiments can be understood by a person of ordinary skill in the art to mean and include a number of interactions between the cation and the cation exchange media over a period of time, during which particular cations can exchange aribitrarily in response to changes in cation concentration in the environment, and within generally established and understood driving forces to attain (or reattain) equilibrium. Without being bound by theory, a total number of cations within an cation exchange media of a core-shell particle is substantially constant; cations can enter and leave the cation exchange media dynamically over time. Within the cation exchange media, cations may diffuse freely within the particle, and/or may be associated with a fixed charge group for a period of time.

Generally, with regard to the persistent selectivity of the compositions of the invention, an effective amount of potassium ion is preferably bound to the compositions of the invention within a potassium-binding period of less than (about) six hours, preferably less than (about) five hours, or less than (about) four hours, or less than (about) three hours, or less than (about) two hours, or less than (about) one hour. Generally, the persistent selectivity of the compositions for potassium ion over inorganic divalent ions (especially magnesium ion and/or calcium ion) is maintained over a magnesium-binding period and/or over a calcium-binding period of more than (about) 18 hours, preferably more than (about) 24 hours, more preferably more than (about) 30 hours, and in some embodiments, more than (about) 36 hours, more than (about) 40 hours, more than (about) 42 hours, more than (about) 48 hours, or more than (about) 72 hours. Various combinations of potassium binding periods (preferably low) with magnesium ion biding periods and/or calcium ion binding periods are contemplated. For example, it is generally preferable that the potassium-binding period is less than (about) 6 hours, and the magnesium-binding period and/or the calcium binding period is more than (about) 18 hours. In some embodiments, the potassium-binding period is less than (about) 4 hours, and the magnesium-binding period and/or the calcium binding period is more than (about) 24 hours. In some embodiments, the potassium-binding period is less than (about) 2 hours, and the magnesium-binding period and/or the calcium binding period is more than (about) 30 hours, or 36 hours, or 42 hours or 48 hours or 72 hours. In some embodiments, the potassium-binding period is less than (about) 1 hour, and the magnesium-binding period and/or the calcium binding period is more than (about) 30 hours, or 36 hours, or 42 hours, or 48 hours, or 72 hours. Other combinations are more fully described herein after.

The combination of a persistent selectivity for potassium ion over divalent ion such as magnesium ion and/or calcium ion, as well as the effective preferential binding for potassium ion over sodium ion, can be more specifically characterized, as follows.

In one first approach, for example, the persistent selectivity and preferential binding can be characterized based on a specific binding profile—defined by the extent of binding of potassium ion over time and the extent of (reduced, retarded or precluded) binding of magnesium ion and/or calcium ion over time. Preferably, for example, the composition (or core-shell particle) can have a specific binding of potassium ion of at least (about) 1.5 mmol/gm, preferably at least (about) 2.0 mmol/gm or 2.5 mmol/gm or 3.0 mmol/gm, or 3.5 mmol/gm or 4.0 mmol/gm or 4.5 mmol/gm or 5.0 mmol/gm, in each case achieved within a potassium-binding period of less than (about) six hours, and in various combination, the composition can have a specific binding of magnesium ion and/or of calcium ion of not more than 5.0 mmol/gm, or not more than 4.0 mmol/gm or not more than 3.0 mmol/gm, preferably not more than 2.0 mmol/gm, more preferably not more than (about) (about) 1.5 mmol/gm, and most preferably not more than (about) 1.0 mmol/gm or not more than (about) 0.75 mmol/gm or not more than (about) 0.5 mmol/gm, in each case maintained over a magnesium-binding period and/or a calcium-binding period of more than (about) eighteen hours. The specific binding can be determined in vivo or can be determined in vitro using one or more assay protocols, preferably where such protocols mimic or are representative of inorganic ion concentrations typical of the gastrointestinal tract, and especially of the lower intestine and/or of the colon. Preferably, the specific binding can be determined using an in vitro assay selected from GI Assay No. I, GI Assay No. II, GI Assay No. III, and combinations thereof, in each case as described and defined below. The potassium-binding period is preferably less than (about) 4 hours, or less than (about) 2 hours, or less than (about) 1 hour, and considered in various combinations, the magnesium-binding period and/or the calcium-binding period is preferably more than (about) 24 hours, or more than (about) 30 hours, or more than (about) 36 hours, or more than (about) 42 hours, or more than (about) 48 hours, or more than 72 hours. For example, in some particularly preferred embodiments, the potassium-binding period is preferably less than (about) 2 hours, and the magnesium-binding period and/or the calcium-binding period is preferably more than (about) 36 hours. In especially preferred embodiments, the potassium-binding period is preferably less than (about) 1 hour, and the magnesium-binding and/or the calcium-binding period is preferably more than (about) 42 hours.

In another second approach, for example, the persistent selectivity and preferential binding of the compositions (or the core-shell particles) of the invention can be characterized based on a relative binding profile—defined by the relative binding of potassium ion as compared to total inorganic cation bound as measured over time, and further defined by the relative (reduced, retarded or precluded) binding of magnesium ion and/or calcium ion as compared to total inorganic cation bound over time. Preferably, for example, the composition (or core-shell particle) can have a relative binding of potassium ion of at least (about) 20% by mole of the total bound cation, preferably at least (about) 30% by mole of the total bound cation, and more preferably of at least (about) 40% by mole of the total bound cation, and even more preferably at least (about) 45% by mole of the total bound cation, or at least (about) 50% by mole of the total bound cation, or at least (about) 55% by mole of the total bound cation, or at least (about) 60% by mole of the total bound cation, or at least (about) 65% by mole of the total bound cation, or at least (about) 70% by mole of the total bound cation, in each case achieved within a potassium-binding period of less than (about) six hours, and in various combination, the composition can have a relative binding of magnesium ion and/or of calcium ion of not more than (about) 80% by mole of the total bound cation, preferably not more than (about) 70% by mole of the total bound cation, more preferably not more than (about) 60% by mole of the total bound cation, and even more preferably not more than (about) 40% by mole of the total bound cation, more still more preferably not more than (about) 35% by mole of the total bound cation, or not more than (about) 30% by mole of the total bound cation, or not more than (about) 25% by mole of the total bound cation, or not more than (about) 20% by mole of the total bound cation, or not more than (about) 15% by mole of the total bound cation, or not more than (about) 10% by mole of the total bound cation, or not more than (about) 5% by mole of the total bound cation, in each case maintained over a magnesium-binding period and/or a calcium-binding period of more than (about) eighteen hours. The relative binding can be determined in vivo or can be determined in vitro using one or more assay protocols, preferably where such protocols mimic or are representative of inorganic ion concentrations typical of the gastrointestinal tract, and especially of the lower intestine and/or of the colon. Preferably, the relative binding can be determined using an in vitro assay selected from GI Assay No. I, GI Assay No. II, GI Assay No. III, and combinations thereof, in each case as described and defined below. The potassium-binding period is preferably less than (about) 4 hours, or less than (about) 2 hours, or less than (about) 1 hour, and considered in various combinations, the magnesium-binding period and/or the calcium-binding period is preferably more than (about) 24 hours, or more than (about) 30 hours, or more than (about) 36 hours, or more than (about) 42 hours, or more than (about) 48 hours, or more than (about) 72 hours. For example, in some particularly preferred embodiments, the potassium-binding period is preferably less than (about) 2 hours, and the magnesium-binding period and/or the calcium-binding period is preferably more than (about) 36 hours. In especially preferred embodiments, the potassium-binding period is preferably less than (about) 1 hour, and the magnesium-binding and/or the calcium-binding period is preferably more than (about) 42 hours.

In a third approach, for example, the persistent selectivity and preferential binding of the compositions (or the core-shell particles) of the invention can be characterized based on a permselectivity relative to equilibrium values of ion binding. That is, if the core-shell particles of the invention are allowed to equilibrate for a period of time, the composition (or the core-shell particles) may eventually bind cations to an extent similar to the core alone. Hence, in one embodiment, the shell component has a permeation rate for potassium ion sufficiently high to allow potassium ion to achieve a high level of binding (but perhaps non-equilibrium level of binding) during the mean average residence time in the environment (e.g., in the colon), while the shell component has permeation rate for competing inorganic cations (e.g. $Mg^{2+}$, and/or $Ca^{2+}$) which is lower, such that the competing divalent cations do not achieve or approach their equilibrium binding levels to significant extent during the mean average residence time. For such embodiments, one can define a measure of the time persistence of permselectivity. In particular, such time persistence can be the time needed to reach between (about) 20% and (about) 80% (i.e., $t_{20}$ to $t_{80}$) of the extent of binding at equilibrium in conditions reflecting the colon electrolyte profile. Preferably, the composition (or core-shell particle) can have a time persistence for potassium ion (and monovalent cations in general), defined as the time needed to reach (about) 20% or 50% or 80% of the equilibrium binding, $t_{20}$ or $t_{50}$ or $t_{80}$, of not more than (about) six hours, preferably not more than (about) 5 hours, or not more than (about) 4 hours, or not more than (about) 2 hours, or not more than (about) 1 hour, and in various combinations, the composition can have a time persistence for magnesium ion and/or for calcium ion defined as the time needed to reach (about) 20% or 50% or 80% of the equilibrium binding, $t_{20}$, or $t_{50}$ or $t_{80}$, respectively of more than (about) 18 hours, preferably more than (about) 24 hours, or more than (about) 30 hours, or more than (about) 36 hours, or more than (about) 40 hours, or more than (about) 42 hours, or more than (about) 48 hours, or more than (about) 72 hours. In this approach, the extent of binding and the equilibrium binding can be determined in vivo or can be determined in vitro using one or more assay protocols, preferably where such protocols mimic or are representative of inorganic ion concentrations typical of the gastrointestinal tract, and especially of the lower intestine and/or of the colon. Preferably, the extent of binding and the equilibrium binding can be determined using an in vitro assay selected from GI Assay No. I, GI Assay No. II, GI Assay No. III, and combinations thereof, in each case as described and defined below. As applied to determining equilibrium values, such assays be extended to run over a long period of time, preferably at least until the earlier of (i) the time at which no further changes in supernatant ion concentrations can be detected over a continuous twenty-four hour period, or (ii) two weeks.

Persistent Selectivity—Sodium

Additionally, the compositions or core-shell particles (e.g., pharmaceutical compositions) of the present invention can selectively bind sodium ion over competing inorganic divalent ions such as magnesium and/or calcium. In general, sodium ion selectivity generally, and persistent selectivity for sodium ion, in each case over such divalent ions, can be based on and characterized in the same manner as described above in connection with the selectivity and persistence for potassium ion.

In some applications for core-shell particles and compositions for binding sodium in the gastrointestinal tract, the core-shell particles and compositions of the invention may preferentially bind sodium ion over competing potassium ion, particularly in the small intestine where sodium is especially prevalent—and typically at concentrations substantially greater than potassium ion. In such applications, the core-shell particles and compositions of the invention can comprise a core component and a shell component. The core component can be a polymer having a capacity for binding sodium ion. The shell component can be a persistent permselective polymer over magnesium ion and/or calcium ion (having a permeability for sodium ion that is higher than a permeability for magnesium ion and/or calcium ion). The composition (and core-shell particle) can be further characterized by one or more of the following, in various combination: (i) having a capacity for binding an effective amount of sodium ion within a relatively short sodium-binding period representative of the transit time through the small intestine (e.g., generally less than (about) twelve hours); (ii) having a persistent selectivity for retarding (or precluding) binding of divalent cation (e.g., magnesium ion and/or calcium ion) with such retarded (or precluded) binding maintained over a relatively long magnesium-binding period and/or calcium-binding period representative of the transit time through the small intestine and colon (e.g., generally more than (about) twelve hours); and (iii) the shell polymer having a permeability for competing inorganic monovalent ions (e.g., potassium) preferably also for competing divalent ions (e.g., magnesium ion and/or calcium ion) that is effectively modulated by an environment of the gastrointestinal tract (e.g., such as pH at (about) where the composition moves from the small intestine to the colon—where pH typically drops from approximately pH 7.5 to approximately pH 5.5; or e.g., such as pH at (about) where the composition moves from the stomach to the small intestine or such as the increase in pH from the entrance of the small intestine (duodenum) to the end of the small intestine (terminal ileum)), such that further ion exchange (e.g., transport through the shell component) between the sodium-binding core and the environment is substantially reduced or eliminated at and beyond a region of the GI tract, beyond which the sodium concentration decreases from its high value in the small intestine.

Further details and description regarding modulating the permeability of the shell component are provided in the following related applications: U.S. application Ser. No. 11/095,918 filed Mar. 30, 2004, which is a continuation-in-part of U.S. application Ser. No. 10/814,749 filed Mar. 30, 2004.

Robustness.

The core-shell particles of the invention are preferably sufficiently robust to survive in the environment of intended use. In one application, for example, the core-shell particles are sufficiently robust to pass through the gastrointestinal system (or an in-vitro assay representative thereof)—without substantially disintegrating such core shell particle. In preferred embodiments, the shell component of the core-shell composition is essentially robust (e.g., not disintegrated, torn, and/or delaminated) under physiological conditions of the gastrointestinal tract (or in vitro representations or mimics thereof) during a period of time for residence and passage through the gastro-intestinal tract. For example, core-shell particle and the shell component of the core-shell particle is essentially not disintegrated under in vitro conditions selected from the group consisting of (i) an aqueous solution having a pH of (about) 3 over a period of (about) 6 hours, (ii) an aqueous solution having a pH of (about) 8 over a period of (about) 10 hours, (iii) an aqueous solution having a pH of (about) 6 over a period of (about) 20 hours and combinations thereof, in each case at a temperature of (about) 37° C. with agitation.

In some embodiments, the core-shell particles can be robust—with respect to other aspects in addition to not disintegrating, including for example with respect to physical characteristics and/or performance characteristics. Physical characteristics can include particle size, particle size distribution, and/or surface properties, for example, as evaluated visually using microscopes, such as electron microscopes and/or confocal microscopes. Performance characteristics can include specific binding capacity, selectivity (e.g., permselectivity) and persistence. Some preferred in vitro assays that can be used in connection with determining robustness, for example for purposes of tuning a core-shell particle in that regard, include GI Assay No. I, GI Assay No. II, GI Assay No. III, and combinations thereof, in each case as described in detail below.

In some embodiments, the shell component can impart other properties relating to robustness, such as being sufficient resistant to sustain mechanical forces or constraints in connection with swelling of the core polymer and/or in connection with formulation (e.g., compression encountered during tablet formulation).

In embodiments of the invention, the shell component can protect the core component from the external environment such as the gastrointestinal tract. For example, the shell component can protect functional groups (e.g., acid groups) of the core components (e.g., of a core polymer) and prevent exposure thereof to the gastrointestinal environment.

In other embodiments, the core-shell component can comprise the core component, the shell component (for example, comprising crosslinked polyvinylic polymer as described above)), and one or more further shell components overlying the crosslinked polyvinylic polymer. For example, such further shell components can comprise an enteric coating, for example an acid-insoluble polymer which prevents contact between a pharmaceutical substance and the acidic contents of the stomach, but disintegrates in the rising pH of the small intestine or colon and allows the pharmaceutical substance to be released. Suitable examples of enteric coatings are described in the art. For example, see Remington: The Science and Practice of Pharmacy by A. R. Gennaro (Editor), 20$^{th}$ Edition, 2000.

Non-Absorbed

Preferably core-shell particles and the compositions comprising such core-shell particles are not absorbed from the gastro-intestinal tract. The term "non-absorbed" and its grammatical equivalents is not intended to mean that the entire amount of administered polymer is not absorbed. It is expected that certain amounts of the polymer may be absorbed. It is preferred that (about) 90% or more of the polymer is not absorbed, preferably (about) 95% or more is not absorbed, even more preferably (about) 97% or more is not absorbed, and most preferably (about) 98% or more of the polymer is not absorbed.

Counterions

The core-shell particles, and particularly, core polymers and/or shell polymers of the core-shell particle can include one or more counterions. Core polymers having a capacity for binding inorganic monovalent ions can preferably comprise one or more cationic counterions. The cations can be metallic, non-metallic, or a combination thereof. Examples of metallic ions include, but are not limited to, $Ca^{2+}$-form, $H^+$-form, $NH_4^+$-form, $Na^+$-form, or a combination thereof. Examples of non-metallic ions include, but are not limited to, alkylammonium, hydroxyalkylammonium, choline, taurine, carnitine, guanidine, creatine, adenine, and aminoacids or derivatives thereof.

Shell Amount or Thickness/Core-Shell Particle Size

The size of the core-shell particles is not narrowly critical, and can be adapted for a particular environment of interest and/or for a particular application of interest. In particular, the amount of a shell component and/or a thickness of a shell component can be controlled and/or optimized with respect to various characteristics and features described herein, such as specific binding capacity, selectivity, persistence, robustness, etc., in each case, based for example on the guidance provided herein.

Generally, for example, the size of the core-shell particles can typically range from (about) 100 nm to (about) 5 mm, and preferably from (about) 200 nm to (about) 2 mm, or from (about) 500 nm to (about) 1 mm, or from (about) 1 micron to (about) 500 microns. In some embodiments, the size of the core-shell particles are more than (about) 1 microns, more preferred is more than (about) 10 microns, even more preferred is more than (about) 20 microns, and most preferred is more than (about) 40 microns. In some embodiments, the size of the core-shell particles are less than (about) 250 microns, more preferred is less than (about) 150 microns. In some embodiments, a particularly preferred size is (about) 100 microns. In some embodiments, particularly preferred size is less than (about) 100 microns, and most preferred is less than (about) 50 microns.

The particle size distribution is not narrowly critical. A relatively narrow particle size distribution can result particles having substantially similar kinetic behavior, with regard to the time for exchange of monovalent cations and the time for exchange of divalent cations. Generally, the particle size distribution can be controlled with respect to kinetics of ion exchange for achieving a desired ion exchange kinetic profile, or with respect to compactibility or bulk density, or other properties of interest for formulation or use. The particle size distribution may be monomodal or multimodal (e.g., comprising a mixture of two or more populations of particles, each population having a well defined and relatively narrow particle size distribution).

The particle shape is likewise not narrowly critical, but can be meaningful in certain embodiments. In one embodiment, for example, for delivery as an oral suspension, the particles can be spherical (e.g. for a reduced perception of roughness or grittiness in the mouth and throat) and the particles can be (about) <200 um in diameter, preferably less than <100 um, and still preferably less than 75, 60, 50, or 40 um. In another embodiment, for example, for a tablet (e.g., a swallowable tablet) or capsule formulation, the particles can have a non-spherical shape and can be irregularly shaped particles, preferably with a relatively broad size distribution, allowing for improved compactibility, higher density, and improved tablet strength.

The amount of shell component, and/or a thickness of a shell component over a surface of the core component is not narrowly critical, and can be adapted for a particular environment of interest and/or for a particular application of interest. In particular, the amount of a shell component and/or a thickness of a shell component can be controlled and/or optimized with respect to various characteristics and features described herein, such as specific binding capacity, selectivity, persistence, robustness, etc., in each case, based for example on the guidance provided herein.

The core-shell particle can preferably comprise a shell component and a core component in a relative amount generally ranging from (about) 1:1000 to (about) 1:2 by weight. In preferred embodiments, the relative amount of shell component to core component can range from (about) 1:500 to (about) 1:4 by weight, or ranging from (about) 1:100 to (about) 1:5 by weight, or ranging from (about) 1:50 to (about) 1:10 by weight.

In some embodiments, the shell component can have a thickness ranging from (about) 0.002 micron to (about) 50 micron, preferably (about) 0.005 micron to (about) 20 microns, or from (about) 0.01 microns to (about) 10 microns. In some embodiments, the shell thickness can be more than (about) 0.5 micron, preferably more than (about) 2 micron, or more than (about) 5 micron. In some embodiments, the shell thickness can be less than (about) 30 micron, preferably less than (about) 20 micron, or less than (about) 10 micron, or less than (about) 5 micron.

In Vitro Assays

The core-shell particles and the compositions of the invention are characterized with respect to various features, such as the extent of binding for a particular cation (e.g., potassium ion or sodium ion), selectivity, and/or persistence. Preferably, such characteristic features of the compositions (or core-shell particles) are determined under a specified set of conditions.

In some cases, such characteristic features of the compositions (or core-shell particles) can be determined using in vitro assay protocols that mimic or are representative of inorganic ion concentrations typical of the gastrointestinal tract, and especially of the lower intestine and/or of the colon. Additionally, the assays may include components which model other species (than inorganic ions) which are commonly found in the gastrointestinal tract. Preferably, such characteristics are determined using an in vitro assay selected from GI Assay No. I, GI Assay No. II, GI Assay No. III, and combinations thereof (i.e., combinations of two or more thereof) defined as follows.

A first assay, referred to herein as GI Assay No. I, is a relatively simple competitive assay involving potassium ion and magnesium ion at equal molar concentrations selected to be generally typical and representative of the concentrations seen in various regions of the intestinal tract, with the concentration of magnesium ion being sufficiently high to be present in excess during the assay (e.g., to avoid substantial depletion of magnesium ion during the assay). This first assay consists essentially of incubating the composition (or the core-shell particle) at a concentration of 4 mg/ml in a first assay solution. The first assay solution comprises, and preferably consists essentially of 55 mM KCl, 55 mM $MgCl_2$ and a buffer, 50 mM 2-morpholinoethanesulfonic acid monohydrate, at a pH of 6.5 and a temperature of 37° C. The composition is incubated for 48 hrs with agitation. The cations bound to the composition are measured, directly or indirectly, over time (e.g., as described below).

A second assay, referred to herein as GI Assay No. II, is a relatively sophisticated competitive assay involving potassium ion and magnesium ion and certain anions (e.g., including anions encountered in the upper gastrointestinal environment) that might modulate the performance of the shell material. This second assay consists essentially of incubating the composition (or core-shell particles) at a concentration of 4 mg/ml in a second assay solution. The second assay solution can comprise and preferably consists essentially of 50 mM KCl, 50 mM $MgCl_2$, 5 mM sodium taurocholate, 30 mM oleate, 1.5 mM citrate, and a buffer, 50 mM 2-morpholinoethanesulfonic acid monohydrate. The composition is incubated at a pH of 6.5 and a temperature of 37° C. for 48 hrs with agitation. The cations bound to the composition are measured, directly or indirectly, over time (e.g., as described below).

A third assay, referred to herein as GI Assay No. III, is an ex vivo assay involving ions present in human fecal water extracts, generally representative of the ion content and concentrations seen in the lower colon. This third (fecal water) assay consists essentially of incubating the composition (or core-shell particles) at a concentration of 4 mg/ml in a fecal water solution. The fecal water solution is a filtered centrifugal supernatant derived by centrifuging human feces for 16 hours at 50,000 g at 4° C. and then filtering the supernatant through a 0.2 um filter. The composition is incubated in the fecal water solution at a temperature of 37° C. for 48 hrs with agitation. The cations bound to the composition are measured, directly or indirectly, over time (e.g., as described below).

In each of the aforementioned assay protocols, GI Assay No. I, GI Assay No. II, and GI Assay No. III, direct measurement of bound cations can be performed by recovering the composition (core-shell particles) and analyzing the ion content thereof, for example, by releasing bound cations by treating with acid or base, and measuring the released cations. In each of the described protocols, indirect measurement of bound cations can be performed by determining the change in ion concentration of the assay solution in the presence and absence of the core-shell particles or composition being evaluated.

Each of these assay protocols (i.e., GI Assay No. I, GI Assay No. II, and GI Assay No. III) describe incubation of the composition (or core-shell particles) at a concentration of 4 mg/mL in assay solutions containing various ions. The concentration of such composition (or the core-shell particles) is not narrowly critical, however, and these assays can alternatively be performed using other concentrations, taking into account, for example, (1) the binding capacity of the core-shell particles assayed, (2) the anticipated dose to be administered, (3) the desired signal-to-noise ratio (which tends to increase with increasing core-shell particle concentration), and (4) the concentration of the target ion within the contents at various locations of the gastrointestinal tract, which for potassium ion tends to increase as a function of distance transited through the gastrointestinal tract (i.e., from the stomach to the jejunum, ileum and then to the colon). Such alternative concentrations may, for example, range from (about) 2 mg/mL to (about) 50 mg/mL in the assay solution. In various embodiments of the assay, the core-shell particle concentration can be 10 mg/mL, 20 mg/mL, or 40 mg/mL. Assays having protocols including these alternative core-shell particle concentrations can be used with any of the embodiments of the invention described herein.

Determining Permeability

Methods for determining permeability coefficients are known. For example, see, W. Jost, *Diffusion in Solids, Liquids and Gases*, Acad. Press, New-York, 1960). For example, the ion permeability coefficient in a shell polymer can be measured by casting the polymer as a membrane over a solid porous material, subsequently contacted with a physiological solution (donor) containing the ions of interest, and measuring steady state permeation rates of said ions, across the membrane in the acceptor solution. Membrane characteristics can then be optimized to achieve the best cooperation in terms of selectivity and permeation rate kinetics. Structural characteristics of the membrane can be varied by modifying, for example, the polymer volume fraction (in the swollen membrane), the chemical nature of the polymer(s) and its properties (hydrophobicity, crosslinking density, charge density), the polymer blend composition (if more than one polymer is used), the formulation with additives such as wetting agents, plasticizers, and/or the manufacturing process.

Tuning of Permselectivity/Persistence

As discussed above, permselectivity and/or persistence of shell polymers for inorganic monovalent ion over inorganic divalent ion can generally be engineered and optimized (i.e., tuned) for an environment of interest. In particular, the shell component can be adapted to have a reduced permeability for higher valency cations (divalent cations such as magnesium ion and calcium ion) compared to permeability for monovalent cations, for an environment in which the core-shell particles will be applied. $Mg^{++}$ and $Ca^{++}$ hydrated ions have a large size compared with monovalent cations such as $K^+$ and $Na^+$ as indicated below in Table 2 (Nightingale E. R., J. Phys. Chem., 63, (1959), 1381-89).

TABLE 2

| Metal ions | Hydrated radii (angstroms) |
|---|---|
| $K^+$ | 3.31 |
| $NH_4^+$ | 3.31 |
| $Na^+$ | 3.58 |
| $Mg^{++}$ | 4.28 |
| $Ca^{2+}$ | 4.12 |

The differences in size and electronic properties of inorganic cations can be the basis for differences in permeability that allow for discriminating between such cations in an environment of interest, and for a period of interest. Generally, the permeability of the shell polymer to alkaline-earth cations can be altered by changing the average pore size, charge density and hydrophobicity of the membrane.

Some approaches for effecting reduced permeabilities to divalent cations are generally known in the art, including for example from previous studies on cation-exchange membranes for electrodialysis (e.g. Sata et al, J. Membrane Science, 206 (2002), 31-60). Disclosed methods are usually based on pore size exclusion and electrostatic interaction and combination thereof.

When the mesh size of the shell material is in the same size range as the solute dimensions, the diffusion of a bulkier divalent cation through the shell component can be significantly slowed down. For example, experimental studies (Krajewska, B., Reactive and Functional polymers 47, 2001, 37-47) report permeation coefficients in cellulose ester or crosslinked chitosan gel membranes for both ionic and non-ionic solutes. These studies show a lower permeation rate for bulkier solutes when membrane mesh size nears solute dimensions. The polymer volume fraction in a swollen (e.g., hydrated) resin is a good indicator of the mesh size within the composition; theoretical studies have shown, for example, that mesh size usually scales with $\phi^{-3/4}$, where $\phi$ is the polymer volume fraction in the shell component swollen in a solution. The membrane swelling ratio, in turn, depends on factors which include the hydrophobicity, crosslinking density, charge density, and solvent ionic strength.

Among approaches for tuning permeability, differentiation based on electronic properties of the target monovalent ions and the competing divalent ions can include a shell polymer that comprises or consists essentially of a cationic polyelectrolyte. For example, a thin layer of a cationic polyelectrolyte can be physically adsorbed to create a strong electrical field that repels more highly charged cations such as $Mg^{++}$ and $Ca^{++}$ (while having less repulsion effect on less charged cations such as $K^+$ and $Na^+$. Preferred cationic polyelectrolytes include homopolymers or copolymers having a vinylic repeat unit such as vinylamine repeat unit. Other suitable cationic polyelectrolytes, for example that can be used in combination with the preferred cationic polyelectrolytes include but are not limited to, homopolymers or copolymers with a repeat unit selected from ethyleneimine, propyleneimine, allylamine, vinylpyridines, alkyaminoalkyl(meth)acrylates, alkyaminoalkyl(meth)acrylamides, aminomethylstyrene, chitosan, adducts of aliphatic amine or aromatic amine with electrophiles (e.g., such as epichlorhydrin, alkylhalides or epoxides) and wherein the amine is optionally a quaternized form. Adducts of aliphatic amine or aromatic amine with alkyldihalides are also referred to as ionenes.

In another approach, the permselectivity of the core-shell particle can also be controlled by pH, for example by varying the pH (or by taking advantage of a pH variation in an environment of interest) to realize a corresponding change in core polymer charge density or shell polymer charge density, and/or to realize a corresponding change in the swelling ratio of the core polymer or the shell polymer with the rate or extent of protonation or deprotonation. In particular, core polymers or shell polymers can have ion exchange properties that vary with the local pH of the environment. For example, core particles comprising core polymers can have a relative low binding capacity at gastric pH (e.g., as low as 2 to 3) and have a relatively high binding capacity at pH greater than (about) 5.5. In one preferred embodiment, the core polymers of the invention can have a fraction of capacity available at pH lower than (about) 3, (e.g., (about) 0-10% of the full capacity to the extent affected by pH (i.e. measured at pH (about) 12)). The fraction of capacity available can be larger, for example greater than (about) 50% of the full capacity, at pH greater than (about) 4, and preferably greater than (about) 5 or greater than (about) 5.5.

Some systems for core-shell particles can combine positive charges and hydrophobicity. For example, preferred shell polymers can include amine functional polymers, such as those disclosed above, which are optionally alkylated with hydrophobic agents. In some cases, the alkylating agents can comprise two or more amine-reactive moieties, and operate as a crosslinking alkylating agent. In some cases, alkylating agents can be introduced through crosslinking reaction with hydrophobic crosslinking agent, such as diglycidyl aniline.

Alkylation involves reaction between the nitrogen atoms of the polymer and the alkylating agent (usually an alkyl, alkylaryl group carrying an amine-reactive electrophile).

Preferred alkylating agents are electrophiles such as compounds bearing functional groups such as halides, epoxides, esters, anhydrides, isocyanate, or $\alpha,\beta$-unsaturated carbonyls. They have the formula $R_x$ where R is a $C_1$-$C_{20}$ alkyl (preferably $C_4$-$C_{20}$), $C_1$-$C_{20}$ hydroxy-alkyl (preferably $C_4$-$C_{20}$ hydroxyalkyl), $C_6$-$C_{20}$ aralkyl, $C_1$-$C_{20}$ alkylammonium (preferably $C_4$-$C_{20}$ alkyl ammonium), or $C_1$-$C_{20}$ alkylamido (preferably $C_4$-$C_{20}$ alkyl amido) group and X includes one or more electrophilic groups. By "electrophilic group" it is meant a group which is displaced or reacted by a nitrogen atom in the polymer during the alkylation reaction. Examples of preferred electrophilic groups, X, include halide, epoxy, tosylate, and mesylate group. In the case of, e.g., epoxy groups, the alkylation reaction causes opening of the three-membered epoxy ring.

Examples of preferred alkylating agents include a $C_3$-$C_{20}$ alkyl halide (e.g., an n-butyl halide, n-hexyl halide, n-octyl halide, n-decyl halide, n-dodecyl halide, n-tetradecyl halide, n-octadecyl halide, and combinations thereof); a $C_1$-$C_{20}$ hydroxyalkyl halide (e.g., an 11-halo-1-undecanol); a $C_1$-$C_{20}$ aralkyl halide (e.g., a benzyl halide); a $C_1$-$C_{20}$ alkyl halide ammonium salt (e.g., a (4-halobutyl)trimethylammonium salt, (6-halohexyl)trimethyl-ammonium salt, (8-halooctyl) trimethylammonium salt, (10-halodecyl)trimethylammonium salt, (12-halododecyl)-trimethylammonium salts and combinations thereof); a $C_1$-$C_{20}$ alkyl epoxy ammoniumn salt (e.g., a (glycidylpropyl)-trimethylammonium salt); and a $C_1$-$C_{20}$ epoxy alkylamide (e.g., an N-(2,3-epoxypropane)butyramide, N-(2,3-epoxypropane) hexanamide, and combinations thereof). Benzyle halide and dodecyl halide are more preferred.

The alkylation step on the polyamine shell precursor can be carried out in a separate reaction, prior to the application of the shell onto the core beads. Alternatively, the alkylation can be done once the polyamine shell precursor is deposited onto the core beads. In the latter case, the alkylation is preferably performed with an alkylating agent that includes at least two electrophilic groups X so that the alkylation also induces crosslinking within the shell layer. Preferred polyfunctional alkylation agents include di-halo alkane, dihalo polyethylene glycol, and epichlorohydrine. Other crosslinkers containing acyl chlorides, isocyanate, thiocyanate, chlorosulfonyl, activated esters (N-hydroxysuccinimide), or carbodiimide intermediates, are also suitable.

Typically, the level of alkylation is adjusted depending upon the nature of the polyamine precursor and the size of the alkyl groups used on alkylation. One factor that can affect the desired level of alkylation includes the insolubility of the shell polymer under conditions of the gastrointestinal tract. In particular, a low pH as prevalent in the stomach tends to solubilize alkylated polyamine polymers having a pH of ionization of (about) 5 and above. For solubility considerations, a higher extent of alkylation and/or a higher chain length alkyl are preferred. As an alternative, one may use an enteric coating to protect the shell material against acidic pH. The enteric coating can be released when the core-shell particles are passed into the lower gastrointestinal tract, such as the intestine. Another factor that can affect the desired extent of alkylation includes the desired permselectivity profile/persistence. For example, when the extent of alkylation is low, the persistence of the permselectivity for competing ions (e.g. $Mg^{2+}$, $Ca^{2+}$) can be relatively shorter, for example, shorter than the typical residence time in the colon. Conversely when the extent of alkylation (or the weight fraction of hydrophobes) is high, then the shell polymer can become less permeable to inorganic cations, and can have a longer persistence. If the extent of alkylation is too high, the shell polymer material can become almost impermeable to most inorganic cations (e.g., and thus, the rate of equilibration or of approaching equilibration for $K^+$ can become undesirably long). Preferably, the degree of alkylation can be tuned and selected by an iterative approach considering such factors, among others.

In another approach and embodiment for controlling permeability (and in turn, permselectivity and/or persistence), the interaction of the positively charged shell with some of the hydrophobic anions present the GI can achieve a higher level of permeability and/or persistence (for example, as characterized by an increase in $t_{20}$ or $t_{80}$ value for $Mg^{2+}$ and $Ca^{2+}$). Such hydrophobic anions include bile acids, fatty acids and anionic protein digests. Alternatively, anionic surfactants can provide the same or similar benefit. In this embodiment, the core-shell particle is either administered as is (for example into a gastrointestinal environment in which such fatty acids or bile acids or salts thereof can interact with the shell polymer in vivo), or alternatively, the core-shell particle can be formulated with fatty acids or bile acid salts or even synthetic anionic detergents such as, but not limited to, alkyl sulfate, alkyl sulfonate, and alkylaryl sulfonate.

In more detail, the shell polymer of a core-shell composition can have a permselectivity controlled at least in part by passive absorption while passing through the upper GI tract. Many components present in the GI tract including components of the diet, metabolites, secretion, etc. are susceptible to adsorb onto and within the shell in a quasi-irreversible manner and can strongly modify the permeability pattern of the shell. The vast majority of these soluble materials are negatively charged and show various levels of hydrophobicity. Some of those species have a typical amphiphilic character, such as fatty acids, phospholipids, bile salts and can behave as surfactants. Surfactants can adsorb non-specifically to surfaces through hydrophobic interactions, ionic interaction and combinations thereof. In this embodiment, this phenomenon is used to change the permeability of the polymeric composition upon the course of binding potassium ions. In one embodiment fatty acids can be used to modify the permeability of the shell and in another embodiment bile acids can be used. Fatty acids and bile acids both form aggregates (micelles or vesicles) and can also form insoluble complexes when mixed with positively charged polymers (see e.g. Kaneko et al, *Macromolecular Rapid Communications* (2003), 24(13), 789-792). Both fatty acids and bile acids exhibit similarities with synthetic anionic surfactants and numerous studies report the formation of insoluble complexes between anionic surfactants and cationically charged polymers (e.g. Chen, L. et al, *Macromolecules* (1998), 31(3), 787-794). In this embodiment, the shell material is selected from copolymers containing both hydrophobic and cationic groups, so that the shell forms a complex with anionically charged hydrophobes typically found in the GI tract, such as bile acids, fatty acids, bilirubin and related compounds. Suitable compositions also include polymeric materials described as bile acids sequestering agents, such as those reported in U.S. Pat. Nos. 5,607,669; 6,294,163; and 5,374,422; Figuly et al, *Macromolecules*, 1997, 30, 6174-6184. The formation of the complex induces a shell membrane collapse which in turn can lower the diffusion of bulky divalent cations, while preferably leaving the permeation of potassium unchanged.

In yet another embodiment, the permeability of the shell polymer of a core-shell composition can be modulated by enzymatic activity in the gastro-intestinal tract. There are a number of secreted enzymes produced by common colonic microflora. For example *Bacteroides, Prevotella, Porphyromonas*, and *Fusobacterium* produce a variety of secreted enzymes including collagenase, neuraminidase, deoxyribonuclease [DNase], heparinase, and proteinases. In this embodiment, the shell comprises a hydrophobic backbone with pendant hydrophilic entities that are cleaved off via an enzymatic reaction in the gut. As the enzymatic reaction proceeds, the polymer membrane becomes more and more hydrophobic, and turns from a high swollen state, high permeability rate material to a fully collapsed low hydration membrane with minimal permeability to bulky hydrated cations such as $Mg^{++}$ and $Ca^{++}$. Hydrophilic entities can be chosen from natural substrates of enzymes commonly secreted in the GI tract. Such entities include amino acids, peptides, carbohydrates, esters, phosphate esters, oxyphosphate monoesters, O- and S-phosphorothioates, phosphoramidates, thiophosphate, azo groups and the like. Examples of enteric enzymes susceptible to chemically alter the shell polymer include, but are not limited to, lipases, phospholipases, carboxylesterase, glycosidases, azoreductases, phosphatases, amidases and proteases. The shell can be permeable to potassium ions until it enters the proximal colon and then the enzymes present in the proximal colon can react chemically with the shell to reduce its permeability to the divalent cations.

Generally, regardless of the particular approach(es) adopted for controlling or tuning the permselectivity and/or persistence of the core-shell particle, the permselective shell polymer membranes of the invention can be optimized by studying their permselectivity profile as a function of polymer compositions and physical characteristics.

Permselectivity is preferably measured in conditions close to those prevailing in the milieu of use (e.g. colon). In a typical experiment, the donor solution is a synthetic fluid with an ionic composition, osmolality, and pH mimicking the colonic fluid, or alternatively, an animal fluid collected through ileostomy or coleostomy, or by extraction of fluid from a tube which is threaded into the GI tract from the mouth or anus. In another embodiment, the membrane is sequentially contacted with fluids that model the conditions found in the different parts of the GI tract, i.e. stomach, duodenum, jejunum, and ileum. In yet another embodiment, the shell is deposited on a cation exchange resin bead under the proton form by microencapsulation method and contacted with a sodium hydroxide aqueous solution. By monitoring pH or conductivity the rate of permeation of NaOH across the membrane is then computed. In another embodiment, the resin is preloaded with lithium cations and the release of lithium and absorption of sodium, potassium, magnesium, calcium and ammonium are monitored by ion chromatography. Some preferred in vitro assays that can be used in connection with measuring permselectivity, for example, for purposes of tuning a core-shell particle in that regard, include GI Assay No. I, GI Assay No. II, GI Assay No. III, and combinations thereof, in each case as described in detail above.

Shell Polymers

Other Embodiments

Although the shell polymer preferably comprises a crosslinked polymer (i.e., homopolymer or copolymer), such as a crosslinked hydrophilic polymer, or a crosslinked polyvinylic polymer, in some embodiments of the invention the shell polymer can more generally comprise polymers (i.e., homopolymers or copolymers) of other monomer repeat units, and can more generally be crosslinked or non-crosslinked polymers. The shell polymer can form a crosslinked gel with a three-dimensional network structure where chains are crosslinked through covalent bonds, ionic or other bonds (e.g., hydrogen bonds, or hydrophobic interactions). Preferably, polymer molecules (polymer chains) are crosslinked through covalent bonds. Generally, the shell polymer can be a film-forming polymer. A shell polymer of the invention can generally comprise a natural or a synthetic polymer.

In some embodiments, the shell polymer can generally comprise an amine functional polymer (a polymer having repeat units comprising one or more amine functional groups). Generally, amine functional groups can optionally be in quaternized form. The amine functional polymers can optionally be alkylated with one or more hydrophobic agents, details of which (e.g., preferred alkylating agents, alkylation protocols, extent of alkylation, etc.) are described above in connection with controlling/tuning permselectivity and persistence, and can be likewise applied in connection herewith.

In some embodiments, the shell polymer can have a repeat unit(s) selected, for example, from one or more of ethyleneimine, propyleneimine, allylamine, vinylpyridines, alkyaminoalkyl(meth)acrylates, alkyaminoalkyl(meth)acrylamides, aminomethylstyrene, chitosan, adducts of aliphatic amine or aromatic amine with electrophiles (e.g., such as epichlorhydrine, alkylhalides or epoxides) an ionenes.

In some embodiments, the shell polymer can comprise a polyvicinalamine.

In some embodiments, the shell polymer can comprise a polymer having a repeat units comprising one or more charged moieties, and in some cases, preferably one or more charged moieties other than a (protonated) amine moiety. For example, the shell polymer can comprise a polymer having a repeat units comprising one more sulfonium moieties.

In some embodiments, the shell polymer can comprise repeat units having hydrophobic groups or moieties. For example, the shell polymer can comprise repeat units of hydrophobic monomers (e.g. long chain alcohol (meth)acrylates, N-alkyl(meth)acrylamide).

In some embodiments, the shell polymer can have repeat units having groups or moieties that ionize subject to pH change. For example, the shell polymer can comprise repeat units of basic monomers. In some embodiments, such basic monomers can ionize at low pH and remain neutral beyond their pKa (e.g. vinyl-pyridine, dialkylaminoethyl(meth)acrylamide).

In some embodiments, shell polymers can comprise repeat units including each of hydrophobic monomers and acidic monomers. In some embodiments, relative amounts of hydrophobic monomers and acidic monomers can be balanced. For example, relative ratios of hydrophobic monomers to acidic monomers can range, for example, from (about) 1:2 to (about) 2:1, and preferably from (about) 2:3 to (about) 3:2. Such systems are extensively described in the literature. For example, see Kraft et al. *Langmuir*, 2003, 19, 910-915; Ito et al, *Macromolecule*, (1992), 25, 7313-7316. The relative amount hydrophobic monomers and acidic monomers can be controlled to obtain physical characteristics and performance characteristics as described above (for example, in connection with robustness and/or controlling/tuning of permselectivity and persistence).

In other embodiments, the shell material can be chemically identical to the core polymer of the core component, but with increasing crosslink density as considered outward from core component to shell component.

In some embodiments, the shell component can be a shell polymer in a brush configuration—rather than a film forming polymer. Such polymer brush shells components can comprise individual polymer strands covalently attached to the core component at termini of the polymer strands. In such embodiments, mesh size can be dictated by the density of chains anchored onto the surface of the core component, and by molecular weight of the polymer strands of the shell component. Polymer brush design variables controlling permeability of polymer brush shell components to solutes of various sizes and/or weights are known in the art. For example, see WO 0102452 (and references therein).

Generally, the shell component can comprise a crosslinked polymer, including crosslinked polymers of the various embodiments of the shell as described herein. The crosslinking agents can generally be the same as those described above in connection with polyvinylic polymers such as polyvinylamine polymers.

Generally, the various embodiments of shell polymers as described herein are examples, and non-limiting. Generally, the various embodiments of shell polymers as described herein can be used in various permutations and combinations with each other. Generally, the shell polymers can be selected and optimized from among the various embodiments of shell polymers as described herein and from other polymers known in the art, in each case to obtain physical characteristics and performance characteristics as described above (for example, in connection with robustness and/or controlling/tuning of permselectivity and persistence) for a core-shell composite such as a core-shell particle.

Core Polymers

Other Embodiments

The polymeric core can alternatively comprise other monovalent ion-binding polymers. In some embodiments, the monovalent-ion-binding polymers comprise acid groups in their protonated or ionized form, such as sulfonic (—SO$_3^-$), sulfuric (—OSO$_3^-$), carboxylic (—CO$_2^-$), phosphonic (—PO$_3^-$), phosphoric (—OPO$_3^-$), or sulfamate (—NHSO$_3^-$). Preferably, the fraction of ionization of the acid groups is greater than (about) 75% at the physiological pH in the colon and the potassium binding capacity is greater than (about) 5 mmol/gm. Preferably the ionization of the acid groups is greater than (about) 80%, more preferably it is greater than (about) 90%, and most preferably it is (about) 100%. In certain embodiments the acid containing polymers contain more than one type of acid groups. In certain embodiments the acid containing polymers are administered in their anhydride form and generate the ionized form when contacted with physiological fluids.

In some other embodiments, a pK$_a$-decreasing group, preferably an electron-withdrawing substituent, is located adjacent to the acid group, preferably it is located in the alpha or beta position of the acid group. The preferred electron-withdrawing substituents are a hydroxyl group, an ether group, an ester group, or an halide atom, and most preferably F. Preferred acid groups are sulfonic (—SO$_3^-$), sulfuric (—OSO$_3^-$), carboxylic (—CO$_2^-$), phosphonic (—PO$_3^-$), phosphoric (—OPO$_3^-$), or sulfamate (—NHSO$_3^-$). Other preferred polymers result from the polymerization of alpha-fluoro acrylic acid, difluoromaleic acid, or an anhydride thereof.

Examples of other suitable monomers for monovalent-ion-binding polymers for core polymers are disclosed in the related application U.S. application Ser. No. 11/096,209 filed Mar. 30, 2005, incorporated herein by reference in this regard. For example, some of such core polymers have repeat units disclosed in Table 3.

TABLE 3

| | Molar mass per charge | Theoretical capacity | Fraction of titrable H @ pH 3 | Fraction of titrable H @ pH 6 | Expected Capacity @ pH 3 | Expected Capacity @ pH 6 |
|---|---|---|---|---|---|---|
| 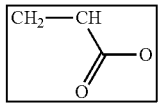 | 71 | 14.1 | 0.05 | .35 | 0.70 | 4.93 |
| 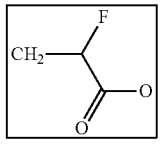 | 87 | 11.49 | 0.2 | 0.95 | 2.3 | 10.92 |
| 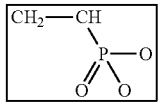 | 53 | 18.9 | 0.25 | 0.5 | 4.72 | 9.43 |
| 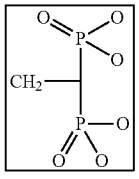 | 47.5 | 21.1 | 0.25 | 0.5 | 5.26 | 10.53 |
| 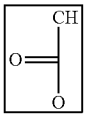 | 57 | 17.5 | 0.1 | 0.5 | 1.75 | 8.77 |
| 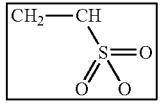 | 107 | 9.3 | 1 | 1 | 9.35 | 9.35 |
| 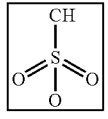 | 93 | 10.8 | 1 | 1 | 10.75 | 10.75 |

TABLE 3-continued

| | Molar mass per charge | Theoretical capacity | Fraction of titrable H @ pH 3 | Fraction of titrable H @ pH 6 | Expected Capacity @ pH 3 | Expected Capacity @ pH 6 |
|---|---|---|---|---|---|---|
| 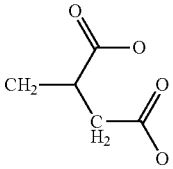 | 63 | 15.9 | 0 | 0.4 | 0 | 6.35 |
| 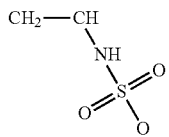 | 125 | 8 | 1 | 1 | 8 | 8 |
| 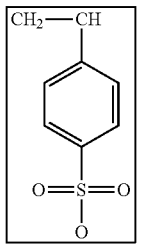 | 183 | 5.5 | 1 | 1 | 5.46 | 5.46 |
| 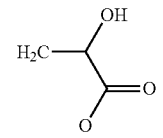 | 87 | 11.49 | .1 | .6 | 1.14 | 6.89 |

The core polymer can alternative by selected from other suitable cation exchange polymers, including for example:

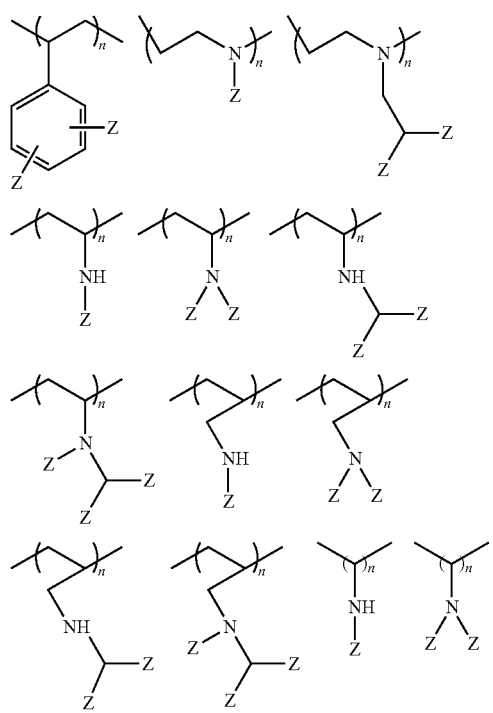

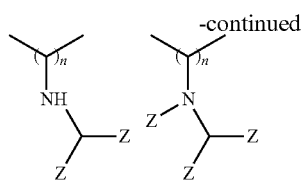

wherein n is equal to or greater than one and Z represents either $SO_3H$ or $PO_3H$. Preferably n is (about) 50 or more, more preferably n is (about) 100 or more, even more preferred is n (about) 200 or more, and most preferred is n (about) 500 or more.

Core polymers can comprise repeat units of suitable phosphonate monomers including vinyl phosphonate, vinyl 1,1 bis phosphonate, and ethylenic derivatives of phosphonocarboxylate esters, oligo(methylenephosphonates), and hydroxyethane-1,1-diphosphonic acid. Methods of synthesis of these monomers are well known in the art.

Core polymers can also comprise sulfamic (i.e. when $Z=SO_3H$) or phosphoramidic (i.e. when $Z=PO_3H$) polymers. Such polymers can be obtained from amine polymers or monomer precursors treated with a sulfonating agent such as sulfur trioxide/amine adducts or a phosphonating agent such as $P_2O_5$, respectively. Typically, the acidic protons of phosphonic groups are exchangeable with cations, like sodium or potassium, at pH of (about) 6 to (about) 7.

Core polymers can comprise free radical polymers derived from monomers such as vinyl sulfonate, vinylphosphonate, or vinylsulfamate.

The core polymers of the invention can also include cation exchange resins comprising from naturally occurring polymers, such as saccharide polymers and semi-synthetic polymers, optionally functionalized to create ion exchange sites on the backbone or on the pendant residues. Examples of polysaccharides of interest include materials from vegetal or animal origins, such as cellulosic materials, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan. Most preferred are polymers that do not degrade under the physiological conditions of the gastrointestinal tract and remain non-absorbed, such as carboxymethylcellulose, chitosan, and sulfoethylcellulose.

Generally, the core component comprising core polymers can be formed by polymerization processes using either homogeneous or heterogeneous mode: in the former case a crosslinked gel is obtained by reacting the soluble polymer chains with a crosslinker, forming a bulk gel which is either extruded and micronized, or comminuted to smaller sized particles. In the former case, the particles are obtained by emulsification or dispersion of a soluble polymer precursor, and subsequently crosslinked. In another method, the particles are prepared by polymerization of a monomer in an emulsion, suspension, miniemulsion or dispersion process. The continuous phase is either an aqueous vehicle or an organic solvent. When a suspension process is used, any suitable type of variants is possible, including methods such as "templated polymerization," "multistage' seeded suspension," all of which yielding mostly monodisperse particles. In one particular embodiment, the beads are formed using a "jetting" process (see U.S. Pat. No. 4,427,794), whereby a "tube of liquid containing a monomer plus initiator mixture is forced through a vibrating nozzle into a continuous phase. The nozzles can be arranged in spinning turret so as to force the liquid under centrifugal force.

Synthesis of Core-Shell Particles

The shell is component can be formed over a surface of the core component. Preferably, the shell component can be formed over an entire exposed surface of a core component, especially in embodiments where the core component comprises a particle. Preferably, the shell component can be substantially uniformly formed (e.g., coated) over a surface of the core component. In some embodiments, the shell component can have an essential absence of pinholes or substantial macroporosity.

Generally, the shell (or a shell precursor for a crosslinked shell) can be formed by chemical or non-chemical processes. Non-chemical processes include spray coating, fluid bed coating, solvent coacervation in organic solvent or supercritical $CO_2$, solvent evaporation, spray drying, spinning disc coating, extrusion (annular jet) or layer by layer formation. Examples of chemical processes include interfacial polymerization, grafting from, grafting unto, and core-shell polymerization.

Crosslinked shells can generally be formed by crosslinking a shell polymer using a crosslinking agent under crosslinking conditions. For example, a (non-crosslinked) shell precursor can be formed as described above by a chemical or a non-chemical process, and crosslinked. The crosslinking can be a separate independent step (typically in a separate, independent reaction zone), or can be integrated with a chemical or non-chemical processes, for example as described above. A typical process for forming a crosslinked shell polymer over a polymer core can include, for example, a layer-by-layer process in which a charged core material such as a cation-binding polymer (e.g., a cation exchange resin) is contacted with a shell polymer such as a polyelectrolyte of opposite charge to form a polymer complex. The contacting step can be repeated, optionally with intermittent drying steps, until a multilayer shell polymer is deposited on a core surface. The composite material comprising the multilayer shell polymer formed over the core is then physically isolated, optionally washed or otherwise worked up, and subsequently, crosslinked in a separate independent step, and typically in an independent reaction zone.

Preferred Methods for Shell Preparation—Multiphase In-Situ Crosslinking

In a preferred process, a core-shell composite (such as a core-shell particle) comprising a core component and a crosslinked shell polymer formed over a surface of the core component is prepared using a multiphase process with in situ crosslinking.

The preferred process can comprise, in a general first embodiment, forming a core-shell intermediate comprising a core component, and a shell polymer associated with a surface of the core component, the core-shell intermediate being formed for example in a first liquid phase. The core-shell intermediate is phase-isolated from a bulk portion of the first liquid phase. Preferably, the core-shell intermediate is phase-isolated using a second liquid phase, the second liquid phase being substantially immiscible with the first liquid phase. Preferably, the second liquid phase can be a non-solvent for the shell polymer, such that the shell polymer remains substantially within the first liquid phase comprising the core-shell intermediate. The phase-isolated core-shell intermediate is contacted with a crosslinking agent under crosslinking conditions (to crosslink the shell polymer associated with the surface of the core component). The resulting product is the core-shell composite comprising a cross-linked shell polymer over a surface of a core component.

In one preferred second embodiment, the core component can be a polymeric core component comprising a core polymer, and preferably a hydrophilic polymer. The first liquid phase can be a first aqueous phase comprising an aqueous solution. The core component can be hydrated in the first aqueous phase. Shell polymer, preferably a hydrophilic shell polymer, can be dissolved or substantially dissolved in the aqueous solution. The shell polymer can be allowed to interact with a surface of the hydrated core component to form a hydrated core-shell intermediate in the first aqueous phase. The hydrated core-shell intermediate can be phase-isolated from a bulk portion of the first aqueous phase. Preferably, the hydrated core-shell intermediate is phase-isolated using a second liquid phase. Preferably, the second liquid phase is substantially immiscible with the first aqueous phase. Preferably, the hydrophilic shell polymer is substantially insoluble in the second liquid phase. Preferably, the second liquid phase can comprise a crosslinking agent. The phase-isolated, hydrated core-shell intermediate is contacted with a crosslinking agent under crosslinking conditions (to crosslink the shell polymer interacting with the surface of the core component) to form the core-shell composite.

In some embodiments, it can be advantageous to remove at least a portion of the first liquid phase media. For example, in embodiments in which the first liquid phase is a first aqueous phase, the first liquid phase media can be dehydrated. Without being bound by theory not specifically recited in the claims, such removal of first liquid phase media (e.g., dehydration) can facilitate association of the shell polymer with a surface of the core component (e.g., can facilitate interaction of a shell polymer, such as a dissolved shell polymer, with a surface of the hydrated core component. Without being bound by theory not specifically recited in the claims, such removal of first phase liquid media (e.g., dehydration) may also favorably affect phase isolation. The removal (e.g., dehydration)

can occur before, during and/or after phase isolation. Preferably, the removal (e.g., dehydration) is at least concurrent with shell-polymer association and/or interaction with core component, and/or with phase isolation and/or with the crosslinking reaction. Most preferably, the dehydration occurs after phase isolation and simultaneously with crosslinking, such that the shell component hydrophilic polymer is restricted to occupy a decreasing volume as the crosslinking progresses, resulting in a higher crosslink density and/or smaller mesh size as a result of crosslinking in a less-swollen state.

Preferably, therefore, the various embodiments of the process for preparing a core-shell composite (including but not limited to the general first embodiment and the preferred second embodiment (as described above) as well as further embodiments (as described below)) can further comprise removing at least a portion of the first liquid phase (e.g., a portion of a first liquid of the first liquid phase). In embodiments in which the first liquid phase is a first aqueous phase, the method can further comprise dehydrating to remove water.

In another general third embodiment, for example, a core-shell composite comprising a polymeric core component and a crosslinked polymeric shell component can be prepared as follows. A first phase is prepared comprising a polymeric core component and a shell polymer in a first liquid, the shell polymer being dissolved or substantially dissolved in the first liquid. A second phase is prepared comprising a crosslinking agent in a second liquid. The second liquid is substantially immiscible with the first liquid. Preferably, the shell polymer is substantially insoluble in the second liquid. The first phase and the second phase can be combined to form a heterogeneous multiphase media. (Preferably, formation of the heterogeneous multiphase media phase-isolates a core-shell intermediate (comprising a core component and a shell polymer associated with a surface of the core component)). At least a portion of the first liquid is removed from the heterogeneous multiphase media. The shell polymer is crosslinked with the crosslinking agent (on a surface of the core component) to form the core-shell composite in the multiphase media.

In another preferred fourth embodiment, the core component can be a polymeric core component comprising a core polymer, and preferably a hydrophilic polymer. The first liquid phase can be a first aqueous phase (comprising an aqueous solution). The core component can be hydrated in the first aqueous phase. Shell polymer, preferably a hydrophilic shell polymer, can be dissolved or substantially dissolved in the first aqueous phase (in the aqueous solution). The first aqueous can be combined and mixed with a second phase. The second phase can comprise a crosslinking agent. The second phase can preferably be substantially immiscible with the first aqueous phase, such that combining and mixing forms a heterogeneous multiphase media. The shell polymer can preferably be substantially insoluble in the second phase. The heterogeneous multiphase media is preferably dehydrated. The shell polymer is crosslinked with the crosslinking agent (on a surface of the core component) to form the core-shell composite.

In another preferred fifth embodiment, the core-shell composite is formed without physically separating the hydrated core-shell intermediate from a bulk portion of the aqueous solution in the presence of the aqueous solution. Briefly, the method can comprise hydrating a core component in an aqueous solution, the core component comprising a (hydrophilic) core polymer, dissolving a shell polymer in the aqueous solution (where preferably the shell polymer is a hydrophilic shell polymer), and allowing the shell polymer to interact with a surface of the hydrated core component to form a hydrated core-shell intermediate in the aqueous solution. Without physically separating the hydrated core-shell intermediate from a bulk portion of the aqueous solution, the hydrated core-shell intermediate is contacted with a crosslinking agent under crosslinking conditions to form the core-shell composite.

In further embodiments, the core-shell composite can be prepared advantageously be effecting some steps concurrently with each other. For example, in a further set of embodiments, the method for preparing a core-shell composite can comprise hydrating a core component (preferably comprising a hydrophilic core polymer) in an aqueous solution, and dissolving or substantially dissolving a shell polymer in the aqueous solution. The shell polymer can preferably be a hydrophilic shell polymer. The method can further comprise any two or all three of the following steps (i), (ii) and/or (iii) being effected concurrently: (i) allowing the shell polymer to interact with a surface of the hydrated core component to form a hydrated core-shell intermediate, (ii) contacting the hydrated core-shell intermediate with a crosslinking agent under crosslinking conditions, such that a core-shell composite is formed, and (iii) removing water from the aqueous solution. Specifically, for example, further sixth embodiment comprises concurrently (i) allowing the shell polymer (preferably a hydrophilic polymer, and preferably dissolved or substantially dissolved in an aqueous solution) to interact with a surface of the hydrated core component to form a hydrated core-shell intermediate, and (ii) contacting the hydrated core-shell intermediate with a crosslinking agent under crosslinking conditions, such that a core-shell composite is formed. A further seventh embodiment can comprise concurrently (i) contacting the hydrated core-shell intermediate (formed by allowing a shell polymer (preferably a hydrophilic polymer, and preferably dissolved or substantially dissolved in an aqueous solution) to interact with a surface of a hydrated core component) with a crosslinking agent under crosslinking conditions, such that a core-shell composite is formed, and (ii) removing water from the aqueous solution. A further eight embodiment can comprise concurrently effecting each of (i) allowing the shell polymer (preferably a hydrophilic polymer, and preferably dissolved or substantially dissolved in an aqueous solution) to interact with a surface of the hydrated core component to form a hydrated core-shell intermediate, (ii) contacting the hydrated core-shell intermediate with a crosslinking agent under crosslinking conditions, such that a core-shell composite is formed, and (iii) removing water from the aqueous solution.

Preferably, in a preferred ninth embodiment, the core-shell composite can be prepared advantageously by forming the core-shell composite without substantially forming crosslinked shell polymer aggregates in a bulk portion of the aqueous solution. Such method can further comprise hydrating a core component in an aqueous solution (e.g, the core component comprising a hydrophilic core polymer), dissolving a shell polymer in the aqueous solution (e.g., the shell polymer being a hydrophilic shell polymer), allowing the shell polymer to interact with a surface of the hydrated core component to form a hydrated core-shell intermediate, and contacting the hydrated core-shell intermediate with a crosslinking agent under crosslinking conditions, without forming the crosslinked shell aggregates in a bulk portion of the aqueous solution.

Further details, features and characteristics of the methods are described hereinafter that can be used in each permutation and various combination with the aforementioned general and preferred embodiments and features described therein Preferred shell polymers can be as described above (in connection with the description for the core-shell particles).

Preferred core components can be inorganic or organic core components. Especially preferred core components are core polymers as described above (in connection with the description for the core-shell particles).

Preferred crosslinking agents can be as described above (in connection with the description for the core-shell particles). Preferably, the molar ratio of the feed (or amount) of crosslinking agent to shell polymer (e.g., to repeat units of the shell polymer or to crosslinkable functional groups of the shell polymer) is not less than 1:1, and preferably is not less than (about) 2:1, or not less than (about) 3:1, or not less than (about) 3.5:1 or not less than (about) 4:1. In some embodiments, the molar ratio of the feed (or amount) of crosslinking agent to shell polymer (e.g., to repeat units of the shell polymer or to cross-linkable functional groups of the shell polymer) is even higher, including not less than (about) 4.5:1, or not less than (about) 5:1 or not less than (about) 6:1. Without being bound by theory not recited in the claims, a substantial excess of crosslinking agent can facilitate contacting of the (hydrated) core-shell intermediate with the crosslinking agent. The particular ratio/amount for a particular system can be determined, for example, as described above to obtain preferred physical characteristics and/or performance characteristics, in each case as described above (in connection with the description for the core-shell particles).

The crosslinking conditions are not narrowly critical, and can generally be determined based on the particular crosslinking agent employed, the shell polymer, and other factors well known in the art. Generally, the crosslinking can be effected at a temperature sufficient to thermally initiate and/or sustain crosslinking of the shell polymer in the method. For example, the temperature can be increased to initiate crosslinking, for example, to a temperature ranging from (about) 70° C. to (about) 100° C. Alternatively, the temperature during the addition of the crosslinking reagent can be (about) 50° C. to (about) 90° C. The reaction temperature can then possibly be adjusted to a temperature ranging from (about) 70° C. to (about) 120° C.; preferably from (about) 85° C. to (about) 110° C. The reaction mixture is heated for (about) 1 to about 12 hours at the temperature described above. The high temperature may be constrained by considerations involving the volatility of the liquid phases and/or the pressure of the system.

Preferably, liquid removal such as dehydration can be effected using one or more unit operations known in the art. In a preferred approach, for example, a liquid can be removed by distillation process, including for example azeotropic distillation, to selectively remove a liquid of the (shell polymer containing) first phase without substantially removing a liquid of the (cross-linker containing) second phase.

Preferably, the multiphase media can be agitated (e.g., stirred) in connection with any embodiment described herein, using equipment and protocols known in the art. Without being bound by theory not recited in the claims, and without limitation, such agitation can facilitate phase-isolation, and contacting of crosslinking agent with the core-shell intermediate.

In any case, the multiphase in situ crosslinking method can further comprise one or more work-up steps, such as separating the formed core-shell composite from the heterogenous, multiphase mixture, and purifying, for example by washing in one or more solvents.

In a particularly preferred approach, a core-shell composite comprising a polymeric core component and a crosslinked polymeric shell component can be prepared as follows. A first aqueous phase is prepared comprising a polymeric core, such as polystyrenesulfonate core (e.g., commercially available as Dowex), and a polyvinylic shell polymer (e.g., polyvinylamine) dissolved in a first aqueous solution. Separately, a second phase is prepared comprising a crosslinking agent, preferably a hydrophobic crosslinking agent (e.g., N,N-diglycidylaniline) in a second organic phase, or preferably a crosslinking agent with preferential partition (e.g., epichlorohydrine, N,N-diglycidylaniline) in a second organic phase, in each case such as a second organic phase comprising toluene, xylene, etc. The first phase and the second phase are combined to form a heterogeneous multiphase media. Preferably, the heterogenous mixture is mixed, for example, by stirring, and crosslinking conditions are initiated by raising the system temperature to (about) 85 C for (about) 2 hours. Following, the multiphase media is dehydrated to remove water, preferably for example using a Dean-Starke distillation at a temperature of (about) 110 C. The shell polymer is crosslinked with the crosslinking agent (on a surface of the core component) to form the core-shell composite in the multiphase media. The core-shell composite is isolated, for example by decanting the liquid portion of the multiphase media. The core-shell composite is then washed, for example, in separate steps with methanol, and subsequently with water.

Such multiphase in situ crosslinking method offers substantial advantages over convention processes. Generally, for example, the method provides for improved control over the amount and/or thickness and/or uniformity of the crosslinked shell polymer formed over a surface of the core component. Notably, for example, as compared to layer-by-layer process involving separate steps of adsorption and subsequent crosslinking, a greater amount/thickness of a shell polymer can be formed on a core component using the multiphase in situ crosslinking method, as described herein. In some embodiments, the shell thickness using the method of the invention can be 10 times more, or 50 times more or even 100 times more or even 500 times more than the thickness achievable with such layer-by-layer process. Likewise, as compared to recirculated fluidized bed (Wurster) coating approaches, a smaller amount/thickness of a shell polymer can be formed (e.g., as a layer and preferably as a uniform layer) on a core component using the multiphase in situ crosslinking method, as described herein. In some embodiments, the amount of shell material of the core-shell composite prepared using the method of the invention can be (about) 5% less, or (about) 10% less or (about) 15% less than that achievable using typical recirculated fluidized bed processes (based, in each case, by weight of shell component relative to weight of the core component of the core-shell composite). Accordingly, the method provides a unique approach for preparing core-shell composites having a different, and commercially meaningful amount/thickness of crosslinked shell polymer. In particular, the method can be used to prepare core-shell composite materials having a shell thickness in the ranges as generally recited above, and in preferred embodiments, for example, the method can prepare shell components having a thickness ranging from (about) 0.002 micron to (about) 50 micron, preferably (about) 0.005 micron to (about) 20 microns, or from (about) 0.01 microns to (about) 10 microns. Additionally, the multiphase in situ crosslinking method offers a scaleable, commercially reasonable approach for preparing such core-shell composites.

Other Methods for Shell Preparation

In fluid bed coating, typically the core beads are kept in a recirculating fluidized bed (Wurster type) and sprayed with a coating solution or suspension. The coating polymer can be used as a solution in alcohols, ethylacetate, ketones, or other suitable solvents or as latex. Conditions and formulations/compositions are typically optimized so as to form a tight and homogeneous membrane layer, and insure that no cracks are formed upon swelling when the particles are contacted with the aqueous vehicle. It is preferred that the membrane polymer can yield to the volume expansion and elongates so as to accommodate the dimension change. This can be aided by selecting a shell polymer composition which swells to some extent upon contact with water, and becomes heavily plasticized by the water. Polymer membranes have an elongation at break greater than 10%, preferably greater than 30%. Examples of this approach are reported in Ichekawa H. et al, International Journal of Pharmaceuticals, 216 (2001), 67-76.

Solvent coacervation is described in the art. For example, see Leach, K. et al., J. Microencapsulation, 1999, 16(2), 153-167. In this process, typically two polymers, core polymer and shell polymer are dissolved in a solvent which is further emulsified as droplets in an aqueous phase. The droplet interior is typically a homogeneous binary polymer solution. The solvent is then slowly driven off by careful distillation. The polymer solution in each droplet undergoes a phase separation as the volume fraction of polymer increases. One of the polymer migrates to the water/droplet interface and forms a more- or less perfect core-shell particle (or double-walled microsphere).

Solvent coacervation is another method that can be employed to deposit a controlled film of shell polymer onto the core. In one embodiment, the coacervation technique consists in dispersing the core beads in a continuous liquid phase containing the shell material in a soluble form. The coacervation process then consists of gradually changing the solvency of the continuous phase so that the shell material becomes increasingly insoluble. At the onset of precipitation some of the shell material ends up as a fine precipitate or film at the bead surface. The change in solvency can be triggered by a variety of physical chemistry means such as, but not limited to, changes in pH, ionic strength (i.e. osmolality), solvent composition (through addition of solvent or distillation), temperature (e.g when a shell polymer with a LCST (lower critical solution temperature) is used), pressure (particularly when supercritical fluids are used). More preferred are solvent coacervation processes when the trigger is either pH or solvent composition. Typically when a pH trigger event is used and when the polymer is selected from an amine type material, the shell polymer is first solubilized at low pH. In a second step the pH is gradually increased to reach the insolubility limit and induce shell deposition; the pH change is often produced by adding a base under strong agitation. Another alternative is to generate a base by thermal hydrolysis of a precursor (e.g. thermal treatment of urea to generate ammonia). The most preferred coacervation process is when a ternary system is used comprising the shell material and a solvent/non-solvent mixture of the shell material. The core beads are dispersed in that homogeneous solution and the solvent is gradually driven off by distillation. The extent of shell coating can be controlled by on-line or off-line monitoring of the shell polymer concentration in the continuous phase. In the most common case where some shell material precipitates out of the core surface either in a colloidal form or as discrete particle, the core-shell particles are conveniently isolated by simple filtration and sieving. The shell thickness is typically controlled by the initial core to shell weight ratio as well as the extent of shell polymer coacervation described earlier. The core-shell beads can then be annealed to improve the integrity of the outer membrane as measured by competitive binding.

Supercritical $CO_2$ coating is described in the art. For example, see Benoit J. P. et al, J. Microencapsulation, 2003, 20(1)87-128. This approach is somewhat a variant of the solvent coacervation. First the shell coating material is dissolved in the supercritical $CO_2$, and then the active is dispersed in that fluid in super-critical conditions. The reactor is cooled down to liquid $CO_2$ conditions wherein the shell material is no longer soluble and precipitates on the core beads. The process is exemplified with shell materials selected from small molecules such as waxes and paraffins. The core-shell material is recovered as a powder.

The spinning disc coating technique is based on forming a suspension of the core particles in the coating, then using a rotating disc to remove the excess coating liquid in the form of small droplets, while a residual coating remains around the core-particles. See U.S. Pat. No. 4,675,140.

In the layer by layer process, a charged core material is contacted with a polyelectrolyte of opposite charge and a polymer complex is formed. This step is repeated until a multilayer is deposited on the core surface. Further crosslinking of the layers are optional.

Interfacial polymerization consists of dispersing the core material containing one reacting monomer in a continuous phase containing a co-reacting monomer. A polymerization reaction takes place at the core interface creating a shell polymer. The core can be hydrophilic or hydrophobic. Typical monomer used for that purpose can include diacylchlorides/diamines, diisocyanates/diamines, diisocyanates/diols, diacylchlorides/diols and bischloroformate and diamines or diols. Trifunctional monomers can also be used to control the degree of porosity and toughness of the membranes.

In yet another embodiment, the shell is formed by contacting the ion exchange material with a polymer dispersion of opposite charge (i.e. the core material is typically charged negatively and the shell positively), and filter the bead particles and anneal them in a fluidized bed at a temperature higher than the transition temperature (or softening point) of the shell polymer. In this embodiment the polymer dispersion is a latex or a polymer colloidal dispersion of particle size in the micron to sub-micron range.

In one further embodiment, the shell material comprises treating the acid containing core material or its derivatives such as methyl ester or acyl chloride with reactive monomer or polymer. Preferably the acid reactive material is a polymer and more preferably a polyamine: for instance a carboxylated core polymer is treated with polyethyleneimine at high temperature in an organic solvent to create amide bonds between the COOH groups and the NH and $NH_2$ groups. It can also be useful to activate the acid functions to facilitate the amide bond formation, e.g. by treating COOH or $SO_3H$ groups with thionylchloride or chlorosulfonic acid to convert said groups into their acid chloride forms. See Sata et al., Die Angewandte Makromolekulare Chemie 171, (1989) 101-117 (Nr2794).

The process of "grafting from" involves an active site capable of initiating polymerization on the core surface and polymer chains are grown from the surface in monolayers. Living polymerization methods such as nitroxide-mediated living polymerizations, ATRP, RAFT, ROMP are most suitable, but non living polymerizations have also been applied.

In the process of "grafting onto" a small molecule (typically an electrophile, such as epoxy, isocyanate, anhydride, etc.) is brought in contact with the polymeric core material, said core carrying reactive species (typically nucleophile groups such as amine, alcohol, etc.). The thickness of the shell thus formed is controlled by the rate of diffusion of the shell small molecule precursor and the rate of reaction with the core. Slow-diffusing/highly reactive species tend to confine the reaction within a short distance from the core surface thus producing a thin shell. Whereas, fast-diffusing/slow reacting species tend to invade the entire core with no defined shell and form a gradient rather than a sharp shell to core boundary.

Core-shell polymerizations can be emulsion polymerization, suspension/miniemulsion polymerization, or dispersion polymerization. All these processes employ free radical polymerizations. In emulsion polymerization, the polymerization takes place in aqueous medium with a surfactant, monomer with a low water solubility, and a water soluble free radical initiator. Polymer particles are formed by micellar or homogeneous nucleation or both. Core shell particles can be formed theoretically by feeding the core monomer first and the shell monomer second as long as the monomer is spontaneously consumed as it is fed ("starved regime"). The potassium binding core beads are preferably made from a water insoluble monomer (e.g. alkylester of a-fluoro-acrylic acid).

In suspension/mini-emulsion polymerization, the free radical initiator is soluble with the monomer. Monomer and initiator are pre-dissolved and then emulsified in droplet stabilized with either surfactant or amphiphilic polymers. This method allows one pre-formed polymer (e.g. the shell polymer) to be dissolved as well. When the reaction proceeds, the shell polymer and the core polymer phase separate to form the desired core-shell particles.

In dispersion polymerization, both the monomer and the initiator are soluble in the continuous phase (usually an organic solvent). A block copolymer is used as a steric stabilizer. The polymer particles are formed by homogenous nucleation and subsequent growth. Particle size are on the 1 to 10 microns range and mono-dispersed.

In a preferred process of dispersion, polymerization employs a refinement reported in Stover H. et al, Macromolecules, 1999, 32, 2838-2844, described thereafter: The shell monomer contains a large fraction of divinyl monomer, such as 1,4 divinylbenzene, while the core particles present some polymerizable double bond on their surface; the shell polymerization mechanism is based on the formation of short oligoradicals in the continuous phase, which are captured by the double bond present on the particle surface. The oligomers themselves contain non-reacted insaturation that replenish the surface in reactive double bonds. The net result is a formation of a crosslinked shell with a sharp boundary with the shell and the core material.

In one embodiment, a core-shell composition of the invention is synthesized by forming the cation exchange core in a conventional inverse suspension process using suitable monomers; decorating the particle surface with reactive double bonds by post-reacting with the acidic group present on the particle core; and dispersing in typical dispersion polymerization solvent such as acetonitrile (e.g. a non-solvent for the cation-exchange core polymer) and adding a polymerizing mixture of DVB or EGDMA with a functional monomers.

Use of Core-Shell Compositions/Methods of Treatment

The methods and compositions described herein are suitable for treatment of hyperkalemia caused by disease and/or use of certain drugs.

In some embodiments of the invention, the compositions and methods described herein are used in the treatment of hyperkalemia caused by decreased excretion of potassium, especially when intake is not reduced. A common cause of decreased renal potassium excretion is renal failure (especially with decreased glomerular filtration rate), often coupled with the ingestion of drugs that interfere with potassium excretion, e.g., potassium-sparing diuretics, angiotensin-converting enzyme inhibitors (ACEIs), non-steroidal anti-inflammatory drugs, heparin, or trimethoprim. Impaired responsiveness of the distal tubule to aldosterone, for example in type IV renal tubular acidosis observed with diabetes mellitus as well as sickle cell disease and/or chronic partial urinary tract obstruction is another cause of reduced potassium secretion. Secretion is also inhibited in diffuse adrenocortical insufficiency or Addison's disease and selective hypoaldosteronism. Hyperkalemia is common when diabetics develop hypoteninemic hypoaldosteronism or renal insufficiency (Mandal, A. K. 1997. Hypokalemia and hyperkalemia. Med Clin North Am. 81:611-39).

In certain preferred embodiments, the potassium binding polymers described herein are administered chronically. Typically, such chronic treatments will enable patients to continue using drugs that cause hyperkalemia, such as potassium-sparing diuretics, ACEI's, non-steroidal anti-inflammatory drugs, heparin, or trimethoprim. Also, use of the polymeric compositions described herein will enable certain patient populations, who were unable to use hyperkalemia causing drugs, to use such drugs.

In certain chronic use situations, the preferred potassium binding polymers used are those that are capable of removing less than (about) 5 mmol of potassium per day or in the range of (about) 5-(about) 10 mmol of potassium per day. In acute conditions, it is preferred that the potassium binding polymers used are capable of removing (about) 15-(about) 60 mmol of potassium per day.

In certain other embodiments, the compositions and methods described herein are used in the treatment of hyperkalemia caused by a shift from intracellular to extracellular space. Infection or trauma resulting in cell disruption, especially rhabdomyolysis or lysis of muscle cells (a major potassium store), and tumor lysis can result in acute hyperkalemia. More often, mild-to-moderate impairment of intracellular shifting of potassium occurs with diabetic ketoacidosis, acute acidosis, infusion of argentine or lysine chloride for the treatment of metabolic alkalosis, or infusion of hypertonic solutions such as 50% dextrose or mannitol. β-receptor blocking drugs can cause hyperkalemia by inhibiting the effect of epinephrine.

In certain other embodiments, the compositions and methods described herein are used in the treatment of hyperkalemia caused by excessive intake of potassium. Excessive potassium intake alone is an uncommon cause of hyperkalemia. Most often, hyperkalemia is caused by indiscriminate potassium consumption in a patient with impaired mechanisms for the intracellular shift of potassium or renal potassium excretion. For example, sudden death among dialyzed patients who are noncompliant in diet can be attributed to hyperkalemia.

In the present invention, the potassium-binding polymers and the core-shell compositions can be co-administered with other active pharmaceutical agents. This co-administration can include simultaneous administration of the two agents in the same dosage form, simultaneous administration in separate dosage forms, and separate administration. For example, for the treatment of hyperkalemia, the potassium-binding polymers and the core-shell compositions can be co-administered with drugs that cause the hyperkalemia, such as potassium-sparing diuretics, angiotensin-convening enzyme inhibitors, non-steroidal anti-inflammatory drugs, heparin, or trimethoprim. The drug being co-administered can be formulated together in the same dosage form and administered simultaneously. Alternatively, they can be simultaneously administered, wherein both the agents are present in separate formulations. In another alternative, the drugs are administered separately. In the separate administration protocol, the drugs may be administered a few minutes apart, or a few hours apart, or a few days apart.

The term "treating" as used herein includes achieving a therapeutic benefit and/or a prophylactic benefit. By therapeutic benefit is meant eradication, amelioration, or prevention of the underlying disorder being treated. For example, in a hyperkalemia patient, therapeutic benefit includes eradication or amelioration of the underlying hyperkalemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of a potassium-binding polymer to a patient suffering from hyperkalemia provides therapeutic benefit not only when the patient's serum potassium level is decreased, but also when an improvement is observed in the patient with respect to other disorders that accompany hyperkalemia like renal failure. For prophylactic benefit, the potassium-binding polymers may be administered to a patient at risk of developing hyperkalemia or to a patient reporting one or more of the physiological symptoms of hyperpkalemia, even though a diagnosis of hyperpkalemia may not have been made.

The pharmaceutical compositions of the present invention include compositions wherein the potassium binding polymers are present in an effective amount, i.e., in an amount effective to achieve therapeutic or prophylactic benefit. The actual amount effective for a particular application will depend on the patient (e.g., age, weight, etc.), the condition being treated, and the route of administration. Determination of an effective amount is well within the capabilities of those skilled in the art, especially in light of the disclosure herein.

The effective amount for use in humans can be determined from animal models. For example, a dose for humans can be formulated to achieve gastrointestinal concentrations that have been found to be effective in animals.

Generally, the dosages of the potassium binding polymers (or for sodium binding polymers) in animals will depend on the disease being, treated, the route of administration, and the physical characteristics of the patient being treated. Dosage levels of the potassium binding polymers for therapeutic and/ or prophylactic uses can be from (about) 0.5 gm/day to (about) 30 gm/day or (about) 0.5 gm/day to (about) 25 gm/day. It is preferred that these polymers are administered along with meals. The compositions may be administered one time a day, two times a day, or three times a day. Most preferred dose is (about) 15 gm/day or less. A preferred dose range is (about) 5 gm/day to (about) 20 gm/day, more preferred is (about) 5 gm/day to (about) 15 gm/day, even more preferred is (about) 10 gm/day to (about) 20 gm/day, and most preferred is (about) 10 gm/day to (about) 15 gm/day. The dose may be administered with meals.

In some embodiments, the amount of potassium bound by the core-shell compositions is greater than the amount if the core component, i.e., potassium binding polymer is used in the absence of the shell. Hence, the dosage of the core component in some embodiments is lower when used in combination with a shell compared to when the core is used without the shell. Hence, in some embodiments of the core-shell pharmaceutical compositions, the amount of core component present in the core-shell pharmaceutical composition is less than the amount that is administered to an animal in the absence of the shell component.

In preferred embodiments, the monovalent ion-binding polymers described herein have a decreased tendency to cause side-effects such as hypernatremia and acidosis due to the release of detrimental ions. The term "detrimental ions" is used herein to refer to ions that are not desired to be released into the body by the compositions described herein during their period of use. Typically, the detrimental ions for a composition depend on the condition being treated, the chemical properties, and/or binding properties of the composition. For example, the detrimental ion could be $H^+$ which can cause acidosis or $Na^+$ which can cause hypernatremia. Preferably the ratio of target monovalent ions (e.g., potassium ion or sodium ion) bound to detrimental cations introduced is 1: (about) 2.5 to (about) 4.

In preferred embodiments, the monovalent ion-binding polymers described herein have a decreased tendency to cause other detrimental side-effects, such as gastrointestinal discomfort, constipation, dyspepsia, etc.

Advantageously, the potential of off-target effects, such as inadvertently removing clinically relevant amounts of Ca and Mg can be reduced by the core-shell particles and compositions of the invention (relative to use of cation exchange binders in the absence of a shell). Notably, a number of studies have been reported in the literature that demonstrate calcium ion and magnesium ion removal by cation binding resins. See, for example, Spencer, A. G. et al. Cation exchange in the gastrointestinal tract. *Br Med J.* 4862:603-6 (1954); see also Evans, B. M., et al. Ion-exchange resins in the treatment of anuria. *Lancet.* 265:791-5 (1953). See also Berlyne, G. M., et al. Cation exchange resins in hyperkalaemic renal failure. *Isr J Med. Sci.* 3:45-52 (1967); see also McChesney, E. W., Effects of long-term feeding of sulfonic ion exchange resin on the growth and mineral metabolism of rats. Am J Physiol. 177:395-400 (1954). In particular, studies evaluating hypocalcaemia ('Tetany') induced by treatment with polystyrene sulfonate resin have been reported. See Angelo-Nielsen K, et al., Resonium A-induced hypocalcaemic tetany. Dan Med. Bull. September; 30(5):348-9 (1983); see also Ng Y Y, et al., Reduction of serum calcium by sodium sulfonated polystyrene resin, J Formos Med. Assoc. May; 89(5):399-402 (1990). Because the compositions and coreshell particles of the invention are selective over such magnesium ions and calcium ions, the present invention can reduce the risk of hypocalcemia and hypomagnesemia.

The compositions described herein can be used as food products and/or food additives. They can be added to foods prior to consumption or while packaging to decrease levels of potassium and/or sodium, and be removed prior to consumption so that the compositions and bound potassium and/or sodium are not ingested. Advantageously, in such application, a selective core/shell composition will release less counterion into the food or beverage, and remove less Mg and Ca, then a non-selective composition. Thus removal of potassium and/ or sodium can be accomplished with the use of less material, and with reduced undesirable 'off target' alteration of the ionic composition of the food or beverage. The compositions can also be used in fodder for animals to lower $K^+$ levels (or Na+ levels), which lowering of K+ levels is for example desirable for example in fodders for pigs and poultry to lower the water secretion.

Formulations and Routes of Administration

The polymeric compositions and core-shell compositions described herein or pharmaceutically acceptable salts thereof can be delivered to the patient using a wide variety of routes or modes of administration. The most preferred routes for administration are oral, intestinal, or rectal.

Generally, in some embodiments, the core-shell particles can be encased or included in a bag or sachet (e.g., in a dialysis bag, or in a paper bag). In some embodiments, the core-shell particles can be formulated in a support media such as a microporous matrix or polymer gel. In some embodiments, the core-shell particles can be formulated as a suspension or dispersion in a liquid media. Such suspension or dispersion can be uniform or non-uniform. In some embodiments, the core-shell particles can be formulated as hollow fibers, as vesicles, as capsules, as tablet, or as a film.

If necessary, the polymers and core-shell compositions may be administered in combination with other therapeutic agents. The choice of therapeutic agents that can be co-administered with the compounds of the invention will depend, in part, on the condition being treated.

The polymers (or pharmaceutically acceptable salts thereof) may be administered per se or in the form of a pharmaceutical composition wherein the active compound(s) is in admixture or mixture with one or more pharmaceutically acceptable carriers, excipients or diluents. Pharmaceutical compositions for use in accordance with the present invention may be formulated in conventional manner using one or more physiologically acceptable carriers compromising excipients and auxiliaries which facilitate processing of the active compounds into preparations which can be used pharmaceutically. Proper formulation is dependent upon the route of administration chosen.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions, wafers, and the like, for oral ingestion by a patient to be treated. In one embodiment, the oral formulation does not have an enteric coating. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, microcrystalline cellulose, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For administration orally, the compounds may be formulated as a sustained release preparation. Numerous techniques for formulating sustained release preparations are known in the art.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for administration.

In some embodiments the polymers of the invention are provided as pharmaceutical compositions in the form of chewable tablets. In addition to the active ingredient, the following types of excipients are commonly used: a sweetening agent to provide the necessary palatability, plus a binder where the former is inadequate in providing sufficient tablet hardness; a lubricant to minimize frictional effects at the die wall and facilitate tablet ejection; and, in some formulations a small amount of a disintegrant is added to facilitate mastication. In general excipient levels in currently-available chewable tablets are on the order of 3-5 fold of active ingredient(s) whereas sweetening agents make up the bulk of the inactive ingredients.

The present invention provides chewable tablets that contain a polymer or polymers of the invention and one or more pharmaceutical excipients suitable for formulation of a chewable tablet. The polymer used in chewable tablets of the invention preferably has a swelling ratio while transiting the oral cavity and in the esophagus of less than (about) 5, preferably less than (about) 4, more preferably less than (about) 3, more preferably less than 2.5, and most preferably less than (about) 2. The tablet comprising the polymer, combined with suitable excipients, provides acceptable organoleptic properties such as mouthfeel, taste, and tooth packing, and at the same time does not pose a risk to obstruct the esophagus after chewing and contact with saliva.

In some aspects of the invention, the polymer(s) provide mechanical and thermal properties that are usually performed by excipients, thus decreasing the amount of such excipients required for the formulation. In some embodiments the active ingredient (e.g., polymer) constitutes over (about) 30%, more preferably over (about) 40%, even more preferably over (about) 50%, and most preferably more than (about) 60% by weight of the chewable tablet, the remainder comprising suitable excipient(s). In some embodiments the polymer comprises (about) 0.6 gm to (about) 2.0 gm of the total weight of the tablet, preferably (about) 0.8 gm to (about) 1.6 gm. In some embodiments the polymer comprises more than (about) 0.8 gm of the tablet, preferably more than (about) 1.2 gm of the tablet, and most preferably more than (about) 1.6 gm of the tablet. The polymer is produced to have appropriate strength/friability and particle size to provide the same qualities for which excipients are often used, e.g., proper hardness, good mouth feel, compressibility, and the like. Unswelled particle size for polymers used in chewable tablets of the invention is less than (about) 80, 70, 60, 50, 40, 30, or 20 microns mean diameter. In preferred embodiments, the unswelled particle size is less than (about) 80, more preferably less than (about) 60, and most preferably less than (about) 40 microns.

Pharmaceutical excipients useful in the chewable tablets of the invention include a binder, such as microcrystalline cellulose, colloidal silica and combinations thereof (Prosolv 90), carbopol, providone and xanthan gum; a flavoring agent, such as sucrose, mannitol, xylitol, maltodextrin, fructose, or sorbitol; a lubricant, such as magnesium stearate, stearic acid, sodium stearyl fumurate and vegetable based fatty acids; and, optionally, a disintegrant, such as croscarmellose sodium, gellan gum, low-substituted hydroxypropyl ether of cellulose, sodium starch glycolate. Other additives may include plasticizers, pigments, talc, and the like. Such additives and other suitable ingredients are well-known in the art; see, e.g., Gennaro A R (ed), *Remington's Pharmaceutical Sciences*, 20th Edition.

In some embodiments the invention provides a pharmaceutical composition formulated as a chewable tablet, comprising a polymer described herein and a suitable excipient. In some embodiments the invention provides a pharmaceutical composition formulated as a chewable tablet, comprising a polymer described herein, a filler, and a lubricant. In some embodiments the invention provides a pharmaceutical composition formulated as a chewable tablet, comprising a polymer described herein, a filler, and a lubricant, wherein the filler is chosen from the group consisting of sucrose, mannitol, xylitol, maltodextrin, fructose, and sorbitol, and wherein the lubricant is a magnesium fatty acid salt, such as magnesium stearate.

The tablet may be of any size and shape compatible with chewability and mouth disintegration, preferably of a cylindrical shape, with a diameter of (about) 10 mm to (about) 40 mm and a height of (about) 2 mm to (about) 10 mm, most preferably a diameter of (about) 22 mm and a height of (about) 6 mm.

In one embodiment, the polymer is pre-formulated with a high Tg/high melting point low molecular weight excipient such as mannitol, sorbose, sucrose in order to form a solid solution wherein the polymer and the excipient are intimately mixed. Method of mixing such as extrusion, spray-drying, chill drying, lyophilization, or wet granulation are useful. Indication of the level of mixing is given by known physical methods such as differential scanning calorimetry or dynamic mechanical analysis.

Methods of making chewable tablets containing pharmaceutical ingredients, including polymers, are known in the art. See, e.g., European Patent Application No. EP373852A2 and U.S. Pat. No. 6,475,510, and Remington's Pharmaceutical Sciences, which are hereby incorporated by reference in their entirety.

In some embodiments, the polymers are provided as dry powders in the form of a sachet or packet, which can be mixed with water or another beverage of the patients choosing. Optionally the powder may be formulated with agents for providing improved sensory attributes, such as viscosity, flavor, odor, color, and mouth feel, when the powder is mixed with water.

In some embodiments the polymers of the invention are provided as pharmaceutical compositions in the form of liquid formulations. In some embodiments the pharmaceutical composition contains an ion-binding polymer dispersed in a suitable liquid excipient. Suitable liquid excipients are known in the art; see, e.g., *Remington's Pharmaceutical Sciences*.

In this specification, the terms "about" and "around" are to signify that in one embodiment, the respective exact value is designated, while in another embodiment, the approximate value is designated. Thus, for example, "at least about 1,000" shall, in one embodiment, be interpreted to mean "at least 1,000" and, in another embodiment, be interpreted to mean "at least approximately 1,000."

DEFINITIONS

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

Unless otherwise indicated, the alkyl groups described herein are preferably lower alkyl containing from one to eight carbon atoms in the principal chain and up to 20 carbon atoms. They may be substituted or unsubstituted and straight or branched chain or cyclic and include methyl, ethyl, propyl, butyl, pentyl, hexyl and the like.

Unless otherwise indicated, the alkenyl groups described herein are preferably lower alkenyl containing from two to eight carbon atoms in the principal chain and up to 20 carbon atoms. They may be substituted or unsubstituted and straight or branched chain or cyclic and include ethenyl, propenyl, butenyl, pentenyl, hexenyl, and the like.

Unless otherwise indicated, the alkynyl groups described herein are preferably lower alkynyl containing from two to eight carbon atoms in the principal chain and up to 20 carbon atoms. They may be substituted or unsubstituted and straight or branched chain and include ethynyl, propynyl, butynyl, pentynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are preferred aryl moieties.

The term "alkaryl" as used herein denote optionally substituted alkyl groups substituted with an aryl group. Exemplary aralkyl groups are substituted or unsubstituted benzyl, ethylphenyl, propylphenyl and the like.

The term "carboxylic acid" refers to a RC(O)OH compound where R can be hydrogen, or substituted or unsubstituted alkyl, alkenyl, alkynyl, aryl, substituted aryl.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring. Preferably, the heterocyclo or heterocyclic moieties have 5 or 6 atoms in each ring, at least one of which is a heteroatom. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring. Preferably, the heteroaryl moieties have 5 or 6 atoms in each ring, at least one of which is a heteroatom. The heteroaryl group preferably has 1 or 2 oxygen atoms and/or 1 to 4 nitrogen atoms and/or 1 or 2 sulfur atoms in the ring, and is bonded to the remainder of the molecule through a carbon. Exemplary heteroaryls include furyl, thienyl, pyridyl, oxazolyl, isoxazolyl, oxadiazolyl, pyrrolyl, pyrazolyl, triazolyl, tetrazolyl, imidazolyl, pyrazinyl, pyrimidyl, pyridazinyl, thiazolyl, thiadiazolyl, biphenyl, naphthyl, indolyl, isoindolyl, indazolyl, quinolinyl, isoquinolinyl, benzimidazolyl, benzotriazolyl, imidazopyridinyl, benzothiazolyl, benzothiadiazolyl, benzoxazolyl, benzoxadiazolyl, benzothienyl, benzofuryl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "quaternary ammonium" as used herein describe an organic nitrogen moiety in which a central nitrogen atom is covalently bonded to four organic groups.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, acyl, acyloxy, nitro, amino, amido, nitro, cyano, ketals, acetals, esters and ethers.

EXAMPLES

The following examples are intended to illustrate certain embodiments within the scope of the invention. These examples are not intended to be limiting in any respect on the subject matter defined by the claims.

Example 1

Preparation of Core-Shell Particles Having Crosslinked Polyvinylamine Shell (2 gm/100 ml Scale) (Reference ID #253)

This example illustrates the preparation of a core-shell particle comprising a core component comprising polystyrenesulfonate and a shell component comprising a crosslinked polyvinylamine, using a multiphase in situ crosslinking process with 2 gm core polymer and epichlorhydrin crosslinker in a 100 ml scale reactor.

Shell Polymer.

Polyvinylamine (Mw, 340,000; >90% hydrolyzed) was provided by BASF under trade name, lupamin9095 (20~22 wt % in aqueous solution). As described herein, more than 90% of the polyvinylformamide was hydrolyzed (or deprotected) to produce polyvinylamine, but the balance of the polymer contained formamide groups, thus, a copolymer of polyvinylamine and polyvinylamide was used. In each example where the polymer was described as 90% hydrolyzed, this copolymer was generally the starting material. The solution was diluted with nanopure water to 2.5 wt %. The solution pH was adjust to pH8.5 by using 33.3 wt % NaOH before coating.

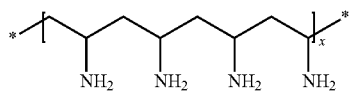

Polyvinylamine, PVAm: a linear high molecular weight and water soluble polymer

Core Polymer.

A polystyrenesulfonate material, Dowex 50WX4-200, was supplied from Aldrich. It was washed extensively in 1M HCl to convert it to the H-form. It was then washed extensively in 1M NaOH. Excess NaOH was removed by washing in H$_2$O. The resins were lyophilized and stored in a desiccator.

Crosslinking Agent.

Epichlorohydrin (ECH) was purchased from Aldrich and used as received.

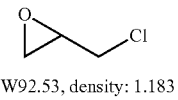

FW92.53, density: 1.183

Reactor.

100 ml round bottom flask.

Multiphase In-Situ Crosslinking.

To a 100 ml round bottom flask were charged 2 gm of Dowex(Na) beads (core polymer) and 6 ml of 2.5 wt % aqueous solution of Lupamin 9095 (pH8.5) (shell polymer) to form a first mixture. The first mixture was gently stirred for 10 minutes. Then a separate, second mixture comprising 6 ml of toluene and 0.584 ml of ECH was added to the first mixture. The combined heterogeneous multiphase reaction mixture was stirred vigorously at 85° C. oil bath for 24 hours, and cooled to room temperature.

Workup.

The solvent was decanted to recover the coated beads. The beads were washed with 10 ml of methanol for ~10 minutes, then washed with 10 ml of water for 3 times. The beads were isolated by filtration, and then freeze-dried for 3 days.

Yield.

About 1.8 gm of core-shell particles were obtained.

Example 2

Preparation of Core-Shell Particles Having Crosslinked Polyvinylamine Shell (100 gm/1 Liter Scale) (Reference ID #293)

This example illustrates the preparation of a core-shell particle comprising a core component comprising polystyrenesulfonate and a shell component comprising a crosslinked polyvinylamine, using a multiphase in situ crosslinking process with 100 gm core polymer and epichlorhydrine crosslinker in a 1 liter scale reactor.

Shell Polymer.

A polyvinylmine solution (Mw, 45,000; >90% hydrolyzed) was provided by BASF under trade name, lupamin5095 (20~22 wt % in aqueous solution). The solution was diluted with nanopure water to 2.5 wt %. The solution pH was adjust to pH8.5 by using 33.3 wt % NaOH before coating.

Core Polymer.

The core polymer was a polystyrenesulfonate material, Dowex 50WX4-200, as described in connection with Example 1.

Crosslinking Agent.

The crosslinking agent was epichlorohydrin (ECH). The ECH was provided in a toluene solution (8.9% in v/v) by mixing 29.2 ml of ECH with 300 ml of toluene.

Reactor:

A 1 L jacketed ChemGlass reactor was fitted with a stirrer and a reaction vessel. To this reactor was connected an internal temperature probe, a nitrogen inlet, a syringe pump, and a 100 ml Dean-Stark distillation trap with condenser and an attached bubbler. Temperature was controlled by a Julabo FP40-ME circulator with Solvay Solexis H-Galden ZT180

Heat Transfer Fluid (a hydrofluoropolyether). A Maximum difference of 20° C. was allowed between the internal and jacket temperature.

Multiphase In-Situ Crosslinking.

To the above described 1 L reactor were charged 100 gm of dry Dowex(Na) beads (core polymer) and 300 ml of 2.5 wt % lupamin5095 aqueous solution (shell polymer) as a first mixture. The first mixture was stirred by the mechanical stirrer at 200 rpm and heated from room temperature to 50° C. in 0.5 hour. The temperature of the first mixture was maintained at 50° C., and then 330 ml of a second mixture comprising the 8.9% ECH in toluene solution was added dropwise to first mixture in one hour while stirring at a stirring speed of 400 rpm, forming a multiphase heterogeneous mixture. The reaction temperature was increased to 85° C. and maintained at this temperature for 3 hours. Subsequently, water was removed from the heterogenous multiphase reaction mixture by azeotropic distillation under internal temperature of 110° C. for a period of 2 hours, allowing for concurrent dehydration of the multiphase mixture and further crosslinking. About 110 ml of water was removed from the reactor under this procedure. Following the crosslinking reaction, the reaction mixture was cooled to 25° C. over 2 hours.

Workup.

The resulting beads were purified and isolated as follows. Toluene was decanted from the cooled mixture to recover the resulting core-shell particle. (Some core-shell particle was lost while decanting the solvent.) Then 500 ml of methanol was added to the mixture under stirring for 30 min. Stirring was stopped to allow the beads to settle down at the bottom. Again the liquid phase, methanol, was decanted. Then 800 ml of water was added to the beads and mixed under stirring for 30 min. Afterward, water was decanted. The water washing sequence was performed 3 times. The slurry comprising the beads was poured into a 600 ml fritted funnel and excess water was removed under reduced pressure. The wet beads were frozen at 80° C. and freeze dried.

Yield.

About 98 gm of core-shell particle were obtained.

Example 3

Preparation of Core-Shell Particles Having Crosslinked Polyvinylamine Shell (4 gm/100 ml scale) (Reference ID #291)

This example illustrates the preparation of a core-shell particle comprising a core component comprising polystyrenesulfonate and a shell component comprising a crosslinked polyvinylamine, using a multiphase in situ crosslinking process with 4 gm core polymer and N,N-diglycidylaniline crosslinker in a 100 ml scale reactor.

Shell Polymer.

A polyvinylmine solution (Mw, 45,000; >90% hydrolyzed) was provided by BASF under trade name, lupamin5095 (20~22 wt % in aqueous solution). The solution was diluted with nanopure water to 2.5 wt %. The solution pH was adjust to pH8.5 by using 33.3 wt % NaOH before coating.

Core Polymer.

The core polymer was a polystyrenesulfonate material, Dowex 50WX4-200, as described in connection with Example 1.

Crosslinking Agent.

N,N-diglycidylaniline (N,N-DGA) was used as received from Aldrich.

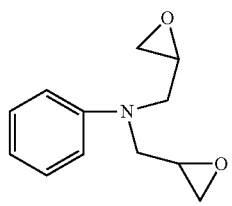

FW: 205.26; density, 1.153

Reactor:

100 ml round bottom flask, fitted with a distillation trap.

Multiphase In-Situ Crosslinking.

To a 100 ml of round bottom flask were charged 4 gm of Dowex(Na) beads (core polymer) and 12 ml of 2.5 wt % solution of Lupamin 5095 (pH8.5) (shell polymer) to form a first mixture. The first mixture was gently stirred for 10 minutes. Then a second mixture comprising 12 ml of toluene and 1.32 ml of N,N'-DGA were added to the first mixture, forming a heterogeneous multiphase reaction mixture. The multiphase reaction mixture was stirred vigorously at 85° C. oil bath for 3 hours, followed by removing water by azeotropic distillation at 120° C. for 40 minutes. After one-fourth of the water was removed from the reaction flask, the reaction was stopped. The multiphase reaction mixture was allowed to cool down to room temperature.

Workup.

The resulting beads were purified and isolated as follows. The solvent was decanted. The beads were washed with 20 ml of methanol for ~10 minutes, then washed with 20 ml of water. This water wash sequence was repeated 3 times. The beads were isolated by filtration, and then freeze-dried for 3 days.

Yield.

The yield was not determined.

Example 4

Binding Performance of Core-Shell Particles Having Crosslinked Polyvinylamine Shell This example illustrates the binding capacity of the core-shell particles prepared in Example 1, Example 2 and Example 3 for binding of potassium ion in the presence of magnesium ion, as determined by in vitro assays representative of the gastrointestinal tract. Control samples were commercially available polystyrenesulfonate cation resin (Dowex 50W X4-200(Na) 100 um beads—without a shell component).

The assays and results are described below. The following Table 4 identifies, in summary form, the samples evaluated in this Example 4, their source, their internal sample reference number, and the various figures reporting the results for the various samples.

TABLE 4

|  | Source | Sample Ref. No. | Assay No. 1 (NI) | Assay No. 2 (KSPIF) | Assay No. 3 (FW) |
|---|---|---|---|---|---|
| Control (Dowex(Na)) | commercial | control | FIG. 1 | FIG. 5 | FIG. 9 |
| [xPVAm/ Dowex(Na)] | Example 1 | #253 (FL253) | FIG. 2 | FIG. 6 | FIG. 10 |
| [xPVAm/ Dowex(Na)] | Example 2 | #293 (FL293) | FIG. 3 | FIG. 7 | FIG. 11 |
| [xPVAm/ Dowex(Na)] | Example 3 | #291 (FL291) | FIG. 4 | FIG. 8 | FIG. 12 |

Example 4A

Binding Performance as Determined Using Assay No. I

In this example, the binding characteristics of the core-shell particles of Examples 1 through 3 were determined using the in vitro assay substantially the same as that designated as GI Assay No. I as described above. This assay was a competitive assay involving potassium ion and magnesium ion at equal concentrations selected to be generally typical and representative of the concentrations seen in various regions of the intestinal tract. A Dowex(Na) core without the shell polymer was used as a control.

Briefly, in this assay, core-shell particles were incubated at a concentration of 4 mg/ml in an assay solution (50 mM KCl, 50 mM $MgCl_2$ and a buffer, 50 mM 2-morpholinoethanesulfonic acid monohydrate) at a pH of 6.5 and a temperature of 37° C. for 48 hrs with agitation. The cations bound to the composition were determined over time, at intervals of 2 hours, 6 hours, 24 hours and 48 hours.

The results are shown in FIGS. 1 through 4. As referenced in the figures, this GI Assay No. I is alternatively referred to as an NI assay (non-interferring assay) and/or as being run under NI conditions.

The binding data for this assay for the control Dowex(Na) core—alone, without a shell polymer, is shown in FIG. 1. As demonstrated therein, Dowex(Na) core, without shell polymer, bound $K^+$ in an amount of about 0.5 meq/gm, and bound $Mg^{++}$ in an amount of more than about 3.5 meq/gm about under the conditions of this assay. These values were substantially unchanged over the duration of time from 2 hrs to 48 hrs. In this FIG. 1 (and generally re each of FIGS. 2 through 12), a negative binding capacity for sodium (shown as a negative number for ions bound in mEq/g) represents the sodium exchanged off the polymer. This provided an internal control for total binding capacity and rate of exchange.

Figure 2:
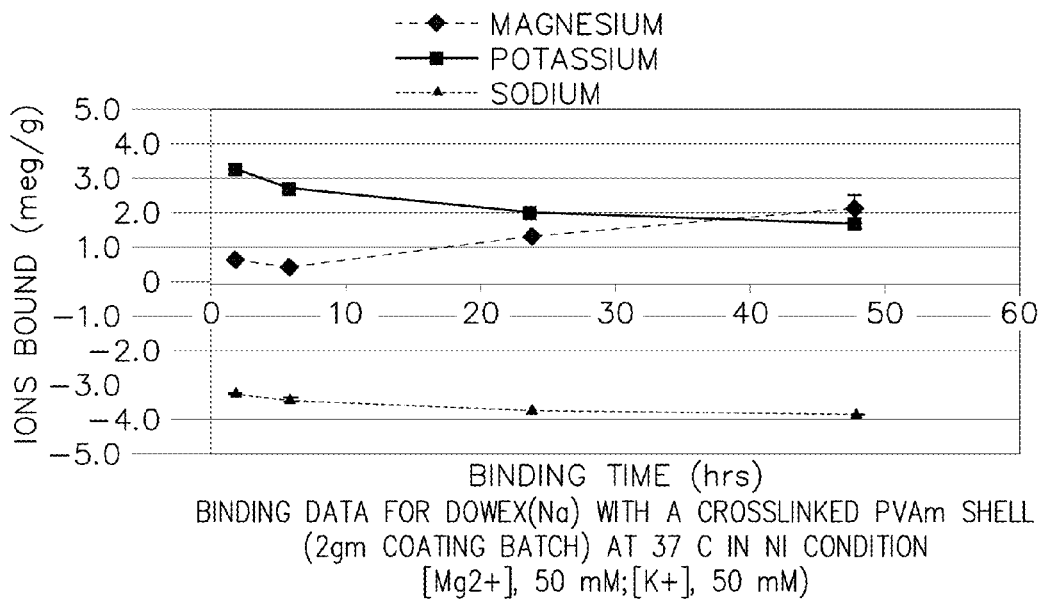

FIG. 2 shows the binding profile from this assay for core-shell particles comprising crosslinked polyvinylamine shell polymer on a Dowex (Na) core polymer (e.g., referred to herein using shorthand notation [xPVAm/Dowex(Na)]) as prepared in Example 1 (Ref #253). At a duration of 2 hours, a $K^+$ binding of 3.3 meq/gm and a $Mg^{2+}$ binding about 0.5 meq/gm were observed for these core-shell particles. Relatively minor changes were observed at a duration of 6 hours. Over a time period from more than about six hours to the end of the study, binding of $Mg^{2+}$ increased gradually, and binding of $K^+$ decreased. Notably, however, binding of $K^+$ was >2 meq/gm at a duration of 6 hours and at a duration of 24 hours. At 24 hours duration $Mg^{2+}$ binding of about 1.5 meq/gm was observed. At 48 hrs, a $K^+$ binding value of 1.6 meq/gm was observed. Compared with binding value for the control [Dowex(Na)] beads (0.5 meq/gm), this data represents a $K^+$ binding value of about 3-fold improvement at the duration of 48 hours.

Figure 3:
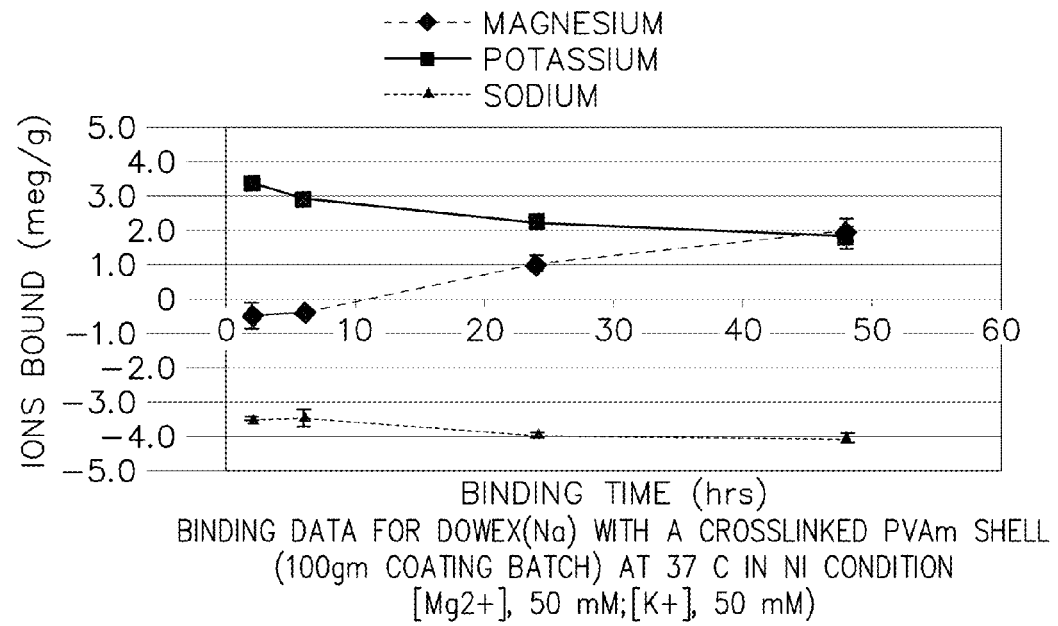

FIG. 3 shows the binding profile from this assay for the core-shell particle [xPVAm/Dowex(Na)] prepared in Example 2 (Ref #293). The profile evidences about the same (if not slightly improved) selectivity and persistence performance as shown in FIG. 2 for the core-shell as prepared in Example 1. The data demonstrates the reproducibility and the scalability of the multiphase in-situ crosslinking method, since substantially similar results were obtained using the core-shell particle prepared in Example 1 (2 gm core polymer/100 ml reactor) and in Example 2 (100 g core polymer/1 L reactor).

Figure 4:
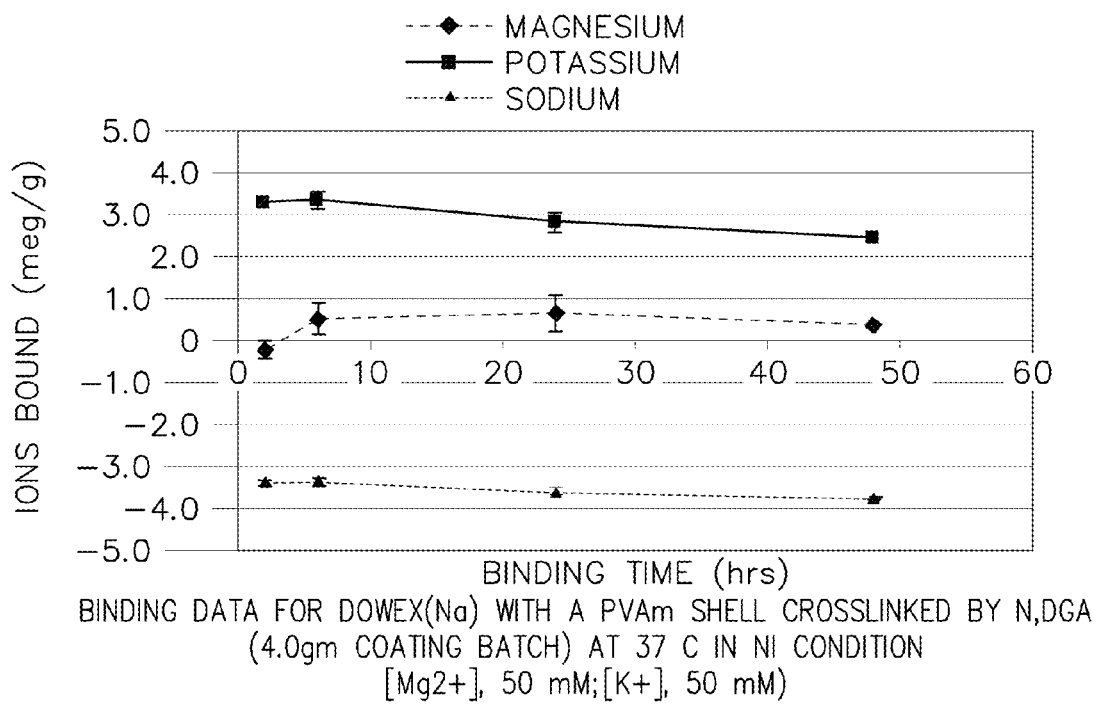

FIG. 4 shows the resulting binding profile from this assay for core-shell particles [xPVAm/Dowex(Na)] prepared in Example 3 (Ref #291) using N,N-DGA crosslinker. This core-shell particle demonstrated a substantial extent of $K^+$ binding under these assay conditions throughout the 48 hour measurement period. Significantly, these crosslinked core-shell particles with xPVAm shell polymer have a remarkably persistent permselectivity for potassium ion binding over magnesium ion binding under the conditions of this assay.

Example 4B

Binding Performance as Determined Using Assay No. II

In this example, the binding characteristics of the core-shell particles of Examples 1 through 3 were determined using the in vitro assay designated as GI Assay No. II. This assay was a competitive assay involving potassium ion and magnesium ion and certain additional anions typical in the upper gastrointestinal environment. A Dowex(Na) core without the shell polymer was used as a control.

In this assay, core shell particles were incubated at concentration of 4 mg/ml in an assay solution (50 mM KCl, 50 mM $MgCl_2$, 5 mM sodium taurocholate, 30 mM oleate, 1.5 mM citrate, and a buffer, 50 mM 2-morpholinoethanesulfonic acid monohydrate) at a pH of 6.5 and a temperature of 37° C. for 48 hrs with agitation. The cations bound to the composition were determined over time, at intervals of 2 hours, 6 hours, 24 hours and 48 hours.

The results are shown in FIGS. 5 through 8. As referenced in the figures, this GI Assay No. II is alternatively referred to a K-SPIF assay (potassium specific interfering assay) and/or as being run under K-SPIF conditions.

The binding data for this assay for the control Dowex(Na) core—without a shell polymer, is shown in FIG. 5. As demonstrated therein, the Dowex(Na) core bound potassium ion in an amount of about 0.8 meq/gm, but bound almost 4 meq/gm magnesium ion under the conditions of the assay. The binding capacity of these control beads was substantially unchanged over the duration of the 48 hour study.

FIG. 6 shows the binding profile from this assay for core-shell particles [xPVAm/Dowex(Na)] prepared in Example 1 (Ref #253). These core-shell particles bound $K^+$ in an amount of ~3.0 meq/gm over the first 6 hours. At 24 hours and 48 hours, the core-shell particles bound $K^+$ in an amount of about ~2.5 meq/gm (24 hrs timepoint) and in an amount of about slightly ≥2.0 meq/gm (48 hrs timepoint). The core-shell particles bound a smaller amount of Mg++, particularly over the 2 hour, 6 hour and 24 hour durations, each of which was ≤2 meq/gm under the conditions of this assay. At the 48 hour duration, the amount of Mg++ bound was slightly <2.0 meq/gm under the assay conditions. These data are generally consistent with, if not slightly improved relative to, the corresponding data from GI Assay No. I (See FIG. 2), demonstrating desirable performance characteristics in a relatively more complex assay.

Figure 7:
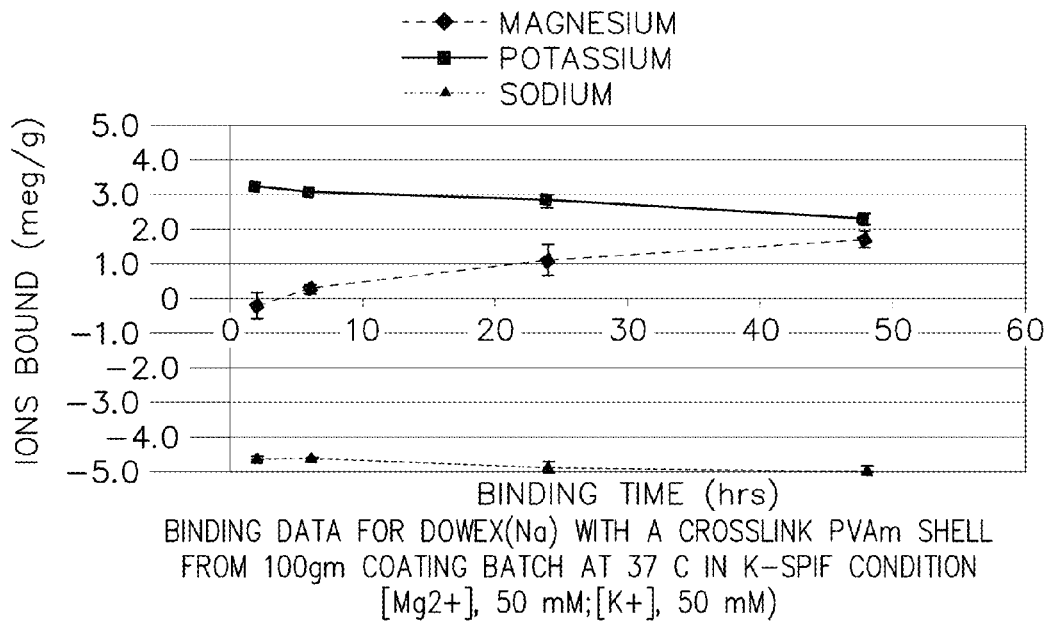

FIG. 7 shows the binding profile from this assay for the core-shell particle [xPVAm/Dowex(Na)] prepared in Example 2 (Ref #293). This data shows $K^+$ binding of 3.0 meq/gm for this core-shell particle for each of the 2 hour, 6 hour and 24 hour timepoints. This data also demonstrates persistent permselectivity for potassium ion over magnesium ion for well beyond 24 hours. For example, even at 48 hrs, the magnesium ion is bound in an amount of slightly <2.0. This data also demonstrates the reproducibility and the scalability of the multiphase in-situ crosslinking method. (Compare results of FIG. 6 based on core-shell compositions of Example 1 (2 gm core polymer/100 ml reactor) with the results of FIG. 7 based on core-shell compositions of Example 2 (100 g core polymer/1 L reactor).

Figure 8:
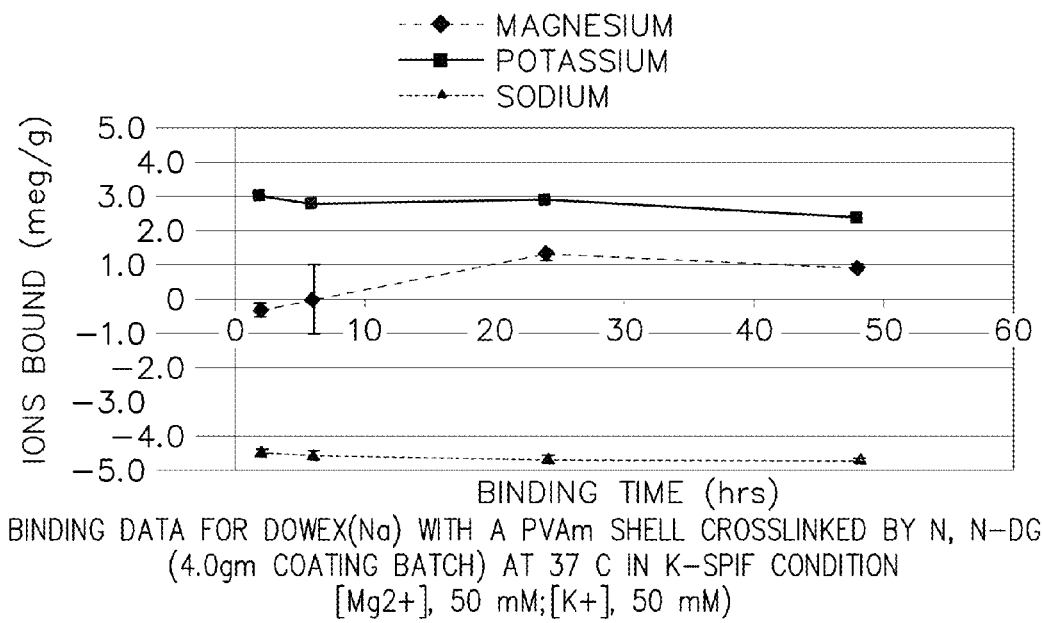

FIG. 8 shows the resulting binding profile from this assay for core-shell particles [xPVAm/Dowex(Na)] prepared in Example 3 (Ref #291) using N,N-DGA crosslinker. The core-shell particle demonstrated a substantial extent of $K^+$ binding under these assay conditions throughout the 48 hour measurement period. Significantly, these crosslinked core-shell particles with xPVAm shell polymer have a remarkably persistent permselectivity for potassium ion binding over magnesium ion binding under the conditions of this assay.

Example 4C

Binding Performance as Determined Using Assay No. III

In this example, the binding characteristics of the core-shell particles of Examples 1 through 3 were determined using the in vitro assay designated as GI Assay No. III. This assay was an ex vivo assay involving ions present in human fecal water extracts, generally representative of the ion content and concentrations seen in the lower colon. A Dowex(Na) core without the shell polymer was used as a control.

In this fecal water assay, core-shell particles at a concentration of 4 mg/ml were incubated in a fecal water solution at a temperature of 37° C. for 48 hrs with agitation. The fecal water solution was obtained by centrifuging human feces for 16 hours at 50,000 g at 4° C. and then filtering the resultant supernatant through a 0.2 um filter. The cations bound to the composition were determined over time.

The results are shown in FIGS. 9 through 12. As referenced in the figures, this GI Assay No. III is alternatively referred to as a FW assay (fecal water assay) and/or as being run under FW conditions.

Figure 9:
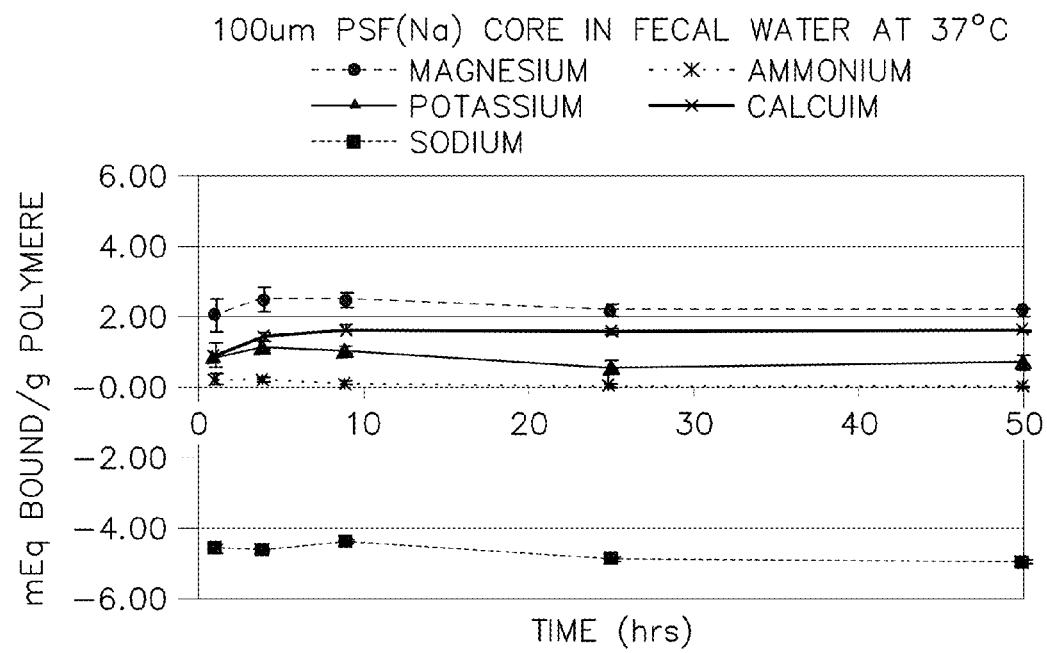

The binding data for this assay for the control Dowex(Na) core—without a shell polymer, is shown in FIG. 9. As demonstrated therein, the Dowex(Na) core bound potassium ion in an amount of between about 0.5 to about 0.8 meq/gm, but bound both calcium ion and magnesium ion, considered collectively, in an amount of about ~3.5 meq/gm under the conditions of the fecal water assay. The binding capacities of these control beads was substantially unchanged over the duration of the study.

Figure 10:
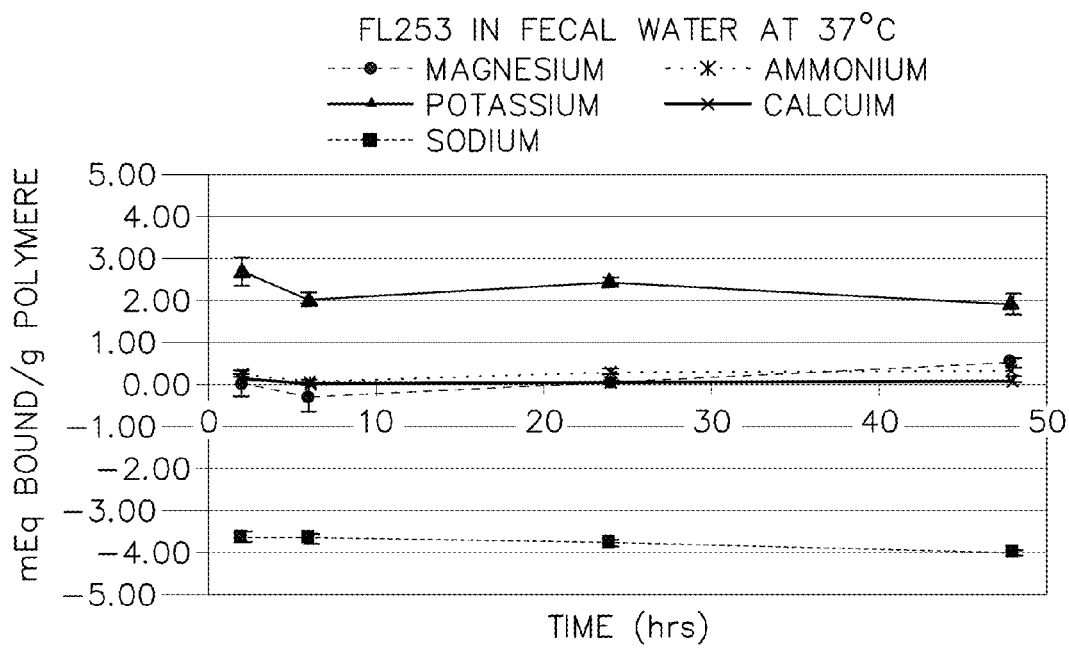

FIG. 10 shows the binding profile from this assay for core-shell particles [xPVAm/Dowex(Na)] prepared in Example 1 (Ref #253). These core-particles [xPVAm/Dowex(Na)] bound potassium ion in an amount of more than about 2.0 through the 48 hour study, representing a 2.5-fold improvement in potassium binding capacity under these conditions when compared to core alone (FIG. 9). These core-shell particles also effectively minimized binding of both calcium ion and magnesium ion, each being bound in an amount of less than 0.5 meq/gm, in each case under the conditions of this fecal water assay. The binding capacities of these core-shell particles varied only moderately over the duration of the study, exemplifying the persistent permselectivity of the core-shell particles.

FIG. 11 shows the binding profile from this assay for the core-shell particle [xPVAm/Dowex(Na)] prepared in Example 2 (Ref #293). These core-particles [xPVAm/Dowex (Na)] bound potassium ion in an amount of more than about 2.0 through about 40 hours, and in a slightly lower amount at 48 hours, representing a 2-fold to 2.5-fold improvement in potassium binding capacity under these conditions when compared to core alone (FIG. 9). These core-shell particles also effectively minimized binding of both calcium ion and magnesium ion, each being bound in an amount of less than 0.5 meq/gm, in each case under the conditions of this fecal water assay. The binding capacities of these core-shell particles varied only moderately over the duration of the study, exemplifying the persistent permselectivity of the core-shell particles.

FIG. 12 shows the resulting binding profile from this assay for core-shell particles [xPVAm/Dowex(Na)] prepared in Example 3 (Ref #291). The core-particles [xPVAm/Dowex (Na)] bound potassium ion in an amount of about 2.0, representing a greater than 2-fold improvement in potassium binding capacity under these conditions when compared to core alone (FIG. 9), and effectively precluded binding of both calcium ion and magnesium ion, each being bound in a negligible, in each case under the conditions of this fecal water assay. The binding capacities of these core-shell particles was virtually unchanged over the duration of the study, demonstrating persistent permselectivity of the core-shell particles through the 48 hour study.

Example 5

Scanning Electron Microscope (SEM) Images of Core-Shell Particles Having Crosslinked Polyvinylamine Shell Scanning electron microscope (SEM) images were taken of the core-shell particles [xPVAm/Dowex (Na)] prepared in Examples 1 through 3. These images illustrate relatively uniform shell surfaces.

FIGS. 13A and 13B show SEM images of the core-shell particle [xPVAm/Dowex (Na)] prepared in Example 1 (Ref #253) at relatively low magnification (FIG. 13A) and at relatively high magnification (FIG. 13B).

FIGS. 14A and 14B show SEM images of the core-shell particle [xPVAm/Dowex (Na)] prepared in Example 2 (Ref #293) at relatively low magnification (FIG. 14A) and at relatively high magnification (FIG. 14B).

FIGS. 15A and 15B show SEM images of the core-shell particle [xPVAm/Dowex (Na)] prepared in Example 3 (Ref #291) at relatively low magnification (FIG. 15A) and at relatively high magnification (FIG. 15B).

FIGS. 16A and 16B show SEM images of the a [Dowex (Na)] particle—without a shell component (used as a control in the experiments of Example 4) at relatively low magnification (FIG. 16A) and at relatively high magnification (FIG. 16B).

Example 6

Confocal Images of Core-Shell Particles Having Crosslinked Polyvinylamine Shell

Confocal images were taken of the core-shell particles [xPVAm/Dowex (Na)] prepared in Example 1 and Example 2. A confocal image was also taken of a Dowex(Na) polystyrenesulfonate cation resin bead—without shell polymer.

Briefly, the polymeric core-shell particles were stained with AlexaFluor 488 (Molecular Probes, OR Cat#A10436), 1 mg in 200 ml buffer. They were then washed briefly to remove unbound fluorophore. The prepared particles were imaged using a Zeiss 510 UV/Vis Meta Confocal Microscope.

Figure 17A:
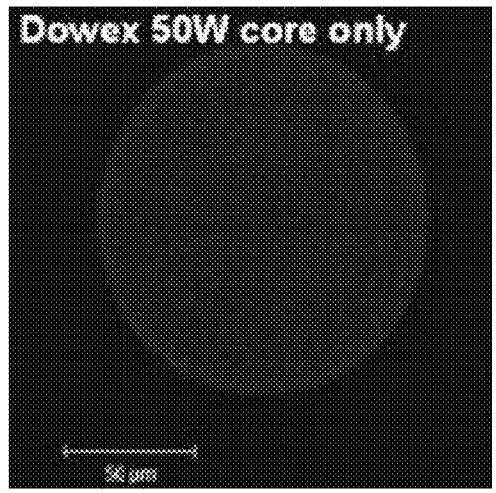
FIGS. 17A through 17C show confocal images of the core particle alone—without shell [Dowex(Na)] (FIG. 17A), of the core-shell particle [xPVAm/Dowex (Na)] prepared in Example 2 (Ref #293) (FIG. 17B), and of the core-shell particle [xPVAm/Dowex (Na)] prepared in Example 1 (Ref #253) (FIG. 17C).
Figure 17B:
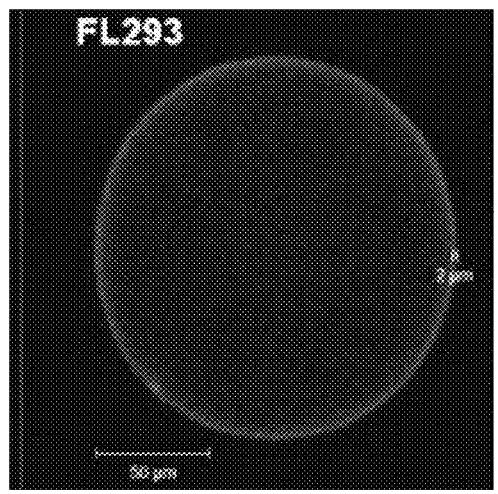
Figure 17C:
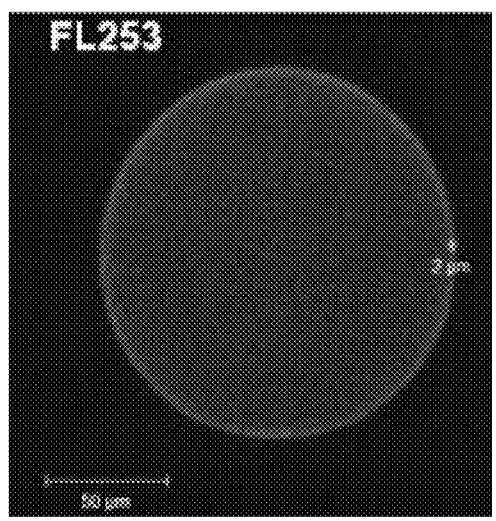

FIGS. 17A through 17C show confocal images of the core particle alone—without shell [Dowex(Na)] (FIG. 17A), and of the core-shell particle [xPVAm/Dowex (Na)] prepared in Example 2 (Ref #293) (FIG. 17B), and of the core-shell particle [xPVAm/Dowex (Na)] prepared in Example 1 (Ref #253) (FIG. 17C). Size bars of 50 um and 2 um are indicated in the FIGS. 17A through 17C.

These images demonstrate a uniform shell component comprising a shell polymer formed as a relatively thin film (having a film thickness of about 2 um) over a polymeric core component (FIG. 17B and FIG. 17C) having a size of about ~120 um.

Example 7

Example for Preparation of Core-Shell Particles by Coating Polystyrene Sulfonate (PSS or Dowex(Na)) with Crosslinked Polyvinylamine (PVAm) in 500 Gm Scale at 5 L Reactor (Coating ID: #340)

This example illustrates the preparation of core-shell particles (or beads) comprising a core component comprising polystyrenesulfonate and a shell component comprising a crosslinked polyvinylamine, using a multiphase in situ crosslinking process with 500 grams core polymer and epichlorohydrin crosslinker in a 5 liter scale reactor.

Shell Materials.

Polyvinylamine solution (Mw, 45,000; >90% hydrolyzed) was provided by BASF under trade name lupamin5095 (20~22 wt. % in aqueous solution). The solution was diluted with nanopure water to 2.5 wt. %. The solution pH was adjusted to pH 8.5 by using 33.3 wt. % sodium hydroxide (NaOH) before coating.

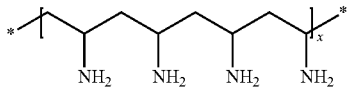

Polyvinylamine, PVAm: a linear high molecular weight and water soluble polymer

Core Materials.

Dowex 50WX4-200 was supplied from Aldrich. It was washed extensively in 1M HCl to convert it to the $H^+$-form. It was then washed extensively in 1M NaOH to convert it to the Na form. Excess NaOH was removed by washing in $H_2O$. The resins were lyophilized and stored in a desiccator.

Cross Linker.

Epichlorohydrin (ECH) and other chemicals were purchased from Aldrich and used as received.

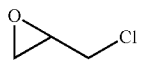

FW92.53, density: 1.183

ECH in toluene solution (22.6% in v/v) was prepared by mixing 146 ml of ECH with 500 ml of toluene Reactor:

The coating and crosslinking of Dowex(Na) with polyvinylamine was carried out in a 5 L jacketed, modified Buchi reactor. The reactor was fitted with an internal temperature probe, a nitrogen inlet, a syringe pump, a 1000 mL Dean Stark trap with condenser and an attached bubbler, a mechanical stirrer, and a steel ball valve outlet. Temperature was controlled by a Julabo FP4O-ME circulator with Solvay Solexis H-Galden ZT180 Heat Transfer Fluid (a hydrofluoropoly-ether). A maximum difference of 20° C. was allowed between the internal and jacket temperatures.

Coating/Crosslinking Procedure.

Dry Dowex(Na) beads (500 grams) and 1500 ml of 2.5 wt. % lupamin5095 aqueous solution was charged to a 5 L reactor. The mixture was stirred by a mechanical stirrer at 200 rpm for 30 minutes and 500 ml of toluene was added. The reaction temperature was raised to 85° C. and 646 ml of 22.6% ECH in toluene was added drop wise to the bead mixture over one hour with stirring at 600 rpm. The internal oil temperature was increased to 110° C. to remove water by azeotropic distillation over 6 hours. The reaction mixture was then cooled to 25° C. over 2 hours and about 700 ml of water was removed under this procedure.

Purification and Isolation.

Toluene was decanted from the cooled mixture and 3 L of methanol was added to the mixture under stirring for 30 minutes. Stirring was stopped to allow the beads to settle and again the methanol liquid phase was decanted. This procedure was repeated twice. Water (3 L) was added to the beads and mixed under stirring for 30 minutes, then the water was decanted followed by water washing (3×3 L). The slurry beads were poured into 3000 mL fritted funnel and excess water was removed under reduced pressure. The wet beads were frozen and dried.

Yield.

About 480 grams of dry coated beads were obtained.

Characterization of Coated Beads.

Figure 18A:
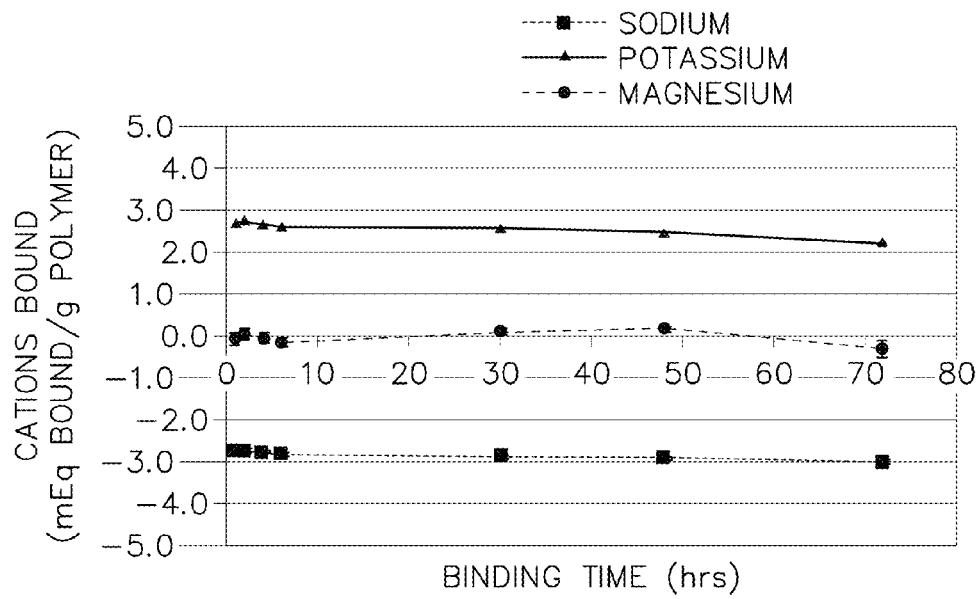
FIG. 18(a) is a graph showing binding profiles for beads having a Dowex(Na) core with a crosslinked polyvinylamine (PVAm) shell (500 gram coating batch) at 37° C. using Assay No. I (non-interfering (NI) conditions) where the bead concentration was 10 mg/ml.
Figure 18B:
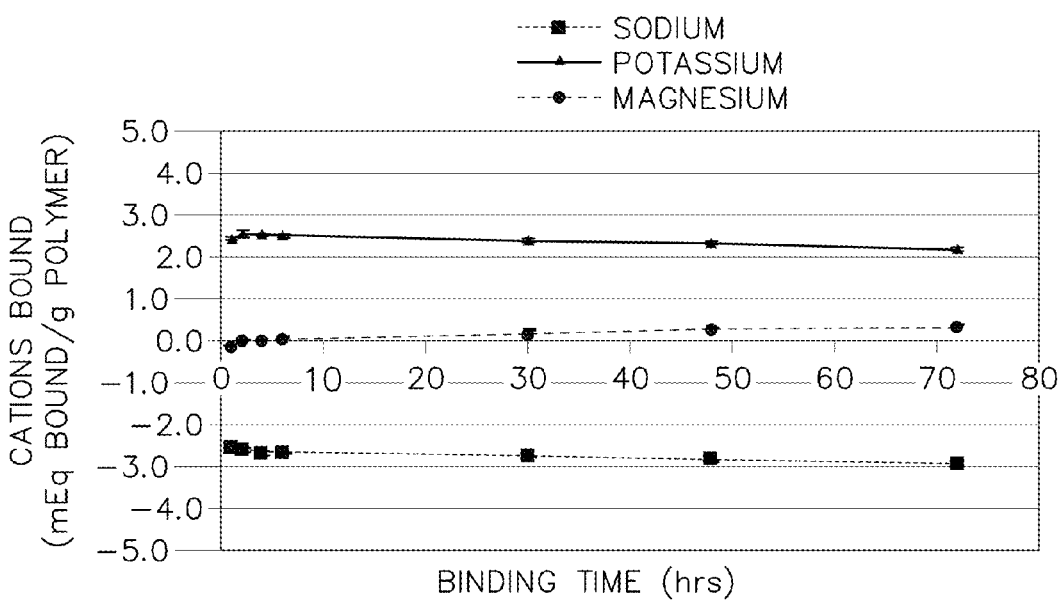
FIG. 18(b) is a graph showing binding profiles for beads having a Dowex(Na) core with a crosslinked polyvinylamine (PVAm) shell (500 gram coating batch) at 37° C. using Assay No. II (potassium specific interfering assay (K-SPIF) conditions) where the bead concentration was 10 mg/ml.

The core-shell particles prepared under conditions described in this example were tested by Assay No. I (as described above in Example 4A and referred to as non-interfering (NI) conditions) and by Assay No. II (as described above in Example 4B and referred to as potassium specific interfering assay (K-SPIF) conditions). Graphs showing the binding profiles for beads prepared by the method described in this example and tested under NI and K-SPIF conditions are shown in FIGS. 18(a) and 18(b), respectively. Under each set of conditions, the crosslinked polyvinylamine/Dowex (Na) beads showed persistent and selective potassium ion binding up to and including 72 hours.

The coated beads prepared according to this method were also characterized by X-ray photoelectron spectroscopy (XPS). The XPS data generally indicates the composition of the core-shell particles tested and differentiates the primary, secondary, tertiary, and quaternary nitrogen atoms in the polyvinylamine shell. Sample FL337 was prepared according to the process above wherein the ratio of the crosslinking agent (ECH) to the number of nitrogens in the polyvinylamine was 1:1. Sample EC64028 was prepared according to the process above, except the ECH:N (in PVAm) was 4:1. The XPS data is summarized in Table 5.

TABLE 5

XPS Results for PSS Core with PVAm shell

| Sample | | C—N #1 | C—N #2 | $NR_4^+Cl^-$ (R = H or alkyl) | Total |
|---|---|---|---|---|---|
| EC64028 (ECH/PVAm: 4/1) | % N | 44 | 46 | 10 | 100 |
|  | Atomic |  |  |  | 11 |
| (treated with 0.2N NaOH) | % | 5 | 5 | 1 |  |
| FL337(ECH/PVAm: 1/1) | % N | 47 | 44 | 10 | ~100[a] |
|  | Atomic |  |  |  | 13 |
| (treated with 0.2 N NaOH) | % | 6 | 6 | 1 |  |
| EC64028(ECH/PVAm: 4/1) | % N | 32 | 55 | 13 | 100 |
|  | Atomic |  |  |  | 11 |
| (without treating with base) | % | 4 | 6 | 1 |  |

TABLE 5-continued

XPS Results for PSS Core with PVAm shell

| Sample | | C—N #1 | C—N #2 | $NR_4^+Cl^-$ (R = H or alkyl) | Total |
|---|---|---|---|---|---|
| FL337 (ECH/PVAm: 1/1) | % N Atomic | 33 | 61 | 6 | 100 |
| (without treating with base) | % | 5 | 8 | 1 | 14 |

[a]approximate due to rounding errors

Example 8

Binding Profiles of Core-Shell Particles Comprising a PSS Core and a Crosslinked PVAm Shell in a Fecal Extract Assay Collection and Preparation of Fecal Extracts.

Fecal samples were supplied by a healthy male volunteer of Caucasian descent. Fecal samples were collected in 1-gallon Ziploc bags and immediately mixed and transferred into PPCO Oak Ridge centrifuge tubes (Nalgene/Nunc 3319-0050). The fecal samples (representing several days' collection) were centrifuged at 21,000 rpm for 20 hours at 4° C. (Beckman JS-25.50 rotor in Beckman-Coulter Avanti J-E centrifuge). The resulting supernatant was pooled and filtered using a Nalgene 0.2 um disposable filter unit. The fecal extract was frozen at −20° C. until needed.

Method to Determine Cation Binding of Core-Shell Beads in Fecal and Colonic Extracts.

The fecal extract was thawed in a room temperature water bath and stirred on a magnetic stir plate. Penicillin G/Streptomycin (Gibco, 15140-122) was added to a final concentration of 100 Units/ml of Penicillin G and 100 ug/ml of streptomycin. Sodium azide was added to a final concentration of 100 ug/ml. Addition of antibiotics and sodium azide discouraged bacterial and/or fungal growth during the assay.

Core-shell particle polymer samples were added to 16×100 mm glass tubes in duplicate, with each tube receiving about 50 mg of dried, accurately weighed sample. While stirring, fecal extract was dispensed into the tubes to produce a final concentration of 10 mg of test sample per mL of extract. The extract was additionally dispensed into duplicate tubes containing no test sample. All tubes were incubated for 72 hours at 37° C., rotating on a rotisserie mixer. At 6 hours, 24 hours, 48 hours and 72 hours, 25 uL of each sample were diluted into 475 uL of Milli-Q purified water (1:20 dilution). The diluted samples were then filtered by centrifugation at 13,200 rpm through Microcon YM-3 filter units (3000 MWCO) for 1 hour. Filtrates were transferred to a 1 mL 96-well plate and submitted for analysis of cation concentrations by ion chromatography. The Dowex beads were coated by various crosslinked polyvinylamine (PVAm) shell polymers. PVAm shell FL293 was prepared by the process described in example 2, wherein the ECH:N ratio was 4:1; PVAm shell FL294 was prepared by the process described in example 2 wherein an ECH:N in PVAm ratio of 5:1 was used, and PVAm shell FL298 was prepared by the process described in example 2 wherein an ECH:N in PVAm ratio of 3:1 was used.

Ion Chromatography Method for Measurement of Cation Concentrations in Fecal and Colonic Extracts.

The cation concentrations in fecal and colonic extract samples were analyzed using a strong cation exchange column set (Dionex CG16 50×5 mm ID and CS16 250×5 mm ID), on a Dionex ICS2000 system equipped with a Dionex WPS3000 auto sampler, DS3 conductivity flow cell and CSRS-Ultra II 4 mm Suppressor. The ion chromatography detection method included an isocratic elution using 30 mM of methanesulfonic acid at a flow rate of 1 mL/minute, and the total run time was 30 minutes per sample.

Data Analysis.

Cation binding was calculated as $(C_{start} - C_{eq})/(C_{beads} *$ valency of the ion), where $C_{start}$ is the starting concentration of cation in the fecal or colonic extract (in millimolar), $C_{eq}$ is the concentration of cation remaining in the sample at equilibrium after exposure to the test agent (in millimolar), and $C_{beads}$ corresponds to the concentration of the test agent in the extract (in mg/mL). The valencies of potassium and ammonium were considered to be 1 (i.e., 1 equivalent per mole) and the valencies of calcium and magnesium were considered to be 2 (i.e., 2 equivalents per mole). All samples were tested in duplicate with values reported as an average (Avg)±the square root of the pooled variance in $C_{start}$ and $C_{eq}$ (Table 6, FIG. 19). The pooled variance is calculated using the following equation $$s_P^2 = \frac{(n_1 - 1)s_1^2 + (n_2 - 1)s_2^2}{n_1 + n_2 - 2}$$

wherein $s_P^2$ is the pooled variance, $s_1^2$ and $s_2^2$ represent the variances of the first and second samples, respectively, and $n_1$ and $n_2$ represent the number of data in the first and second samples.

Results.

The presence of crosslinked polyvinylamine shells on a core of Dowex 50W X4-200 increased the amount of potassium and ammonium bound by the material, measured in mEq of cation bound per gram of binding material, at time points measured from 6 hours to 72 hours (Table 6, FIG. 19). The amount of divalent cations bound (magnesium and calcium) was correspondingly reduced by the presence of these shells.

TABLE 6

Average Binding Capacity as mEq bound/g bead (beads tested at 10 mg/ml):

| | | | | | | Error = SQRT of the pooled variance | | | |
|---|---|---|---|---|---|---|---|---|---|
| Sample | Time (hr) | Potassium | Ammonium | Magnesium | Calcium | Potassium Error | Ammonium Error | Magnesium Error | Calcium Error |
| Na- | 6 | 0.98 | 0.14 | 1.74 | 0.97 | 0.132 | 0.049 | 0.216 | 0.093 |
| Dowex | 24 | 0.92 | 0.13 | 1.89 | 1.03 | 0.090 | 0.038 | 0.252 | 0.022 |

TABLE 6-continued

Average Binding Capacity as mEq bound/g bead (beads tested at 10 mg/ml):

| Sample | Time (hr) | Potassium | Ammonium | Magnesium | Calcium | Potassium Error | Ammonium Error | Magnesium Error | Calcium Error |
|---|---|---|---|---|---|---|---|---|---|
| 50w X4-200 core | 48 | 1.12 | 0.21 | 2.01 | 1.04 | 0.058 | 0.018 | 0.165 | 0.067 |
|  | 72 | 1.19 | 0.24 | 1.96 | 1.04 | 0.140 | 0.033 | 0.220 | 0.044 |
| FL293 | 6 | 2.18 | 0.41 | 0.01 | 0.13 | 0.061 | 0.010 | 0.140 | 0.121 |
|  | 24 | 2.10 | 0.42 | 1.05 | 0.47 | 0.087 | 0.040 | 0.255 | 0.021 |
|  | 48 | 1.41 | 0.31 | 1.18 | 0.52 | 0.054 | 0.019 | 0.143 | 0.044 |
|  | 72 | 1.45 | 0.31 | 1.54 | 0.65 | 0.267 | 0.055 | 0.258 | 0.113 |
| FL294 | 6 | 2.20 | 0.44 | 0.35 | 0.19 | 0.042 | 0.007 | 0.045 | 0.092 |
|  | 24 | 1.67 | 0.33 | 0.96 | 0.39 | 0.070 | 0.037 | 0.238 | 0.045 |
|  | 48 | 1.50 | 0.34 | 1.35 | 0.57 | 0.034 | 0.016 | 0.106 | 0.059 |
|  | 72 | 1.44 | 0.33 | 1.55 | 0.62 | 0.074 | 0.020 | 0.115 | 0.027 |
| FL298 | 6 | 2.12 | 0.42 | 0.40 | 0.18 | 0.072 | 0.022 | 0.012 | 0.087 |
|  | 24 | 1.60 | 0.32 | 1.10 | 0.45 | 0.127 | 0.047 | 0.322 | 0.039 |
|  | 48 | 1.26 | 0.25 | 1.40 | 0.54 | 0.086 | 0.032 | 0.220 | 0.071 |
|  | 72 | 1.37 | 0.31 | 1.76 | 0.69 | 0.025 | 0.015 | 0.071 | 0.033 |

Example 9

Binding Profiles of Core-Shell Particles (Beads) Comprising a PSS Core and a Crosslinked PVAm Shell in a Fecal Extract Assay A number of fecal binding experiments were performed essentially as described in Example 8, with two differences as follows. First, binding was measured at a polymer concentration of 4 mg per ml of fecal extract rather than 10 mg per ml of fecal extract. Second, time points were taken at 2, 6, 24, and 48 hours. The results are presented in Table 7. The Dowex beads were coated by various crosslinked polyvinylamine (PVAm) shell polymers. PVAm shell FL253 was prepared by the process described in example 1; PVAm shell FL275 was prepared by the process described in example 1 except a 5 g scale was used, and PVAm shell FL291 was prepared by the process described in example 3.

Example 10

Binding Profiles of Beads Comprising a PSS Core and a Crosslinked PVAm Shell in a Colonic Extract Assay A binding experiment was performed essentially as described in Example 8, with one difference. Instead of a fecal sample, the sample used was colonic fluid provided by a female volunteer who had recently undergone a colostomy that removed part of her terminal colon, through use of a colostomy bag. The results of this study are presented in Table 8. PVAm shells FL293, FL294, and FL298 are described above in example 8.

TABLE 7

Average Binding Capacity as mEq bound/g bead (beads tested at 4 mg/ml):

| Sample | Time (hr) | Potassium | Ammonium | Magnesium | Calcium | Potassium Error | Ammonium Error | Magnesium Error | Calcium Error |
|---|---|---|---|---|---|---|---|---|---|
| FL253 | 2 | 2.70 | 0.28 | 0.02 | 0.16 | 0.35 | 0.06 | 0.27 | 0.03 |
|  | 6 | 2.06 | 0.06 | −0.30 | 0.07 | 0.12 | 0.05 | 0.35 | 0.08 |
|  | 24 | 2.47 | 0.08 | 0.05 | 0.30 | 0.08 | 0.03 | 0.04 | 0.07 |
|  | 48 | 1.94 | 0.07 | 0.52 | 0.30 | 0.23 | 0.03 | 0.13 | 0.06 |
| FL275 | 2 | 2.03 | 0.19 | −0.05 | 0.03 | 0.62 | 0.08 | 0.48 | 0.11 |
|  | 6 | 1.18 | −0.18 | −0.45 | 0.00 | 0.24 | 0.08 | 0.41 | 0.07 |
|  | 24 | 1.79 | −0.06 | 0.28 | 0.25 | 0.09 | 0.03 | 0.17 | 0.08 |
|  | 48 | 1.27 | −0.01 | 0.76 | 0.20 | 0.51 | 0.09 | 0.44 | 0.18 |
| FL291 | 2 | 2.86 | 0.30 | 0.19 | 0.11 | 0.35 | 0.06 | 0.20 | 0.01 |
|  | 6 | 1.96 | −0.10 | −0.68 | 0.02 | 0.13 | 0.02 | 0.02 | 0.04 |
|  | 24 | 1.97 | −0.07 | −0.47 | 0.10 | 0.09 | 0.04 | 0.14 | 0.07 |
|  | 48 | 1.78 | 0.00 | 0.13 | 0.14 | 0.23 | 0.03 | 0.19 | 0.05 |
| FL293 | 2 | 2.86 | 0.22 | −0.49 | −0.09 | 0.38 | 0.06 | 0.19 | 0.01 |
|  | 6 | 2.22 | −0.03 | −0.74 | 0.00 | 0.16 | 0.02 | 0.03 | 0.02 |
|  | 24 | 2.77 | −0.02 | −0.13 | 0.24 | 0.48 | 0.04 | 0.36 | 0.11 |
|  | 48 | 1.64 | −0.07 | 0.50 | 0.27 | 0.36 | 0.05 | 0.31 | 0.07 |

TABLE 8

Average Binding Capacity as mEq bound/g bead (beads tested at 10 mg/ml):

| Sample | Time (hr) | Potassium | Ammonium | Magnesium | Calcium | Potassium Error | Ammonium Error | Magnesium Error | Calcium Error |
|---|---|---|---|---|---|---|---|---|---|
| Na-Dowex 50w X4-200 core | 6 | 1.54 | 0.42 | 0.89 | 1.07 | 0.120 | 0.026 | 0.092 | 0.147 |
|  | 24 | 1.39 | 0.33 | 0.92 | 1.11 | 0.156 | 0.053 | 0.167 | 0.247 |
|  | 48 | 1.41 | 0.34 | 0.95 | 1.14 | 0.072 | 0.034 | 0.179 | 0.210 |
|  | 72 | 1.65 | 0.38 | 0.97 | 1.16 | 0.058 | 0.005 | 0.079 | 0.168 |
| FL293 | 6 | 2.32 | 0.58 | 0.15 | 0.25 | 0.047 | 0.014 | 0.055 | 0.094 |
|  | 24 | 2.00 | 0.50 | 0.40 | 0.60 | 0.127 | 0.055 | 0.180 | 0.240 |
|  | 48 | 1.62 | 0.41 | 0.52 | 0.75 | 0.130 | 0.047 | 0.183 | 0.216 |
|  | 72 | 1.51 | 0.39 | 0.64 | 0.84 | 0.120 | 0.040 | 0.090 | 0.169 |
| FL294 | 6 | 2.24 | 0.55 | 0.25 | 0.32 | 0.042 | 0.007 | 0.025 | 0.095 |
|  | 24 | 1.55 | 0.41 | 0.43 | 0.58 | 0.162 | 0.049 | 0.174 | 0.241 |
|  | 48 | 1.89 | 0.48 | 0.69 | 0.84 | 0.096 | 0.041 | 0.180 | 0.210 |
|  | 72 | 1.77 | 0.47 | 0.74 | 0.90 | 0.133 | 0.029 | 0.125 | 0.169 |
| FL298 | 6 | 2.16 | 0.59 | 0.30 | 0.35 | 0.272 | 0.045 | 0.118 | 0.134 |
|  | 24 | 1.99 | 0.45 | 0.57 | 0.67 | 0.119 | 0.046 | 0.168 | 0.257 |
|  | 48 | 1.50 | 0.40 | 0.66 | 0.80 | 0.078 | 0.031 | 0.187 | 0.227 |
|  | 72 | 2.06 | 0.52 | 0.81 | 0.89 | 0.379 | 0.053 | 0.154 | 0.177 |

Example 11

The Effect of Core-Shell Particles (Comprising Cross-Linked Polyvinylamine Shell on a Polystyrene Sulfonate Core) on Cation Excretion in Swine Test Articles.

Sodium-form polystyrene sulfonate (Kayexalate; Newton Pharmacy, Canada) and Y5017N6 (a blend of crosslinked polyvinyl amine-coated sodium-form polystyrene sulfonate beads (Dowex 50WX4-200); bead batches FL332, FL336 and FL327). Batches FL332 and FL335 were prepared by the process described in example 7 and FL327 was prepared by a similar process (as in example 7) except the crosslinking agent (ECH) was added at a temperature of 50° C.

Study Design.

Figure 20:
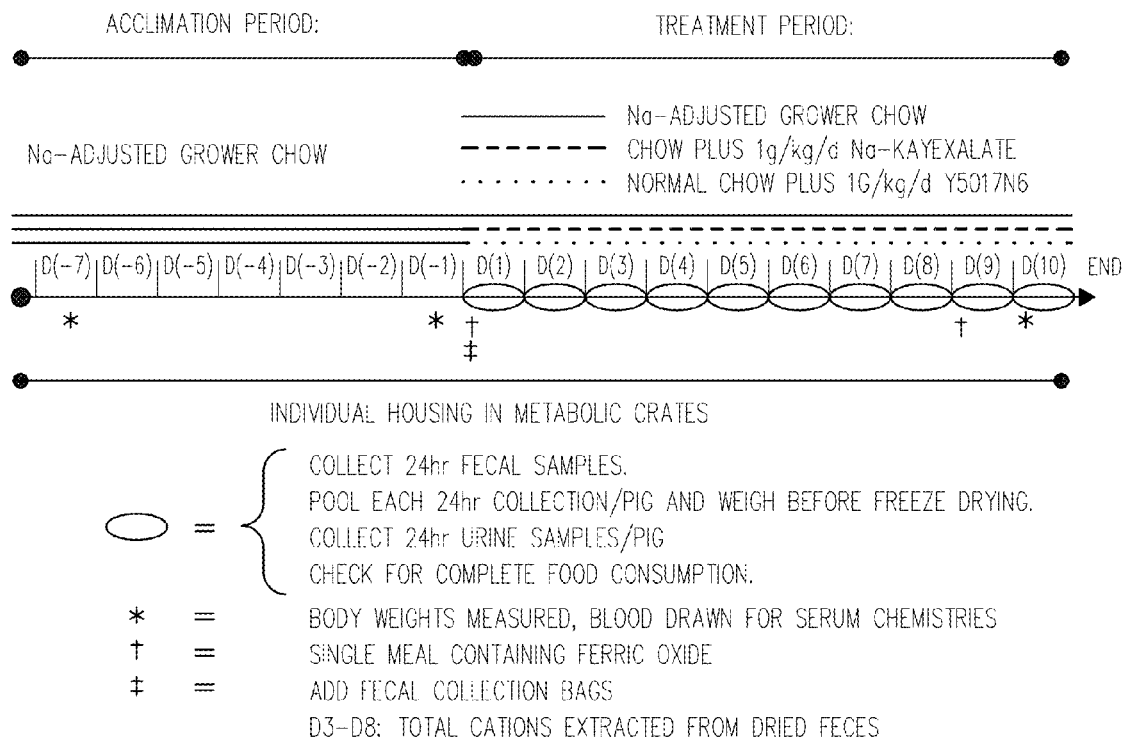
FIG. 20 is a schematic of the study design for testing the effect of crosslinked polyvinylamine shells on cation excretion in swine.

The overall study design is shown in FIG. 20. Eighteen pigs were placed in metabolic crates, which allow separation and collection of total fecal and urine output. They were acclimated for a period of seven days on normal swine grower chow, with additional sodium added to account for the sodium present as the counterion in Y5017N6. Seven animals were then continued on the sodium-adjusted grower chow, while four animals were switched to normal grower chow supplemented with Y5017N6 to give a daily dose of 1 g/kg/d and another seven animals were switched to normal grower chow supplemented with Kayexalate (sodium-form polystyrene sulfonate) to give a daily dose of 1 g/kg/d. A bolus of ferric oxide was given along with the first meal on day D(1) and on day D(9) as an indicator of transit time. Urine and feces were collected and pooled by day beginning on day D(1) and running through the end of the study. The cation content of urine and feces was measured on days D(3) through D(8) and the effect of Y5017N6 treatment versus the control group on urine and fecal cation excretion was determined.

Animal Assignments.

Eighteen approximately 9-week old intact grower barrow swine (Camborough 15 or 22 dams× Terminal Sire boars; PIC Canada Inc.) weighing approximately 25 kg were used in this study Animals that had obvious health problems (e.g. weak, lame, hernia, diarrhea) or ridglings were excluded from the study. Seven pigs were randomly allocated to the control and Kayexalate treatments. Four pigs were randomly assigned to the Y5017N6 treatment. The pigs were housed in metabolic crates for the duration of the study, which allowed separation and collection of all urine and feces excreted by the animals. Three dietary treatments (one control diet, and two test diets) were offered during one treatment period in this study. During the treatment period, the treatment groups were fed a grower diet supplemented with 1 gram of Kayexalate or of Y5017N6 per kilogram of body weight. The control group was fed a standard grower diet supplemented with the appropriate amount of sodium bicarbonate to supply the same amount of sodium per kg diet as that provided by the Kayexalate and Y5017N6.

Acclimation Period.

Prior to the acclimation period, the pigs were fed a standard production diet. At the start of acclimation period, the 18 pigs were weighed, selected and ranked by weight. During the acclimation period, pigs were trained to consume all food offered. Three days before the Test Diet Period, the amounts actually fed to each pig were adjusted according to their body weight at the beginning of the acclimation period, so that given the fixed inclusion rate each pig on each treatment diet received 1 g Kayexalate or Y5017N6/kg body weight/day. The amount fed to the pigs on the control diet was adjusted in the same manner. This amount of feed then remained constant for each pig for the remainder of the study. Throughout the entire study, daily feed allowances for individual pigs were divided in two equal sizes and offered at approximately 08:30 and 15:30.

Test Diet Period.

After acclimation, the eleven test pigs were switched to a diet containing one gram of Kayexalate or Y5017N6 per kilogram of body weight. The seven control pigs remained on the control (acclimation) diet. These diets were for ten days.

Collection Period.

Feces and urine was collected and pooled by animal and by day. A plastic bag held in place around the anus of the pig by rings attached to the skin collected the feces. Each bag of fecal sample was individually weighed prior to being frozen at approximately −20° C. Feces was collected continuously until the end of the treatment period. For each individual pig, the appearance of the first red feces due to the second ferric oxide bolus terminated fecal collection. The urine was collected via a collection tray located underneath the metabolic crate of each pig. A funnel attached under each tray drained into plastic bottles containing approximately 20 mL of HCl. Urine was collected continuously until the offering of the second ferric oxide bolus. The weight of urine collected was recorded twice each day of the collection period. Each daily (24 hr) fecal and urine sample for each pig was kept separate from the rest of the samples for that pig.

Once the Collection Period was complete, the individual frozen fecal specimens were thawed, thoroughly mixed (i.e. each 24-hour sample was mixed, but kept separate from the other 24-hour samples) and freeze-dried. The freeze-dried fecal samples were ground through a 1 mm screen to reach homogeneity for analysis.

Analysis of Cation Content in Urine and Feces.

Lyophilised fecal samples were extracted for 48 hrs in 1M HCl. The samples were clarified by centrifugations and the supernatant was analysed by flame spectroscopy for cation content. Urine samples were thawed, thoroughly mixed, and diluted 1/30 into 50 mM HCl. The diluted, mixed samples were filtered and analysed for cation content by ion chromatography. The effect of Test Articles on cation excretion was calculated by comparing average cations excreted in the control group with cations excreted in the test groups during days D(3) through D(8) for feces and D(1) through D(8) for urine. The fecal analysis period encompassed the days after the last appearance of the first ferric oxide bolus in the feces and before treatment ceased at the end of the treatment period.

Results.

Figure 21A:
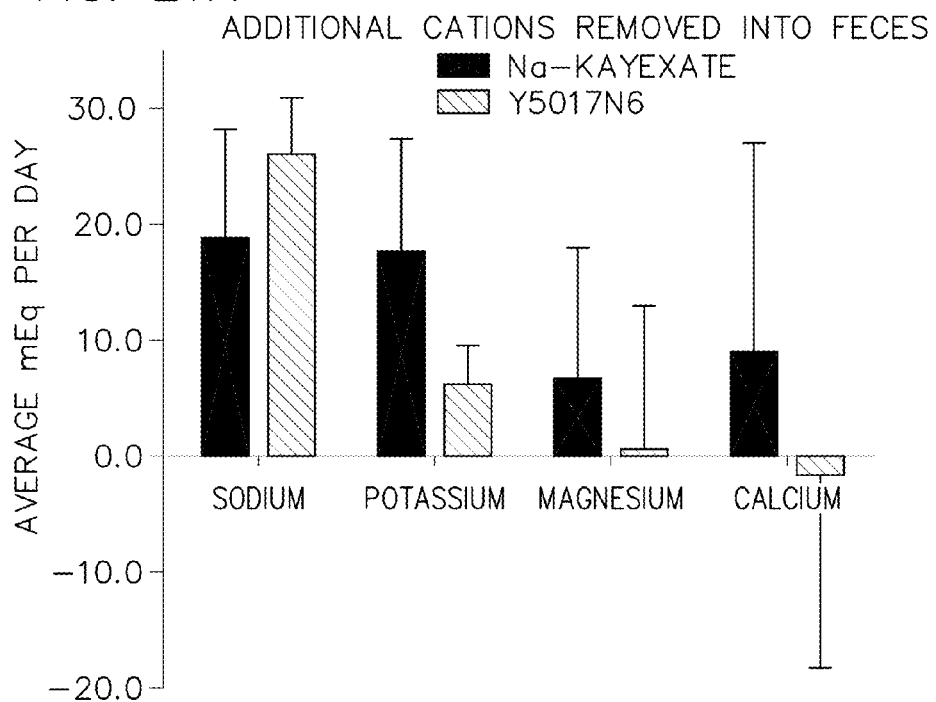
FIG. 21(a) is a graph showing the excretion of sodium, potassium, magnesium, and calcium ions in feces of swine.
Figure 21B:
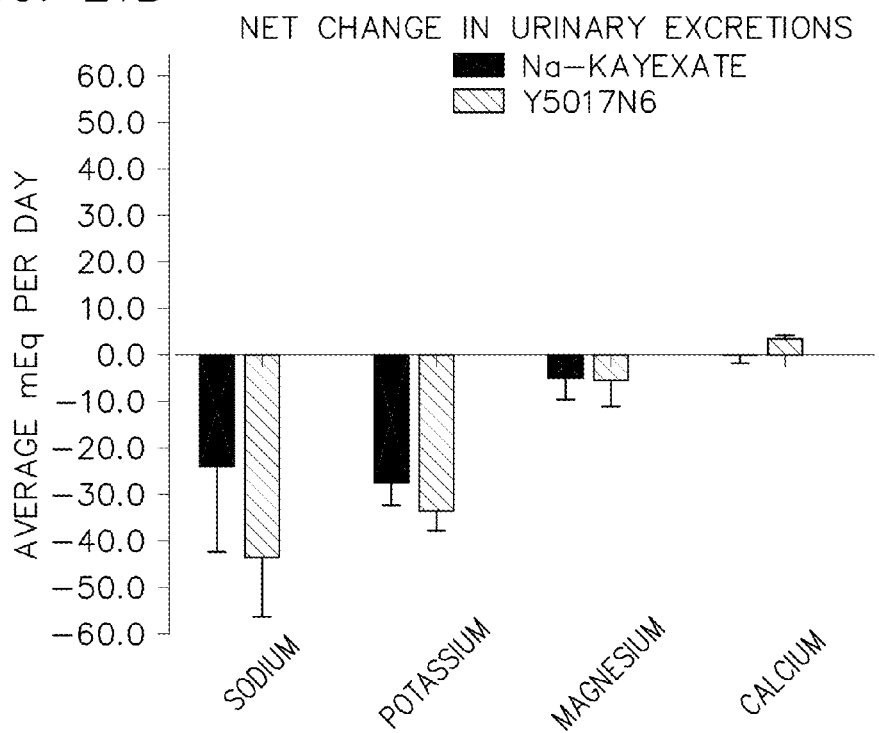
FIG. 21(b) is a graph showing the excretion of sodium, potassium, magnesium, and calcium ions in urine of swine.

Dosing of about 1 g/kg/d Kayexalate resulted in an increased fecal excretion of sodium, potassium, magnesium and calcium into the feces of swine, and a reduction in the excretion of these cations into the urine of swine (FIG. 21(a) and FIG. 21(b)). Y5017N6 also resulted in an increased average sodium and potassium secretion into the feces, and a decreased average sodium, potassium and magnesium excretion in the urine, compared to control feces and urine.

When compared to the Kayexalate-treated group, the Y5017N6 group showed increased sodium secretion in the feces and lower divalent cation excretion. This alteration in fecal excretion was compensated by the expected inverse effect on urinary excretion (i.e. decreased sodium excretion and increased divalent cation excretion). The Y5017N6 treated group showed decreased potassium excretion in the urine compared to Kayexalate, but this was not mirrored by increased potassium excretion in the feces.

Example 12

Effect of Core-Shell Particles (Comprising Cross-Linked Polyvinylamine Shell) on Cation Excretion in Rats Test Articles.

Sodium-form polystyrene sulfonate beads (Dowex 50WX4-200; Sigma-Aldrich, Inc, St. Louis, Mo.) and sodium-form, crosslinked polyvinyl amine-coated polystyrene sulfonate beads from batch FL293 (prepared by the process described in example 2, wherein the ECH:N ratio was 4:1).

Study Design.

Figure 22:
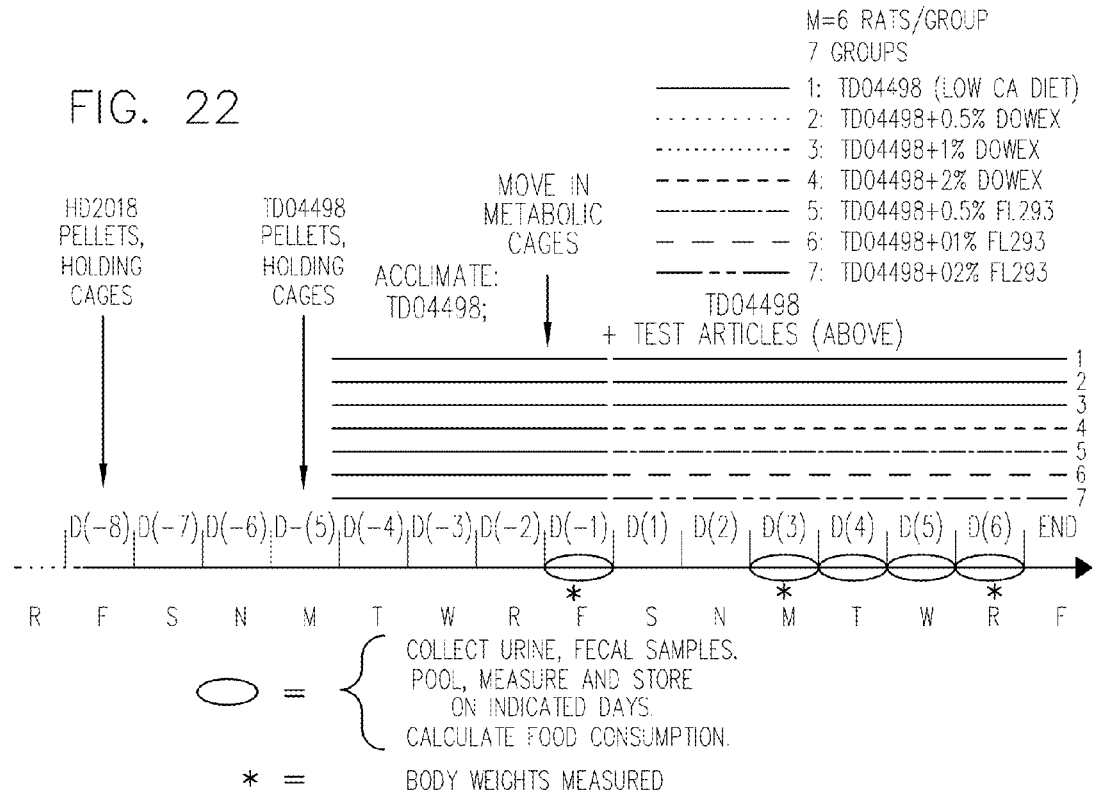
FIG. 22 is a schematic of the study design for testing the effect of crosslinked polyvinylamine shells on cation excretion in rats.

The overall study design is shown in FIG. 22. Forty two rats were placed on normal rodent chow (HD2018; Harlan Teklad Inc., Madison, Wis.). After three days, they were switched to a low calcium diet designed to result in a rat fecal calcium output similar to that of humans (TD04498, Harlan Teklad Inc., Madison, Wis.). After three days acclimation on this diet, the rats were weighed, randomly assigned to seven groups of six animals each and moved to metabolic cages, which allow separation and collection of total fecal and urine. They were acclimated for a further 24 hours. Then, on day D(1) of the study, six groups were switched to TD04498 that had been supplemented with Test Articles as described in FIG. 22 and Table 9. One group (group 1) remained on TD04498. Urine and feces were collected and pooled by day on day D(−1) and on days D(3), D(4), D(5) and D(6). The cation content of urine and feces was measured on days D(3) through D(6) and the effect of Test Article treatment versus the control group on urine and fecal cation excretion was determined.

Diets.

The base diet used in days D(−4) through day D(7) of this study was TD04498. Test articles were was mixed directly into the powder form of TD04498 at 0.5 grams per 100 g of diet (0.5%), 1 gram per 100 g of diet (1%), or at 2 grams per 100 g of diet (2%). The Test Article-supplemented diet was fed to the rats utilizing standard metabolic cage procedures. The actual dose of Test Article consumed on day D(3) by each group is summarized in Table 9.

TABLE 9

Study Group Summary

| Group Number | Number of Animals | Treatment Groups | Actual dose consumed (day 3) g/kg/d |
|---|---|---|---|
| 1 | 6 | non-treatment control | — |
| 2 | 6 | Dowex 0.5% | 0.38 |
| 3 | 6 | Dowex 1.0% | 0.82 |
| 4 | 6 | Dowex 2.0% | 1.51 |
| 5 | 6 | FL293 0.5% | 0.34 |
| 6 | 6 | FL293 1.0% | 0.79 |
| 7 | 6 | FL293 2.0% | 1.62 |

Animals.

Animals used in the study were CD® [Crl: CD® (SD)IGS BR] rats (Charles River, Wilmington, Mass.), 8 weeks of age and approximately 250 g at day D(−1) of the study. Food and water were provided ad libitum.

Methods and Measurements.

Urine electrolytes: Urine samples were diluted 30 fold in 50 mM Hydrochloric Acid and then filtered (Whatman 0.45 micron PP filter plate, 1000×g for 10 minutes). The cation concentrations in these urine samples were analyzed using a strong cation exchange column set (Dionex CG16 50×5 mm ID and CS16 250×5 mm ID), on a Dionex ICS2000 system equipped with a Dionex AS50 auto sampler, DS3 conductivity flow cell and CSRS-Ultra II 4 mm Suppressor. The ion chromatography detection method included an isocratic elution using 31 mM methanesulfonic acid at a flow rate of 1 mL/minute, and the total run time was 33 minutes per sample.

Fecal Electrolytes:

After collection from the metabolic cages, the feces were frozen at minus 20° C. The frozen feces were lyophilized and the dry weight was measured. The entire dried twenty-four hour fecal sample was homogenized with a mortar and pestle and stored at room temperature.

To a 15 mL conical tube, 200 mg of homogenized feces and 10 mL of 1N HCl was added. The fecal mixture was incubated for approximately 40 hours on a rotisserie mixer at room temperature. A sample of fecal supernatant was isolated after centrifugation (2000×g, 15 minutes) and then filtered (Whatman 0.45 micron PP filter plate, 1000×g for 10 minutes). The filtrate was diluted 2 fold with Milli-Q $H_2O$.

Filtrate cation content was measured by inductively coupled plasma optical emission spectrometry (ICP-OES) using a Thermo Intrepid II XSP Radial View. Samples were infused into the spray chamber using a peristaltic pump and CETAC ASX-510 autosampler. An internal standard, yttrium (10 ppm in 1M hydrochloric acid), was employed for correcting variation in sample flow as well as plasma conditions. The emission lines that were used for quantifying different cations are listed in Table 10:

TABLE 10

Emission lines for quantifying cations by ICP-OES

| Element | Wavelength (Internal Standard) |
|---|---|
| Calcium | 184.0 nm (224.3 nm) |
| Magnesium | 285.2 nm (224.3 nm) |
| Sodium | 589.5 nm (437.4 nm) |
| Potassium | 766.4 nm (437.4 nm) |

Data Analysis.

Fecal electrolytes were calculated in milliequivalents per day (mEq/day) using the following equation.

$$mEq/day = \left(\frac{(mEq/L \text{ electroylte} \times \text{assay volume }(L))}{(g \text{ feces in assay})}\right) \times \left(\frac{\text{Total g feces}}{\text{Day}}\right)$$

In the above equation, mEq/L electrolyte was the reported concentration of an electrolyte by the ICP after adjusting for dilution factor and valence, and total g feces per day was the amount of feces collected in a 24 hour period after lyophilization.

Urinary electrolytes were calculated in mEq electrolyte excreted per day (mEq/day) using the following equation: (mEq electrolyte per L)*(24 hour urine volume). Effect of treatment was calculated by subtracting the average values from the control group from the values in the treatment groups.

Data is presented using means±standard deviation, and/or by bar charts of average values with standard deviations represented by error bars. The mean result from each group was determined by averaging the combined mEq/day electrolyte values from treatment day D(3) through day D(6) for each animal and then averaging this average result for each treatment group.

Statistical analysis was performed using GraphPad Prism v4.03 (GraphPad Software, Inc., San Diego, Calif.). Probability (p) values were calculated using one-way ANOVA with Tukey's post test to compare groups.

Figure 23A:
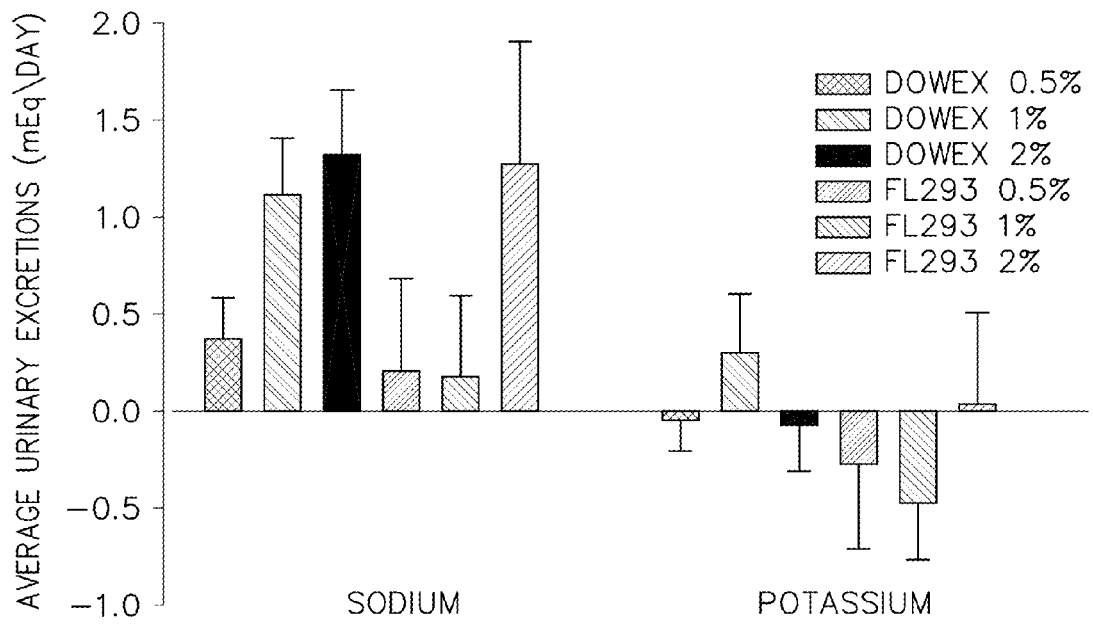
FIG. 23(a) is a graph showing the excretion of sodium and potassium ions in urine of rats.

Results for sodium and potassium cations in rat urine are presented in Table 11A and FIG. 23(a).

TABLE 11A

| | Sodium | | Potassium | |
|---|---|---|---|---|
| | Average | Std. Dev | Average | Std. Dev |
| Dowex 0.5% | 0.37 | 0.21 | −0.04 | 0.16 |
| Dowex 1.0% | 1.11 | 0.30 | 0.31 | 0.29 |
| Dowex 2.0% | 1.33 | 0.33 | −0.08 | 0.24 |
| FL293 0.5% | 0.21 | 0.48 | −0.27 | 0.45 |
| FL293 1.0% | 0.17 | 0.42 | −0.47 | 0.31 |
| FL293 2.0% | 1.28 | 0.63 | 0.02 | 0.50 |

Figure 23B:
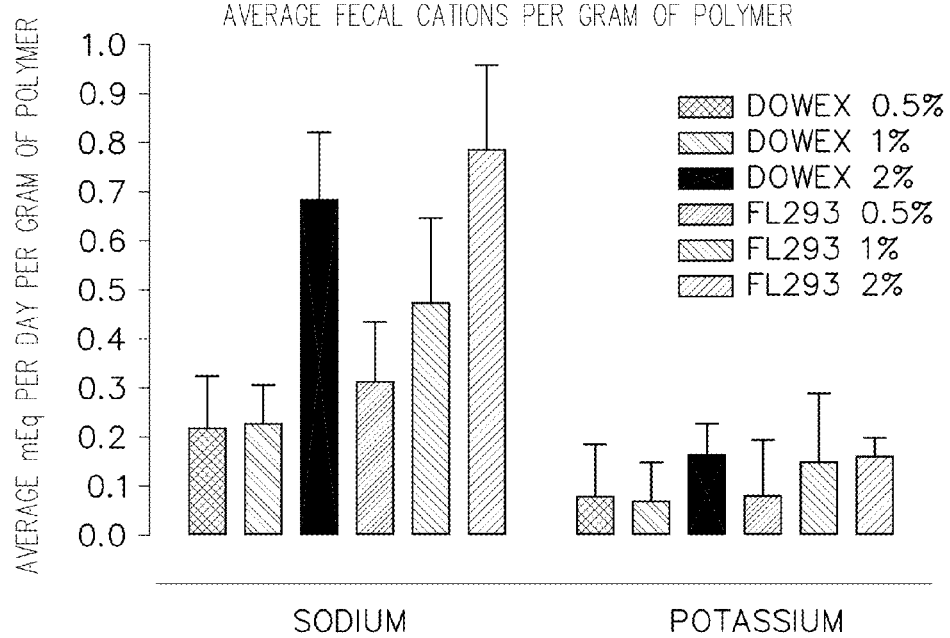
FIG. 23(b) is a graph showing the excretion of sodium and potassium ions in feces of rats.
Figure 24A:
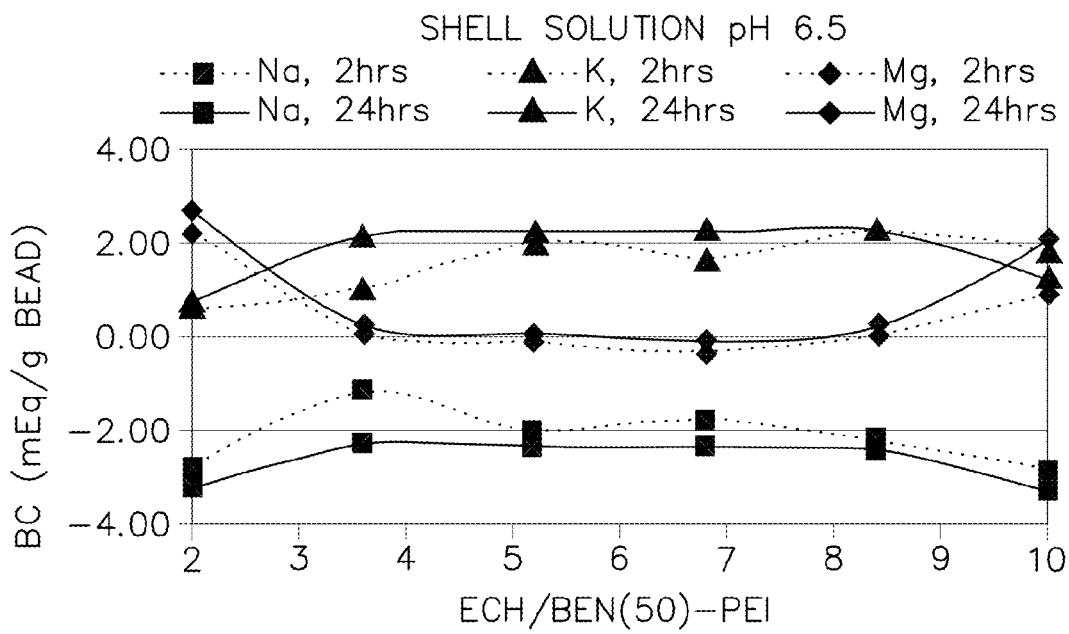
FIG. 24(a) is a graph showing the effect of the ECH/Ben (50)-PEI ratio on cation binding of a core-shell particle containing a Dowex(Na) core with a crosslinked Ben(50)-PEI shell with an aqueous shell solution of pH 6.5 during coating.
Figure 24B:
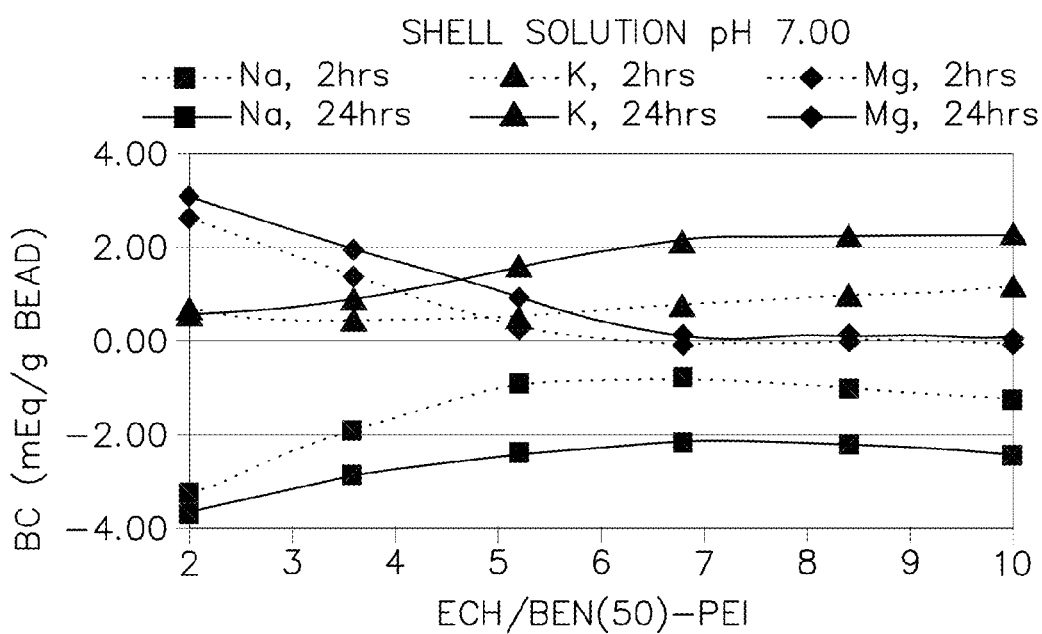
FIG. 24(b) is a graph showing the effect of the ECH/Ben (50)-PEI ratio on cation binding of a core-shell particle containing a Dowex(Na) core with a crosslinked Ben(50)-PEI shell with an aqueous shell solution of pH 7 during coating.
Figure 24C:
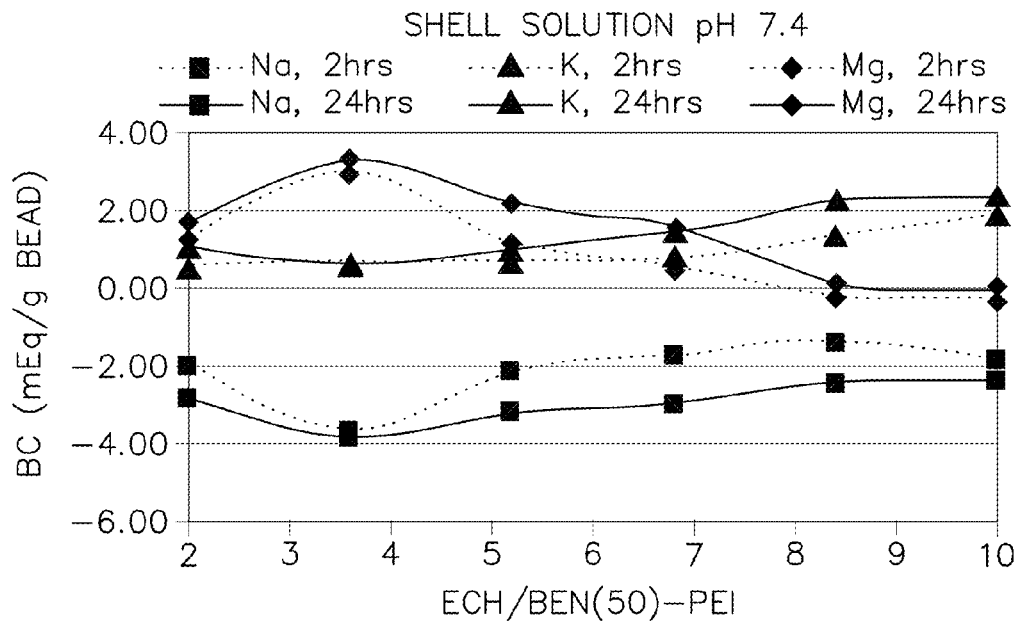
FIG. 24(c) is a graph showing the effect of the ECH/Ben (50)-PEI ratio on cation binding of a core-shell particle containing a Dowex(Na) core with a crosslinked Ben(50)-PEI shell with an aqueous shell solution of pH 7.4 during coating.
Figure 24D:
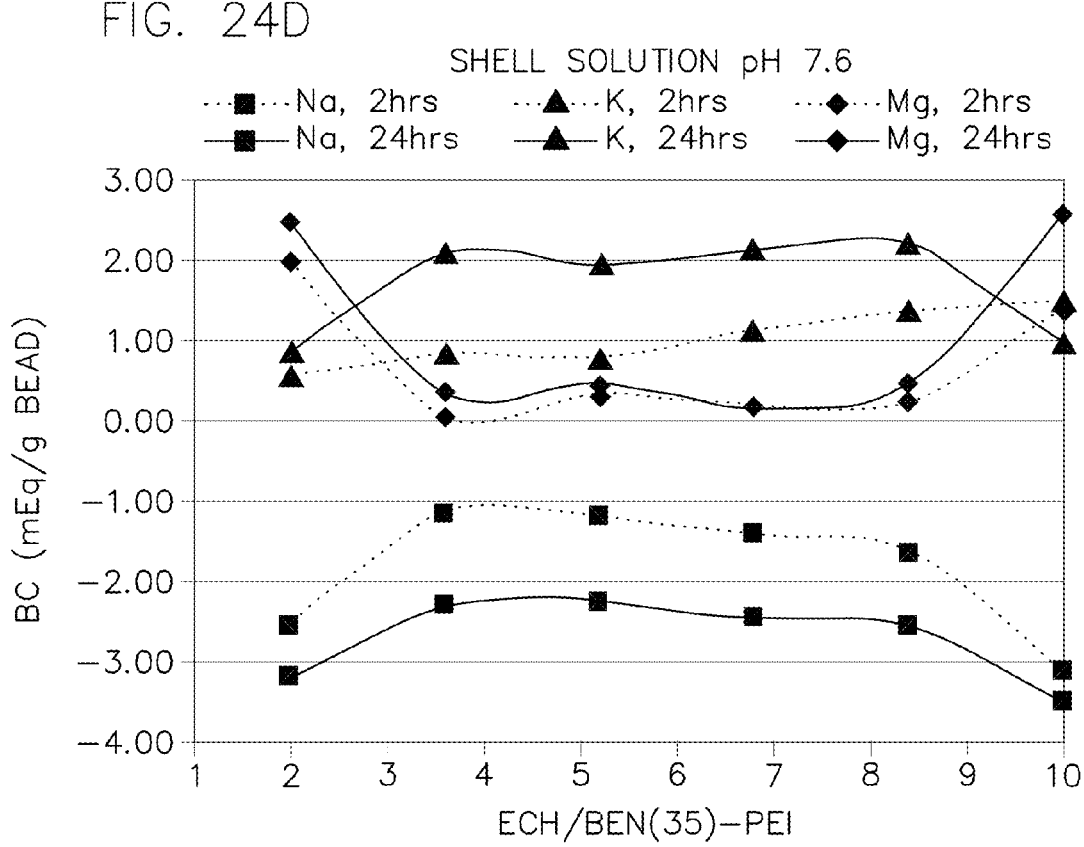
FIG. 24(d) is a graph showing the effect of the ECH/Ben (35)-PEI ratio on cation binding of a core-shell particle containing a Dowex(Na) core with a crosslinked Ben(35)-PEI shell with an aqueous shell solution of pH 7.6 during coating.

Results for sodium and potassium cations in the feces are presented in Table 11B and FIG. 23(b).

TABLE 11B

| | Sodium | | Potassium | |
|---|---|---|---|---|
| | Average | Std. Dev | Average | Std. Dev |
| Dowex 0.5% | 0.22 | 0.11 | 0.07 | 0.11 |
| Dowex 1.0% | 0.23 | 0.08 | 0.07 | 0.08 |
| Dowex 2.0% | 0.69 | 0.14 | 0.17 | 0.06 |
| FL293 0.5% | 0.31 | 0.12 | 0.08 | 0.12 |
| FL293 1.0% | 0.48 | 0.17 | 0.15 | 0.14 |
| FL293 2.0% | 0.79 | 0.18 | 0.16 | 0.04 |

Conclusions.

FL293 dosed at 1% resulted in the greatest reduction in urinary potassium excretion of all groups. Treatment with either Dowex or FL293 resulted in an increase in sodium urinary excretion, due to the increased sodium dosed as a counter-ion in the Test Articles.

On average, FL293 dosed at 1% resulted in 112% more potassium excretion and 111% more sodium excretion in the feces per gram of polymer dosed, when compared to Dowex dosed at the same level. This represents a statistically significant difference with respect to sodium ($p<0.05$).

Example 13

Core-Shell Particles Having a PSS Core and a Crosslinked Benzylated-Polyethyleneimine (Ben-PEI) Shell Prepared by Multiphase Process with In Situ Crosslinking Core Polymer.

The core polymer was PSS in the form of Dowex(Na). Dowex (H) 50W×4-200 was supplied from Aldrich and was converted to Dowex(Na) before it was coated with shell polymer.

Shell Polymer.

The shell polymer was Ben-PEI with benzylation degrees from 35 to 80%, by mole. These shell polymers were synthesized and named as Ben(35)-PEI, Ben(50)-PEI, Ben(65)-PEI, and Ben(84)-PEI, to correspondingly represent polyethyleneimine polymer benzylated at about 35 mol % (Ben(35)-PEI), at about 50 mol %, (Ben(50)-PEI), at about 65 mol % (Ben(65)-PEI), and at about 84 mol % Ben(84)-PEI, respectively. The solubility of a vinyl benzylated PEI polymer (R=vinyl in the structure below) was also tested and it is labeled v-Ben (40)-PEI.

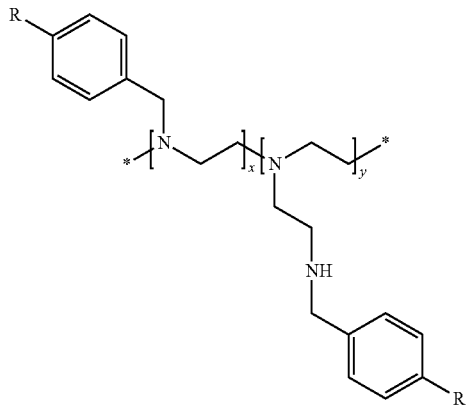

Generally, these shell polymers were prepared by weighing PEI-10K (27.83 g, Polysciences) into a 250 mL 3-necked flask, followed by addition of 23.77 g of NaHCO$_3$, 71.31 g of ethanol, and 0.02 g of t-butyl catechol to the flask. The flask was set up in the hood and fitted with a reflux condenser, a bubbler, and an overhead stirrer. The flask was heated to 70° C. and either benzyl chloride or vinyl-benzyl chloride was added in the appropriate amount over a 2 hour period. The reaction was allowed to heat at this temperature for 24 hours and then the reaction mixture was allowed to cool for 6 hours. Methylene chloride was added to the reaction mixture with stirring and then the mixture was allowed to settle for 12 hours. The solid sodium salts were removed by filtration through coarse, fast flow rate, fluted, filter paper. The resulting solution was centrifuged at 1000 rpm for 1 hour. The clear solution was decanted and added to hexanes to precipitate the functionalized polymer. The polymer was washed several times with hexanes, dried under reduced pressure at 26° C. for 24 hours, and used as is. 51.0 g of polymer was isolated.

Crosslinking Agent.

Epichlorohydrin (ECH) was used; it and other chemicals were purchased from Aldrich and used as received.

Shell Solubility Properties.

An investigation of the shell solubility was conducted to screen shell materials for use in a multiphase coating process with in situ crosslinking. Preferably for such process, the shell can be substantially soluble in the water phase and substantially insoluble in the organic phase. Shell solution pH does affect the water solubility of the shell polymers. The solubility data for Ben-PEI with different benzylation degrees is listed in Table 9.

As shown in Table 12, Ben-PEI having low degrees of benzylation was soluble in water and insoluble in organic solvents such as toluene, hexanes, and dodecane. With increased benzylation degree, water solubility for Ben-PEI decreased. However, water solubility for Ben-PEI can be altered by lowering the solution pH. For example, Ben(65)-PEI is soluble in water when the shell solution pH is below 6.5. By way of further example, Ben(80)-PEI is sparingly soluble in water independent of the pH. As described below, Ben(35)-PEI and Ben(50)-PEI were screened to explore the multiphase coating process with in situ crosslinking.

TABLE 12

Solubility profile of benzylated PEI

| Ben-PEI (benzylation degree) | Solubility | | | |
|---|---|---|---|---|
| | H2O | Toluene | Hexane | Dodecane |
| 35 | yes up to pH 9 | No | No | No |
| 45 | up to pH 8.5 | No | No | No |
| 50 | up to pH 8.0 | Swollen | No | No |
| 65 | up to pH 6.5 | Swollen | No | No |
| 80 | Swollen | Yes | Swollen | Swollen |
| V-Ben(40)-PEI | Swollen | Swollen | No | No |

Variations for the Multiphase Coating Process with In Situ Crosslinking.

Experiments investigating coating with crosslinking were conducted in a library format of 4×6 reactors, where the crosslinking agent/shell polymer ratio and shell solution pH varied from well to well. The crosslinking agent/shell polymer ratio is based on the number of equivalents of crosslinking agent per nitrogen atom in the shell polymer. Each well contained about 300 mg of Dowex(Na) beads, which were premixed with 2.5 wt. % aqueous Ben(35)-PEI or Ben(50)-PEI. The amount of shell was 7.5 wt. % compared to the weight of Dowex(Na) beads. A solution of ECH in an organic solvent such as hexanes was added. Each well was heated to 85° C. and reacted at this temperature for 10 hours. The coated beads were washed with methanol three times and washed with water twice. The beads were freeze-dried for screening in non-interfering MES buffer solution of 50 mM KCl and 50 mM MgCl$_2$. Coating quality was evaluated by determining its degree of persistent selective binding of potassium ion over magnesium ion. These results are shown in FIGS. 24($a$) to 24($d$).

Figure 25A:
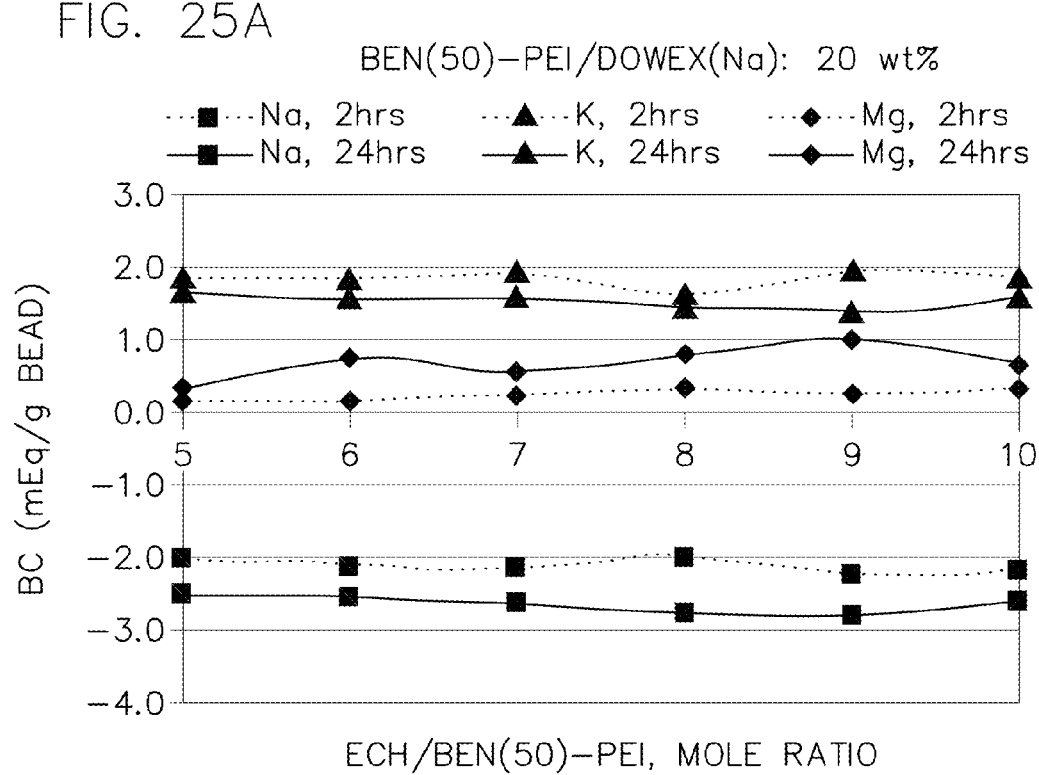
FIG. 25(a) is a graph showing the effect of the ECH/Ben (50)-PEI ratio on cation binding of a core-shell particle containing a Dowex(Na) core with a crosslinked Ben(50)-PEI shell where 20 wt. % of shell polymer was used during coating.
Figure 25B:
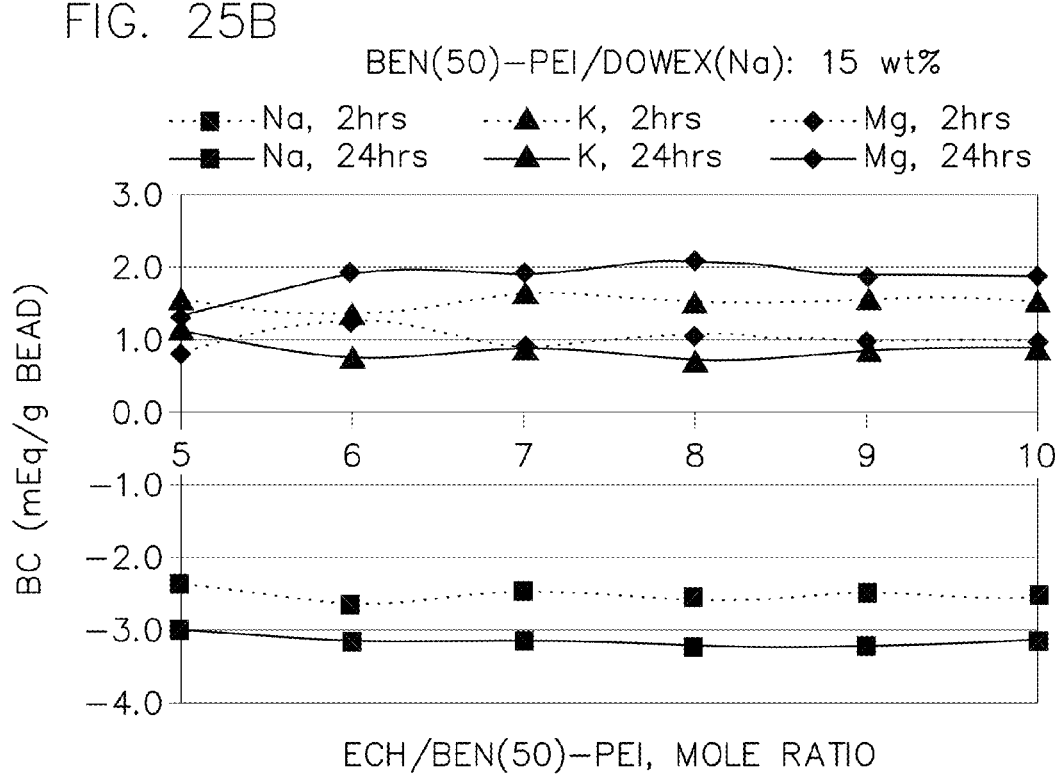
FIG. 25(b) is a graph showing the effect of the ECH/Ben (50)-PEI ratio on cation binding of a core-shell particle containing a Dowex(Na) core with a crosslinked Ben(50)-PEI shell where 15 wt. % of shell polymer was used during coating.
Figure 25C:
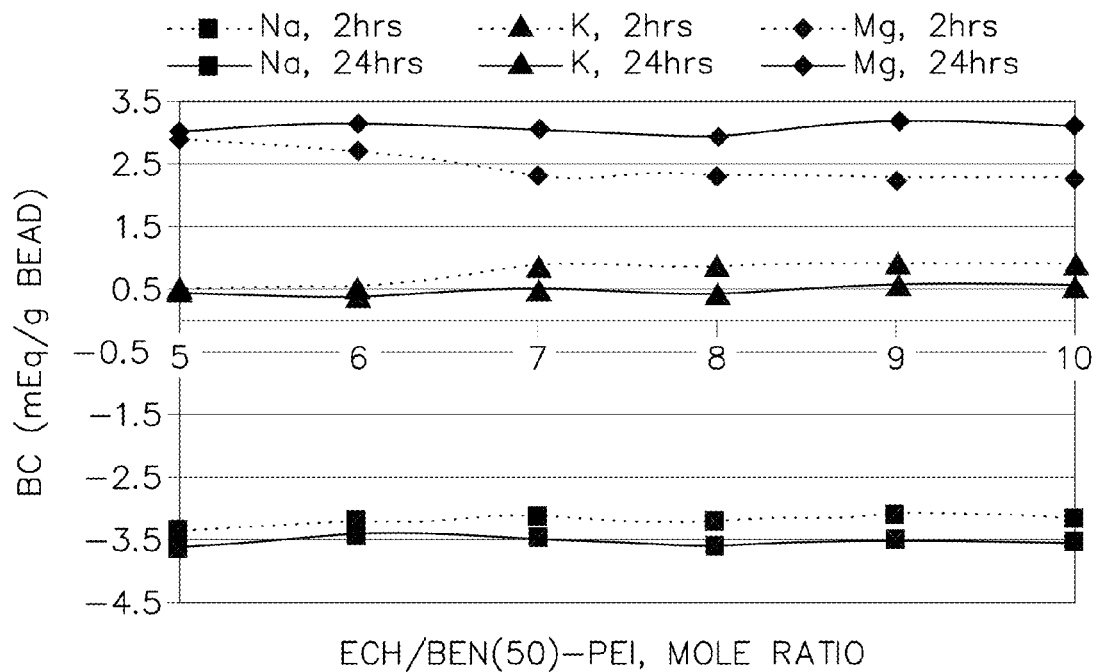
FIG. 25(c) is a graph showing the effect of the ECH/Ben (50)-PEI ratio on cation binding of a core-shell particle containing a Dowex(Na) core with a crosslinked Ben(50)-PEI shell where 10 wt. % of shell polymer was used during coating.

Other coating experiments were carried out to evaluate the effect of coating thickness on shell binding performance. These experiments were also performed in a library format of 4×6 reactors. The shell solution contained 10 wt. % of Ben (50)-PEI and the Dowex(Na) beads were premixed with a predetermined amount of shell solution. To these mixtures, a hexanes solution of ECH was added. This coating procedure was similar to the previous procedure described in this example. Binding results are shown in FIGS. 25($a$) to 25($c$).

FIG. 24($a$) depicts the effect of ECH/Ben(50)-PEI ratio on the binding performance of the crosslinked core-shell beads. At a low ECH/Ben(50)-PEI ratio, the coated beads do not show selective potassium ion binding; they perform more like core beads having no shell polymer. With increasing ECH/Ben(50)-PEI ratio, the coated beads show selective binding of potassium ion over magnesium ion at duration of 2 and 24 hours. The binding curves also show that the coated beads bind potassium ion persistently, which reflects a good coating quality and good shell composition. With further increased ECH/Ben(50)-PEI ratio, shell binding selectivity for potassium ion over magnesium ion decreases with time. A suitable ECH/Ben(50)-PEI ratio range of from about 3.6 to about 8.4 generally provides a shell that has the desired selectivity for monovalent ions.

FIG. 24($b$) and FIG. 24($c$) show more binding data for Dowex(Na) cores having crosslinked Ben(50)-PEI shell that were prepared from shell solutions of pH 7.0 and 7.4, respectively. These figures show that coating quality is sensitive to the shell solution pH. Under these conditions, desirable Ben (50)-PEI coating quality is obtained at a shell solution pH between 6.5 and 7.0. If the shell solution pH is too high, the interface interaction between the shell and core will be weakened due to the deprotonation of the shell. However, if the shell solution pH is too low, crosslinking will not be as effective due to the strong interface interaction between the core and shell. Therefore, in this system, particular pH ranges provide the desired properties of coating coverage and acceptable degree of crosslinking.

FIG. 24($d$) shows the effect of the ECH/Ben(35)-PEI ratio on the binding performance of the crosslinked core-shell beads. A similar range of ECH/Ben(35)-PEI ratios was observed as compared to the ECH/Ben(50)-PEI ratio ranges described above. However, Ben(35)-PEI could be acceptably coated and crosslinked at a higher pH than Ben(50)-PEI.

FIGS. 25($a$) to 25($c$) show the binding performance of the crosslinked Ben(50)-PEI/Dowex(Na) particles with shell coating amounts of 20 wt. %, 15 wt. %, and 10 wt. %, respectively. A thicker shell with 20 wt. % shell polymer on the Dowex(Na) beads showed desirable potassium ion binding selectivity and binding persistence up to 24 hours (FIG. 25($a$)). When there is 15 wt. % shell polymer on a Dowex(Na) core, the binding selectivity was more desirable at 2 hours with decreasing selectivity for monovalent ions over divalent ions at 24 hours. Use of a 10 wt. % shell polymer on a Dowex(Na) core did not show selective binding of monovalent ions over divalent ions even at 2 hours. These results show that the shell coating thickness is one factor for preparing a composition that provides selective and persistent binding of monovalent ions over divalent ions.

Example 14

Coating of Benzylated PEI by Solvent Coacervation

Core Polymer.
Dowex(Na): Dowex (H) 50WX4-200 was supplied from Aldrich and was converted to Dowex(Na) or Dowex(K) before shell coating.
Shell Polymer.
Benzylated PEI (Ben-PEI) shells having various benzylation degrees from 20 to 84 were prepared and named Ben(35)-PEI, Ben(50)-PEI, Ben(65)-PEI, and Ben(84)-PEI.

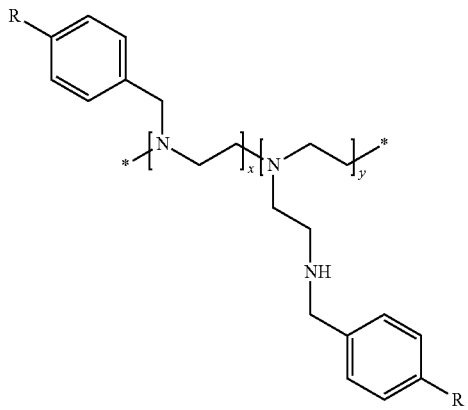

Figure 26A:
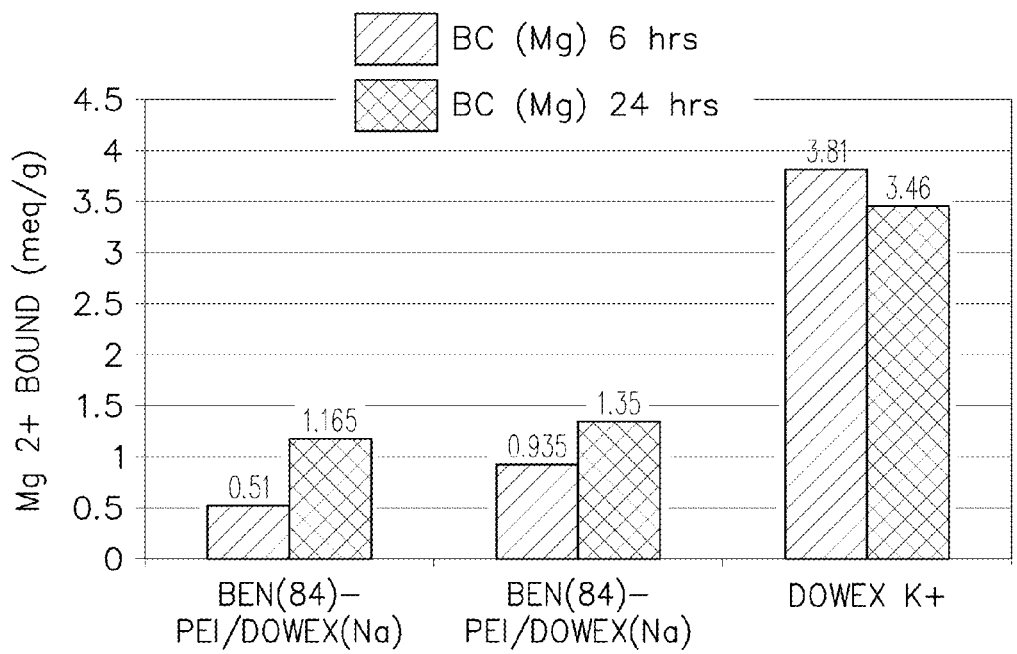
FIGS. 26(a) and 26(b) are graphs showing the magnesium ion binding profile of Ben(84)-PEI shells on Dowex(K) cores prepared by solvent coacervation.
Figure 26B:
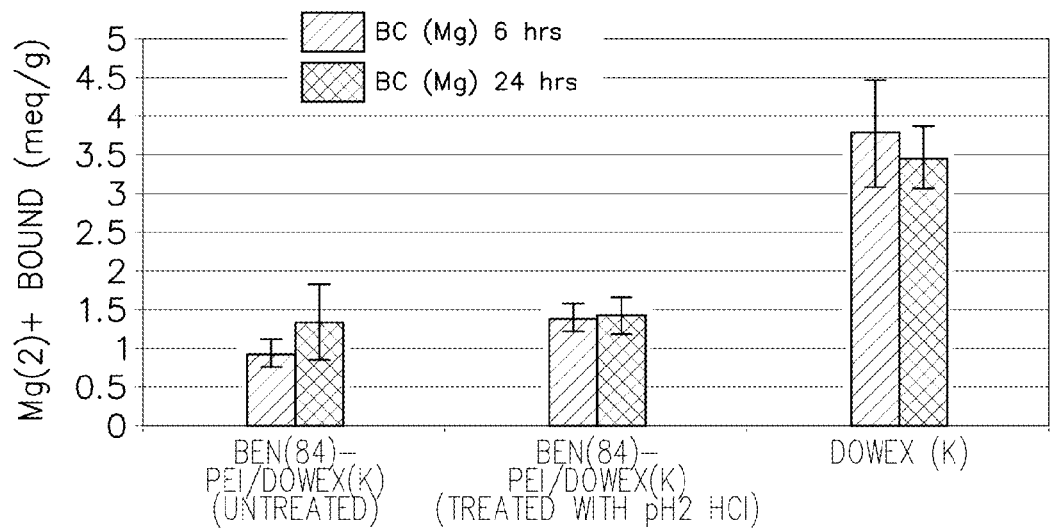

Coating Ben-PEI on Dowex(K).
Many experiments were conducted using a Dowex(K) core to explore coating methods. Coating quality was evaluated by binding experiments in a donor solution of 50 mM KCl and 50 mM $MgCl_2$ at a bead concentration of 4 mg/ml.
Experiments investigating two coacervation methods were performed to produce Ben-PEI-coated Dowex beads. The first was the controlled precipitation of shell materials onto beads that was driven by a solvent composition change called "solvent coacervation." The second was the controlled precipitation of shell materials onto beads by pH change.
Coating Dowex(K) with Ben(84)-PEI by Solvent Coacervation.
The shell solution was prepared as follows: 5 grams of Ben(84)-PEI was dissolved in 178 ml of methanol, then 59.3 ml of water was added. The mixture was adjusted to pH 3 by adding 6M HCl. The final polymer concentration was 2.5 wt. %. For coating experiments, 1 gram of Dowex(Na) was mixed with 3 gm of 2.5 wt. % Ben(84)-PEI solution. The shell and core were mixed for 5 minutes and methanol was removed by rotary evaporation. The coated beads were isolated, washed, and dried. Results of the binding measurements using these core-shell particles are shown in FIG. 26(a). Good coating quality was observed by lower magnesium ion as compared to core only beads.
FIG. 26(b) depicts the stability of Ben(84)-PEI coated Dowex(K) beads under acid conditions representative of the acidic conditions in the stomach. The core-shell beads were exposed to aqueous HCl at pH 2 for 6 hours, and then isolated and dried. Binding selectivity was tested for the post-treated beads at the same conditions described above. The shell coating was stable and magnesium ion binding was suppressed at 6 hours and 24 hours.

Figure 27A:
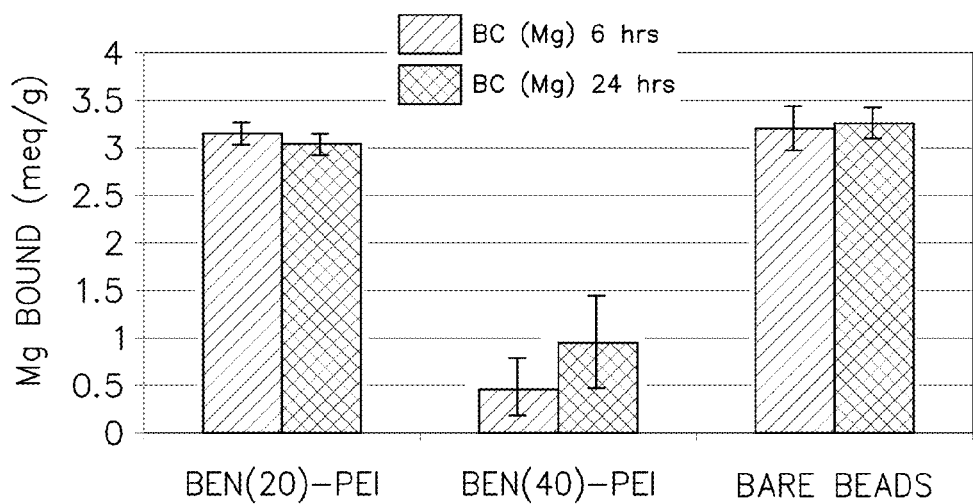
FIG. 27(a) is a graph showing the magnesium ion binding profile of core-shell particles having a Ben(20)-PEI shell, a Ben(40)-PEI shell, or no shell on a Dowex(K) core.
Figure 27B:
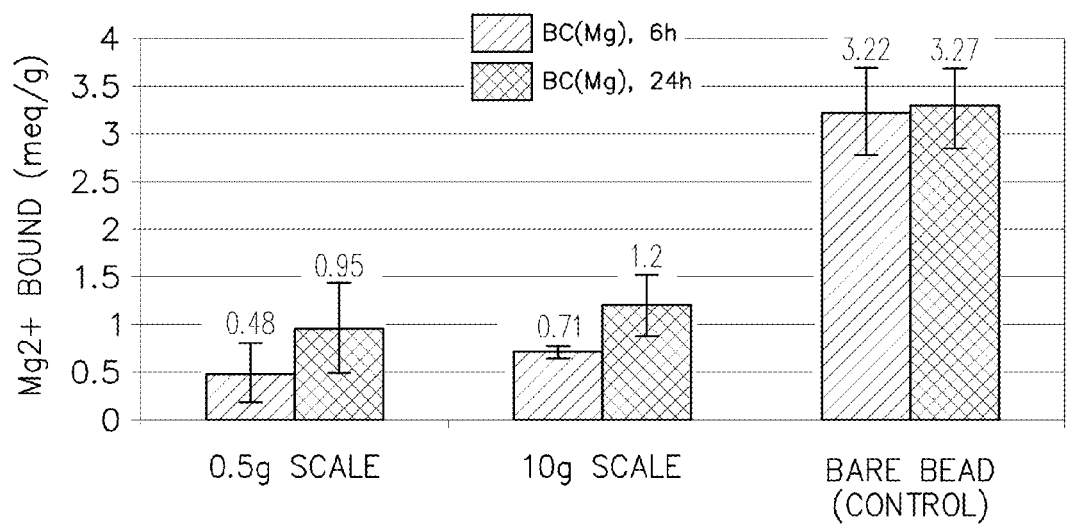
FIG. 27(b) is a graph showing the magnesium ion binding profile of core-shell particles having a Ben(40)-PEI shell and a Dowex(K) core where the particles were prepared on a 0.5 gram or a 10 gram scale.
Figure 28A:
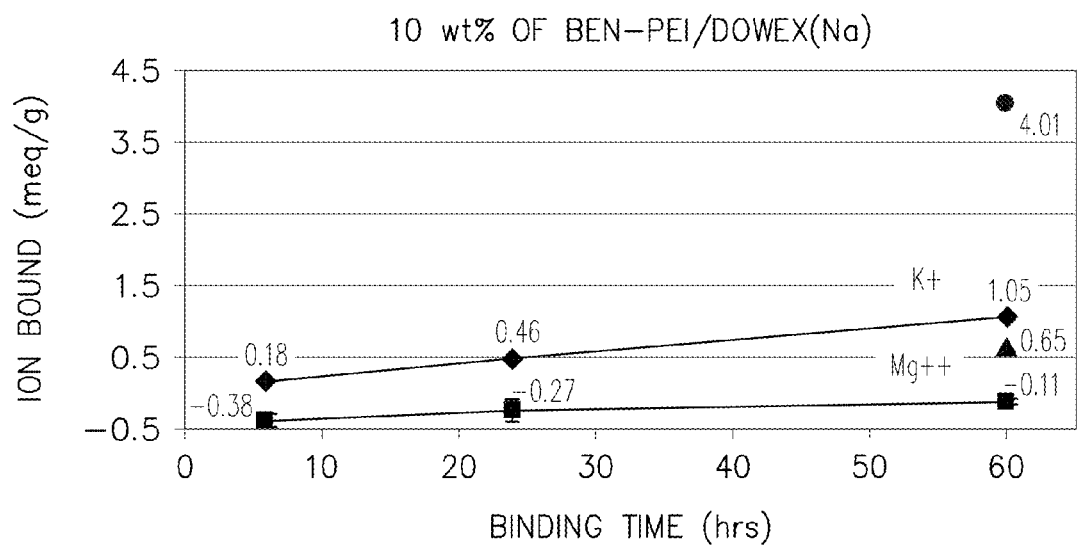
FIG. 28(a), 28(b), 28(c) are graphs showing the potassium ion and magnesium ion binding profiles where the shell thickness is varied. Shell thicknesses approximated by the ratio of shell material to core material (expressed as wt. %) are 10 wt. % Ben(84)-PEI, 2 wt. % Ben(84)-PEI, and 7.6 wt. % Ben (65)-PEI, respectively.
Figure 28B:
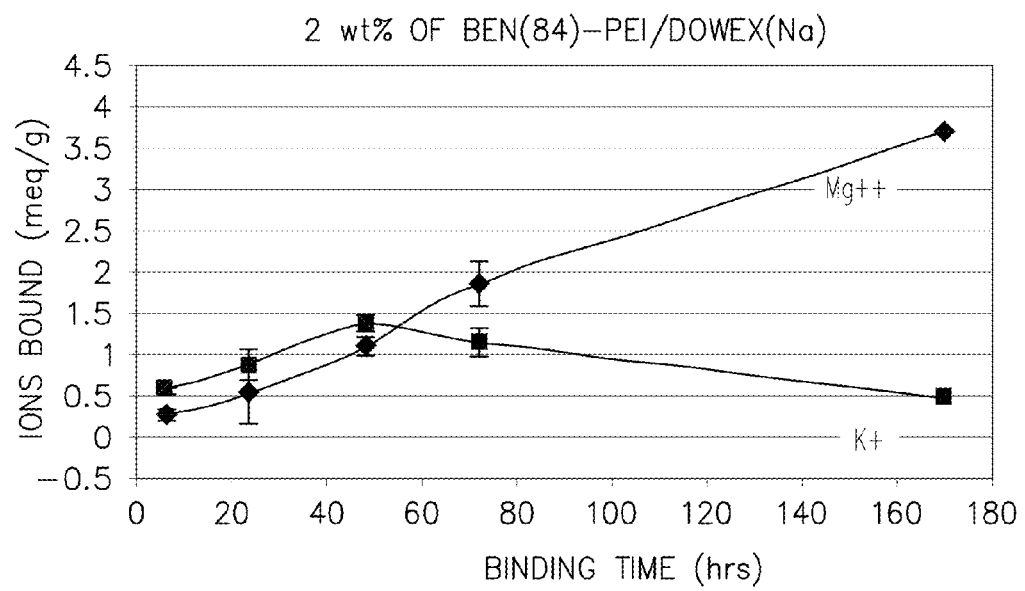
Figure 28C:
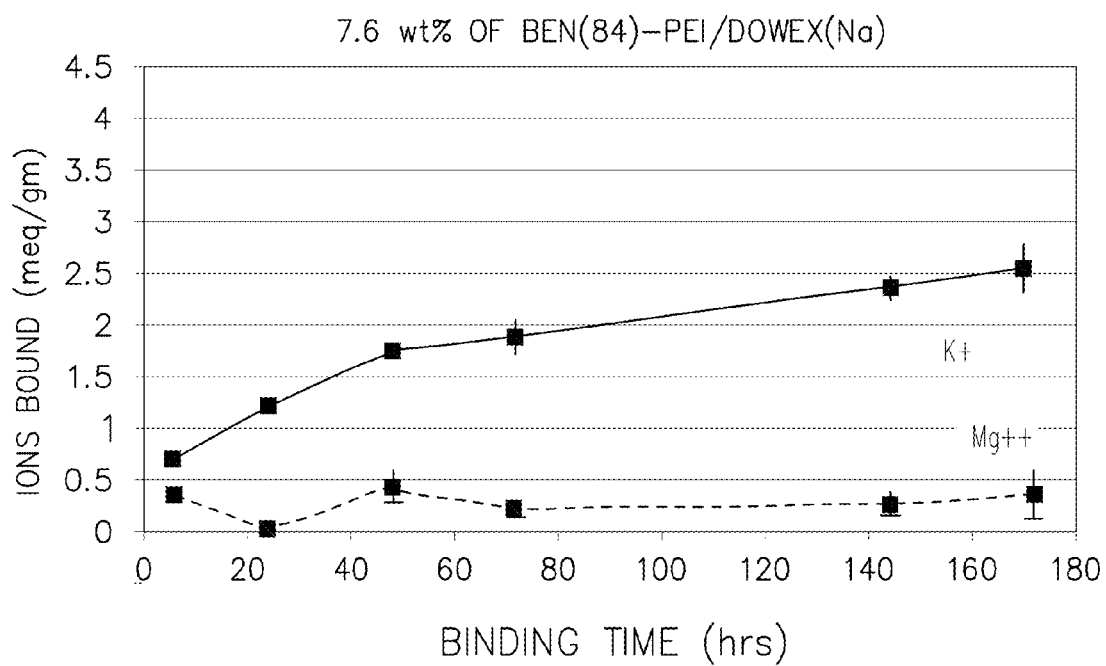

Coating Dowex(K) with Benzylated PEI by Controlled Precipitation Induced by pH Change.
5.0 grams of Ben-PEI shell having about 20% and about 40% benzylation was dissolved in 195 grams of neutral water to get a 2.5 wt. % solution. For coating experiments, 1 gram of Dowex(Na) was mixed with 4 grams of 2.5 wt. % Ben-PEI solution. An aqueous solution of NaOH (0.1 M) was added drop wise to the mixture of Dowex(K) beads and shell solution until the shell solution became turbid. The beads were isolated, washed with neutral water, and dried. Binding was measured in 50 mM KCl and 50 mM $MgCl_2$. FIG. 27(a) shows the results of the binding experiments. This controlled precipitation method for 40% benzylated PEI showed better shell quality.
Coating Dowex(K) With Ben(40)-PEI by this controlled precipitation method was further conducted on a scale of 0.5 grams and 10 grams. Binding data in FIG. 27(b) showed that this coating method could provide core-shell particles having acceptable properties on this larger scale.
Coating Dowex(Na) with Ben-PEI:
The coating procedure was similar to the coating of Dowex (K). The binding study was conducted in 50 mM KCl and 50 mM $MgCl_2$. Using $Na^+$-loaded Dowex(Na) beads would better reflect the shell ion selective and permeable nature because potassium could exchange through the shell to interact with the core polymer.
FIGS. 28(a) and 28(b) show the binding data of Ben(84)-PEI coated Dowex(Na) beads having different shell thicknesses. The procedure for the coating is similar that described in the section Coating Dowex(K) with Ben(84)-PEI by solvent coacervation above. Sample in FIG. 27(a) has 10 wt. % of Ben(84)-PEI compared with core. The sample in FIG. 28(b) has a 2 wt. % of Ben(84)-PEI compared with Dowex (Na) core. A 10 wt. % Ben(84)-PEI coating on Dowex(Na) shows relatively slow binding kinetics for potassium ions with good binding selectivity of potassium ion over magnesium ion. Decreasing the shell thickness to 2 wt. % Ben(84)-PEI increased the binding kinetics (or ion permeability) for potassium ions and a maximum binding of potassium ions was observed at a binding duration of 48 hours.
FIG. 28(c) shows the binding data for Ben(65)-PEI coated Dowex(Na) beads. Persistent binding selectivity for potassium ions over magnesium ions was observed.

Example 15

Quaternization of Benzyl Functionalized Polyethyleneimine that has a Benzyl Content of 84 Mole % (Bz-PEI-84) with Methyl Iodide An array of different ionic methyl quaternized amine levels on a Ben(84)-PEI shell polymer. The procedure to prepare an array of methyl quaternized benzyl-polyethyleneimine was implemented in an eight well reactor, where the amount of the reactants was varied from well to well as indicated in Table 13. Entries in the table correspond to the weight of chemicals that were used in the reaction well. Ben-PEI corresponds to benzyl functionalized polyethyleneimine that has a benzyl content of 84 mole % of molecular weight 10K (from Polysciences) and prepared using the following procedure. PEI-10K (27.83 g; Polysciences) and 23.77 g of $NaHCO_3$ was weighed into was weighed into a 250 mL 3 necked flask and 71.31 g of ethanol was placed into the flask. The flask was then set up in the hood and fitted with a reflux condenser, a bubbler and an overhead stirrer. The flask was heated to 70° C. Benzyl chloride (59.58 mL) was added over a 2 hour period. The reaction mixture was allowed to heat at this temperature for 24 hours and then the reaction mixture was allowed to cool for 6 hours. Methylene chloride was added to the flask and reaction mixture was thoroughly stirred and then allowed to settle for 12 hours. The solid sodium salts were removed by filtration through coarse, fast flow rate, fluted, filter paper. The resulting solution was centrifuged at 1000 rpm for 1 hour. The clear solution was decanted and added to hexanes to precipitate the functionalized polymer. The polymer was washed several times with hexanes (500 mL). The polymer was dried under reduced pressure at 26° C. for 24 hours and was used as is. 51.0 g of polymer was isolated.

Methyl iodide was used as the reactant at the appropriate concentration of Ben-PEI. The reaction was conducted in a bulk format (i.e, all the reactants were added into the same vial), in a 14 mL vial, with an overhead stirrer, and was temperature controlled. The reactor was heated to 70° C., in air for 20 hours. The product polymer was isolated by adding methylene chloride to the vials. The clear solution was added to hexanes to precipitate the quaternized polymer. The polymer was dried under reduced pressure at 26° C. for 24 hours. The polymer was then washed three times in a saturated sodium chloride solution to exchange the iodide on the polymer for chloride. The polymers were then washed an additional three times in deionized water to remove excess sodium chloride. The samples were then dried under reduced pressure for 24 hours.

The swelling ratio of a polymer was measured by placing a polymer into a previously weighed vial. Water was added to this vial and the polymer was allowed to soak for 6 hours. Excess water was removed and the vial was weighed and the weight was recorded. The wet polymer in the vial was placed into a lyophilizer for 24 hours to dry the polymer. The weight of the dry polymer was obtained. The swelling value recorded was obtained by subtracting the weight of the dry polymer from the weight of the water swollen polymer and dividing this resulting value by the weight of the dry polymer. The glass transition temperature ($T_g$) was measured using differential scanning calorimetry (DSC). These polymer swelling ratio and glass transition temperatures are presented in Table 14.

TABLE 13

Units are in grams.

| Col | Ben-PEI(84) | MeOH | MeI |
|---|---|---|---|
| 1 | 1.032 | 3.096 | 0.127 |
| 2 | 0.702 | 2.106 | 0.260 |
| 3 | 0.803 | 2.409 | 0.496 |
| 4 | 0.687 | 2.060 | 0.593 |
| 5 | 0.528 | 1.585 | 0.587 |
| 6 | 0.620 | 1.859 | 0.841 |
| 7 | 0.947 | 2.840 | 1.519 |
| 8 | 0.728 | 2.184 | 1.348 |

TABLE 14

| Sample number | Moles of MeI to N on PEI | Swelling g of water/g of gel | $T_g$ onset | $T_g(½)$ |
|---|---|---|---|---|
| 1 | 0.100 | 1.491 | 19.390 | 24.080 |
| 2 | 0.242 | 1.092 | 35.060 | 39.300 |
| 3 | 0.384 | 1.000 | 38.000 | 40.000 |
| 4 | 0.526 | 1.533 | 51.700 | 52.540 |
| 5 | 0.668 | 1.426 | 55.200 | 57.200 |
| 6 | 0.810 | 1.345 | 45.900 | 54.300 |
| 7 | 0.952 | 1.080 | 43.000 | 45.030 |
| 8 | 1.100 | 1.400 | 43.300 | 42.300 |

Coating of Dowex with Quaternized Benzyl-Polyethyleneimine.

Figure 29:
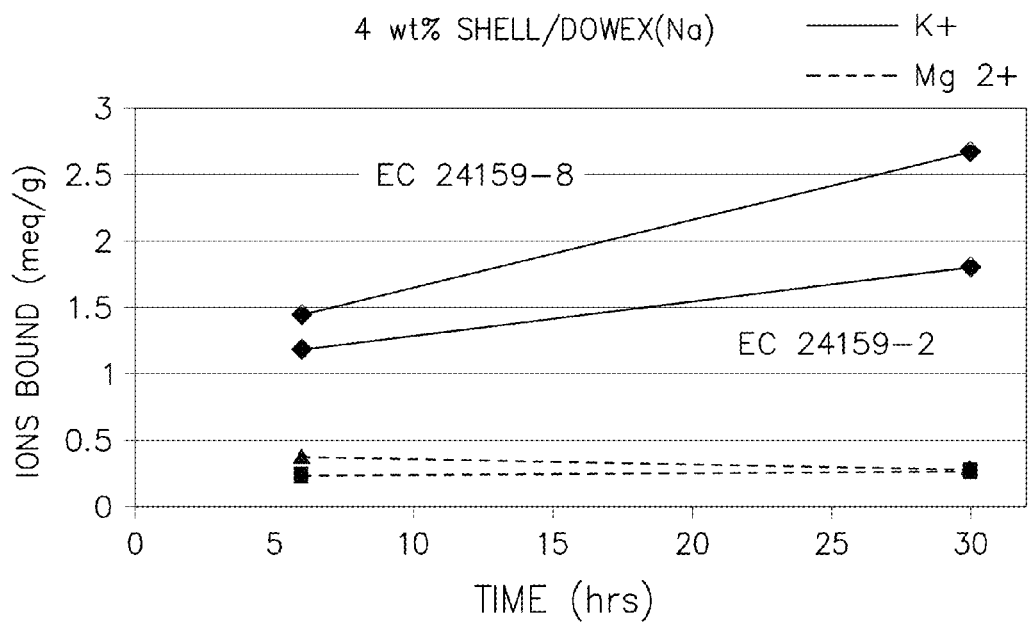
FIG. 29 is a graph showing the potassium ion and magnesium ion binding profiles for two samples having a Dowex core and Ben-PEI shells of differing quaternization degrees. The EC-24159-2 sample has a lower quaternization degree than the EC-24159-8.

The shell polymer, Ben(84)-PEI, was dissolved in a methanol and water mixture (3:1). Concentrated HCl (0.22 g) was added per gram of shell polymer. For this process, 10 wt. % of shell polymer with respect to core was used in the experiment. The shell and core were mixed for 5 minutes. Water and methanol were removed by using a rotary evaporator (bath temperature set at 60° C.). In this example, 4 wt. % of shell polymer was placed on the core. The coated Dowex beads were used "as is." FIG. 29 shows a binding isotherm for two Dowex samples that contain shells of differing quaternization degrees. The shell is described in the figure as EC24159-8: Sample 8 table 13, Ben(84)-PEI with high quaternization degree and EC24159-2: Sample 2 table 13 Ben(84)-PEI with low quaternization degree. It is observed from the figure that a higher quaternization gave faster exchanging kinetics with sustained selectivity relative to the lower quaternized material.

Example 16

Preparation of an Array of Vinyl-Benzyl Functionalized Polyethyleneimine (v-Ben-PEI)

The procedure to prepare an array of functionalized polyethyleneimine was implemented in an eight well reactor, where the nature of the reactants were varied from well to well as indicated in Table 15. Entries in the table correspond to the weight of chemicals that were used in the reaction well. PEI corresponds to polyethyleneimine of molecular weight 10K (from Polysciences). The reaction was conducted in a bulk format (i.e., all the reactants were added into the same vial), in a 14 mL vial, with an overhead stirrer, and was temperature controlled. The reactor was heated to 70° C., in air for 20 hours. The product polymer was isolated by adding methylene chloride to the vials. The $NaHCO_3$ was removed by passing the reactant solution through coarse, fast flow rate, fluted, filter paper. The resulting solution was centrifuged at 1000 rpm for 1 hour. The clear solution was decanted and added to hexanes to precipitate the functionalized polymer. The polymer was dried under reduced pressure at 26° C. for 24 hours.

NMR analysis was achieved by dissolving the resulting polymer from a reaction element as described above in a 50/50 by weight solution of deuterated methanol and chloroform. Results for the measured integration peaks of each spectral region are given. The swelling value of a polymer was measured by placing a polymer into a preweighed vial. Water was added to this vial and the polymer was allowed to soak for 6 hours. Excess water was removed and the vial was weighed and the weight was recorded. The wet polymer in the vial was placed into a lyophilizer for 24 hours to dry the polymer. The weight of the dry polymer was obtained. The swelling value recorded was obtained by subtracting the weight of the dry polymer from the weight of the water swollen polymer and dividing this resulting value by the weight of the dry polymer.

TABLE 15

Components used to prepare v-Ben-PEI

| Col | PEI | EtOH | NaHCO₃ | vinyl-benzyl chloride. |
|---|---|---|---|---|
| | Library: Unit: g | | | |
| 1.00 | 1.37 | 3.03 | 2.02 | 0.49 |
| 2.00 | 1.07 | 3.23 | 2.15 | 0.86 |
| 3.00 | 1.22 | 3.33 | 2.22 | 1.53 |
| 4.00 | 1.07 | 3.18 | 2.12 | 1.82 |
| 5.00 | 0.90 | 3.38 | 2.25 | 1.95 |
| 6.00 | 1.06 | 3.53 | 2.35 | 2.77 |
| 7.00 | 0.81 | 3.14 | 2.09 | 2.50 |
| 8.00 | 0.62 | 3.21 | 2.14 | 2.19 |

TABLE 16

NMR analysis and solubility/swelling results of v-Ben-PEI.

| Sample number (Col) | Moles of BzCl to N on PEI | Solvent | 7 ppm | 4-3 ppm | 3-2 ppm | Swelling: g of water per g of polymer |
|---|---|---|---|---|---|---|
| 1 | 0.1 | CDCl₃/MeOD | 4 | 1.5 | 18.9 | |
| 2 | 0.226 | CDCl₃/MeOD | 4 | 1 | 5.8 | |
| 3 | 0.352 | CDCl₃/MeOD | 4 | 1.8 | 7.9 | 1.90 |
| 4 | 0.478 | CDCl₃/MeOD | 4 | 0.57 | 1.65 | 1.00 |
| 5 | 0.61 | CDCl₃/MeOD | 4 | 1.1 | 1.64 | 0.85 |
| 6 | 0.74 | CDCl₃/MeOD | 4 | 1.42 | 2.57 | 0.15 |
| 7 | 0.87 | CDCl₃/MeOD | 4 | 1.59 | 2.28 | 0.20 |
| 8 | 1 | CDCl₃/MeOD | 4 | 1.4 | 1.51 | 0.25 |

Example 17

Scale Up of v-Ben-PEI Example Between Samples 3 and 4 of Example 16 Containing a Vinyl Benzyl Content of 40 Mole %

PEI-10K (27.83 g, Polysciences) was weighed into a 250 mL 3-necked flask, followed by addition of 23.77 g of NaHCO₃, 71.31 g of ethanol, and 0.02 g of t-butyl catechol to the flask. The flask was set up in the hood and fitted with a reflux condenser, a bubbler, and an overhead stirrer. The flask was heated to 70° C. and vinyl-benzyl chloride was added over a 2 hour period. The reaction was allowed to heat at this temperature for 24 hours and then the reaction mixture was allowed to cool for 6 hours. Methylene chloride was added to the reaction mixture with stirring and then the mixture was allowed to settle for 12 hours. The solid sodium salts were removed by filtration through coarse, fast flow rate, fluted, filter paper. The resulting solution was centrifuged at 1000 rpm for 1 hour. The clear solution was decanted and added to hexanes to precipitate the functionalized polymer. The polymer was washed several times with hexanes. The polymer was dried under reduced pressure at 26° C. for 24 hours and was used as is. 51.0 g of polymer was isolated.

Example 18

Coating of Core-Shell Particles Comprising Dowex Core with a v-Ben-PEI Having a Vinyl Benzyl Content of 40 Mole %

The shell, v-Ben-PEI was dissolved in a methanol and water mixture (3:1). Concentrated HCl (0.22 g) was added per gram of shell. Shell polymer (10 wt. %) with respect to core polymer was used in the experiment. The shell and core were mixed for 5 minutes. Water and methanol were removed by using a rotary evaporator (bath temperature set at 60° C.) and the dried beads were used as is.

Example 19

Crosslinking v-Ben-PEI Shells on Dowex Cores

Variation of epichlorohydrin crosslinker content. The shell was stabilized on the core using a salting out process for vinyl-benzyl functionalized polyethyleneimine (v-Ben-PEI) coated on Dowex. A batch of Dowex beads were coated (solution coating procedure described in Example 18) with polyethyleneimine functionalized with 40 mol % vinyl-benzyl chloride so that the shell made up 10% of the core-shell final weight, described in table 17 as EC64010A. The coated beads were placed into an eight well reactor, where the nature of the reactants were varied from well to well as indicated in Table 17. Entries in the table correspond to the weight of chemicals that were used in the reaction well. A liquid dispensing robot was used to add the solutions and liquid components of the reaction. A solution of 0.2M sodium chloride (NaCl_s) was used along with neat epichlorohydrin (X-EP-1). The tubes containing the coated Dowex beads plus the reactants were then placed into an eight well parallel reactor. The reactor was flushed with nitrogen and sealed. The reactor was heated to 80° C. for 12 hours with stirring (250 rpm). The tubes were taken out of the reactor and placed in a library holder. The reactant solution was removed and the resulting products were washed with water (2×10 mL) and methanol (2×10 mL). The library was then dried overnight under reduced pressure. The samples were then screened at 10 mg bead/mL of assay solution by Assay No. I (described in more detail in Example 4A). The potassium ion and magnesium ion binding capacities for the samples are presented in Table 18. Values that are higher than the control Dowex (0.70 for K) indicate that the shell survived the washing process and was crosslinked. When the shell performs desirably, high potassium binding capacity is accompanied by lower magnesium binding.

TABLE 17

Components used to prepare crosslinked v-Ben-PEI
Library: ec64010

| Well No. | NaCl_s (g) | X-EP-1 (g) | Dowex + shell (g) | Shell at 10% (g) | Moles X-EP-1 | Mole N on shell | Molar ratio of X-EP-1 to N |
|---|---|---|---|---|---|---|---|
| 1 | 2.10 | 0.042 | 0.42 | 0.042 | 0.00045 | 0.00037 | 1.243 |
| 2 | 2.50 | 0.088 | 0.5 | 0.05 | 0.00095 | 0.00043 | 2.175 |

TABLE 17-continued

Components used to prepare crosslinked v-Ben-PEI
Library: ec64010

| Well No. | NaCl_s (g) | X-EP-1 (g) | Dowex + shell (g) | Shell at 10% (g) | Moles X-EP-1 | Mole N on shell | Molar ratio of X-EP-1 to N |
|---|---|---|---|---|---|---|---|
| 3 | 2.45 | 0.123 | 0.49 | 0.049 | 0.00132 | 0.00043 | 3.107 |
| 4 | 2.15 | 0.140 | 0.43 | 0.043 | 0.00151 | 0.00037 | 4.039 |
| 5 | 1.90 | 0.152 | 0.38 | 0.038 | 0.00164 | 0.00033 | 4.971 |
| 6 | 2.20 | 0.209 | 0.44 | 0.044 | 0.00226 | 0.00038 | 5.903 |
| 7 | 1.95 | 0.215 | 0.39 | 0.039 | 0.00232 | 0.00034 | 6.836 |
| 8 | 2.00 | 0.250 | 0.4 | 0.04 | 0.00270 | 0.00035 | 7.768 |

TABLE 18

Ion binding results

| Time | 1 EC 64010#A1 | 2 EC 64010#A2 | 3 EC 64010#A3 | 4 EC 64010#A4 | 5 EC 64010#A5 | 6 EC 64010#A6 | 7 EC 64010#B1 | 8 EC 64010#B2 |
|---|---|---|---|---|---|---|---|---|
| [Mg2+] mmol/g | | | | | | | | |
| 3 | 2.254 | 2.232 | 1.323 | 0.626 | 0.031 | −0.034 | 0.001 | 0.021 |
| 6 | 2.321 | 2.282 | 1.620 | 0.879 | 0.170 | −0.108 | 0.000 | 0.071 |
| 24 | 2.393 | 2.441 | 1.949 | 1.186 | 0.329 | −0.008 | −0.031 | 0.161 |
| [K+] mmol/g | | | | | | | | |
| 3 | 0.455 | 0.441 | 0.453 | 0.534 | 0.653 | 0.963 | 1.438 | 2.285 |
| 6 | 0.494 | 0.465 | 0.501 | 0.697 | 1.024 | 1.389 | 1.844 | 2.648 |
| 24 | 0.428 | 0.467 | 0.620 | 1.074 | 1.949 | 2.366 | 2.533 | 2.893 |
| [Na+] mmol/g | | | | | | | | |
| 3 | −2.673 | −2.598 | −1.877 | −1.253 | −0.813 | −1.045 | −1.484 | −2.354 |
| 6 | −2.786 | −2.670 | −2.044 | −1.492 | −1.178 | −1.478 | −1.893 | −2.688 |
| 24 | −3.026 | −2.842 | −2.398 | −2.086 | −2.203 | −2.401 | −2.607 | −2.876 |

Example 20

Scale Up of Core-Shell Particle Comprising Crosslinked-Shell and Dowex Core

The epichlorohydrin crosslinker content was 7.76 molar equivalent for each nitrogen on v-Ben-PEI. The shell polymer was stabilized on the core using a salting out process for vinyl-benzyl functionalized polyethyleneimine (v-Ben-PEI) coated on Dowex. Into a 3-necked, 0.5 L round bottom flask was weighed 50.4 grams of Dowex beads that are coated with 10 weight % of a v-Ben-PEI shell (using the coating procedure described in example 3). The flask was fitted with an overhead stirrer, a condenser, a bubbler, and a temperature probe. Then, 251 grams of 0.2 molar solution of NaCl in water and 31.44 g of neat epichlorohydrin was added to the flask. The reaction was allowed to stir at 100 RPM for 10 minutes at room temperature with a nitrogen purge. The reaction was then allowed to heat up to 85° C. and maintained at this temperature for 12 hours. The reaction was allowed to cool and the supernatant liquid was removed. The beads are washed with water, methanol, methylene chloride, ethanol, and finally with water 3 times. The beads were dried using reduced pressure. Weight of dry isolated core shell bead 54.3 grams. Binding data in a NI buffer is given in table 19.

TABLE 19

Binding capacities for core-shell beads.
Binding Capacity (BC)(mEq/g bead): (beads tested at 10 mg/ml)

| Sample Description | $Na^+$ BC (mEq/g) at timepoint (hr): | | $K^+$ BC (mEq/g) at timepoint (hr): | | $Mg^{2+}$ BC (mEq/g) at timepoint (hr): | |
|---|---|---|---|---|---|---|
| | 2 | 24 | 2 | 24 | 2 | 24 |
| EC85081-1 | −2.092 | −2.388 | 1.998 | 1.787 | 0.148 | 0.871 |
| EC85081-2 | −2.110 | −2.421 | 1.974 | 1.759 | 0.065 | 0.766 |

Example 21

Coating of a Fluoroacrylate Based Bead with Vinyl-Benzyl Polyethyleneimine

A solution of vinyl-benzyl polyethyleneimine (preparation described in example 17) was dissolved in an aqueous methanol solution so as to give a final polymer content of 2.5 wt. %. The final composition was 6 gram v-Ben-PEI, 1.42 gram HCl, and 234 gram methanol/water (3:1 mass %). Using a Wurster coater (fluidized bed) 40 grams of fluoroacrylate based beads were coated with vinyl-benzyl-polyethyleneimine. Samples were taken during the coating process and the WO90805A beads contained a 20 wt. % v-Ben-PEI coating; the WO90805B beads contained a 30 wt. % v-Ben-PEI coating; the WO90805C beads contained a 37 wt. % v-Ben-PEI coating; and the WO90805D beads contained a 40 wt. % v-Ben-PEI coating. Binding profiles from Assay No. I (NI) are presented table 20.

TABLE 20

Ion binding profiles for various v-Ben-PEI shells on a FAA core

| Time | W090805A | W090805B | W090805C | W090805D | Uncoated standard bead |
|---|---|---|---|---|---|
| $Mg^{2+}$ mmol/g of bead | | | | | |
| 2 | 5.505 | 5.193 | 4.470 | 4.495 | 6.533 |
| 6 | 5.234 | 4.759 | 4.404 | 4.669 | 6.869 |
| $K^+$ mmol/g of bead | | | | | |
| 2 | 1.323 | 1.496 | 1.280 | 1.269 | 0.819 |
| 6 | 0.979 | 1.010 | 0.988 | 1.086 | 0.950 |
| $Na^+$ mmol/g of bead | | | | | |
| 2 | 5.336 | 4.838 | 4.591 | 4.675 | 7.219 |
| 6 | 5.396 | 4.979 | 4.686 | 4.706 | 7.121 |

The following procedure was implemented in a four well reactor that was equipped with controlled liquid dispensing capabilities. The nature of the reactants were varied from well to well as indicated in Table 21. The "Dowex beads+vBzPEI" is a Dowex bead that was coated with 10 wt. % v-Ben-PEI (shell synthesis from Example 17) using the solution coating process as described in Example 18. The coated beads were placed into the reaction vials. Then, 0.2 molar sodium chloride water solution and epichlorohydrin was added to the vial. The vials were placed into the reactor. The reactor was programmed to heat to 80° C. for 12 hours. After 6 hours, the whole amount of neat methyl iodide (MeI) was added to the reaction vial in the amounts described in Table 21. The reaction was run under an atmosphere of nitrogen. After the full reaction time, the reactor was allowed to cool, and the samples were taken out of the vials and placed into labeled centrifuge tubes. The bead products were washed with water (45 mL), methanol (45 mL), water (45 mL), 0.2 M NaCl (45 mL) (to exchange the iodide for chloride) and water (45 mL) twice. The excess water was decanted and the bead products were dried under reduced pressure. The beads were screened in Assay No. I (NI) "as is" after 24 hours of drying. The screening results are summarized in Table 22.

TABLE 21

Library: ec10324

| Row | Dowex + vBzPEI (g) | Shell at 10 wgt % (g) | NaCl_s (g) | X-EP-1 (g) | Moles of N on shell | MeI (g) | Moles of X-EP-1 to N on shell | Moles of MeI to N on shell |
|---|---|---|---|---|---|---|---|---|
| 1 | 0.770 | 0.077 | 3.850 | 0.308 | 0.00067 | 0.000 | 4.970 | 0.000 |
| 2 | 0.650 | 0.065 | 3.250 | 0.260 | 0.00057 | 0.172 | 4.970 | 2.143 |
| 3 | 0.720 | 0.072 | 3.600 | 0.288 | 0.00063 | 0.381 | 4.970 | 4.286 |
| 4 | 0.750 | 0.075 | 3.750 | 0.300 | 0.00065 | 0.595 | 4.970 | 6.428 |

Example 22

Alkylation of Crosslinked Polyethyleneimine Shell of a Core-Shell Particle with Methyl Iodide The presence of permanently quaternized amines in the shell polymer of a core-shell particle was demonstrated to have a beneficial effect on monovalent ion permeability while maintaining permselectivity over divalent ions. Quaternization can be achieved by crosslinking (e.g., see Example 19) or by alkylation or by a combination thereof, including for example by a process of exhaustive alkylation (*Langmuir* 1996, 12, 6304-6308). Methyl iodide was used to alkylate amine functionality of an epichlorhydrin-crosslinked polyethyleneimine shell of a core-shell particle Methyl iodide is known to form quaternized structures with alkyl amines (*J. Am. Chem. Soc.* 1960, 82, 4651). In this experiment, core-shell particles were prepared in the manner described for sample 5 from Example 19.

TABLE 22

Binding Capacity (mEq/g bead): (beads tested at 10 mg/ml)

| | Na BC (mEq/g) at timepoint (hr): | | K BC (mEq/g) at timepoint (hr): | | Mg BC (mEq/g) at timepoint (hr): | |
|---|---|---|---|---|---|---|
| Well no. | 2 | 24 | 2 | 24 | 2 | 24 |
| 1 | −1.14 | −2.00 | 0.42 | 1.22 | 0.69 | 0.77 |
| 2 | −1.51 | −2.26 | 1.57 | 2.34 | −0.09 | 0.10 |
| 3 | −1.99 | −2.35 | 2.15 | 2.29 | 0.03 | 0.21 |
| 4 | −2.11 | −2.33 | 2.31 | 2.20 | −0.06 | 0.27 |

Figure 30:
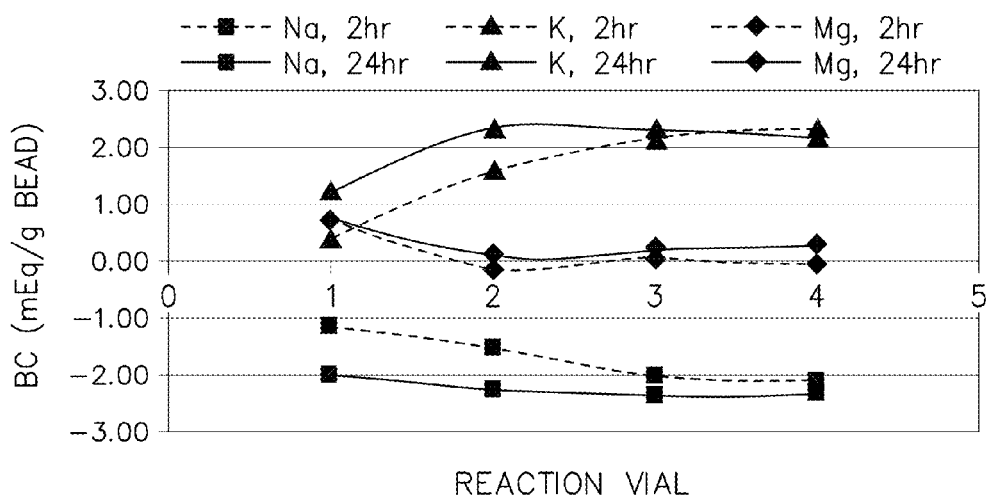
FIG. 30 is a graph showing the potassium ion, magnesium ion, and sodium ion binding profiles for samples having a Dowex core and Ben-PEI shells having different degrees of permanent quaternization.

The data from Table 22 is shown in FIG. 30.

Example 23

X-Ray Photoelectron Spectroscopy (XPS) Analysis

The core-shell particles identified below in Table 23 were also characterized by X-ray photoelectron spectroscopy (XPS).

TABLE 23

| Sample ID | Molar equivalents of X-EP-1 added | Sample preparation description |
|---|---|---|
| EC64005C3 | 4.9 | Example 19; Table 17 well 5 |
| EC85002C | 7.76 | Example 20 |
| EC85075 | 0 | Example 17 |

XPS data generally indicates the composition of the core-shell particles tested and differentiates the primary, secondary, tertiary, and quaternary nitrogen atoms in the polyethyleneimine shell. The core-shell particle samples were washed with 1.0 Molar sodium hydroxide (to remove any hydrochloride salt from the bead particles). The wash sequence was 0.3 g with 5 mL 1.0 M NaOH, 5 mL water, and 5 mL methanol. Then the core-shell particles were dried under reduced pressure.

Figure 31:
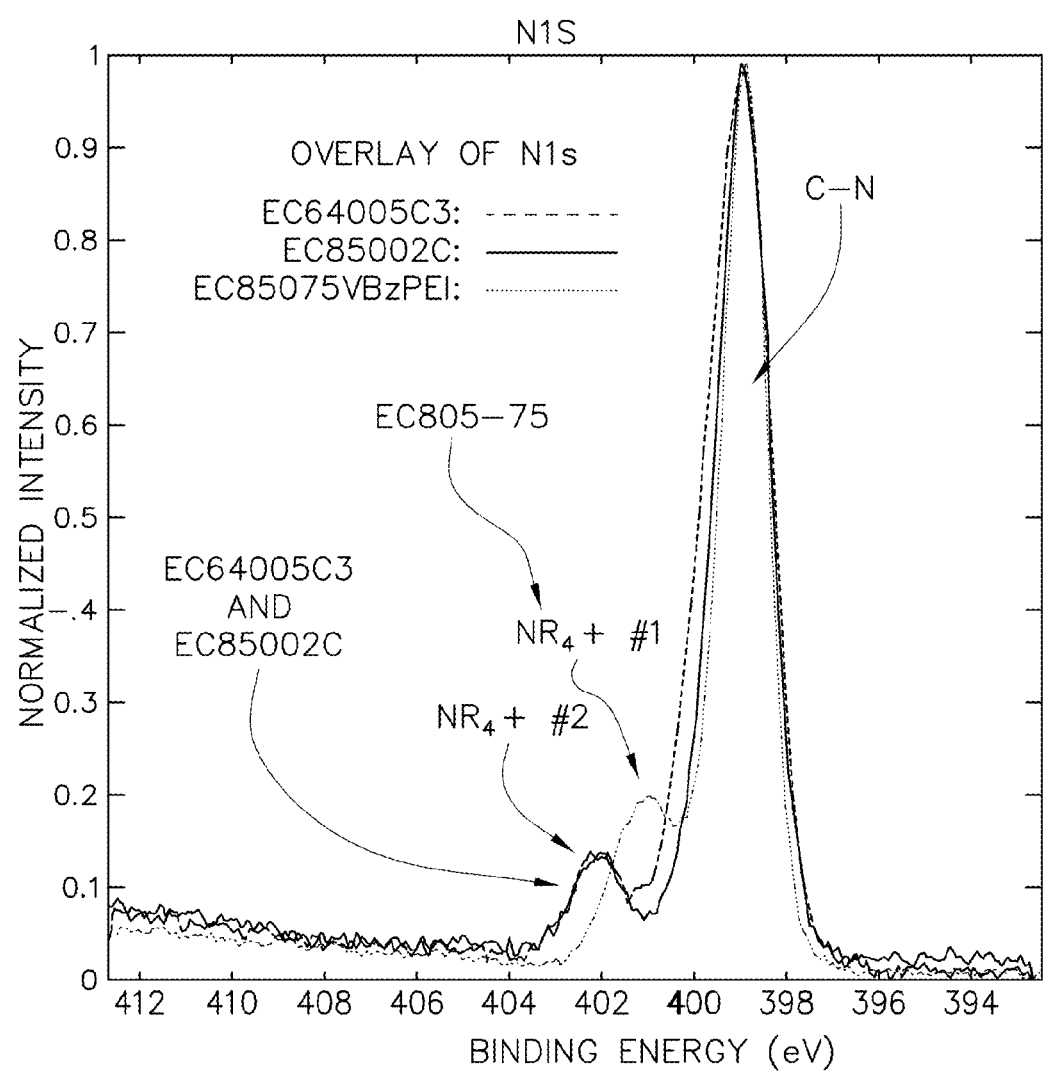
FIG. 31 is a graph showing the relative intensities and the energy (in eV) of the electrons occupying the nitrogen is orbital for nitrogen atoms attached to different numbers of organic groups.

Sample EC64005C3 was a Dowex bead coated with a v-Bz-PEI and crosslinked with epichlorohydrin prepared according to the process wherein the ratio of the crosslinking agent (epichlorohydrin, (X-EP-1)) to the number of nitrogens in the polyethyleneimine was 1:4.9. Sample EC85002c was a Dowex bead coated with a v-Bz-PEI and crosslinked with epichlorohydrin prepared according to the process where the X-EP-1:N was 7.76:1. Sample EC85075 was the v-Bz-PEI coating alone. The XPS data which is displayed in FIG. 31 is summarized in Table 24.

TABLE 24

XPS Results for PSS Core with v-Bz-PEI shell

| Sample | | C-N #1 (399.1-399.2 eV) | C-N #2 (400.0 ev-400.2 ev) | $NR_4^+$ #1 (401.5 eV) | $NR_4^+$ #2 (402.2 ev) | Total |
|---|---|---|---|---|---|---|
| EC64005C3 | % N | 68 | 24 | — | 8 | 100 |
| | At %[b] | 7 | 3 | — | 1 | 11 |
| EC85002C | % N | 82 | 10 | — | 8 | 100 |
| | At % | 7 | 1 | — | 1 | 9 |
| EC85075 | % N | 76 | 9 | 15 | — | 100 |
| VBzPEI | At % | 11 | 1 | 2 | — | ~15[a] |

From an XPS data base, $NR_4$ #1 corresponds to protonated amine. Also from an XPS data base, $NR_4$ #2 corresponds to quaternized amines. C-N #1 and C-N #2 correspond to primary, disubstituted, and trisubstituted amines. From table 24, it can be deduced that quaternary structures are present on the core-shell particles having a Dowex core coated with v-Bz-PEI and then crosslinked with epichlorohydrin when compared with the starting polyamine coating that has not been exposed to epichlorohydrin (EC85075 v-Bz-PEI).

The examples demonstrate the invention, and some of its various objects and advantages. The examples are illustrative an non-limiting. A person of ordinary skill in the art will appreciate other alternatives within the scope of invention, as defined the claims hereof.

What is claimed is:

1. A method for removing potassium from a patient in need thereof comprising administering a potassium-binding particle in an oral dosage form to the patient, the potassium-binding particle comprising a microporous or mesoporous material, the particle having an average in vitro binding capacity of at least about 2.5 mmol per gram for binding potassium, and the patient being administered a dose from about 0.5 grams per day to about 20 grams per day, wherein the microporous or mesoporous material comprises a zeolite.

2. The method of claim 1 wherein the dose is from about 0.5 grams per day to about 15 grams per day.

3. The method of claim 1 wherein the dose is from about 5 grams per day to about 20 grams per day.

4. The method of claim 1 wherein the dose is from about 5 grams per day to about 15 grams per day.

5. The method of claim 1 wherein the dose is from about 10 grams per day to about 20 grams per day.

6. The method of claim 1 wherein the dose is from about 10 grams per day to about 15 grams per day.

7. The method of claim 1 wherein the potassium-binding particle has an average in vitro binding capacity of at least about 3.0 mmol per gram.

8. The method of claim 1 wherein the potassium-binding particle has an average in vitro binding capacity of at least about 3.5 mmol per gram.

9. A method of treating hyperkalemia in a patient in need thereof comprising administering a potassium-binding particle in an oral dosage form to the patient, the potassium-binding particle comprising a microporous or mesoporous material, the particle having an average in vitro binding capacity of at least about 2.5 mmol per gram for binding potassium, and the patient being administered a daily dose from about 0.5 grams per day to about 20 grams per day, wherein the microporous or mesoporous material comprises a zeolite.

10. The method of claim 9 wherein the dose is from about 0.5 grams per day to about 15 grams per day.

11. The method of claim 9 wherein the dose is from about 5 grams per day to about 20 grams per day.

12. The method of claim 9 wherein the dose is from about 5 grams per day to about 15 grams per day.

13. The method of claim 9 wherein the dose is from about 10 grams per day to about 20 grams per day.

14. The method of claim 9 wherein the dose is from about 10 grams per day to about 15 grams per day.

15. The method of claim 9 wherein the potassium-binding particle has an average in vitro binding capacity of at least about 3.0 mmol per gram.

16. The method of claim 9 wherein the potassium-binding particle has an average in vitro binding capacity of at least about 3.5 mmol per gram.

17. The method of claim 1 wherein the potassium-binding particle retains at least 5% of the bound potassium.

18. The method of claim 1 wherein the potassium-binding particle retains at least 25% of the bound potassium.

19. The method of claim 9 wherein the potassium-binding particle retains at least 5% of the bound potassium.

20. The method of claim 9 wherein the potassium-binding particle retains at least 25% of the bound potassium.

21. A method for removing potassium from a patient in need thereof comprising administering a potassium-binding particle in an oral dosage form to the patient, the potassium-binding particle comprising a zeolite, the particle having an average in vitro binding capacity of at least about 2.5 mmol per gram for binding potassium, and the patient being administered a dose from about 0.5 grams per day to about 20 grams per day.

22. The method of claim 21 wherein the potassium-binding particle has an average in vitro binding capacity of at least about 3.0 mmol per gram.

23. The method of claim 21 wherein the potassium-binding particle has an average in vitro binding capacity of at least about 3.5 mmol per gram.

24. A method of treating hyperkalemia in a patient in need thereof comprising administering a potassium-binding particle in an oral dosage form to the patient, the potassium-binding particle comprising a zeolite, the particle having an average in vitro binding capacity of at least about 2.5 mmol per gram for binding potassium, and the patient being administered a daily dose from about 0.5 grams per day to about 20 grams per day.

25. The method of claim 24 wherein the potassium-binding particle has an average in vitro binding capacity of at least about 3.0 mmol per gram.

26. The method of claim 24 wherein the potassium-binding particle has an average in vitro binding capacity of at least about 3.5 mmol per gram.

\* \* \* \* \*

UNITED STATES PATENT AND TRADEMARK OFFICE
CERTIFICATE OF CORRECTION

PATENT NO. : 9,301,974 B2  
APPLICATION NO. : 14/053725  
DATED : April 5, 2016  
INVENTOR(S) : Michael J. Cope et al.

Page 1 of 1

It is certified that error appears in the above-identified patent and that said Letters Patent is hereby corrected as shown below:

On the title page of the patent, Item 72, Inventors:

Michael J. Cope  
Paul Mansky  
Futian Liu  
Han-Ting Chang  
Dominique Charmot  
Eric Connor  
Kalpesh Biyani  
Mingjun Liu  
Tony Kwok-Kong Mong  
Yan Chen should read Michael J. Cope  
Paul Mansky  
Futian Liu  
Han-Ting Chang  
Dominique Charmot  
Eric Connor  
Kalpesh Biyani  
Mingjun Liu  
Tony Kwok-Kong Mong  
Yan Chen  
Gerrit Klaerner  
Jerry M. Buysse Signed and Sealed this  
Seventh Day of June, 2016

Michelle K. Lee  
*Director of the United States Patent and Trademark Office*